United States Patent
Sadovsky et al.

(10) Patent No.: US 9,593,334 B2
(45) Date of Patent: Mar. 14, 2017

(54) USE OF THE CHROMOSOME 19 MICRORNA CLUSTER (C19MC) FOR TREATING VIRAL DISEASE AND PROMOTING AUTHOPHAGY

(71) Applicant: University of Pittsburgh—Of the Commonwealth System of Higher Education, Pittsburgh, PA (US)

(72) Inventors: Yoel Sadovsky, Pittsburgh, PA (US); Carolyn Coyne Candrilli, Jefferson Hills, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/383,222

(22) PCT Filed: Mar. 6, 2013

(86) PCT No.: PCT/US2013/029420
§ 371 (c)(1),
(2) Date: Sep. 5, 2014

(87) PCT Pub. No.: WO2013/134416
PCT Pub. Date: Sep. 12, 2013

(65) Prior Publication Data
US 2015/0045412 A1    Feb. 12, 2015

Related U.S. Application Data

(60) Provisional application No. 61/607,899, filed on Mar. 7, 2012.

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |

(52) U.S. Cl.
CPC ........ *C12N 15/1131* (2013.01); *C12N 15/113* (2013.01); *C12N 15/1132* (2013.01); *C12N 15/1133* (2013.01); C12N 2310/141 (2013.01)

(58) Field of Classification Search
CPC ... A61K 48/00; C12N 2310/11; C12N 15/113
See application file for complete search history.

(56) References Cited

U.S. PATENT DOCUMENTS 7,795,419 B2    9/2010 Bentwich et al.

FOREIGN PATENT DOCUMENTS

WO    WO 2011/023413    3/2011

OTHER PUBLICATIONS

Bortolin-Cavaille et al., "C19MC microRNAs are Processed from Introns of Large Pol-II, Non-Protein-Coding Transcripts," *Nucl. Acids Res.*, vol. 37:3464-3473, 2009.
Chen et al., "Inhibition of c-FLIP Expression by miR-512-3p Contributes to Taxol-Induced Apoptosis in Hepatocellular Carcinoma Cells," *Oncology Reports*, vol. 23:1457-1462, 2010.
Noguer-Dance et al., "The Primate-Specific microRNA Gene Cluster (C19MC) is Imprinted in the Placenta," *Human Mol. Genetics*, vol. 19:3566-3582, 2010.
Saito et al., "Chromatin Remodeling at Alu Repeats by Epigenetic Treatment Activates Silenced *microRNA-512-5p* with Downregulation of *Mcl-1* in Human Gastric Cancer Cells," *Oncogene*, vol. 28:2738-2744, 2009.
Santhakumar et al., "Combined Agonist-Antagonist Genome-Wide Functional Screening Identifies Broadly Reactive Antiviral microRNAs," *Proc. Natl. Acad. Sci.*, vol. 107:13830-13835, 2010.
Bayer et al., "Human trophoblasts confer resistance to viruses implicated in perinatal infection," *Am J Obstet Gynecol* 212(1):71. e1-8, 2015.
Delorme-Axford et al., "Human placental trophoblasts confer viral resistance to recipient cells," *Proc Natl Acad Sci USA* 110(29):12048-12053, 2013.
Delorme-Axford et al., "Autophagy as a mechanism of antiviral defense at the maternal-fetal interface," *Autophagy* 9(12):2173-2174, 2013.
Mouillet et al., "The role of trophoblastic microRNAs in placental viral infection," *Int J Dev Biol* 58:281-289, 2014.

*Primary Examiner* — Amy Bowman
(74) *Attorney, Agent, or Firm* — Klarquist Sparkman, LLP

(57) ABSTRACT

It is disclosed herein that cultured primary placental human trophoblast (PHT) cells are highly resistant to infection by a number of disparate viruses, and confer this resistance to non-placental recipient cells by exosome-mediated delivery of microRNAs (miRs). PHT cells express high levels of unique, primate-specific miRNAs, expressed from the chromosome 19 miRNA cluster (C19MC). It is further disclosed herein that C19MC miRNAs are packaged within PHT-derived exosomes and attenuate viral replication in recipient cells by inducing autophagy. Thus, provided herein are methods of inhibiting, treating or preventing microbial infections by administering one or more miRs of the C19MC. Also provided are methods of inducing autophagy in a cell by contacting the cell with one or more miRs of the C19MC.

16 Claims, 13 Drawing Sheets

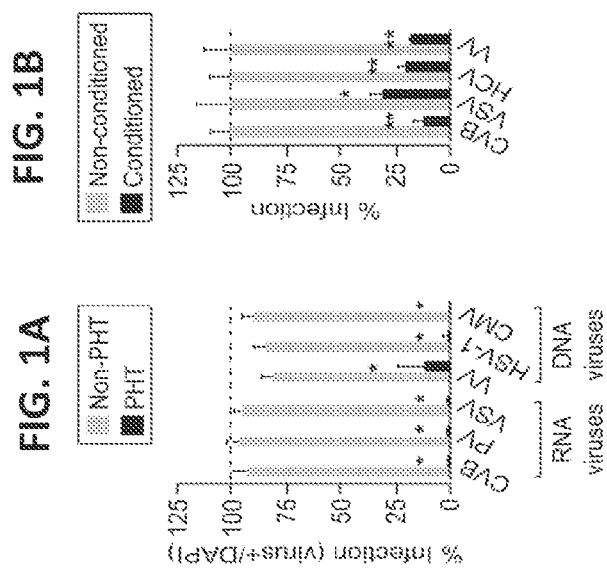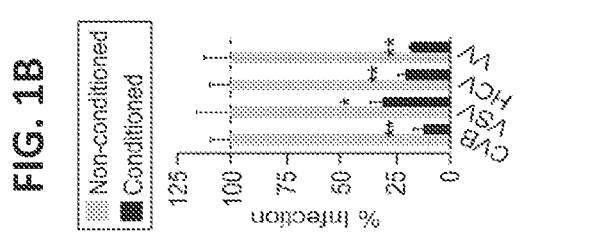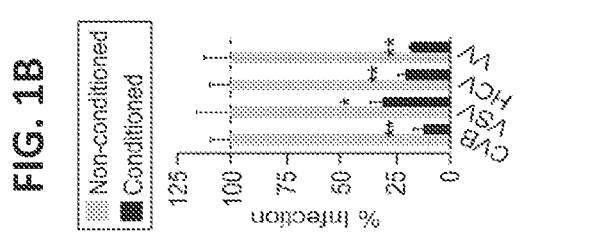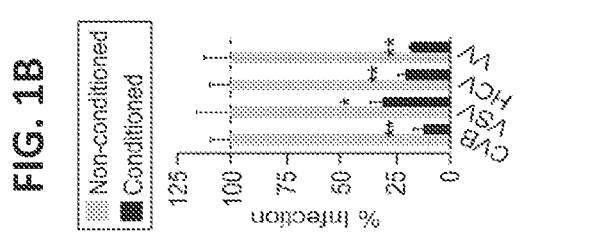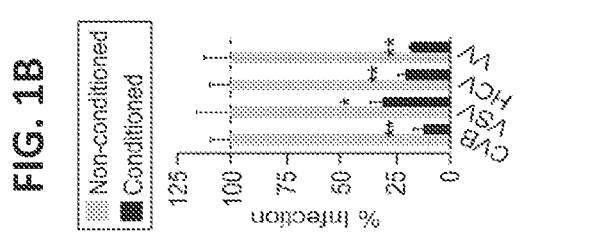

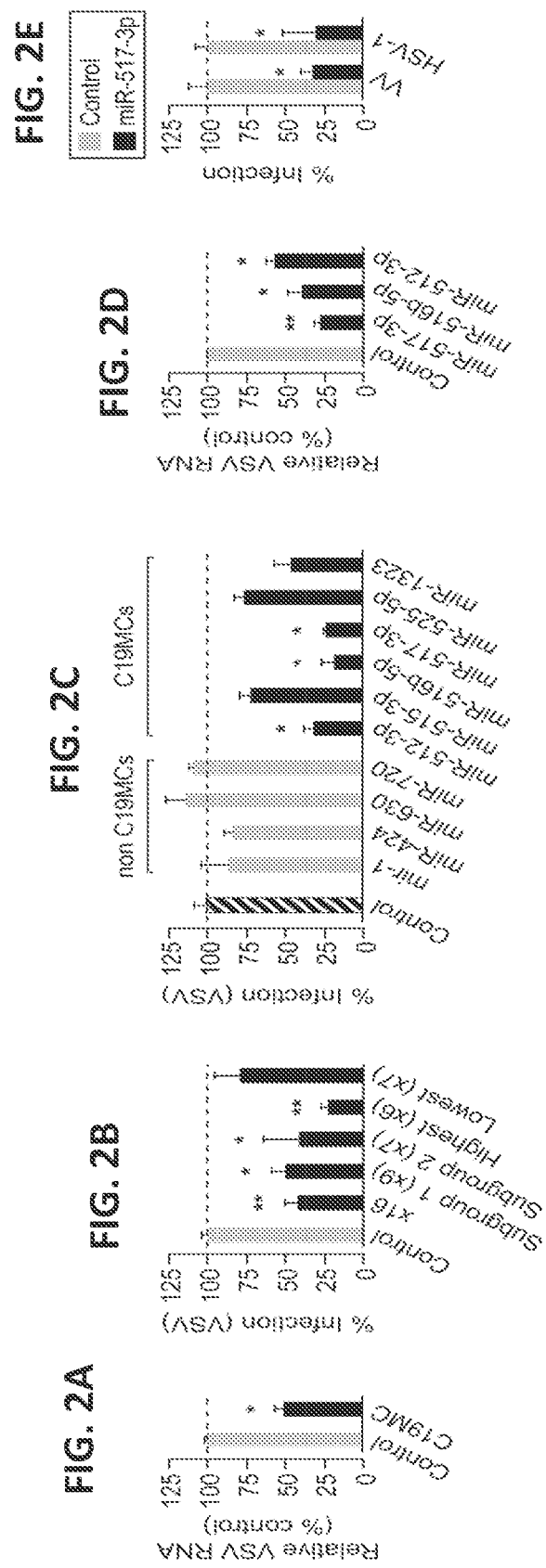

FIG. 3A
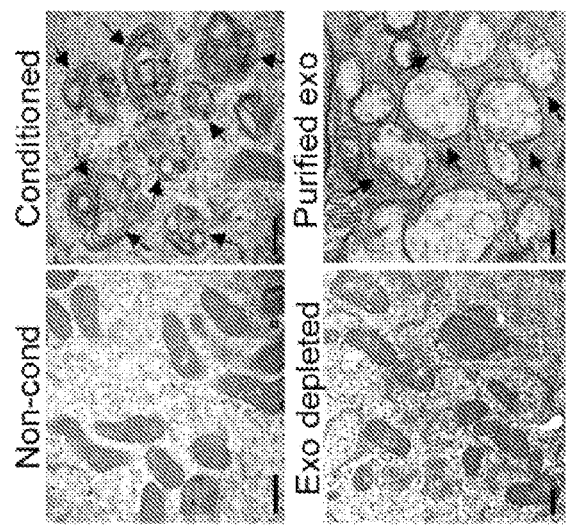
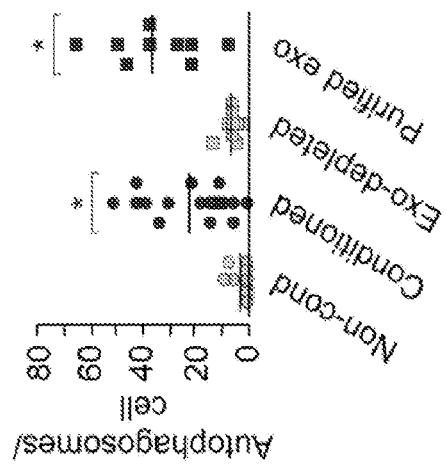
FIG. 3B
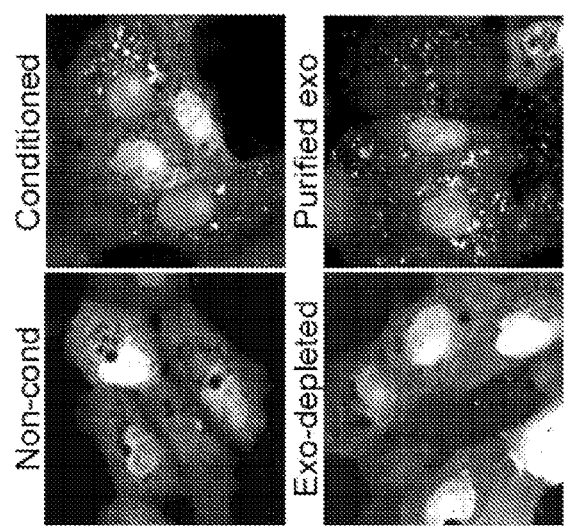
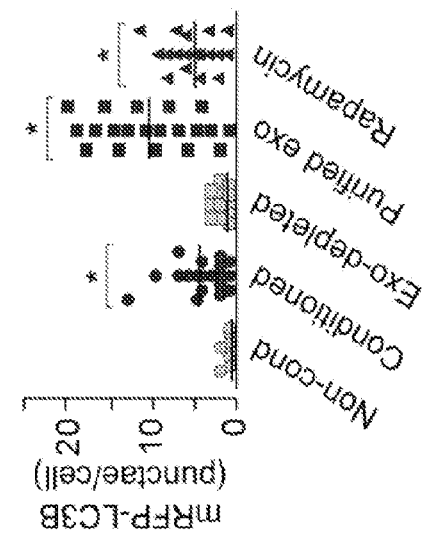

FIG. 3C
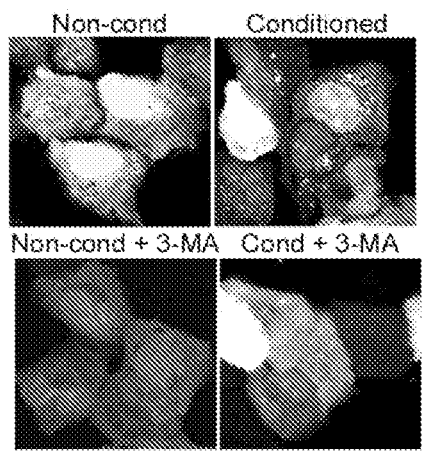
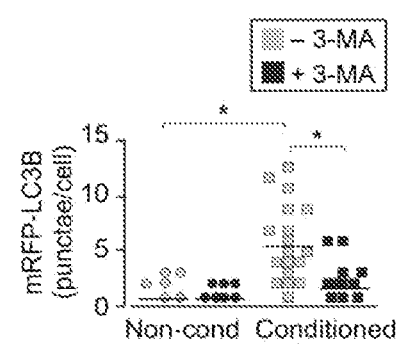
FIG. 3D
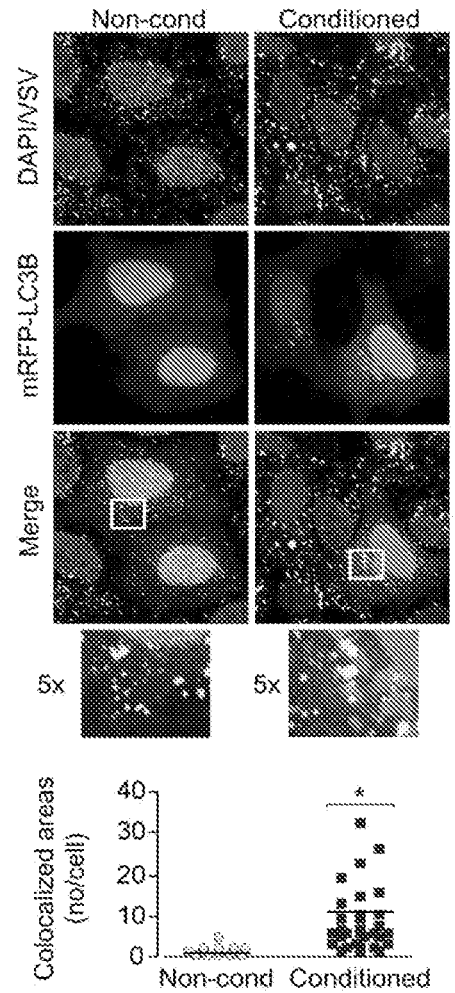

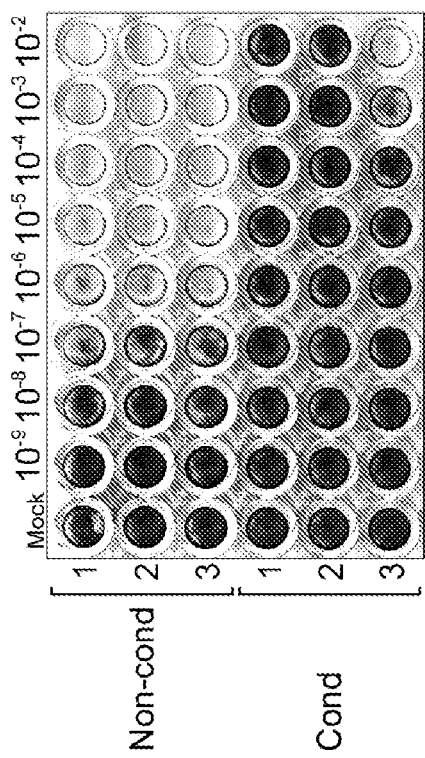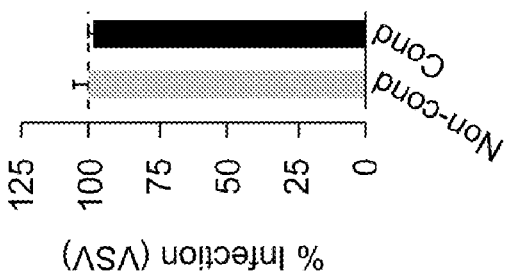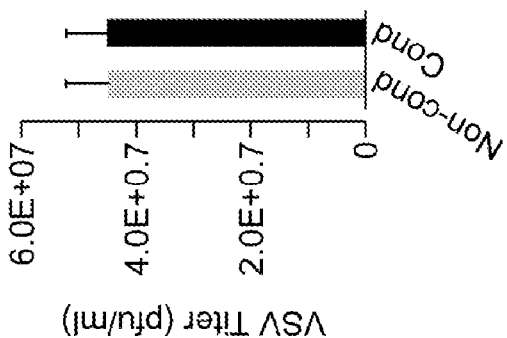

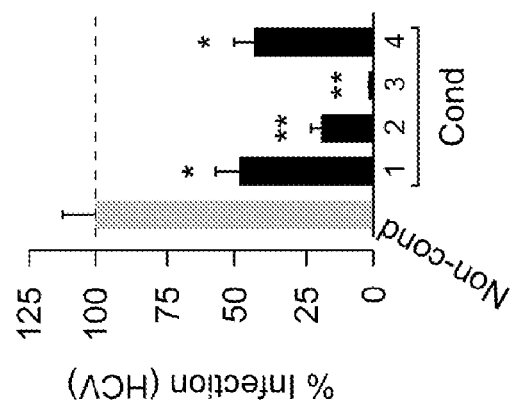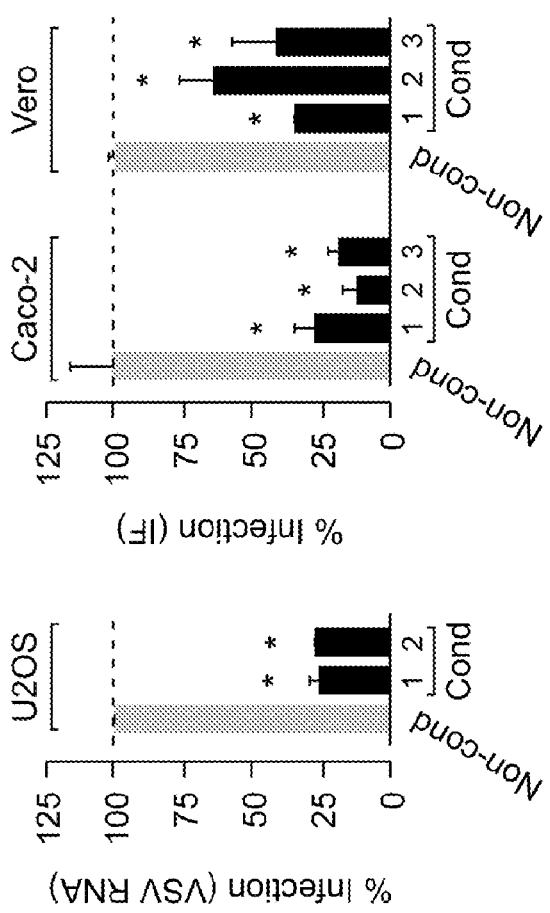

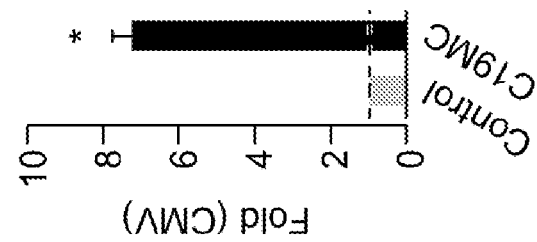
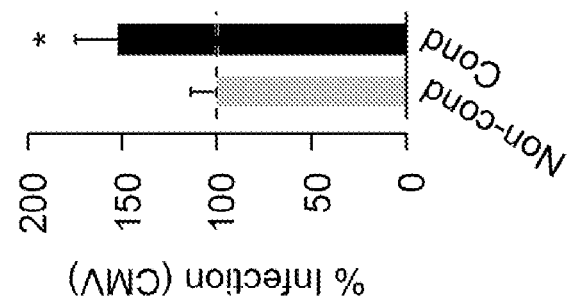
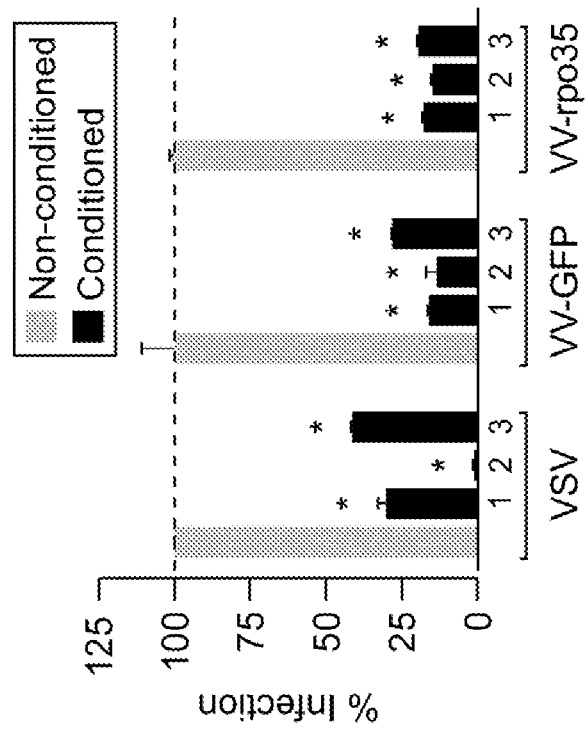

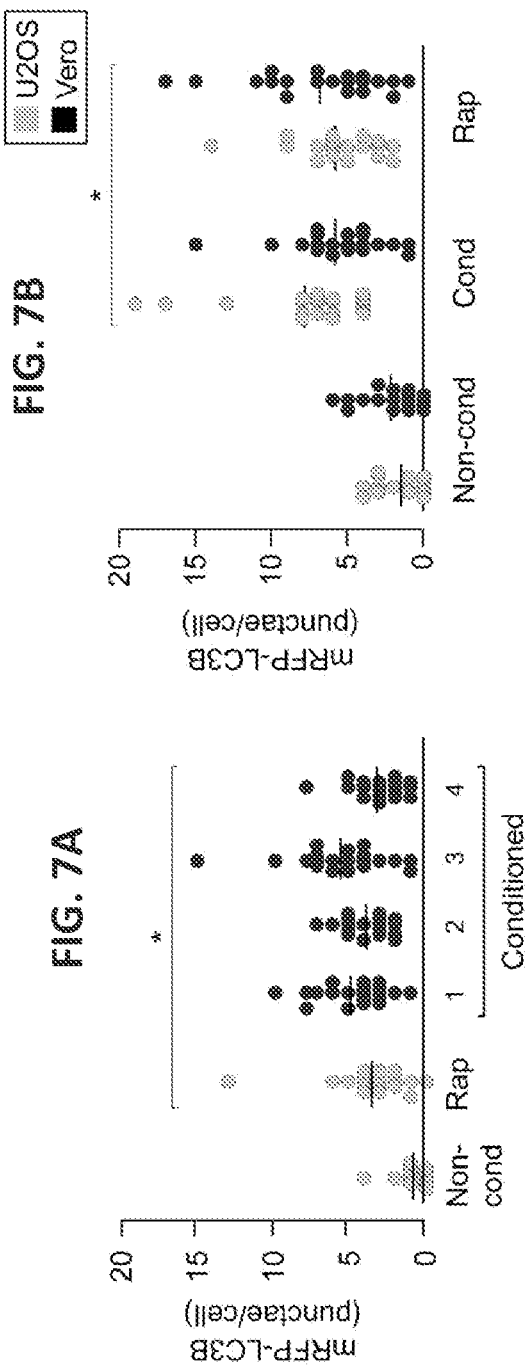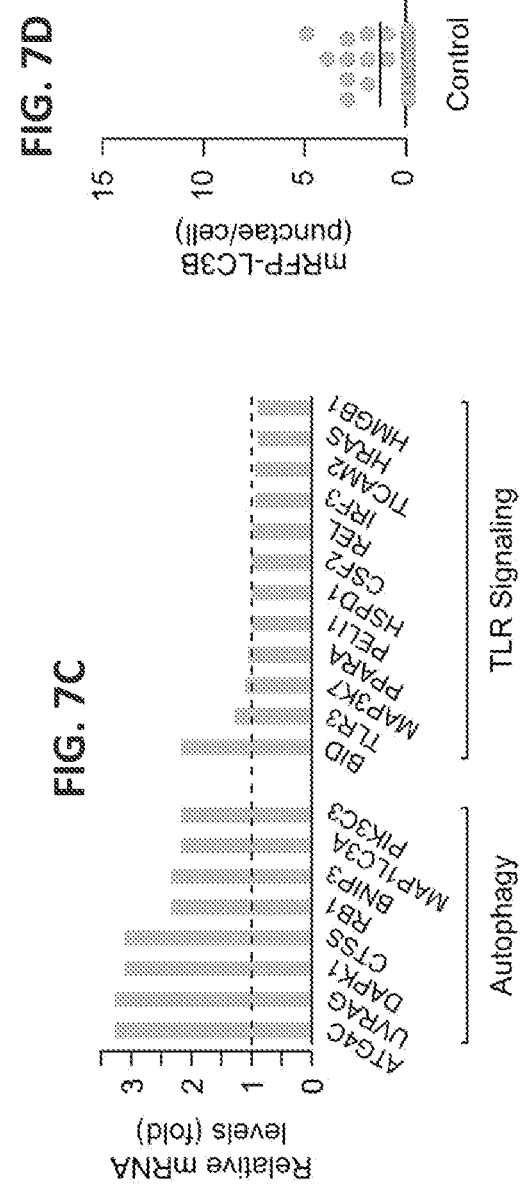

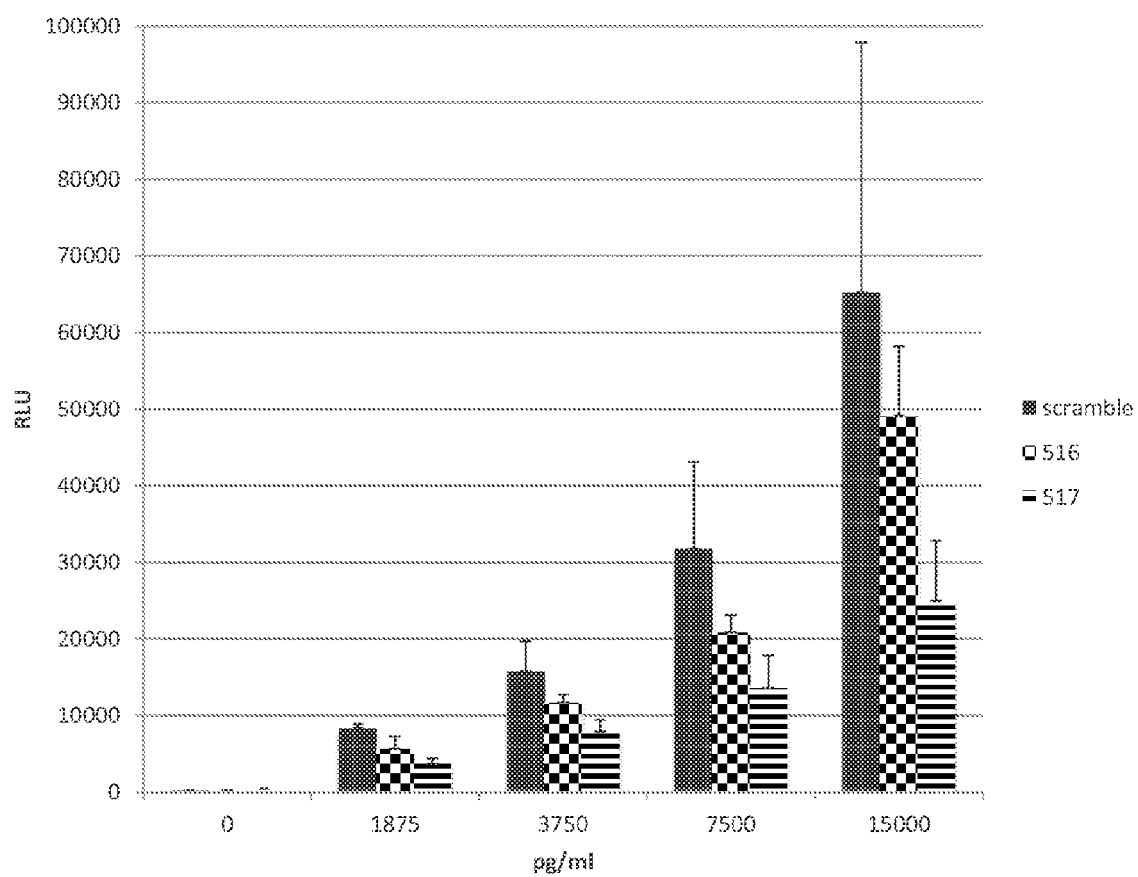

USE OF THE CHROMOSOME 19 MICRORNA CLUSTER (C19MC) FOR TREATING VIRAL DISEASE AND PROMOTING AUTHOPHAGY

CROSS REFERENCE TO RELATED APPLICATIONS

This application claims the benefit of U.S. Provisional Application No. 61/607,899, filed Mar. 7, 2012, which is herein incorporated by reference in its entirety.

ACKNOWLEDGMENT OF GOVERNMENT SUPPORT

This invention was made with government support under grant numbers AI081759 and HD065893 awarded by the National Institutes of Health. The government has certain rights in the invention.

FIELD

This disclosure concerns the use of microRNAs encoded by the primate-specific chromosome 19 miRNA cluster (C19MC) for the prophylaxis and/or treatment of microbial infection and diseases associated with autophagy.

BACKGROUND

Strategies to reduce the risk of fetal infection are of critical importance during pregnancy, where maternal to fetal transmission of microbes can have devastating consequences to the developing embryo, ranging from fetal infection, induced preterm delivery, structural or functional congenital anomalies, miscarriages and stillbirths (Ornoy and Tenenbaum, Reprod Toxicol 21, 446-457, 2006; Silingardi et al., Am J Forensic Med Pathol 30, 394-397, 2009; Euscher et al., Obstet Gynecol 98, 1019-1026, 2001). Additionally, pathogenic infections can compromise maternal health and jeopardize the pregnancy even in the absence of fetal transmission. The physical barrier interfacing the maternal and fetal blood systems within human hemochorial placenta villi include the trophoblast bilayer, basement membrane, stromal cells and fetal capillary endothelial cells. The multinucleated, terminally differentiated villous syncytiotrophoblasts are bathed directly in the maternal blood, and mediate the crucial exchange of gases, nutrients, and waste products between the mother and fetus, produce crucial hormones, and immunologically guard the developing fetus. These cells, along with the less differentiated cytotrophoblasts, constitute the first line of feto-placental defense against invading microbes.

Intrauterine transmission of viruses is likely to occur by at least four potential routes: (a) transmission across the placental villous trophoblasts by hematogenous spread or ascending infection, (b) placental transfer of infected macrophages from the maternal blood, (c) transfer of viruses via paracellular routes and/or (d) transmission of viruses from the infected maternal endothelial microvasculature to endovascular extravillous cytotrophoblasts. In general, little is known regarding the defense mechanisms employed by placental trophoblasts to defend against viral infections. Additionally, as antiviral therapeutics are generally ineffective in preventing intrauterine viral infections, elucidating the nature of these mechanism(s), as well as the underpinnings of viral counter-measures, is critical for designing therapeutic strategies aimed at preventing fetal and maternal viral disease.

Mammalian cells utilize diverse defense mechanisms to combat microbial pathogens. One crucial mechanism is the induction of autophagy, an evolutionarily conserved lysosomal degradation pathway that has been associated with an array of cellular functions, including cell death (Beaulation and Lockshin, J Morphol 154:39-57, 1977; Liang et al., Nature 402:672-676, 1999), tumorigenesis (Qu et al., J Clin Invest 112:1809-1820, 2003), and neurodegeneration (Hara et al., Nature 441:885-889, 2006; Komatsu et al., Nature 441:880-884, 2006). Autophagy also degrades intracellular foreign microbial invaders (a process sometimes referred to as xenophagy or virophagy). The cascade of events that culminate in autophagy begin with the formation of a double membrane organelle, the autophagosome, and ends in the degradation of engulfed material via the fusion of autophagosomes with late endosomes and/or lysosomes. The degradation of microbes via the fusion of autophagosomes with lysosomes is a key component in the antimicrobial effects of autophagy, yet the sequestration of viruses into autophagosomes can also direct MHC class II presentation (English et al., Nat Immunol 10:480-487, 2009), the production of antiviral type I interferons downstream of toll-like receptor 7 engagement (Lee et al., Science 315: 1398-1401, 2007), and even altered T-cell signaling (Nedjic et al., Nature 455:396-400, 2008). It is becoming clear that autophagy functions at the crossroads of many aspects of cell survival, and is likely a fundamental component of antiviral signaling.

SUMMARY

It is disclosed herein that microRNAs (miRs) of the C19MC cluster promote viral resistance and induce autophagy of recipient cells.

Provided herein is a method of inhibiting or treating a microbial infection in a subject by selecting a subject with a microbial infection or at risk for contracting a microbial infection; and administering to the subject a therapeutically effective amount of one or more miRs encoded by the C19MC, thereby inhibiting or treating the microbial infection. In some embodiments, the one or more miRs are administered by administering a nucleic acid molecule encoding the entire C19MC or a biologically active portion thereof, for example a portion that encodes one or more miRs that promote viral resistance and induce autophagy. In non-limiting examples, the one or more miRs include miR-517-3p, miR-1323, miR-516b-5p, miR-525-5p, miR-512-3p, or miR-515-3p, or any combination thereof.

Also provided herein is a method of inducing autophagy in a cell by contacting the cell with an effective amount of one or more miRs encoded by the C19MC, thereby inducing autophagy in the cell. In some embodiments, the method is an in vitro method. In other embodiments, the method is an in vivo method that includes administering to a subject an effective amount of one or more miRs encoded by the C19MC, or a nucleic acid molecule encoding the C19MC or a biologically active portion thereof. In non-limiting examples, the subject suffers from a disease associated with a deficiency in autophagy and/or a disease that may be ameliorated by enhancing autophagy.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E: Conditioned primary human trophoblast (PHT) medium and exosomes confer viral resistance to recipient cells. (FIG. 1A) PHT or non-PHT cells were infected with a panel of viruses, including coxsackievirus B (CVB), poliovirus (PV), vesicular stomatitis virus (VSV), vaccinia virus (VV), herpes simplex virus-1 (HSV-1), or cytomegalovirus (CMV). Non-PHT cells were as follows: HeLa (CVB, PV), U2OS (VSV, HSV-1, and VV), and human foreskin fibroblasts (HFF, CMV). Shown are the percent infected cells (assessed by immunofluorescence (IF); *p<0.0001). (FIG. 1B) Non-PHT recipient cells were exposed for 24 h to non-conditioned or conditioned PHT medium, and then infected with CVB, VSV, HCV, or VV. Non-PHT cells were as follows: HFF (CVB), U2OS (VSV, VV), and Huh 7.5 (HCV). Shown are the percent of infected cells, assessed by IF (CVB, VSV), luciferase assay (HCV), or RT-qPCR (VV); *p<0.05, **p<0.005. (FIG. 1C, left) Cells were exposed to non-conditioned or conditioned PHT medium for 24 h, then infected with VSV or CVB. (FIG. 1C, right) Primary cells were infected with VSV following exposure to non-conditioned or conditioned PHT medium (*p<0.05, **p<0.005). (FIG. 1D) Conditioned PHT medium was subjected to heat inactivation or sonication prior to 24 h exposure to Vero cells, then infected with VSV. Percent infection assessed as in (A); (*p<0.0001). (FIG. 1E) U2OS cells were exposed for 24 h to non-conditioned, conditioned, exosome-depleted conditioned medium, exosomes purified from PHT, JEG-3, or from three preparations of murine dendritic cell (DC), and then infected with VSV. Percent infection assessed as in (A); (*p<0.0005), each PHT exosome preparation was derived from a different placental preparation.

FIGS. 2A-2E: PHT and exosomal C19MC miRNAs confer viral resistance to recipient cells. (FIG. 2A) U2OS cells stably expressing control- or C19MC-bacterial artificial chromosome (BAC) were infected with VSV (infection levels assessed by RT-qPCR, *p<0.0001). (FIG. 2B) U2OS cells were transfected with C19MC miRNA mimics that represent the miRNA sub-groups detailed in Table 2 or control mimics, and then infected with VSV (shown as percent infected cells, assessed by IF; *p<0.05, **p<0.001). (FIG. 2C) U2OS cells, transfected with mimics of the six highest expressed C19MC miRNAs, scrambled control, or non-C19MC (miR-1, -424, -630, -720) miRNA mimics, were infected with VSV (infection level assessed by IF or qPCR; *p<0.0005). (FIG. 2D) U2OS cells, transfected with mimics of the top three antiviral C19MC miRNAs or with scrambled control mimics, were infected with VSV (infection assessed by RT-qPCR; *p<0.05, **p<0.0001). (FIG. 2E) U2OS cells, transfected with scrambled control or miR-517-3p mimic, were infected with VV or HSV-1; infection assessed as in (D) (*p<0.0001).

FIGS. 3A-3D: PHT-derived exosomes induce autophagy in recipient cells. (FIG. 3A) U2OS cells transfected with mRFP-LC3b were exposed to non-conditioned-, PHT conditioned-, exosome-depleted conditioned PHT medium, or purified PHT exosomes for 24 h, and LC3b punctae formation was assessed by confocal microscopy. Shown are confocal micrographs (top) and quantification of mRFP-LC3b punctae per cell (bottom) (*p<0.0001). (FIG. 3B, top) Electron micrographs of cells exposed to non-conditioned or conditioned PHT medium (Vero), exosome-depleted conditioned PHT medium (Vero), or purified PHT exosomes (U2OS). Arrows denote autophagosomes. Bar=500 nm. (FIG. 3B, bottom) Quantification of electron micrographs of cells exposed to non-conditioned (Vero and U2OS), conditioned PHT media samples (Vero and U2OS), exosome-depleted conditioned medium (Vero), or purified PHT exosomes (U2OS) (*p<0.0001). (FIG. 3C) U2OS cells transfected with mRFP-LC3b were exposed to non-conditioned or conditioned PHT medium in the absence or presence of 3-methyladenine (3-MA) for 8 h, and LC3b punctae formation was assessed by confocal microscopy. Shown are confocal micrographs (top) and quantification of mRFP-LC3b punctae (bottom) (*p<0.0005). (FIG. 3D, top) Immunofluorescence images of VSV entry into U2OS cells transiently transfected with mRFP-LC3b exposed to non-conditioned (left) or conditioned (right) PHT medium (inset, 5× magnification). (FIG. 3D, bottom) Quantification of the extent of colocalization between VSV particles and mRFP-LC3B positive punctae (*p<0.0001).

(FIG. 4A, top) Electron micrographs of U2OS cells transfected with scrambled control or the six highest expressed C19MC miRNA mimics (Table 2). Black arrows denote autophagosomes and/or autolysosomes. Bar=500 nm. (FIG. 4A, bottom) Quantification of electron micrographs shown at top (*p<0.005), or in PHT cells. (FIG. 4B) U2OS cells were transfected with mRFP-LC3b and either scrambled control or the six highest expressed C19MC miRNA mimics. Shown are confocal micrographs (top) and quantification of mRFP-LC3b punctae per cell (bottom) (*p=0.0005). (FIG. 4C, left) Electron micrographs of U2OS cells transfected with scrambled control or the most potent antiviral miRNA mimics. Black arrows denote autophagosomes and/or autolysosomes. Bar=500 nm. (FIG. 4C, right) Quantification of adjacent electron micrographs (*p<0.005). (FIG. 4D, top) A representative immunoblot for p62 or GAPDH in U2OS cells stably transfected with either control Del- or C19MC-BAC. (FIG. 4D, bottom) Densitometry of p62 levels (normalized to GAPDH) from three independent immunoblots as described above (*p<0.05).

(FIG. 5A) U2OS cells transfected with scrambled control or miRNA mimics of the six most prevalent C19MC miRNA mimics. Cells were exposed to 3-MA before and during VSV infection. Relative VSV RNA was analyzed by RT-qPCR (*p<0.0005). (FIG. 5B, top) U2OS cells stably expressing control- or C19MC-BAC transfected with scrambled control siRNA or beclin-1 siRNA for 72 h were infected with VSV, and relative infection was determined by RT-qPCR (*p<0.05, determined using ANOVA with Bonferroni correction). (FIG. 5B, bottom) Immunoblots for beclin-1 or actin in cells transfected as described above. (FIG. 5C) PHT cells were treated with 3-MA for 60 min prior to infection with green fluorescent protein (GFP)-VSV (in the presence of 3-MA). Relative VSV RNA was analyzed by RT-qPCR (*p<0.005). Data are representative of four independent experiments.

FIGS. 6A-6H: Medium from different preparations of PHT cells confers an antiviral effect on recipient cells. (FIG. 6A) Tissue culture infectious dose 50 (TCID50) assays for VSV in Vero cells pretreated for 24 h with non-conditioned medium (top, in triplicate) or three independent preparations of conditioned PHT medium (bottom). Cells were infected in the indicated dilution of virus in the presence of non-conditioned or conditioned medium for approximately 40-45 h and then stained with crystal violet. (FIG. 6B) Vero cells were exposed to non-conditioned (Non-cond) or conditioned (Cond) medium isolated from BeWo cells for 24 h and then infected with VSV. Shown is the percent of infected cells (as assessed by IF). (FIG. 6C) VSV was incubated in non-conditioned or conditioned PHT medium (in the absence of cells) for 1 h at 37° C. then a plaque assays performed. Shown are VSV titers (in pfu/mL). (FIG. 6D, left) U2OS cells were exposed to non-conditioned (Non-cond) or conditioned media (Cond) from two independent PHT preparations and infected with VSV. Relative VSV RNA was assessed by RT-qPCR (*p<0.0001). (FIG. 6D, right) Caco-2 or Vero cells were exposed to conditioned (Cond) medium isolated from four independent preparations of PHT cells for 24 h prior to infection with VSV. Shown is the percent of infected cells (as assessed by IF; *p<0.0005). (FIG. 6E) Huh7.5 cells were exposed to non-conditioned or conditioned medium isolated from four independent preparations of PHT cells for 24 h prior to infection with HCV. Shown is percent infection as assessed by luciferase assay (*p<0.005, p≤0.0005). (FIG. 6F**) U2OS cells exposed to non-conditioned or conditioned PHT medium were infected with VSV or VV for approximately 6 h. Relative VSV or VV (early gene rpo35 or early gene GFP) RNA was assessed by RT-qPCR (*p<0.0001). (FIG. 6G) HFF cells were exposed to non-conditioned (Non-cond) or conditioned (Cond) PHT media for 24 h before and during infection with CMV. Shown is the percent of infected cells (assessed by IF; *p<0.05). (FIG. 6H) U2OS cells stably expressing control- or C19MC-BAC were infected with CMV, and infection levels assessed by RT-qPCR. Data are shown as fold-change over control (*p<0.0001). In all panels, data are displayed as mean±SD, and are representative of experiments performed a minimum of three times.

FIGS. 7A-7D: Medium from PHT cells induces autophagy in recipient cells. (FIG. 7A) Vero cells were transfected with mRFP-LC3b and at 24 h post-transfection were exposed for 24 h to either non-conditioned (Non-cond) or conditioned medium isolated from four independent PHT preparations. Cells were exposed to rapamycin (Rap) as a positive control. Shown are the levels of autophagic induction as determined by quantification of mRFP-LC3b positive punctae by confocal microscopy (*p<0.0001). (FIG. 7B) Vero and U2OS cells were transfected with mRFP-LC3b and then exposed to non-conditioned (Non-cond) or conditioned PHT medium (Cond) 24 h post-transfection. Cells were exposed to rapamycin (Rap) as a positive control. Shown are the levels of autophagic induction as determined by quantification of mRFP-LC3b positive punctae by confocal microscopy (*p<0.0001). (FIG. 7C) Relative mRNA levels in U2OS cells exposed to non-conditioned or conditioned PHT medium for 24 h, and analyzed using autophagy or toll-like receptor (TLR)-targeted RT-qPCR arrays. (FIG. 7D) U2OS cells stably expressing a control- or C19MC-BAC were transfected with mRFP-LC3b, fixed after 48 h, and analyzed for mRFP-LC3b punctae by confocal microscopy (*p<0.0001).

FIG. 10 is a graph showing inhibition of HIV replication in cells transfected with control (scrambled), miR-517-3p (517), or miR-516-5p (516) mimics. TZM-bl cells were transfected for 48 h prior to infection with HIV-1. Cells were then infected with serial dilutions of HIV for 48 h, and infection levels were assessed by Tat-induced luciferase reporter gene expression, in triplicate. The results represent one independent experiment, performed in triplicate.

SEQUENCE LISTING

Figures 4A, 4B, 4C, 4D:
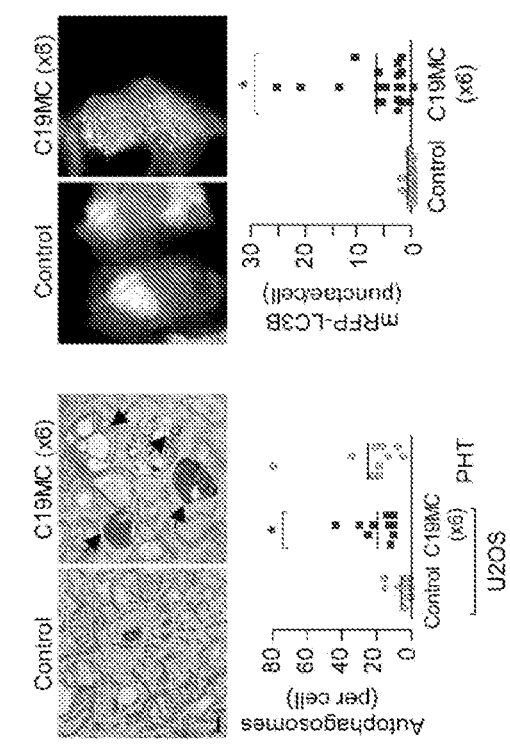
FIGS. 4A-4D: C19MC miRNAs induce autophagy.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 25, 2013, 217 KB, which is incorporated by reference herein. In the accompanying sequence listing:

SEQ ID NOs: 1-59 are nucleotide sequences of miRNAs found in the C19MC.

SEQ ID NO: 60 is the nucleotide sequence of the human genomic DNA insert in the BAC RP11-1055O17 clone containing region q13-42 of chromosome 19.

SEQ ID NOs: 61-82 are qPCR primers.

DETAILED DESCRIPTION

I. Abbreviations

BAC bacterial artificial chromosome
C19MC chromosome 19 microRNA cluster
CMV cytomegalovirus
Ct cycle threshold
CTB cholera toxin B
CVB coxsackievirus B
DAPI 4',6-diamino-2-phenylindole
DC dendritic cell
ELISA enzyme-linked immunosorbent assay
EM electron microscopy
FBS fetal bovine serum
GFP green fluorescent protein
hCG human chorionic gonadotropin
HCV hepatitis C virus
HFF human foreskin fibroblast
HIV human immunodeficiency virus
HSV herpes simplex virus
IF immunofluorescence
IFN interferon
ISRE interferon stimulated responsive element
3-MA 3-methyladenine
miR microRNA
miRNA microRNA
MOI multiplicity of infection
PEI polyethylenimine
PHT primary human trophoblasts
PV poliovirus
RNAi RNA interference
RT-qPCR reverse transcriptase quantitative polymerase chain reaction
TCID50 tissue culture infectious dose 50
TLR toll-like receptor
VSV vesicular stomatitis virus
VV vaccinia virus
YFP yellow fluorescent protein II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a nucleic acid molecule or a microRNA), by any effective route. Exemplary routes of administration include, but are not limited to, injection (such as subcutaneous, intramuscular, intradermal, intraperitoneal, intrathecal and intravenous), oral, intraductal, sublingual, rectal, transdermal, intranasal, vaginal and inhalation routes.

Autophagy: A lysosomal degradation pathway that is one of the primary mechanisms for maintaining cellular homeostasis. Autophagy, which means "to eat oneself," is a self-cannibalization pathway that is known to be anti-microbial, functioning as a key innate immune pathway to degrade intracellular foreign microbial pathogens by a process termed antimicrobial autophagy or xenophagy. A diverse group of RNA and DNA viruses, bacteria and protozoa are sensitive to autophagy. Autophagy is also known to be deficient in a number of human diseases, such as inflammatory bowel disease, Crohn's disease, alcoholic liver disease, Parkinson's disease, Alzheimer's disease, heart disease, diabetes and obesity.

Figure 8:
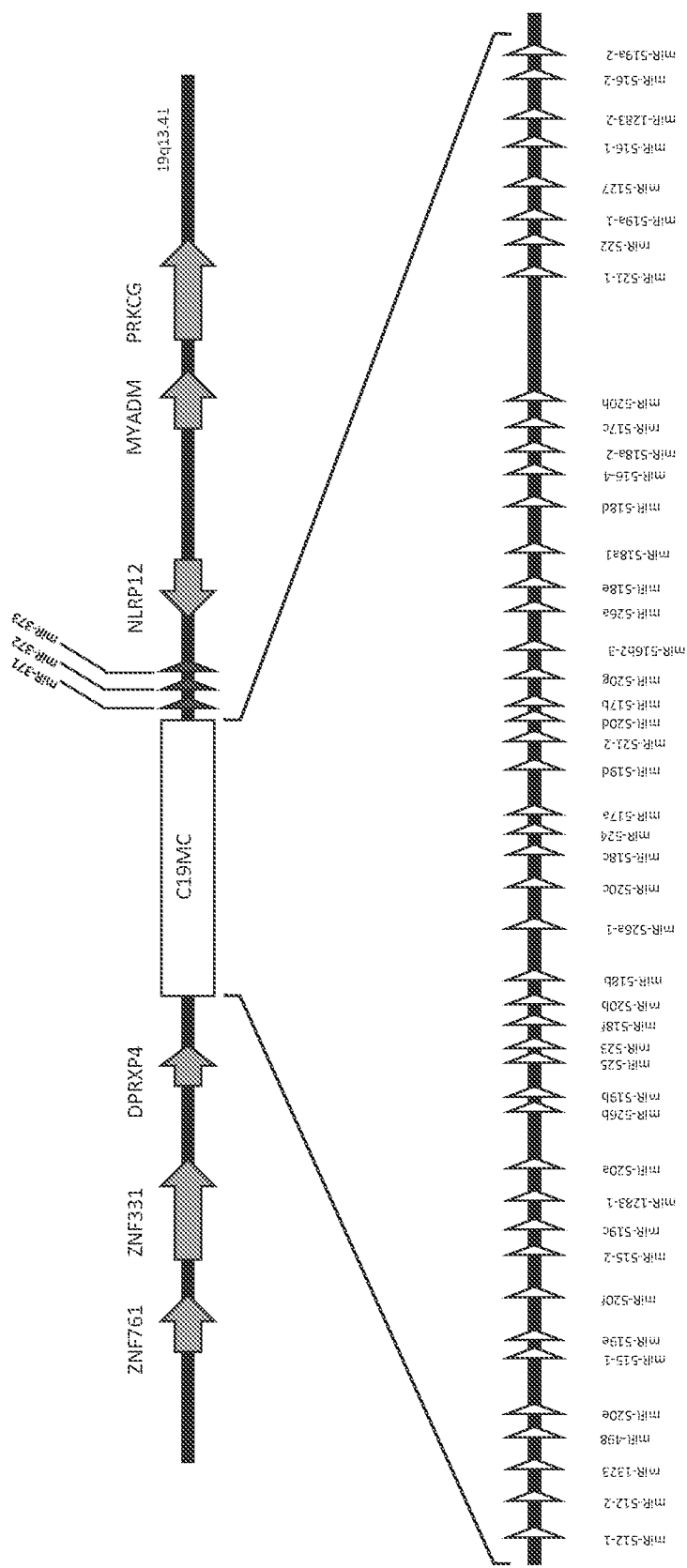
FIG. 8 is a schematic of the genomic organization of the primate-specific C19MC.

Chromosome 19 miRNA cluster (C19MC): A unique cluster of 46 primate-specific miRNA genes encoded by an approximately 100 kb region on chromosome 19 (19q13.41). The genomic organization of C19MC is shown in FIG. 8. A list of the mature miRNAs (miRs) encoded by the genes in the cluster, as well as their sequences, is provided in section V below. In the context of the present disclosure, a "biologically active portion" of the C19MC refers to any portion of the cluster (or any single miR or combination of multiple miRs encoded by the C19MC) that confers increased viral resistance and/or autophagy in a cell. In the context of the present disclosure, an "inhibitory miR" is a miR encoded by the C19MC with anti-microbial activity (and/or the ability to induce autophagy in a cell). Thus, in some examples, an inhibitory miR is a miR that increases viral resistance and/or induces autophagy in a cell. In some embodiments, the inhibitory miR does not inhibit CMV (or does not increase viral resistance to CMV).

Contacting: Placement in direct physical association; includes both in solid and liquid form. As used herein, "contacting" is used interchangeably with "exposed." In some cases, "contacting" includes transfecting, such as transfecting a nucleic acid molecule into a cell.

Exosomes: Small (30-120 nm) endosome-derived membrane vesicles. Exosomes are enriched in miRNAs.

Isolated: An "isolated" biological component (such as a nucleic acid molecule, miRNA, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Microbial infection: Infection by any type of microorganism, including viral, bacterial, fungal and protozoan infections. In some embodiments disclosed herein, the microbial infection is caused by any one of the following viruses, bacteria, fungi or protozoans:

Examples of viruses include, but are not limited to those in the following virus families: Retroviridae (for example, human immunodeficiency virus (HIV), human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus, rubella viruses); Flaviridae (for example, hepatitis C virus, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxyiridae (variola viruses, vaccinia viruses, pox viruses); and Iridoviridae (such as African swine fever virus); Astroviridae; and unclassified viruses or agents (for example, the etiological agents of spongiform encephalopathies, the agent of delta hepatitis (thought to be a defective satellite of hepatitis B virus).

Examples of bacterial pathogens include, but are not limited to: *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

Examples of fungal pathogens include, but are not limited to: *Cryptococcus neoformans, Histoplasma capsulatum*,

*Coccidioides immitis, Blastomyces dermatitidis, Chlamydia trachomatis* and *Candida albicans*.

Other pathogens (such as parasitic pathogens) include, but are not limited to: *Plasmodium falciparum, Plasmodium vivax, Trypanosoma cruzi* and *Toxoplasma gondii*.

MicroRNA: MicroRNAs (also known as miRNAs and miRs) are short RNA sequences expressed from longer transcripts found in the genomes of animals, plants and viruses and at least one single-celled eukaryote (Molnár et al., *Nature* 447:1126-1129, 2007; Zhao et al., *Genes Dev.* 21:1190-1203, 2007). MicroRNAs regulate the expression of target genes by binding to complementary sites in the target gene transcripts to cause translational repression or transcript degradation (Pillai et al., *Trends Cell Biol.* 17:118-126, 2007). These small RNA molecules have been implicated in a number of biological processes related to development, cell proliferation, apoptosis, metabolism, morphogenesis and diseases (Kloosterman and Plasterk, *Dev. Cell* 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 19-24 nucleotides in length and are partially complementary to the 3'UTR (or other regions such as introns, exons or 5'UTR) of one or more target messenger RNAs (mRNAs).

A nomenclature scheme has been well established for microRNAs (Griffiths-Jones et al., *Nucleic Acids Res.* 34:D140-D144, 2006; Ambros et al., RNA 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "150," resulting in a complete name of "hsa-miR-150." Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-181a and miR-181b). In some cases, mature miRNAs from both the 5' and 3' arms of the hairpin precursor are identified, which are designated "3p" or "5p" (such as miR-768-3p and miR-768-5p).

MicroRNA gene product sequences are well described throughout the scientific and patent literature and are available online through miRBase (world wide web at mirbase.org), provided by the University of Manchester (previously provided by the Sanger Institute). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR**, which are sometimes identified by their "3p" or "Sp" annotation, as described above.

In the context of the present disclosure, administering a "miR" to a subject or contacting a cell with a "miR" encompasses administration or contacting with a pri-miRNA, pre-miRNA or mature miRNA, or a nucleic acid molecule encoding a pri-miRNA, pre-miRNA or mature miRNA.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (such as a miR or vector encoding a miR).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Subject: Living multi-cellular vertebrate organisms, a category that includes human and non-human mammals.

Therapeutically effective amount: A quantity of a specified composition, pharmaceutical or therapeutic agent (such as a miR or nucleic acid molecule encoding a miR) sufficient to achieve a desired effect in a subject, or in a cell, being treated with the agent. The effective amount of the agent will be dependent on several factors, including, but not limited to the subject being treated, the disease or condition being treated, and the manner of administration of the therapeutic composition. In some embodiments of the present disclosure, the therapeutically effective amount (or effective amount) of a miR is the amount required to increase viral resistance or induce autophagy.

Transduce, transform or transfect: To introduce a nucleic acid molecule into a cell, such as a miR or a vector encoding a miR. These terms encompass all techniques by which a nucleic acid molecule can be introduced into a cell, including but not limited to, transduction with viral vectors, transfection with plasmid vectors, liposomal-mediated transfection and introduction of naked DNA by electroporation and particle gun acceleration. A transfected or transformed cell is a cell into which has been introduced a nucleic acid molecule by molecular biology techniques. In some examples, the nucleic acid molecule becomes stably replicated by the cell, for example by incorporation of the nucleic acid molecule into the cellular genome, or by episomal replication. In other examples, the nucleic acid molecule is transiently expressed in the cell.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Described herein is the finding that cultured primary human trophoblasts (PHT) are highly resistant to infection by diverse and unrelated viruses. The studies disclosed herein also determined that conditioned PHT culture medium confers resistance to viral infections in permissive non-placental cells, indicating that trophoblast-associated viral resistance is transmissible, and is transferred to recipient cells. It was found that a unique cluster of primate-specific microRNAs (miRNAs), which are highly expressed in human trophoblasts from the human chromosome 19 miRNA cluster (C19MC) (Noguer-Dance et al., *Hum Mol Genet.* 19, 3566-3582, 2010), are packaged within PHT-derived exosomes and confer this viral resistance to recipient cells. It is further shown herein that PHT cells exhibit high rates of resting autophagy, a process involved in the maintenance of cellular homeostasis and an effective cellular countermeasure to suppress viral infections. PHT-derived exosomes and several C19MC miRNAs robustly induce autophagy in non-placental recipient cells, which is required for their resistance to viral infection. Unlike the other viruses that were tested, CMV infection is greatly enhanced by C19MC miRNAs. These findings illuminate a previously unknown pathway employed by human trophoblasts to suppress viral infections and confer viral resistance to non-placental recipient cells, suggesting a novel mechanism for shielding the placenta and maternal-derived recipient cells against viral infections during pregnancy.

IV. Overview of Several Embodiments

Provided herein is a method of inhibiting or treating a microbial infection in a subject. In some embodiments, the method includes selecting a subject with a microbial infection, or at risk for contracting a microbial infection, and administering to the subject a therapeutically effective amount of one or more microRNAs (miRs) encoded by the chromosome 19 miRNA cluster (C19MC). In some embodiments, the method includes direct administration of the one or more miRs encoded by the C19MC. In other embodiments, administering the one or more miRs encoded by the C19MC comprises administering a nucleic acid molecule encoding the C19MC or a biologically active portion thereof. In some examples, the nucleic acid molecule comprises a vector, such as a plasmid vector or a viral vector.

In some embodiments, the microbial infection is a viral infection. The viral infection can be an infection caused by any type of virus. In some examples, the virus is an RNA virus. RNA viruses include, for example, coxsackieviruses (e.g. coxsackievirus A and coxsackievirus B), poliovirus, vesicular stomatitis virus, human immunodeficiency virus, hepatitis C virus, rubella virus and morbilliviruses (such as measles virus). In particular examples, the RNA virus is a coxsackievirus, poliovirus, vesicular stomatitis virus, human immunodeficiency virus or hepatitis C virus. In other examples, the virus is a DNA virus. DNA viruses include, for example, vaccinia virus, herpes simplex viruses (HSV-1 and -2), Epstein-Ban virus, hepatitis B virus, parvovirus and varicella zoster. In particular examples, the DNA virus is a vaccinia virus or a herpes simplex virus. In some embodiments, the virus is not cytomegalovirus (CMV).

In some embodiments, the microbial infection is a bacterial infection. In some examples, the bacteria is *Staphylococcus aureus*, Group A *Streptococcus, Listeria monocytogenes, Bacillus anthracis, Burkholderia pseudomallei, Helicobacter pylori, Salmonella enterica* or *Vibrio cholerae*.

In some embodiments, the microbial infection is a parasitic infection. In some examples, the parasite is the protozoan parasite *Toxoplasma gondii*.

In some embodiments, inhibiting the microbial infection comprises preventing the microbial infection.

In some embodiments, the method comprises inhibiting or preventing intrauterine transmission of the microbial infection.

In some embodiments of the disclosed methods, administration is extrauterine. In other embodiments, administration is intrauterine.

In some examples, the one or more miRs, or nucleic acid molecule encoding the C19MC or biologically active portion thereof, is administered prophylactically to prevent infection. In other examples, the one or more miRs, or nucleic acid molecule encoding the C19MC or biologically active portion thereof, is administered to treat an existing infection.

The one or more miRs administered to the subject can be any single miR or any combination of two or more miRs that are encoded by the C19MC. Similarly, if the subject is administered a nucleic acid molecule comprising the C19MC or biologically active portion thereof, the subject can be administered the entire C19MC or a portion that encodes a single or multiple miRs. The miR genes included in the C19MC are shown in FIG. 8 and listed in Table 1. Table 1 also lists 58 unique mature miR sequences encoded by the miR genes.

In some embodiments, the subject is administered a single miR. In other embodiments, the subject is administered at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50, or at least 55 miRs. In another embodiment, the subject is administered all miRs encoded by the cluster. In particular examples, the miRs are mature miRs.

In other embodiments, the subject is administered a nucleic acid molecule comprising all miR genes of the C19MC (see Table 1). In another embodiment, the subject is administered a nucleic acid molecule encoding a single miR encoded by the C19MC. In yet other embodiments, the subject is administered a nucleic acid molecule encoding at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50, or at least 55 miRs of the C19MC. In particular examples, the miRs are mature miRs.

In some embodiments, the subject is administered the entire C19MC or a nucleic acid molecule encoding the entire C19MC.

In some embodiments, the biologically active portion of the C19MC, or the one or more miRs, comprises miR-517-3p, miR-516b-5p or miR-512-3p. In particular examples, the biologically active portion of the C19MC, or the one or more miRs comprises miR-517-3p, miR-516b-5p, and miR-512-3p. In other particular examples, the biologically active portion of the C19MC, or the one or more miRs comprises miR-517-3p, miR-1323, miR-516b-5p, miR-525-5p, miR-512-3p and miR-515-3p.

In some examples, the biologically active portion of the C19MC, or the one or more miRs, comprises miR-512-3p, miR-516b, miR-517-3p, or any combination of two or more thereof. In particular examples, the biologically active portion of the C19MC, or the one or more miRs, comprises miR-512-3p, miR-516b, miR- and 517-3p. In further examples, a single miR selected from miR-512-3p, miR-516b, miR- and 517-3p is administered to the subject.

In other examples, the biologically active portion of the C19MC, or the one or more miRs, comprises miR-512-3p, miR-515-3p, miR-516b, miR-517-3p, miR-525-5p and miR-1323. In yet other examples, the biologically active portion of the C19MC, or the one or more miRs, comprises miR-1323, miR-512-3p, miR-512-5p, miR-515-3p, miR-515-5p, miR-516b, miR-517-3p, miR-517c, miR-518a-5p, miR-518b, miR-518e, miR-519c-3p, miR-519d, miR-520c-3p, miR-520h and miR-525-5p.

In some examples, the nucleotide sequence of the one or more miRs is at least 95%, at least 96%, at least 97%, at least 98% or at least 99% identical to one or more of SEQ ID NOs: 1-59. In non-limiting examples, the nucleotide sequence of the one or more miRs comprises or consists of one or more of SEQ ID NOs: 1-59.

Further provided herein is a method of inducing autophagy in a cell. In some embodiments, the method includes contacting the cell with an effective amount of one or more miRs encoded by the C19MC. In some embodiments, the method includes directly contacting the cell with the one or more miR molecules. In other embodiments, contacting the cell with the one or more miRs encoded by the C19MC comprises contacting the cell with a nucleic acid molecule encoding the C19MC or a biologically active portion thereof. In some examples, the nucleic acid molecule comprises a vector, such as a plasmid vector a viral vector.

In some embodiments, the method is an in vitro method. In some examples of the in vitro method, the cell is a primary cell. In other examples, the cell is an immortalized cell.

In other embodiments, the method is an in vivo method and contacting the cell comprises administering to a subject an effective amount of one or more miRs encoded by the C19MC, or a nucleic acid molecule encoding the C19MC or a biologically active portion thereof. In some embodiments, the subject suffers from a disease associated with a deficiency in autophagy and/or a disease that can be ameliorated by stimulating autophagy. In particular examples, the disease is inflammatory bowel disease, Crohn's disease, alcoholic liver disease, Parkinson's disease, Alzheimer's disease, heart disease, diabetes or obesity.

The one or more miRs contacted with the cell (in vitro or in vivo) can be any single miR or any combination of two or more miRs that are encoded by the C19MC. Similarly, if the cell is contacted with a nucleic acid molecule encoding the C19MC or biologically active portion thereof, the cell can be contacted with the entire C19MC or a portion that encodes a single or multiple miRs. In some embodiments, the cell is contacted with a single miR. In other embodiments, the cell is contacted with at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50 or at least 55 miRs. In another embodiment, the cell is contacted with all miRs encoded by the C19MC. In particular examples, the miRs are mature miRs.

In other embodiments, the cell is contacted with a nucleic acid molecule comprising all miR genes of the C19MC (see Table 1). In another embodiment, the cell is contacted with a nucleic acid molecule encoding a single miR of the C19MC. In yet other embodiments, the cell is contacted with a nucleic acid molecule encoding at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50 or at least 55 miRs of the C19MC. In particular examples, the miRs are mature miRs.

In some embodiments of the methods of inducing autophagy, the subject is administered the entire C19MC or a nucleic acid molecule encoding the entire C19MC.

In some embodiments of the methods of inducing autophagy, the biologically active portion of the C19MC, or the one or more miRs, comprises miR-517-3p, miR-516b-5p or miR-512-3p. In particular examples, the biologically active portion of the C19MC, or the one or more miRs comprises miR-517-3p, miR-516b-5p, and miR-512-3p. In other particular examples, the biologically active portion of the C19MC, or the one or more miRs comprises miR-517-3p, miR-1323, miR-516b-5p, miR-525-5p, miR-512-3p and miR-515-3p. In some examples, the biologically active portion of the C19MC, or the one or more miRs, comprises miR-512-3p, miR-516b, miR-517-3p, or any combination of two or more thereof. In particular examples, the biologically active portion of the C19MC, or the one or more miRs, comprises miR-512-3p, miR-516b, and miR-517-3p. In further examples, a single miR selected from miR-512-3p, miR-516b, and miR-517-3p is contacted with the cell.

In other examples of the methods of inducing autophagy, the biologically active portion of the C19MC, or the one or more miRs, comprises miR-512-3p, miR-515-3p, miR-516b, miR-517-3p, miR-525-5p and miR-1323. In yet other examples, the biologically active portion of the C19MC, or the one or more miRs, comprises miR-1323, miR-512-3p, miR-512-5p, miR-515-3p, miR-515-5p, miR-516b, miR-517-3p, miR-517c, miR-518a-5p, miR-518b, miR-518e, miR-519c-3p, miR-519d, miR-520c-3p, miR-520h and miR-525-5p.

In some examples of the methods of inducing autophagy, the nucleotide sequence of the one or more miRs is at least 95%, at least 96%, at least 97%, at least 98% or at least 99% identical to one or more of SEQ ID NOs: 1-59. In non-limiting examples, the nucleotide sequence of the one or more miRs comprises or consists of one or more of SEQ ID NOs: 1-59.

In some embodiments of the methods disclosed herein, the one or more miRs, or the nucleic acid molecule encoding the C19MC or biologically active portion thereof, is administered to the subject or contacted with the cell using a liposomal formulation, a cationic lipid or a polypeptide carrier.

In some embodiments of the disclosed methods, the nucleic acid molecule encoding the C19MC or biologically active portion thereof comprises a vector. In some examples, the vector is a plasmid vector. In other examples, the vector is a viral vector. Viral vectors can be of, for example, adenovirus, adeno-associated virus, retrovirus, herpes virus or vaccinia virus origin. Viral vectors can include modified versions of the viruses, such as replication deficient viruses. Suitable vectors, such as gene therapy vectors, are well known in the art. In some examples, the miR is expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the present disclosure can also comprise inducible or regulatable promoters for expression of the miR.

In some embodiments, such as when the miR is administered as a naked nucleic acid molecule, the miR includes modifications, such as nucleotide modifications to increase nuclease resistance, or other modifications to enhance delivery and/or activity of the miR.

The disclosed methods comprise administering a therapeutically effective amount, or contacting a cell with an effective amount, of at least one miR encoded by the C19MC. In some embodiments, the miR is a variant or biologically-active fragment of the miR encoded by the C19MC. Thus, the miR that is administered to a subject or contacted with a cell can be identical to an endogenous (wild-type) miR (including a pri-miRNA, pre-miRNA or mature miRNA) that is encoded by the C19MC, or it can be a variant or biologically-active fragment thereof. As defined herein, a "variant" of a miR refers to a miRNA that has less than 100% identity to a corresponding wild-type miR and possesses one or more biological activities of the corresponding miR. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule), promoting viral resistance or inducing autophagy. The miR variants include species variants and variants that are the consequence of one or more mutations (e.g., a substitution, a deletion, an insertion) in a miR gene. In certain embodiments, the variant is at least about 80%, at least about 85%, at least about 90%, at least about 95%, at least about 96%, at least about 97%, at least about 98%, or at about 99% identical to a corresponding wild-type miR (such as one of the miRs listed in Table 1 or set forth herein as SEQ ID NOs: 1-59).

As used herein, a "biologically-active fragment" of a miR refers to an RNA fragment of a miR that possesses one or more biological activities of a corresponding wild-type miR. As described above, examples of such biological activities include, but are not limited to, inhibition of expression of a target RNA molecule, repressing protein translation, promoting viral resistance or inducing autophagy. In certain embodiments, the biologically-active fragment is at least about 9, at least about 11, at least about 13, at least about 15, at least about 17 or at least about 19 nucleotides in length.

V. Placental miRNAs from Chromosome 19 miRNA Cluster (C19MC)

Akin to other tissues, trophoblast differentiated functions are controlled by transcription factors, epigenetic modifiers and post-transcriptional influences that ultimately shape mRNA and protein expression. These pathways include small modulatory RNAs that interact with target gene 3'UTRs (or other regions of the genes) and promote RNA degradation and translational repression (Ghildiyal et al., *Nat Rev Genet.* 10:94-108, 2009; Huntzinger and Izaurralde, *Nat Rev Genet.* 12:99-110, 2011; Krol et al., *Nat Rev Genet.* 11:597-610, 2010; Friedman et al., *Genome Res* 19:92-105, 2009; Thomas and Lieberman, *Nat Struct Mol Biol* 17:1169-1174, 2010; Vickers et al., *Nat Cell Biol* 13:423-433, 2011; Herranz and Cohen, *Genes Dev* 24:1339-1344, 2010; Bartel, *Cell* 136:215-233, 2009; Carthew and Sontheimer, *Cell* 136:642-655, 2009). Among all small RNAs, previous studies have shown that human trophoblasts produce primarily miRNAs throughout pregnancy, as well as other small RNAs (piRNAs, snRNAs, and snoRNAs) (Mouillet et al., *Placenta* 31:781-784, 2010; Luo et al., *Biol Reprod* 81:717-729, 2009; Mouillet et al., *Birth Defects Res A Clin Mol Teratol* 91:737-743, 2011; Barad et al., *Genome Res* 14:2486-2494, 2004; Pineles et al., *Am J Obstet Gynecol* 196:261, 2007). Many of these miRNAs are stably released into the maternal circulation, suggesting a miRNA-based mechanism for fetal-maternal communication (Mouillet et al., *Placenta* 31:781-784, 2010; Chim et al., *Clin Chem* 54:482-190, 2008).

Approximately 30-40% of placental miRNA species are expressed from defined miRNA clusters (Luo et al., *Biol Reprod* 81:717-729, 2009; Liang et al., *Genomics* 8:166, 2007; Bortolin-Cavaille et al., *Nucleic Acids Res* 37:3464-3473, 2009). Unique among these clusters is a primate-specific, large miRNA cluster (~100 kb, 46 highly-related miRNA genes), expressed from chromosomal region 19q13.41 (Bentwich et al., *Nat Genet.* 37:766-770, 2005). MiRNA members of this chromosome 19 miRNA cluster (C19MC) are expressed throughout human pregnancy, and nearly exclusively in the placenta (Luo et al., *Biol Reprod* 81:717-729, 2009; Liang et al., *Genomics* 8:166, 2007; Bortolin-Cavaille et al., *Nucleic Acids Res* 37:3464-3473, 2009; Chiu et al., *Clin Chem* 52:313-316, 2006). Although the C19MC genomic sequence contains many primate-specific Alu repeats, which may mediate gene rearrangement (Zhang et al., *Mol Biol Evol* 25:1493-1502, 2008; Lehnert et al., *PLoS One* 4:e4456, 2009), secondary structure conservation and low SNP frequency of C19MC suggests that this cluster is evolutionarily stable. Selected placenta-specific miRNA species are found in the maternal blood throughout pregnancy. Their levels are not uniform, and rapidly decline in the first 24 h postpartum (Ng et al., *Proc Natl Acad Sci USA* 100:4748-4753, 2003; Gilad et al., *PLoS One* 3:e3148, 2008).

A schematic of the genomic organization of C19MC is shown in FIG. 8. A list of the specific miRNA genes included in this cluster is provided in the table below. The names and sequences of the mature forms of each miRNA gene are also shown. Many miR genes encode more than one mature product (the "5p" and "3p" products from the 5' and 3' arms, respectively, of the hairpin precursor). In some instances, two different miR genes encode a mature product with the same sequence (for example, see hsa-miR-512-1 and hsa-miR-512-2). All sequences shown in Table 1 were obtained from miRBase (world wide web at mirbase.org) on Feb. 27, 2012. The present disclosure contemplates the use of any microRNA product (a pri-mRNA, pre-miRNA or mature RNA) encoded by any of the genes listed in Table 1.

TABLE 1 miRNAs of the chromosome 19 miRNA cluster

| Gene | Mature miRNA | Sequence of Mature miRNA | SEQ ID NO: |
|---|---|---|---|
| hsa-mir-512-1 | hsa-miR-512-5p | CACUCAGCCUUGAGGGCACUUUC | 1 |
|  | hsa-miR-512-3p | AAGUGCUGUCAUAGCUGAGGUC | 2 |
| hsa-mir-512-2 | hsa-miR-512-5p | CACUCAGCCUUGAGGGCACUUUC | 1 |
|  | hsa-miR-512-3p | AAGUGCUGUCAUAGCUGAGGUC | 2 |
| hsa-mir-1323 | hsa-miR-1323 | UCAAAACUGAGGGGCAUUUUCU | 3 |
| hsa-mir-498 | hsa-miR-498 | UUUCAAGCCAGGGGGCGUUUUUC | 4 |
| hsa-mir-520e | hsa-miR-520e | AAAGUGCUUCCUUUUUGAGGG | 5 |
| hsa-mir-515-1 | hsa-miR-515-5p | UUCUCCAAAAGAAAGCACUUUCUG | 6 |
|  | hsa-miR-515-3p | GAGUGCCUUCUUUUGGAGCGUU | 7 |
| hsa-mir-519e | hsa-miR-519e-5p | UUCUCCAAAAGGGAGCACUUUC | 8 |
|  | hsa-miR-519e-3p | AAGUGCCUCCUUUUAGAGUGUU | 9 |
| hsa-mir-520f | hsa-miR-520f | AAGUGCUUCCUUUUAGAGGGUU | 10 |
| hsa-mir-515-2 | hsa-miR-515-5p | UUCUCCAAAAGAAAGCACUUUCUG | 6 |
|  | hsa-miR-515-3p | GAGUGCCUUCUUUUGGAGCGUU | 7 |
| hsa-mir-519c | hsa-miR-519c-5p | CUCUAGAGGGAAGCGCUUUCUG | 11 |
|  | hsa-miR-519c-3p | AAAGUGCAUCUUUUUAGAGGAU | 12 |
| hsa-mir-1283-1 | hsa-miR-1283 | UCUACAAAGGAAAGCGCUUUCU | 13 |

TABLE 1-continued miRNAs of the chromosome 19 miRNA cluster

| Gene | Mature miRNA | Sequence of Mature miRNA | SEQ ID NO: |
|---|---|---|---|
| hsa-mir-520a | hsa-miR-520a-5p | CUCCAGAGGGAAGUACUUUCU | 14 |
|  | hsa-miR-520a-3p | AAAGUGCUUCCCUUUGGACUGU | 15 |
| hsa-mir-526b | hsa-miR-526b-5p | CUCUUGAGGGAAGCACUUUCUGU | 16 |
|  | hsa-miR-526b-3p | GAAAGUGCUUCCUUUUAGAGGC | 17 |
| hsa-mir-519b | hsa-miR-519b-5p | CUCUAGAGGGAAGCGCUUUCUG | 18 |
|  | hsa-miR-519b-3p | AAAGUGCAUCCUUUUAGAGGUU | 19 |
| hsa-mir-525 | hsa-miR-525-5p | CUCCAGAGGGAUGCACUUUCU | 20 |
|  | hsa-miR-525-3p | GAAGGCGCUUCCCUUUAGAGCG | 21 |
| hsa-mir-523 | hsa-miR-523-5p | CUCUAGAGGGAAGCGCUUUCUG | 22 |
|  | hsa-miR-523-3p | GAACGCGCUUCCCUAUAGAGGGU | 23 |
| hsa-mir-518f | hsa-miR-518f-5p | CUCUAGAGGGAAGCACUUUCUC | 24 |
|  | hsa-miR-518f-3p | GAAAGCGCUUCUCUUUAGAGG | 25 |
| hsa-mir-520b | hsa-miR-520b | AAAGUGCUUCCUUUUAGAGGG | 26 |
| hsa-mir-518b | hsa-miR-518b | CAAAGCGCUCCCCUUUAGAGGU | 27 |
| hsa-mir-526a-1 | hsa-miR-526a | CUCUAGAGGGAAGCACUUUCUG | 28 |
| hsa-mir-520c | hsa-miR-520c-5p | CUCUAGAGGGAAGCACUUUCUG | 29 |
|  | hsa-miR-520c-3p | AAAGUGCUUCCUUUUAGAGGGU | 30 |
| hsa-mir-518c | hsa-miR-518c-5p | UCUCUGGAGGGAAGCACUUUCUG | 31 |
|  | hsa-miR-518c-3p | CAAAGCGCUUCUCUUUAGAGUGU | 32 |
| hsa-mir-524 | hsa-miR-524-5p | CUACAAAGGGAAGCACUUUCUC | 33 |
|  | hsa-miR-524-3p | GAAGGCGCUUCCCUUUGGAGU | 34 |
| hsa-mir-517-3p | hsa-miR-517-5p | CCUCUAGAUGGAAGCACUGUCU | 35 |
|  | hsa-miR-517-3p | AUCGUGCAUCCCUUUAGAGUGU | 36 |
| hsa-mir-519d | hsa-miR-519d | CAAAGUGCCUCCCUUUAGAGUG | 37 |
| hsa-mir-521-2 | hsa-miR-521 | AACGCACUUCCCUUUAGAGUGU | 38 |
| hsa-mir-520d | hsa-miR-520d-5p | CUACAAAGGGAAGCCCUUUC | 39 |
|  | hsa-miR-520d-3p | AAAGUGCUUCUCUUUGGUGGGU | 40 |
| hsa-mir-520g | hsa-miR-520g | ACAAAGUGCUUCCCUUUAGAGUGU | 42 |
| hsa-mir-516b-2 | hsa-miR-516b-5p | AUCUGGAGGUAAGAAGCACUUU | 43 |
|  | hsa-miR-516b-3p | UGCUUCCUUUCAGAGGGU | 44 |
| hsa-mir-526a-2 | hsa-miR-526a | CUCUAGAGGGAAGCACUUUCUG | 28 |
| hsa-mir-518e | hsa-miR-518e-5p | CUCUAGAGGGAAGCGCUUUCUG | 45 |
|  | hsa-miR-518e-3p | AAAGCGCUUCCCUUCAGAGUG | 46 |
| hsa-mir-518a-1 | hsa-miR-518a-5p | CUGCAAAGGGAAGCCCUUUC | 47 |
|  | hsa-miR-518a-3p | GAAAGCGCUUCCCUUUGCUGGA | 48 |
| hsa-mir-518d | hsa-miR-518d-5p | CUCUAGAGGGAAGCACUUUCUG | 49 |
|  | hsa-miR-518d-3p | CAAAGCGCUUCCCUUUGGAGC | 50 |

TABLE 1-continued miRNAs of the chromosome 19 miRNA cluster

| Gene | Mature miRNA | Sequence of Mature miRNA | SEQ ID NO: |
|---|---|---|---|
| hsa-mir-516b-1 | hsa-miR-516b-5p | AUCUGGAGGUAAGAAGCACUUU | 43 |
|  | hsa-miR-516b-3p | UGCUUCCUUUCAGAGGGU | 44 |
| hsa-mir-518a-2 | hsa-miR-518a-5p | CUGCAAAGGGAAGCCCUUUC | 47 |
|  | hsa-miR-518a-3p | GAAAGCGCUUCCCUUUGCUGGA | 48 |
| hsa-mir-517c | hsa-miR-517-5p | CCUCUAGAUGGAAGCACUGUCU | 35 |
|  | hsa-miR-517c-3p | AUCGUGCAUCCUUUUAGAGUGU | 51 |
| hsa-mir-520h | hsa-miR-520h | ACAAAGUGCUUCCCUUUAGAGU | 52 |
| hsa-mir-521-1 | hsa-miR-521 | AACGCACUUCCCUUUAGAGUGU | 38 |
| hsa-mir-522 | hsa-miR-522-5p | CUCUAGAGGGAAGCGCUUUCUG | 53 |
|  | hsa-miR-522-3p | AAAAUGGUUCCCUUUAGAGUGU | 54 |
| hsa-mir-519a-1 | hsa-miR-519a-5p | CUCUAGAGGGAAGCGCUUUCUG | 55 |
|  | hsa-miR-519a-3p | AAAGUGCAUCCUUUUAGAGUGU | 56 |
| hsa-mir-527 | hsa-miR-527 | CUGCAAAGGGAAGCCCUUUC | 57 |
| hsa-mir-516a-1 | hsa-miR-516a-5p | UUCUCGAGGAAAGAAGCACUUUC | 58 |
|  | hsa-miR-516a-3p | UGCUUCCUUUCAGAGGGU | 59 |
| hsa-mir-1283-2 | hsa-miR-1283 | UCUACAAAGGAAAGCGCUUUCU | 13 |
| hsa-mir-516a-2 | hsa-miR-516a-5p | UUCUCGAGGAAAGAAGCACUUUC | 58 |
|  | hsa-miR-516a-3p | UGCUUCCUUUCAGAGGGU | 59 |
| hsa-mir-519a-2 | hsa-miR-519a-3p | AAAGUGCAUCCUUUUAGAGUGU | 56 |

Placental Exosomes

A significant fraction of plasma miRNA is packaged in exosomes. These nanoparticles function as "cargo vehicles" (Valadi et al., Nat Cell Biol 9:654-659, 2007; Simpson et al., Proteomics 8:4083-4099, 2008; Skog et al., Nat Cell Biol 10:1470-1476, 2008) to transfer nucleic acids, proteins, lipids and other biomolecules to proximal and distant tissues (Thery et al., Nat Rev Immunol 9:581-593, 2009; Raposo et al., J Exp Med 183:1161-1172, 1996; Alvarez-Erviti et al., Nat Biotechnol 29:341-345, 2011). Exosomes belong to a large family of intracellular and extracellular microvesicular bodies, ranging in size between >100 nm (apoptotic blebs and microparticles) to approximately 30-120 nm (exosomes). Exosomes can fuse intracellularly with lysosomes to destroy content or fuse with plasma membranes to release exosomal content via exocytosis or ectocytosis (Thery et al., Nat Rev Immunol 2:569-579, 2002; Pan and Johnstone, Cell 33:967-978, 1983; Keller et al., Immunol Lett 107:102-108, 2006). Exosomes are defined by size, cup-shaped form, sucrose gradient buoyancy (1.13-1.19 g/mL), and a detergent-resistant, lipid raft-rich membrane bilayer of proteins, cholesterol, and sphingolipids. Some of the membrane proteins are common, such as cytoskeletal proteins, chaperones, and tetraspanins, including CD9, CD63, CD81, and others specific to the exosome's cell of origin (Simpson et al., Proteomics 8:4083-4099, 2008; Thery et al., Nat Rev Immunol 2:569-579, 2002). Surface proteins may determine exosome specificity to target cells, which they enter via endocytosis-based internalization (Morelli et al., Blood 104: 3257-3266, 2004), cell membrane fusion (Denzer et al., J Immunol 165:1259-1265, 2000), or receptor-ligand interactions (Admyre et al., Eur J Immunol 36:1772-1781, 2006).

Thus, exosomes act as a form of communication among different cell types, with potentially striking consequences to recipient cells (e.g., induction of apoptosis, mediated by the FAS ligand binding to FAS receptors). Relevant to the present disclosure, exosomes were recently found to be enriched for miRNAs (Valadi et al., Nat Cell Biol 9:654-659, 2007; Eldh et al., PLoS One 5:e15353, 2010), akin to virally-mediated intercellular transfer of genetic material, with potential beneficial or harmful consequences (Eldh et al., PLoS One 5:e15353, 2010). The human placenta is known to express microvesicular bodies of diverse sizes, mainly shed as syncytiotrophoblast microparticles, implicated in preeclampsia-related placental apoptosis. Production of exosomes has been studied in first trimester trophoblasts, where exosomes likely contribute to the establishment of maternal immune tolerance, possibly via impaired T-cell signaling, down-regulation of NK cell receptor NKG2D, and enhanced apoptotic pathways through FasL, TRAIL, and PD-L (Luo et al., Biol Reprod 81:717-729, 2009; Taylor et al., J Immunol 176:1534-1542, 2006; Hedlund et al., J Immunol 183:340-351, 2009; Mincheva-Nilsson and Baranov, Am J Reprod Immunol 63:520-533, 2010). The production and function of placental exosomes after the first trimester of human pregnancy, and the role of miRNAs packaged in these exosomes, has not been previously studied.

VI. Administration of miRNAs

A nucleic acid molecule encoding C19MC, or a biologically active portion thereof (including a single miR or multiple miRs), can be administered to a subject in need of treatment using any suitable means known in the art. Nucleic acid-based therapeutic agents can be administered to a subject by any suitable route. In some examples, the nucleic acid molecules are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. In some cases, suitable administration routes are injection, infusion and direct injection into a target tissue.

In the context of the present disclosure, a miR or a nucleic acid molecule encoding C19MC, or a biologically active portion thereof, can be administered to the subject either as naked RNA or DNA in combination with a delivery reagent, or can be encoded by a recombinant plasmid or viral vector. Recombinant plasmids and viral vectors including sequences that express the C19MC or biologically active portion thereof, and techniques for delivering such plasmids and vectors to target cells, are well known in the art.

In some embodiments, liposomes are used to deliver the nucleic acid molecule to a subject. Liposomes can also increase the blood half-life of nucleic acids. Suitable liposomes for use with the present disclosure can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a nucleic acid molecule to a subject. Cationic lipids and polymers that can be used to deliver therapeutic nucleic acid molecules have been described (see, for example, Zhang et al., *J Control Release.* 123(1):1-10, 2007; Vorhies et al., *Methods Mol. Biol.* 480:11-29, 2009; and U.S. Patent Application Publication No. 2009/0306194). Polypeptide carriers can also be used to administer nucleic acid molecules, such as miRs, to a subject (see, for example, Rahbek et al., *J. Gene Med.* 10:81-93, 2008).

Nucleic acid molecules can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils.

Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Administration can be accomplished by single or multiple doses. The dose required will vary from subject to subject depending on the species, age, weight and general condition of the subject, the particular nucleic acid molecule being used and its mode of administration. An appropriate dose can be determined by one of ordinary skill in the art using only routine experimentation.

The following examples are provided to illustrate certain particular features and/or embodiments. These examples should not be construed to limit the disclosure to the particular features or embodiments described.

EXAMPLES

Example 1

Materials and Methods

This example describes the materials and experimental procedures used for the studies described in Example 2.

Cells and PHT Exosome Purification

Primary human trophoblasts (PHT cells) were isolated from normal singleton term placentas using the trypsin-deoxyribonuclease-dispase/Percoll method as described by Kliman et al., with previously published modifications (Kliman et al., *Endocrinology* 118, 1567-1582, 1986; Nelson et al., *Am J Obstet Gynecol* 180, 896-902, 1999). Cells were maintained in DMEM (Sigma) containing 10% fetal bovine serum (FBS, Hyclone, Logan, Utah, USA) and antibiotics at 37° C. in a 5% carbon dioxide ($CO_2$)-air atmosphere. Cells were maintained 72 h after plating, with cell quality monitored both morphologically (by microscopy) and by medium human chorionic gonadotropin (hCG) levels, determined by enzyme-linked immunosorbent assay (ELISA, DRG International, Mountainside, N.J.), showing a characteristic increase in medium hCG as cytotrophoblasts differentiate into syncytiotrophoblasts (Nelson et al., *Am J Obstet Gynecol* 180, 896-902, 1999; Chen et al., *J Biol Chem* 281, 2764-2772, 2006).

For isolation of PHT exosomes, PHT cells were maintained for 48 h in DMEM containing 10% FBS that was ultracentrifuged at 108,000×g for 10 h to deplete pre-existing FBS exosomes. Exosomes were isolated as described previously (Montecalvo et al., *J Immunol* 180, 3081-3090, 2008). Briefly, supernatants from 200 million PHT cells were combined and subsequently centrifuged at 300×g for 5 min, 1,200×g for 10 min, and 10,000×g for 30 min. Exosomes were concentrated by centrifugation at 2,500×g for 25 min using a Vivacell 100 filter (BioExpress, Kaysville, Utah, USA; F-2820-100C), then ultracentrifuged at 108,000×g for 1 h, and the exosome pellet was subsequently ultracentrifuged on top of a 30% sucrose density cushion at 108,000×g for 1 h (Lamparski et al., *J Immunol Methods* 270, 211-226, 2002). The exosomal phase was collected and resuspended in PBS, before ultracentrifugation at 108,000×g for 1 h. The total amount of exosomes was determined by total protein spectrophotometry. Exosome-depleted PHT supernatant was produced by subsequently centrifugation at 300×g for 5 min, 1,200×g for 10 min, 10,000×g for 30 min and 108,000×g for 1.5 h. Exosomes were reconstituted in FBS-exosome depleted complete medium at a ten-fold concentration over conditioned medium.

Human osteosarcoma U2OS, human foreskin fibroblast (HFF), and Huh7.5 cells were cultured in DMEM-H supplemented with 10% FBS and penicillin/streptomycin. Vero African green monkey kidney cells were maintained in DMEM-H supplemented with 5% FBS and penicillin/streptomycin. Caco-2 (ATCC clone) human intestinal epithelial cells were cultured in MEM supplemented with 10% FBS, non-essential amino acids, sodium pyruvate, and penicillin/streptomycin. Immortalized human first trimester extravillous trophoblast cells, provided by C H Graham, Kingston, Ontario, Canada (Graham et al., *Exp Cell Res* 206, 204-211, 1993) were cultured in RPMI-1640 (Cellgro, Manassas, Va., USA), supplemented with 5% bovine growth serum (HyClone) and antibiotics.

Conditioned media from PHT or other cells were harvested between 48-72 h post plating. Conditioned medium was subjected to sonication or heat-inactivation for 30 min at 65° C. Recipient cells were exposed to conditioned medium for ~24 h prior to assay.

Viruses

Experiments were performed with vesicular stomatitis virus (VSV), green fluorescent protein (GFP)-tagged VSV, recombinant yellow fluorescent protein (YFP)-tagged vaccinia virus as described (VV) (Moser et al., *PLoS Pathog* 6, e1000954, 2010), coxsackievirus B3-RD isolate (CVB3-RD) as described (Coyne and Bergelson, *Cell* 124, 119-131, 2006), poliovirus (PV) as described (Coyne et al., *EMBO J.* 26, 4016-4028, 2007), cytomegalovirus (hCMV Towne strain), cell culture grown hepatitis C virus (HCV) expressing firefly luciferase (HCVcc-luc), or GFP-tagged herpes simplex virus-1 (HSV1, strain KOS) as described (Desai and Person, *J Virol* 72, 7563-7568, 1998). VSV was expanded by growth on Vero cells and media was harvested. Viral titers were determined by plaque assays as previously described (Bozym et al., *Cell Host Microbe.* 11:153-166, 2012). Plaque assays were conducted on Vero (VSV and GFP-VSV) or HeLa (CVB) cells. Confluent monolayers were treated with serial dilutions of virus for one hour at 37° C. (VSV) or at room temperature (CVB). Cells were then overlayed with agarose and incubated for 48 h. Plaques were visualized by crystal violet staining and plaques enumerated. HCVcc-luc propagation was performed as described (Liu et al., *J. Virol.* 83:2011-2014, 2009).

Experiments assessing productive virus infection were performed as follows. PHT cells were infected with CVB, PV, VSV, VV, or HSV-1 for 14-15 h (multiplicity of infection (MOI)=5), or CMV for 24 h. Infections were performed with three individual PHT preparations in duplicate. hCMV infections were performed with two individual PHT preparations in triplicate. For 3-MA experiments assessed by RT-qPCR, PHT cells were infected with GFP-VSV for 15 h at MOI=5. For experiments analyzing immediate early viral gene expression measured by RT-qPCR, PHT cells were infected with CVB, VSV, VV, or HSV-1 for 6-7 h at MOI=1. HeLa cells were infected with CVB or PV at an MOI=5 for 8 h. HFF cells were infected with CMV for 24 h, VSV or CVB (MOI=5) for 15 h. Vero cells were infected with VSV CVB for 6 h (MOI=5). Caco-2 cells were infected with VSV or CVB for 7 h (MOI=5). RL-95 cells were infected with CVB for 15 h (MOI=5). For immunofluorescence, U2OS cells were infected with CVB for 7 h (MOI=5), VSV (MOI=5), VV, or HSV-1 (MOI=1) for 15 h. For RT-qPCR, U2OS cells were infected with CMV, VSV, HSV-1 or VV for 5-6 h (MOI=1). Huh7.5 cells were infected with HCVcc as described previously (Liu et al., *J. Virol.* 83:2011-2014, 2009).

miRNA Mimics, Plasmids, and Transfections

Mimics for C19MC miRNAs (miRIDIAN) as well as a non-targeting control miRNA mimic were obtained from Thermo-Fisher (Dharmacon, Lafayette, Colo.) as described (Donker et al., *Mol. Hum. Reprod.* 18(8):417-424, 2012). U2OS cells or other cell lines were transfected with one or multiple miRNA mimics or miRNA mimic negative control (final concentration 6 nM for each miRNA mimic) using DharmaFECT-1 transfection reagent (Thermo Fisher Scientific) or HiPerFect™ (Qiagen) according to manufacturer's instructions. Cells were assayed 48 h post-transfection.

The total concentration of non-targeting control miRNA mimics was adjusted to that of all active miRNA mimics. For siRNA transfections, U2OS cells were reverse transfected using HiPerFect™ transfection reagent (Qiagen). For silencing of beclin-1, 40 nM per well of scrambled non-targeting siRNA (siControl) or beclin-1 siRNA (Cell Signaling, #6222S) were transfected.

Plasmid transfections were performed using X-tremeGENE 9 (Roche) according to manufacturer's protocol. The mRFP-LC3B expression construct was purchased from Addgene (plasmid 21075) and originally constructed by Tamotsu Yoshimori (Kimura et al., *Autophagy* 3, 452-460, 2007). For experiments with conditioned media and purified exosomes, cells were transfected, exposed to media 24 h later, and fixed 48 h post-transfection. For all other experiments, the cells were assayed 48 h post-transfection.

C19MC BAC Preparation and Transfection

The BAC RP11-1055O17 containing 160,970 bp of genomic DNA from region q13-42 of chromosome 19 was obtained from the BACPAC Resource Center located at the Children's Hospital Oakland Research Institute (CHORI) in Oakland, Calif. The BAC clone harbors the entire C19MC miRNA cluster spanning around 100 kb and contains an additional 60 kb of flanking sequences. The nucleotide sequence of the genomic insert in BAC RP11-1055O17 is set forth herein as SEQ ID NO: 60. Recombineering of the BAC was performed as described (Warming et al., *Nucleic Acids Res* 33, e36, 2005). A GFP::zeocin cassette from the pSELECT-GFPzeo-mcs plasmid (InvivoGen, CA), was PCR amplified and cloned into the Hind III and Bam HI sites of pBluescript II SK(+) (pBS-SK). BAC specific homology arms of ~500 bp each were PCR amplified and cloned into pBS-SK using the restriction sites flanking the GFP::zeocin cassette (5' arm: Xho I and Hind III; 3' arm: Bam HI and Xba I). The whole targeting cassette was then PCR amplified, gel purified, and electroporated into the recombinogenic SW 106 bacterial strain containing the recipient BAC. In addition to the construct that was simply tagged with the GFP::zeocin cassette at the 3' end of the C19MC cluster, a BAC with a deletion of the entire C19MC coding sequence was created and used as a control in transfection experiments. By choosing a 5' homology arm located upstream of the miRNA cluster and keeping the same 3' homology arm, the recombination led to the actual deletion (BAC "trimming") of the entire miRNA locus (~100 kb). The construct contain ~60 kb of genomic DNA flanking the GFP::zeocin cassette. Bacteria harboring the BAC with the desired alteration were selected on selective medium with chloramphenicol (12.5 µg/ml) and zeocin (25 µg/ml). The correct BAC constructs, confirmed by using restriction mapping and PCR, were transformed back into DH10B bacterial cells for propagation. BAC DNA for transfection was prepared using the PhasePrep BAC DNA kit following the recommendations from the manufacturer (Sigma).

RNA Isolation, Microarrays and miRNA RT-qPCR

For miRNA analysis, total cellular RNA was purified from cells using miRNeasy Mini Kit (Qiagen, Valencia, Calif.), according to the manufacturer's instructions. Prior to RNA isolation, non-exosomal RNA were degraded using 400 ng/µl RNase at 37° C. for 15 min (Valadi et al., Nat Cell Biol 9, 654-659, 2007). For miRNA analysis, reverse transcription and quantitative PCR (RT-qPCR) of duplicate samples was performed using the miScript PCR system (Qiagen, Valencia, Calif.), following the manufacturer's instructions. Detection of all miRNAs was performed using respective miScript primers (Qiagen, Valencia, Calif.). Dissociation curves were run on all reactions to ensure amplification of a single product. Control $H_2O$ samples were included in all RT and PCR reactions. Total RNA input was normalized using RNU6B RNA as an endogenous control. The fold increase relative to control samples was determined by the 2-ΔΔCt method (Livak and Schmittgen, Methods 25, 402-408, 2001). Microarray analysis of C19MC miRNA expression in PHT cells and in PHT exosomes was performed using Agilent's Human miRNA V3 8×15K arrays.

For analysis of C19MC miRNA targets, total cellular RNA was purified from U2OS or HTR8/Sv-Neo cells using miRNeasy Mini Kit (Qiagen), according to the manufacturer's instructions (Agilent Technologies, Santa Clara, Calif.). The quality of RNA was confirmed using 2100 Bioanalyzer (Agilent Technologies, Santa Clara, Calif.). A total of 100 ng of RNA was used for labeling, generating cyanine 3-labeled lineary amplified cRNA. Six hundred ng of cRNA was used for microarray hybridization as per Agilent protocol, performed using Agilent's SurePrint G3 Hmn GE 8×60K human arrays. Array data were extracted using a High-Resolution C scanner (Agilent) and a GE1 107 (September 09) feature extraction protocol (Agilent).

All data were from the three experimental paradigms were log 2 transformed and normalized separately using the cyclic loess normalization method (Wu et al., BMC Bioinformatics 6:309, 2005). Identical probes targeting the same mRNA transcripts were averaged by probe set intensity values. A moderated student's t test, which is based on an empirical Bayesian algorithm, as implemented in the R package "limma" (G. K. Smyth, "Linear models and empirical Bayes methods for assessing differential expression in microarray experiments," Statistical Applications in Genetics and Molecular Biology, 3:Article 3, 2004) was applied to test, for each gene, if it was differentially expressed between the cells transfected by the empty BAC or by the C19MC BAC. The Storey's q-value method (Storey and Tibshirani, Proc Natl Acad Sci USA 100, 9440-9445, 2003) was used to calculate the adjusted p values for the p values of the moderated t test to control the false discovery rate. Up- or down-regulated genes were subsequently identified that satisfied the following conditions: (1) down (or up) regulation in the C19MC-transfected HTR8 cells with adjusted p values ≤0.05 and log 2 fold change ≤−0.5 (or ≥+0.5), (2) down (or up) regulation in the C19MC-transfected U2OS cells with adjusted p values ≤0.05 and log 2 fold change ≤−0.5 (or ≥+0.5), and (3) down (or up) regulated in the U2OS cells exposed to conditioned medium, with log 2 fold change ≤−0.5 (or ≥+0.5, note that because each group in the U2OS conditioned medium experiment had only one sample, no statistical testing was performed). Finally, the TargetScan miRNA target database (version 6) was searched to identify, among the down regulated genes, those that are predicted targets of at least one of the 4 most abundant C19MC miRNAs: miR-517-3p, miR-517b, miR-516b, and miR-512-3p. All the analyses were performed using the statistical computing program R and its packages (R Development Core Team, 2011. R: A language and environment for statistical computing. R Foundation for Statistical Computing, Vienna, Austria. ISBN 3-900051-07-0).

For cellular mRNA analysis, total RNA was extracted using TRIreagent (MRC) or RNeasy (Qiagen) according to manufacturer's protocol. RNA samples were treated with RNAse-free DNAse (Qiagen). Total RNA was reverse transcribed using iScript cDNA synthesis kit (Bio-Rad) or $RT^2$ First Strand kit (SABiosciences). For each sample, 0.25-1 µg RNA was used for cDNA synthesis. Real-time PCR as performed using iQ SYBR Green Supermix (Bio-Rad) in a Applied Biosystems StepOnePlus real-time PCR machine according to the manufacturer's instructions. Dissociation curves were run on all reactions to ensure amplification of a single product. Gene expression was calculated using the ΔΔCt values with normalization to human actin (ACTGGGACGACATGGAGAAAA, SEQ ID NO: 61; GCCACACGCAGCTC, SEQ ID NO: 62).

Primers used were as follows: VSV (TG-CAAGGAAAGCATTGAACAA, SEQ ID NO: 63; GAG-GAGTCACCTGGACAATCACT, SEQ ID NO: 64), GFP (CACATGAAGCAGCACGACTTCT, SEQ ID NO: 65; AACTCCAGCAGGACCATGTGAT, SEQ ID NO: 66), hCMV Towne strain (GCGGTGGTTGCCCAACAGGA, SEQ ID NO: 67; ACGACCCGTGGTCATCTTTA, SEQ ID NO: 68), ATG4C (TAGAGGATCACGTAATTGCAGGA, SEQ ID NO: 69; GTTGTCAAAGCTGAGCCTTCTAT, SEQ ID NO: 70), UVRAG (ATGCCAGACCGTCTTGA-TACA, SEQ ID NO: 71; TGACCCAAGTATTTCAGC-CCA, SEQ ID NO: 72), PIK3C3 (GAACAACG-GTTTCGCTCTTTG, SEQ ID NO: 73; GCTTCTACATTAGGCCAGACTTT, SEQ ID NO: 74), Tk (ACCCGCTTAACAGCGTCAACA, SEQ ID NO: 75; CCAAAGAGGTGCGGGAGTTT, SEQ ID NO: 76), VV rpo35 early (GCCAATGAGGGTTCGAGTTC, SEQ ID NO: 77; AACAACATCCCGTCGTTCATC, SEQ ID NO: 78), CVB3 (ACGAATCCCAGTGTGTTTTGG, SEQ ID NO: 79; TGCTCAAAAACGGTATGGACAT, SEQ ID NO: 80), and ISG56 (CAACCAAGCAAATGTGAGGA, SEQ ID NO: 81; GGAGACTTGCCTGGTGAAAA, SEQ ID NO: 82).

Autophagy and toll-like receptor qPCR arrays (SABiosciences) were performed with 1 µg RNA per 96 well plate and subjected to RT-qPCR using SYBR/ROX $RT^2$ qPCR 2× master mix (SABiosciences) according to manufacturer's protocol. Gene expression was defined from the threshold cycle (Ct), and relative expression levels were calculated using SABiosciences $RT^2$ Profiler PCR array analysis automated software.

RNA library construction and miRNA sequencing was performed by Ocean Ridge Biosciences (Palm Beach Gardens, Fla.) using extracted RNA. The small RNA libraries were aligned to the NCBI-37 human reference genome using Bowtie, then intersected with the mature miRNA sequenced annotated by miRBase (v.18) using BEDtools. The miRNA counts in each library were normalized using established algorithms (Anders and Huber, *Genome Biol.* 11:R106, 2010). The C19MC miRNAs and the non-C19MC miRNAs in the six libraries were Laplace smoothed by adding 1 to the normalized counts, log 2 transformed, and clustered respectively by the agglomerative hierarchical clustering, using the complete linkage method. Heat maps were then generated separately for the clustered C19MC miRNAs and non-C19MC miRNAs. To quantify the differences in miRNA expression between U2OS cells that were exposed to PHT conditioned medium vs. cells that were exposed to fresh medium, the differential expression test was applied, which assumes that the in all libraries were follow negative binomial distributions (Anders and Huber, *Genome Biol.* 11:R106, 2010), and a shrinkage estimator was used for the dispersion parameters of the miRNAs. The p-values of the tests were adjusted using the Benjamini and Hochberg's method (Hochberg and Benjamini, *J. Roy. Statist. Soc. B.* 57:289-300, 1995) to control for false discovery rate. Statistical analyses were performed using statistical computing software R and the DESeq package of R.

Pharmacological Agents

Cells were pre-treated with 3-methyladenine (3-MA; 5 mM, Sigma) for 30-60 min prior to infection, and cells were incubated with drug throughout the duration of infection. For mRFP-LC3B punctae assays, 3-MA was added for 30 min prior to conditioned or non-conditioned media exposure, and was present throughout. Rapamycin (5 µM, Calbiochem) treatment or serum-starvation with Hank's Balanced salt solution (HBSS) for 4 h was used as a positive control for autophagy.

Immunofluorescence and Confocal Microscopy

Cell monolayers were cultured in 8-well chamber slides (LabTek) at 37° C. Cells were then washed and fixed as indicated with either ice cold methanol, 3:1 methanol-acetone, or 4% paraformaldehyde in PBS and permeabilized with 0.25% Triton X-100 in PBS. Mouse anti-VSV-G and mouse anti-hCMV gB were obtained from Santa Cruz Biotechnology, and mouse anti-enterovirus VP1 (NCL-Entero) was purchased from Novacastra Laboratories. Mouse-anti clathrin heavy chain (CHC) and mouse anti-caveolin 1 (Cav1) antibodies were obtained from BD Transduction Laboratories. Rabbit anti-Dynamin II (DynII) was purchased from Abcam. Fixed monolayers were incubated with primary antibody, washed, incubated with Alexa Fluor-488 or -594-conjugated secondary antibodies (Invitrogen), washed, and then mounted with Vectashield (Vector Laboratories) containing 4',6-diamidino-2-phenylindole (DAN), Cholera toxin B (CTB) conjugated to Alexa Fluor 488 (8 µg/mL; Invitrogen) and transferrin conjugated to Alexa Fluor 594 (Invitrogen) uptake was performed essentially as previously described (Patel et al., *J Virol* 83, 11064-11077, 2009).

Images were captured with an IX81 inverted microscope equipped with a motorized stage or with an Olympus Fluoview 1000 laser scanning confocal microscope. Images of infected cells were taken using an Olympus PlanApo 10×/0.40 NA dry or Apo 20×/0.75 NA dry objective, whereas all other images were taken with an Olympus PlanApo 60×/1.42 NA oil objective.

For virus infection assays, cells were fixed and stained for markers of virus infection (CVB and PV (VP1), VSV (VSV-G), hCMV (gB)) or assessed for GFP-expression (VV-GFP, HSV-1-GFP, VV-YFP). A minimum of three independent fields per condition were counted (at least 600 cells total). Infection levels are reported as the percentage of virus positive cells among the total number of cells, determined by DAPI staining. Quantification of percent virus positive cells was performed using ImageJ (National Institutes of Health) analysis. For LC3B autophagy assays, at least twenty individual cells from a minimum of four independent fields were captured per condition. The total number of mRFP-LC3B-positive punctae were quantified per cell using ImageJ analysis with identical settings per condition, Analysis of the extent of VSV and mRFP-LC3b punctate co-localization was performed using ImageJ.

Electron Microscopy

Cells were washed, fixed with 2.5% gluteraldehyde in PBS for 1 h, then processed for electron microscopy as previously described (Gao et al., *J Biol Chem* 285, 1371-1383, 2010), Sections were imaged using a JEOL JEM 1011 transmission electron microscope (Peabody) using an 80 V fitted with a bottom mount AMT 2k digital camera (Advanced Microscopy Techniques). At least five to ten individual cells were captured per condition. The number of autophagosomes (including amphisomes, autophagosomes, autophagic vacuoles, and autolysosomes) were quantified per cell manually.

Immunoblots

Cells were grown in 6-well plates and lysates were prepared with RIPA buffer (50 mM Tris-HCl [pH 7.4]; 1% NP-40; 0.25% sodium deoxycholate; 150 mM NaCl; 1 mM EDTA; 1 mM phenylmethanesulfonyl fluoride; 1 mg/ml aprotinin, leupeptin, and pepstatin; 1 mM sodium orthovanadate), and insoluble material was precipitated by brief centrifugation. Protein concentration of lysates was determined by BCA protein assay (Thermo Scientific). Lysates containing equal amounts of protein were loaded onto 4-20% Tris-HCl gels (Bio-Rad) and transferred to polyvinylidene difluoride membranes. Membranes were blocked in 5% nonfat dry milk, probed with the indicated antibodies, and developed with horseradish peroxidase-conjugated secondary antibodies (Santa Cruz Biotechnology), and SuperSignal West Pico or Dura, chemiluminescent substrates (Pierce Biotechnology).

For beclin-1 immunoblotting, cells were lysed on ice in a 50 mM Tris-HCl, pH 7.5 buffer that contained 150 mM NaCl and 0.5% NP-40. After centrifugation at 12,000×g at 4° C., the supernatant was subjected to 10% SDS-PAGE, transferred to PVDF membrane, and signal detected using monoclonal antibodies as indicated. Densitometry was performed using Image J.

Reporter Gene Assay

Activation of interferon β (IFNβ) or interferon-stimulated response element (ISRE) promoters was measured by reporter assay. Cells were transfected with 1 µg of DNA/well of a 24 well plate, a 30:1 ratio of IFNβ or ISRE firefly luciferase reporter plasmids to pRL-null (*Renilla* control) as per manufacturer's protocol. Cells were lysed in 100 µL of lysis buffer and the levels of firefly and *Renilla* luciferase levels quantified using the Dual-Luciferase Reporter Assay System (Promega) with a dual injector equipped Synergy 2 SL Luminescence Microplate Reader (BioTek). Levels of firefly luciferase were normalized to control *Renilla* luciferase levels. For poly(I:C) treatment, cells were transfected with 1 µg poly(I:C)/well using XtremeGene-9 for 16 h as per the manufacturer's protocol.

Statistical Analysis

All experiments were performed at least three times, as indicated in the figure legends. Data are presented as mean±standard deviation. Except where specified, Student's t test was used to determine statistical significance for virus infection and autophagy assays when 2 sets were compared, and one-way analysis of variance (ANOVA) with Bonferroni's correction for multiple comparisons were used to determine statistical significance for reporter gene assays. A p<0.05 was determined significant.

Virus Entry Assays

Virus entry assays in PHT cells were performed with CVB and PV as previously described (Coyne and Bergelson, *Cell* 124, 119-131, 2006; Coyne et al., *EMBO J.* 26, 4016-4028, 2007). VV and HSV-1 internalization assays were performed by incubating PHT cells with virus (MOI 25) at 37° C. until fixation at various time points (30, 60, 90 min). VSV entry assays in U2OS cells exposed to either non-conditioned or conditioned PHT medium for 24 h was performed by incubating cells with virus (MOI=500) for 1 h at 37° C. until fixation in 4% PFA followed by permeabilization in 0.1% Triton X-100. VSV particles were visualized with anti-VSV-G antibody.

Modified TCID50 Virus Titering Assays

Vero or PHT cells were seeded to confluence in 96 well plates. Cells were incubated with serial dilutions of the indicated viruses for approximately 40-45 h, then stained with 0.05% crystal violet (in 10% ethanol). For experiments performed with conditioned medium, Vero cells were incubated in non-conditioned or conditioned medium 24 h prior to incubation with virus. Serial dilutions of virus were made in either non-conditioned or conditioned medium, and cells were incubated and developed with crystal violet as described above.

Neutralizing Virus Plaque Assays

VSV virus stock was diluted 1:20 in either non-conditioned or conditioned PHT medium, then incubated at 37° C. for 1 h. Plaques assays were performed on Vero cells. Plaques were visualized after 36 h by staining with crystal violet.

Example 2

Human Placental Trophoblasts Confer Viral Resistance to Recipient Cells by the Release of miRNAs and the Induction of Autophagy This example describes the finding that PHTs are highly resistant to infection by a number of different types of viruses. This resistance is mediated by exosomes containing miRNAs encoded by the primate-specific chromosome 19 miRNA cluster (C19MC).

PHT-Derived Exosomes Protect Recipient Cells from Viral Infection

The studies described herein determined that PHT cells were resistant to infection by a panel of viruses, including coxsackievirus B3 (CVB), poliovirus (PV), vesicular stomatitis virus (VSV), vaccinia virus (VV), herpes simplex virus-1 (HSV-1), and human cytomegalovirus (CMV), when compared to non-PHT cells (FIG. 1A). This lack of viral replication was not due to inefficient viral binding and/or entry, or to defects in common endocytic pathways utilized by viruses for their entry, such as clathrin- or caveolar-mediated pathways. It was found that exposure of diverse non-PHT recipient cells for 24 h prior to infection to PHT conditioned medium (isolated from naïve PHT cells 48-72 h post-plating) decreased the replication of CVB, VSV, hepatitis C virus (HCV), and VV (FIG. 6A). The antiviral effect of conditioned PHT medium was also observed in several physiologically relevant fetal and/or maternal primary cells, including human umbilical vein endothelial cells (HUVEC), human uterine microvascular endothelial cells, human placental fibroblasts, and human foreskin fibroblasts (HFF; FIG. 1C, right panel). In contrast, conditioned medium from other cell types, such as immortalized trophoblast BeWo cells, had no effect (FIG. 6B). This effect was not the result of direct neutralization of the virus as conditioned medium had no direct effect on viral titers (FIG. 6C). Furthermore, antiviral effects were observed across multiple conditioned medium samples isolated from independent and unrelated PHT preparations (FIGS. 6D-6F). Together, these data indicate that PHT cells release specific components to the medium, which are capable of conferring viral resistance to non-placental recipient cells.

To better define the component in conditioned medium of PHT cells that is responsible for conferring viral resistance, the conditioned medium was exposed to heat inactivation or RNAse treatment; however, no effect was observed (FIG. 1D). In contrast, repeated freeze-thawing partly attenuated the effect, and sonication completely abolished the antiviral effect of PHT conditioned medium (FIG. 1D). Because exosomes, which function as "cargo nanovesicles" (Valadi et al., *Nat. Cell. Biol.* 9:654-659, 2007; Skog et al., *Nat. Cell. Biol.* 10:1470-1476, 2008), are characteristically released from trophoblasts and are sensitive to sonication (Donker et al., *Mol. Hum. Reprod.* 18(8):417-424, 2012; Taylor et al., *J. Immunol.* 176:1534-1542, 2006; Montecalvo et al., *J. Immunol.* 180:3081-3090, 2008; Luo et al., *Biol. Reprod.* 81:717-729, 2009; Pegtel et al., *Proc. Natl. Acad. Sci. U.S.A.* 107:6328-6333, 2010), their role in PHT-mediated transfer of viral resistance was examined. It was found that exosomes purified from PHT conditioned medium attenuated VSV infection in recipient cells (FIG. 1E). The antiviral effect was abrogated using exosome-depleted PHT conditioned medium (FIG. 1E). In addition, exosomes isolated from other cell types, such as an immortalized human placental choriocarcinoma cell line (JEG-3) or primary murine dendritic cells, had no effect on viral infection (FIG. 1E). Taken together, these data point to a direct role for PHT-derived exosomes in the transfer of viral resistance to non-placental recipient cells.

C19MC-Associated miRNAs Confer Viral Resistance

The transfer of RNA and/or miRNAs via exosomes may play an important role in exosome-based intercellular communication (Valadi et al., *Nat. Cell. Biol.* 9:654-659, 2007; Pegtel et al., *Proc. Natl. Acad. Sci. U.S.A.* 107:6328-6333, 2010; Zhang et al., *Mol. Cell.* 39:133-144, 2010). The human C19MC is the largest known miRNA cluster, comprising 46 miRNAs that are highly expressed almost exclusively in the human placenta. Moreover, as a group, C19MC miRNAs are also the most abundant miRNA species in trophoblastic exosomes, with a strong correlation between C19MC miRNA levels in PHT cells and in PHT-derived exosomes (Noguer-Dance et al., *Hum. Mol. Genet.* 19:3566-3582, 2010; Donker et al., *Mol. Hum. Reprod.* 18(8):417-424, 2012; Taylor et al., *J. Immunol.* 176:1534-1542, 2006; Mouillet et al., *Placenta.* 31:781-784, 2010). To date, the function of these miRNAs has remained elusive. To test whether the expression of C19MC miRNAs could induce viral resistance in non-PHT cells, which do not naturally express these miRNAs, U2OS cells were stably transfected with a BAC that contained the entire human C19MC cluster. When compared to U2OS cells transfected with a control BAC (that is deficient for the C19MC expression sequence), cells stably expressing C19MC-BAC or cells exposed to PHT conditioned media expressed a higher level of C19MC miRNAs, as confirmed by RNAseq (Table 3), and exhibited resistance to VSV infection (FIG. 2A). Likewise, transient transfection of U2OS cells with miRNA mimics of 16 C19MC-associated miRNAs (representing highly expressed miRNAs, or the two subfamilies of the C19MC; Lin et al., Comput. Biol. Chem. 34:232-241, 2010) markedly reduced VSV infection (FIG. 2B and Table 2). It was also found that transfection of mimics of the six highest expressed C19MCs (Donker et al., Mol. Hum. Reprod. 18(8):417-424, 2012; Taylor et al., J. Immunol. 176:1534-1542, 2006; Mouillet et al., Placenta. 31:781-784, 2010) attenuated VSV infection, whereas transfection with mimics of the lowest expressed seven had no significant effect (FIG. 2B). To define the impact of individual miRNAs, individual mimics from among the highest expressed C19MC miRNAs were expressed, and a significant inhibition of VSV infection was detected with mimics of miR-517-3p, -516b-5p, and -512-3p, but not with mimics of several non-C19MC-associated miRNAs (miR-1, -424, -630, and -720; FIGS. 2C-2D). Likewise, a mimic of miR-517-3p also attenuated infection by the DNA viruses VV and HSV-1 (FIG. 2E).

TABLE 2

Groups of mimics to C19MC miRNAs used in the described experiments. The 16 miRNAs are listed in order of expression level (highest to lowest).

| 16 C19MC miRNAs | Subgroup 1 9 C19MC miRNAs | Subgroup 2 7 C19MC miRNAs | 6 highest expressed C19MC miRNAs | 7 lowest expressed C19MC miRNAs |
|---|---|---|---|---|
| miR-517-3p | miR-517-3p | | miR-517-3p | |
| miR-1323 | | miR-1323 | miR-1323 | |
| miR-516b-5p | | miR-516b-5p | miR-516b-5p | |
| miR-525-5p | | miR-525-5p | miR-525-5p | |
| miR-512-3p | | miR-512-3p | miR-512-3p | |
| miR-515-3p | miR-515-3p | | miR-515-3p | |
| miR-518e | miR-518e | | | |
| miR-515-5p | | miR-515-5p | | |
| miR-517c | miR-517c | | | |
| miR-519c-3p | miR-519c-3p | | | miR-519c-3p |
| miR-520h | miR-520h | | | miR-520h |
| miR-519d | miR-519d | | | miR-519d |
| miR-518b | miR-518b | | | miR-518b |
| miR-512-5p | | miR-512-5p | | miR-512-5p |
| miR-520c-3p | miR-520c-3p | | | miR-520c-3p |
| miR-518a-5p | | miR-518a-5p | | miR-518a-5p |

TABLE 3

Differences in miRNA expression between U2OS cells exposed to conditioned or non-conditioned medium, analyzed by RNAseq*.

| C19MC miRNA | Conditioned medium | Non-conditioned medium | Fold change (CM/FM) | Log2 fold change | p value | p adjusted (BH) |
|---|---|---|---|---|---|---|
| miR-517-3p | 2374.403 | 765.215 | 3.103 | 1.634 | 2.66E−32 | 4.68E−30 |
| miR-519a-3p | 1738.835 | 1144.108 | 1.520 | 0.604 | 9.81E−07 | 4.60E−05 |
| miR-522-3p | 1662.638 | 1245.641 | 1.335 | 0.417 | 0.001083036 | 0.021856025 |
| miR-1323 | 1454.781 | 459.377 | 3.167 | 1.663 | 8.06E−35 | 3.31E−32 |
| miR-516a-5p | 1093.955 | 635.203 | 1.722 | 0.784 | 7.75E−09 | 4.34E−07 |
| miR-521 | 631.942 | 494.047 | 1.279 | 0.355 | 0.014010033 | 0.215579384 |
| miR-1283 | 565.757 | 341.747 | 1.655 | 0.727 | 4.06E−06 | 0.000166442 |
| miR-516b-5p | 424.862 | 188.208 | 2.257 | 1.175 | 1.08E−13 | 9.49E−12 |
| miR-512-3p | 337.442 | 44.576 | 7.570 | 2.920 | 3.44E−38 | 2.48E−35 |
| miR-524-5p | 269.386 | 37.146 | 7.252 | 2.858 | 2.06E−33 | 6.34E−31 |
| miR-515-3p | 249.009 | 17.335 | 14.365 | 3.844 | 4.03E−38 | 2.48E−35 |
| miR-517c-3p | 228.786 | 116.392 | 1.966 | 0.975 | 2.02E−07 | 1.03E−05 |
| miR-525-5p | 216.140 | 26.002 | 8.312 | 3.055 | 2.73E−30 | 4.20E−28 |
| miR-520d-3p | 200.409 | 21.050 | 9.521 | 3.251 | 4.39E−30 | 6.01E−28 |
| miR-520a-3p | 141.669 | 35.908 | 3.945 | 1.980 | 2.43E−14 | 2.50E−12 |
| miR-518e-3p | 122.653 | 16.097 | 7.620 | 2.930 | 4.67E−19 | 5.75E−17 |
| miR-519d | 113.300 | 38.385 | 2.952 | 1.562 | 4.05E−09 | 2.37E−07 |
| miR-518b | 105.055 | 58.196 | 1.805 | 0.852 | 0.000622055 | 0.013434194 |
| miR-518c-3p | 76.726 | 32.194 | 2.383 | 1.253 | 2.34E−05 | 0.000823018 |
| miR-518a-5p | 70.166 | 34.670 | 2.024 | 1.017 | 0.002164332 | 0.040989113 |
| miR-520g | 65.535 | 61.911 | 1.059 | 0.082 | 0.848007306 | 1 |
| miR-518e-5p | 65.366 | 26.002 | 2.514 | 1.330 | 5.44E−05 | 0.001594773 |
| miR-519a-5p | 65.366 | 26.002 | 2.514 | 1.330 | 5.44E−05 | 0.001594773 |
| miR-519b-5p | 65.366 | 26.002 | 2.514 | 1.330 | 5.44E−05 | 0.001594773 |
| miR-519c-5p | 65.366 | 26.002 | 2.514 | 1.330 | 5.44E−05 | 0.001594773 |
| miR-522-5p | 65.366 | 26.002 | 2.514 | 1.330 | 5.44E−05 | 0.001594773 |
| miR-523-5p | 65.366 | 26.002 | 2.514 | 1.330 | 5.44E−05 | 0.001594773 |
| miR-524-3p | 57.113 | 2.476 | 23.063 | 4.527 | 1.85E−13 | 1.42E−11 |
| miR-520h | 54.554 | 34.670 | 1.574 | 0.654 | 0.048469819 | 0.547397683 |
| miR-526b-5p | 48.663 | 28.479 | 1.709 | 0.773 | 0.020670659 | 0.277189278 |
| miR-515-5p | 43.639 | 34.670 | 1.259 | 0.332 | 0.311332029 | 1 |
| miR-498 | 38.128 | 17.335 | 2.199 | 1.137 | 0.003592299 | 0.06503118 |
| miR-527 | 34.719 | 17.335 | 2.003 | 1.002 | 0.032552612 | 0.396755106 |
| miR-526a | 33.466 | 8.667 | 3.861 | 1.949 | 0.000139813 | 0.00374151 |
| miR-519c-3p | 32.153 | 4.953 | 6.492 | 2.699 | 3.16E−06 | 0.000138861 |
| miR-520a-5p | 26.509 | 11.144 | 2.379 | 1.250 | 0.014724591 | 0.223777425 |
| miR-518f-5p | 25.322 | 4.953 | 5.113 | 2.354 | 0.000166051 | 0.004258507 |
| miR-520d-5p | 24.485 | 3.715 | 6.591 | 2.721 | 4.17E−05 | 0.001426038 |
| miR-518a-3p | 24.118 | 17.335 | 1.391 | 0.476 | 0.300976907 | 1 |
| miR-525-3p | 20.871 | 14.859 | 1.405 | 0.490 | 0.270466957 | 1 |

TABLE 3-continued

Differences in miRNA expression between U2OS cells exposed to conditioned or non-conditioned medium, analyzed by RNAseq*.

| C19MC miRNA | Conditioned medium | Non-conditioned medium | Fold change (CM/FM) | Log2 fold change | p value | p adjusted (BH) |
|---|---|---|---|---|---|---|
| miR-519e-5p | 17.257 | 4.953 | 3.484 | 1.801 | 0.008673863 | 0.14013828 |
| miR-518d-5p | 16.733 | 3.715 | 4.505 | 2.171 | 0.005073798 | 0.086747848 |
| miR-520c-5p | 16.733 | 3.715 | 4.505 | 2.171 | 0.005073798 | 0.086747848 |
| miR-518c-5p | 14.673 | 7.429 | 1.975 | 0.982 | 0.150512908 | 1 |
| miR-523-3p | 14.119 | 3.715 | 3.801 | 1.926 | 0.016108611 | 0.241825612 |
| miR-518d-3p | 11.457 | 1.238 | 9.252 | 3.210 | 0.006515171 | 0.108380746 |
| miR-517-5p | 9.017 | 1.238 | 7.282 | 2.864 | 0.018394499 | 0.263298001 |
| miR-512-5p | 8.716 | 8.667 | 1.006 | 0.008 | 1 | 1 |
| miR-518f-3p | 7.288 | 2.476 | 2.943 | 1.557 | 0.215985658 | 1 |
| miR-519b-3p | 7.132 | 4.953 | 1.440 | 0.526 | 0.60445537 | 1 |
| miR-526b-3p | 6.258 | 1.238 | 5.054 | 2.338 | 0.13991013 | 1 |
| miR-520e | 2.789 | 3.715 | 0.751 | −0.414 | 0.91188741 | 1 |
| miR-519e-3p | 1.506 | 0.000 | Inf | Inf | 0.579448235 | 1 |
| miR-520b | 1.458 | 1.238 | 1.177 | 0.235 | 1 | 1 |
| miR-520c-3p | 1.157 | 0.000 | Inf | Inf | 0.94380054 | 1 |
| miR-520f | 0.428 | 0.000 | Inf | Inf | 1 | 1 |
| miR-516a-3p | 0.000 | 0.000 | NA | NA | NA | NA |
| miR-516b-3p | 0.000 | 0.000 | NA | NA | NA | NA |

*Counts were normalized by the median of ratio of the observed counts in each library to the geometric mean of the observed counts of all libraries, as described in Methods. Columns of conditioned and non-conditioned medium represent the mean of the normalized miRNAs counts in those samples.

PHT-Derived Exosomes and C19MC-Associated miRNAs Upregulate Autophagy

Mammalian cells utilize diverse defense mechanisms to combat microbial pathogens. One crucial mechanism is the induction of autophagy, an evolutionarily conserved lysosomal degradation pathway that has been associated with an array of cellular functions. Autophagy also degrades intracellular foreign microbial invaders (a process sometimes referred to as xenophagy) and thus serves as an important cellular response to suppress microbial infections. Exposure of U2OS cells to PHT conditioned medium or to purified PHT-derived exosomes markedly stimulated autophagy, as assessed by the formation of mRFP-LC3b-containing punctae and by electron microscopy, whereas conditioned-medium depleted of PHT-exosomes had no effect (FIGS. 3A-3B and FIG. 7A). In contrast, no effect of PHT conditioned medium or C19MC-miRNAs on type I interferon (IFN) signaling was observed in recipient cells, and antiviral activity of conditioned PHT medium was observed in cells that fail to respond to type I IFNs. In addition, PHT cells themselves also do not exhibit enhanced type I IFN signaling.

Autophagy induction was observed in diverse cell types (FIGS. 3A-3B and FIG. 7B), and was absent in cells exposed to exosome-depleted PHT conditioned medium (FIGS. 3A-3B). In addition, PHT conditioned medium induced the upregulation (>3-fold) of several key pro-autophagy transcripts (e.g., ATG4C, UVRAG, and LC3A) while having no effect on other innate immune pathway components (e.g. toll-like receptors, interferon regulatory factors, cytokine-mediated signaling) in U2OS cells exposed to conditioned PHT medium (FIG. 7C and Table 4), further supporting the induction of autophagy. 3-methyladenine (3-MA), an inhibitor of autophagosome biogenesis, inhibited autophagosome formation in recipient cells exposed to conditioned PHT medium (FIG. 3C). Lastly, incoming VSV particles were trafficked to LC3b-positive punctae formed following exposure of cells to conditioned PHT medium, suggesting that the mislocalization or targeting of incoming viral particles to autophagosomes and/or autolysosome might impact viral replication (FIG. 3D).

TABLE 4

Summary of expression changes in autophagy-related transcripts.

| Gene | Fold-change | Gene | Fold-change |
|---|---|---|---|
| ATG4C | 3.2861 | MAP1LC3B | 1.2209 |
| UVRAG | 3.2696 | CHUK | 1.2054 |
| CCL2 | 3.1764 | HSPA1A | 1.1822 |
| DAPK1 | 3.119 | ATG12 | 1.1791 |
| CTSS | 3.1154 | RIPK2 | 1.1446 |
| EIF2AK2 | 2.5184 | ATG16L1 | 1.1417 |
| RB1 | 2.3295 | PTGS2 | 1.1354 |
| BNIP3 | 2.3171 | TOLLIP | 1.124 |
| MAP1LC3A | 2.1561 | EIF2AK3 | 1.1192 |
| PIK3C3 | 2.1554 | IL8 | 1.1002 |
| BID | 2.149 | UBE2N | 1.0968 |
| AMBRA1 | 1.9193 | MAP3K7 | 1.0954 |
| ARSA | 1.849 | TLR4 | 1.0872 |
| BCL2L1 | 1.7855 | APP | 1.0846 |
| PRKRA | 1.7526 | PPARA | 1.0624 |
| ATG4D | 1.7454 | PELI1 | 1.0265 |
| SQSTM1 | 1.7187 | PRKAA2 | 1.0185 |
| NFKBIA | 1.6335 | FAS | 1.0149 |
| ATG4A | 1.6288 | BECN1 | 1.0139 |
| LY96 | 1.4979 | HSP90AA1 | 1.0107 |
| NFKB1 | 1.45885 | HSPD1 | 0.9957 |
| TBK1 | 1.3469 | CSF2 | 0.9879 |
| TP53 | 1.3446 | HGS | 0.9745 |
| MAP3K1 | 1.3294 | REL | 0.9743 |
| DRAM1 | 1.3204 | CXCR4 | 0.9529 |
| ATG3 | 1.289 | MAPK14 | 0.9497 |
| AKT1 | 1.2812 | IRF3 | 0.9437 |
| TLR3 | 1.2655 | TICAM2 | 0.9347 |
| ATG16L2 | 1.2457 | ATG4B | 0.9261 |
| TGFB1 | 1.2354 | ATG5 | 0.9159 |
| ULK2 | 1.2352 | HRAS | 0.9159 |
| SNCA | 1.2286 | CTSB | 0.9132 |
| HMGB1 | 0.9027 | ATG10 | 0.724 |
| TNFRSF1A | 0.901 | FADD | 0.7218 |
| ELK1 | 0.8971 | BAX | 0.7145 |
| IL1B | 0.8966 | PIK3R4 | 0.7073 |
| UBE2V1 | 0.8948 | MAP2K3 | 0.6992 |
| GABARAP | 0.8913 | HSPA8 | 0.6945 |
| IKBKB | 0.8859 | MAPK8 | 0.68385 |
| PTEN | 0.8814 | ATG7 | 0.6794 |
| EIF4G1 | 0.8792 | MAPK8IP3 | 0.6767 |
| GABARAPL2 | 0.8772 | NFRKB | 0.6665 |
| MAP4K4 | 0.8748 | TAB1 | 0.6663 |

TABLE 4-continued

Summary of expression changes in autophagy-related transcripts.

| Gene | Fold-change | Gene | Fold-change |
|---|---|---|---|
| CD180 | 0.8699 | ULK1 | 0.6621 |
| CLN3 | 0.8339 | TICAM1 | 0.6597 |
| PRKAA1 | 0.8324 | CDKN1B | 0.6285 |
| FAM176A | 0.8304 | TGM2 | 0.6192 |
| TRAF6 | 0.8257 | DRAM2 | 0.6166 |
| MAP2K4 | 0.8234 | RPS6KB1 | 0.6072 |
| NR2C2 | 0.8234 | RGS19 | 0.6005 |
| BCL2 | 0.8218 | NFKB2 | 0.5946 |
| HTT | 0.8135 | TMEM74 | 0.576 |
| TLR6 | 0.809 | ATG9A | 0.5758 |
| ECSIT | 0.804 | CASP8 | 0.57545 |
| BAD | 0.8011 | JUN | 0.5644 |
| BAK1 | 0.7987 | SARM1 | 0.5564 |
| MYD88 | 0.7962 | NFKBIL1 | 0.5528 |
| GAA | 0.7936 | IRAK1 | 0.5404 |
| IRF1 | 0.7825 | FOS | 0.5091 |
| CASP3 | 0.7749 | TP73 | 0.5061 |
| GABARAPL1 | 0.7581 | TNFSF10 | 0.4193 |
| HDAC1 | 0.7541 | IRGM | 0.2952 |
| RAB24 | 0.7351 | TNF | 0.2475 |
| RELA | 0.7325 | ATG9B | 0.2436 |
|  |  | IFNA4 | 0.1286 |

Because a role for C19MC-associated miRNAs was observed in the induction of viral resistance, it was assessed whether these miRNAs could induce autophagy. Transfection of cells with mimics of six of the highest expressed C19MC miRNAs (FIGS. 4A-4B), the entire C19MC (FIG. 7D) or mimics of individual C19MC miRNAs that attenuated viral infection (FIG. 4C), also stimulated autophagy, as observed by mRFP-LC3b punctate formation or by electron microscopy. Furthermore, C19MC-associated induction of autophagy occurred via the upregulation of autophagic flux, as supported by a decrease in p62 levels in cells expressing the entire C19MC (FIG. 4D).

The Antiviral Effects of C19MC-Associated miRNAs Require Autophagy

Figure 5A:
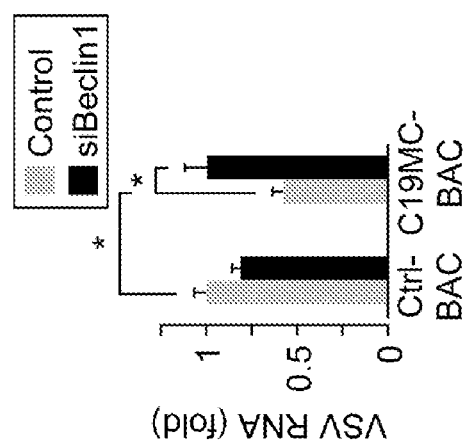
FIGS. 5A-5C: Suppression of autophagy restores C19MC-mediated antiviral effects.
Figure 5B:
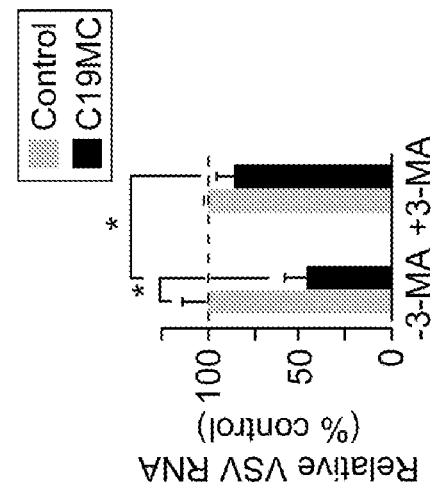
Figure 5C:
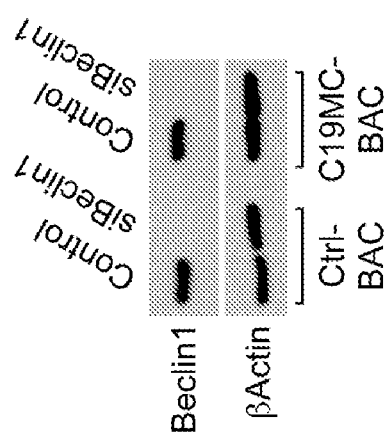

An inhibition of viral replication and a pronounced upregulation of autophagy was observed in cells exposed to PHT conditioned medium and in cells expressing C19MC-associated miRNAs. To determine if the antiviral effects of these conditions involved autophagy, autophagy was suppressed by treatment of cells with 3-MA or by RNA interference (RNAi)-mediated silencing of beclin-1, a key factor in autophagic induction (Liang et al., Nature 402:672-676, 1999). Inhibition of autophagy using 3-MA or by RNAi-mediated silencing of beclin-1 expression significantly restored the level of VSV infection in U2OS cells expressing the entire C19MC (FIGS. 5A-5B). Furthermore, addition of 3-MA to PHT cells enhanced VSV infection (FIG. 5C). These data show that the induction of autophagy is critical for the antiviral effect of C19MC miRNAs.

Discussion

The placenta shields the embryo from the spread of a number of diverse pathogens, including viruses. Disclosed herein is the striking finding that placental trophoblasts transfer viral resistance to non-placental cells. Viral resistance is transferrable via trophoblastic conditioned medium, trophoblastic exosomes, or miRNA members of the C19MC primate-specific cluster. It is shown that multiple members of the C19MC primate-specific miRNA cluster, which is localized to chromosome 19q13.41 and expressed by a specific RNA Pol-II primarily in the placenta (Noguer-Dance et al., Hum Mol Genet. 19, 3566-3582, 2010; Bortolin-Cavaille et al., Nucleic Acids Res 37, 3464-3473, 2009; Bentwich et al., Nat Genet. 37, 766-770, 2005), are packaged within exosomes, which are capable of carrying their nucleic acids and other types of cargo to neighboring or distal targets (Valadi et al., Nat Cell Biol 9, 654-659, 2007). Although the C19MC is the largest known human miRNA cluster, its function remains unknown. Specific members of the C19MC miRNA family are known to be up-regulated in cancers, such as aggressive primitive neuroectodermal brain tumors (miR-517c and miR-520g) (Li et al., Cancer Cell 16, 533-546, 2009), hepatocellular carcinoma (miR-519d) (Formari et al., J Pathol, doi: 10.1002/path.3995, Jan. 19, 2012 [Epub]), breast cancer (miR-516-3p, miR-520c) (Foekens et al., Proc Natl Acad Sci USA 105, 13021-13026, 20081; Huang et al., Nat Cell Biol 10, 202-210, 2008), prostate cancer (miR-520c) (Yang et al., Int J Clin Exp Pathol 2, 361-369, 2009), and thyroid adenomas (Rippe et al., PLoS One 5, e9485, 2010). Thus, the data described herein are the first to suggest a unique role of C19MC miRNA members in an antiviral response that is transferable to either neighboring cells within the placenta such as villous fibroblasts, macrophages or fetal endothelial cells, and to maternal systemic cells, such as maternal endothelial or immune cells. Whereas the nature of recipient cells and the mechanisms of targeting remain unknown, exosome-mediated delivery of C19MC family members may constitute a powerful evolutionary adaptation by which a developing fetus is protected from viral invaders during pregnancy.

Primary human trophoblasts produce robust levels of miRNAs throughout pregnancy, as well as other small RNAs (piRNAs, snRNAs, and snoRNAs) (Mouillet et al., Placenta. 31:781-784, 2010; Luo et al., Biol. Reprod. 81:717-729, 2009; Mouillet et al., Birth Defects Res. A. Clin. Mol. Teratol. 91:737-743, 2011; Barad et al., Genome. Res. 14:2486-2494, 2004; Pineles et al. Am. J. Obstet. Gynecol. 196(3):e261-266, 2007). Many of these miRNAs, including members of the C19MC, are found in the maternal blood throughout pregnancy and rapidly decline in the first 24 h postpartum (Ng et al., Proc. Natl. Acad. Sci. U.S.A. 100, 4748-4753, 2003; Gilad et al., PLoS One. 3:e3148, 2008), suggesting a miRNA-based mechanism for fetal-maternal communication (Mouillet et al., Placenta. 31:781-784, 2010; Chim et al., Clin. Chem. 54:482-490, 2008). The data disclosed herein thus provide evidence for a novel paracrine and/or systemic function of placental trophoblasts—utilizing exosome-mediated transport of a unique set of primate-specific effector miRNAs to directly communicate with maternal cells, and possibly neighboring placental cells, and regulate their immunity to viral infections. It is possible that PHT-derived, C19MC miRNA-containing exosomes specifically target their cargo to a discrete subpopulation of maternal cells, or may aid in the selectively eliciting antiviral responses and upregulating autophagy. Although placental-derived miRNAs are found in low levels in the fetal circulation, it is possible that these miRNAs are sufficient to regulate specific pathways in the developing fetus, such as the induction of autophagy, which is critical for neonatal survival (Kuma et al., Nature. 432:1032-1036, 2004).

The data disclosed herein show that conditioned media from PHT cells, purified PHT-derived exosomes, and miRNA mimics of several members of the C19MC family potently induce autophagy. Autophagy is an important component of host antimicrobial signaling and often functions to restrict viral replication. Although some of the viruses used in the disclosed study (such as CVB (Schlegel et al., J Virol 70, 6576-6588, 1996; Jackson et al., PLoS Biol 3, e156, 2005) and HCV (Dreux et al., Proc Natl Acad Sci USA 106, 14046-14051, 2009)) are thought to benefit from the formation of autophagic vesicles during their replication, these viruses were also sensitive to the antiviral effects of C19MC miRNAs. Unlike the induction of autophagy via an innate immune pathway in response to virus replication, recipient cells exposed to C19MC miRNAs exhibit robust levels of autophagy prior to their first exposure to viruses. Thus, preexisting C19MC-induced autophagosomes, which fuse with lysosomes to become autophagolysosomes, could profoundly impact the ability of incoming viral particles to properly traffic or release their genomes. It was found that PHT cells themselves also exhibit a high level of baseline autophagy which indicates that this mechanism plays a role in conferring viral resistance to these cells. Alternatively or in addition, autophagy may underlie other important functions of placental trophoblasts, such as those related to feto-placental nutrition or neonatal survival.

Recipient cells exposed to C19MC miRNAs exhibit robust levels of autophagy when first exposed to these viruses versus a typical setting in which autophagy would be an innate immune pathway that is upregulated in response to virus replication. Thus, C19MC miRNAs would greatly enhance the formation of autophagosomes, which fuse with lysosomes to become autophagolysosomes at a very early stage in the virus life cycle, which could have profound impacts on the ability of incoming viral particles to properly traffic and/or release their genomes. The high level of constitutive autophagy in primary human trophoblasts also implies that this mechanism confers viral resistance to these cells. Autophagy may underlie other important functions of placental trophoblasts, related to feto-placental nutrition primarily when resources are scarce. For example, autophagy is critically involved in neonatal survival during the period of starvation that occurs immediately post-birth, when the mother's milk supply has not yet been established (Kuma et al., *Nature* 432, 1032-1036, 2004).

Unlike the other viruses tested in the studies disclosed herein, conditioned PHT medium and expression of C19MC miRNAs significantly enhanced hCMV infection (FIGS. 6G-6H), indicating that while C19MC miRNAs attenuate the replication of many viruses, they may function in a proviral manner to enhance the infection of CMV, and possibly other viruses. The findings disclosed herein (FIG. 1A) and the work of others (Chan et al., *Am. J. Pathol.* 161:1371-1381, 2002) suggest that PHT cells are resistant to CMV infection, and studies of CMV-infected placentas suggest that CMV specifically targets invasive and endovascular cytotrophoblasts as a means of entry into the fetal compartment (Chan et al., *Am. J. Pathol.* 161:1371-1381, 2002; Maidji et al., *J. Virol.* 81:4701-4712, 2007; Maidji et al., *Virology* 304:53-69, 2002).

The studies disclosed herein are the first to define an unprecedented role for miRNA members of the C19MC in transferrable autophagy-mediated antiviral responses. The results show that placental-associated C19MC miRNAs are robust inducers of autophagy, a beneficial pathway in states of nutrient deprivation and a powerful suppresser of microbial infections. C19MC-derived placental miRNAs, released into the maternal circulation by exosomes, communicate an antiviral signal to maternal host cells, thus providing an unprecedented mechanism to protect the developing embryo.

Example 3

C19MC microRNAs Inhibits HIV Replication

This example demonstrates that PHT-conditioned media, as well as particular miRs encoded by the C19MC, also are capable of inhibiting infection by human immunodeficiency virus (HIV).

TZM-bl cells are HeLa cell derivatives that express high levels of CD4 and the HIV co-receptors CXCR4 and CCR5. These cells are stably transfected with LTR-driven firefly luciferase and LTR-driven β-galactosidase cassettes. Infection of TZM-bl cells with HIV-1 and HIV-2 isolates results in the induction of luciferase and β-galactosidase, allowing for the detection and quantification of infection.

Figure 9:
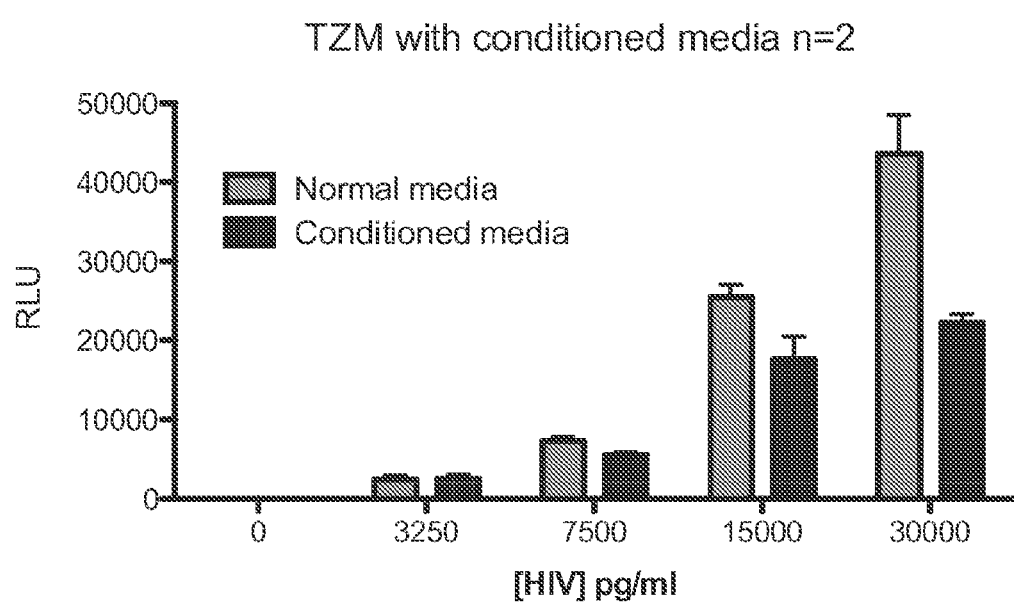
FIG. 9 is a graph showing inhibition of human immunodeficiency virus (HIV) replication by medium from PHT cells. TZM-bl cells were pre-incubated with PHT conditioned medium or control medium for 24 h prior to infection with HIV-1. Cells were then infected with serial dilutions of HIV for 48 h, and infection levels were assessed by Tat-induced luciferase reporter gene expression, in triplicate. The results represent two independent experiments.

TZM-bl cells were pre-incubated with PHT conditioned medium or control medium for 24 h prior to infection with HIV-1. Cells were then infected with serial dilutions of HIV (0, 3250, 7500, 15,000 and 30,000 pg/ml) for 48 h, and infection levels were assessed by Tat-induced luciferase reporter gene expression, in triplicate. As shown in FIG. 9, PHT-conditioned medium inhibited HIV-1 replication, particularly at the higher doses of virus.

In another experiment, TZM-bl cells were transfected with a scrambled control, miR-517-3p, or miR-516-5p mimics for 48 h prior to infection with HIV-1. Cells were then infected with serial dilutions of HIV (1875, 3750, 7500 and 15,000 pg/ml) for 48 h, and infection levels were assessed by Tat-induced luciferase reporter gene expression. As shown in FIG. 10, both miR-517-3p and miR-516-5p inhibited HIV replication at all dilutions of virus that were tested.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of inhibiting or treating a viral infection in a subject, wherein the viral infection is not caused by cytomegalovirus (CMV), comprising:

administering to the subject a therapeutically effective amount of one or more inhibitory microRNAs (miRs) encoded by the chromosome 19 miRNA cluster (C19MC), wherein the one or more inhibitory miRs comprises miR-517-3p, miR-1323, miR-516b-5p, miR-525-5p, miR-512-3p, miR-515-3p, miR-518e, miR-515-5p, miR-517c, or any combination thereof, thereby inhibiting or treating the viral infection.

2. The method of claim 1, wherein administering the one or more inhibitory miRs encoded by the C19MC comprises administering a nucleic acid molecule encoding the C19MC or a biologically active portion thereof.

3. The method of claim 1, wherein the viral infection is an infection by an RNA virus.

4. The method of claim 3, wherein the RNA virus is a coxsackievirus, poliovirus, vesicular stomatitis virus, human immunodeficiency virus or hepatitis C virus.

5. The method of claim 1, wherein the viral infection is an infection by a DNA virus.

6. The method of claim 5, wherein the DNA virus is a vaccinia virus, varicella zoster virus or herpes simplex virus.

7. The method of claim 1, wherein inhibiting the viral infection comprises preventing the viral infection.

8. The method of claim 1, wherein the method comprises inhibiting or preventing intrauterine transmission of the viral infection.

9. The method of claim 1, wherein the subject is administered a nucleic acid molecule encoding the entire C19MC.

10. The method of claim 1, wherein the one or more inhibitory miRs comprises:

(i) miR-517-3p, miR-1323, miR-516b-5p, miR-525-5p, miR-512-3p and miR-515-3p;

(ii) miR-517-3p, miR-516b-5p, and miR-512-3p;

(iii) miR-517-3p;
(iv) miR-516b-5p; or
(v) miR-512-3p.

11. The method of claim 2, wherein the nucleic acid molecule comprises a vector.

12. The method of claim 3, wherein the RNA virus is an alphavirus.

13. The method of claim 12, wherein the alphavirus is chikungunya virus, an equine encephalitis virus, Sindbis virus or rubella virus.

14. The method of claim 3, wherein the RNA virus is a human immunodeficiency virus.

15. The method of claim 1, wherein the one or more inhibitory miRs comprises miR-517-3p, miR-1323, miR-516b-5p, miR-525-5p, miR-512-3p and miR-515-3p.

16. The method of claim 1, wherein the one or more inhibitory miRs comprises miR-517-3p.

* * * * *

UNITED STATES PATENT AND TRADEMARK OFFICE
CERTIFICATE OF CORRECTION

PATENT NO. : 9,593,334 B2
APPLICATION NO. : 14/383222
DATED : March 14, 2017
INVENTOR(S) : Sadovsky et al.

Page 1 of 1

It is certified that error appears in the above-identified patent and that said Letters Patent is hereby corrected as shown below:

In the Specification

Column 1, Line 10, "grant numbers AI081759 and HD065893" should read –grant numbers AI081759, HD065893, and HD071707–

Signed and Sealed this
Twenty-sixth Day of February, 2019

Andrei Iancu
*Director of the United States Patent and Trademark Office*

SEQUENCE LISTING

<160> NUMBER OF SEQ ID NOS: 82

<210> SEQ ID NO 1
<211> LENGTH: 23
<212> TYPE: RNA
<213> ORGANISM: Homo sapiens

<400> SEQUENCE: 1
cacucagccu ugagggcacu uuc                                    23

```
<210> SEQ ID NO 2
<211> LENGTH: 22
<212> TYPE: RNA
<213> ORGANISM: Homo sapiens

<400> SEQUENCE: 2
aagugcuguc auagcugagg uc                                              22

<210> SEQ ID NO 3
<211> LENGTH: 22
<212> TYPE: RNA
<213> ORGANISM: Homo sapiens

<400> SEQUENCE: 3
ucaaaacuga ggggcauuuu cu                                              22

<210> SEQ ID NO 4
<211> LENGTH: 23
<212> TYPE: RNA
<213> ORGANISM: Homo sapiens

<400> SEQUENCE: 4
uuucaagcca gggggcguuu uuc                                             23

<210> SEQ ID NO 5
<211> LENGTH: 21
<212> TYPE: RNA
<213> ORGANISM: Homo sapiens

<400> SEQUENCE: 5
aaagugcuuc cuuuuugagg g                                               21

<210> SEQ ID NO 6
<211> LENGTH: 24
<212> TYPE: RNA
<213> ORGANISM: Homo sapiens

<400> SEQUENCE: 6
uucuccaaaa gaaagcacuu ucug                                            24

<210> SEQ ID NO 7
<211> LENGTH: 22
<212> TYPE: RNA
<213> ORGANISM: Homo sapiens

<400> SEQUENCE: 7
gagugccuuc uuuuggagcg uu                                              22

<210> SEQ ID NO 8
<211> LENGTH: 22
<212> TYPE: RNA
<213> ORGANISM: Homo sapiens

<400> SEQUENCE: 8
uucuccaaaa gggagcacuu uc                                              22

<210> SEQ ID NO 9
<211> LENGTH: 22
<212> TYPE: RNA
<213> ORGANISM: Homo sapiens

<400> SEQUENCE: 9
aagugccucc uuuuagagug uu                                              22
```

<210> SEQ ID NO 10
<211> LENGTH: 22
<212> TYPE: RNA
<213> ORGANISM: Homo sapiens

<400> SEQUENCE: 10
aagugcuucc uuuuagaggg uu                                              22

<210> SEQ ID NO 11
<211> LENGTH: 22
<212> TYPE: RNA
<213> ORGANISM: Homo sapiens

<400> SEQUENCE: 11
cucuagaggg aagcgcuuuc ug                                              22

<210> SEQ ID NO 12
<211> LENGTH: 22
<212> TYPE: RNA
<213> ORGANISM: Homo sapiens

<400> SEQUENCE: 12
aaagugcauc uuuuuagagg au                                              22

<210> SEQ ID NO 13
<211> LENGTH: 22
<212> TYPE: RNA
<213> ORGANISM: Homo sapiens

<400> SEQUENCE: 13
ucuacaaagg aaagcgcuuu cu                                              22

<210> SEQ ID NO 14
<211> LENGTH: 21
<212> TYPE: RNA
<213> ORGANISM: Homo sapiens

<400> SEQUENCE: 14
cuccagaggg aaguacuuuc u                                               21

<210> SEQ ID NO 15
<211> LENGTH: 22
<212> TYPE: RNA
<213> ORGANISM: Homo sapiens

<400> SEQUENCE: 15
aaagugcuuc ccuuuggacu gu                                              22

<210> SEQ ID NO 16
<211> LENGTH: 23
<212> TYPE: RNA
<213> ORGANISM: Homo sapiens

<400> SEQUENCE: 16
cucuugaggg aagcacuuuc ugu                                             23

<210> SEQ ID NO 17
<211> LENGTH: 22
<212> TYPE: RNA
<213> ORGANISM: Homo sapiens

<400> SEQUENCE: 17
gaaagugcuu ccuuuuagag gc                                              22

```
<210> SEQ ID NO 18
<211> LENGTH: 22
<212> TYPE: RNA
<213> ORGANISM: Homo sapiens

<400> SEQUENCE: 18
cucuagaggg aagcgcuuuc ug                                                  22

<210> SEQ ID NO 19
<211> LENGTH: 22
<212> TYPE: RNA
<213> ORGANISM: Homo sapiens

<400> SEQUENCE: 19
aaagugcauc cuuuuagagg uu                                                  22

<210> SEQ ID NO 20
<211> LENGTH: 21
<212> TYPE: RNA
<213> ORGANISM: Homo sapiens

<400> SEQUENCE: 20
cuccagaggg augcacuuuc u                                                   21

<210> SEQ ID NO 21
<211> LENGTH: 22
<212> TYPE: RNA
<213> ORGANISM: Homo sapiens

<400> SEQUENCE: 21
gaaggcgcuu cccuuuagag cg                                                  22

<210> SEQ ID NO 22
<211> LENGTH: 22
<212> TYPE: RNA
<213> ORGANISM: Homo sapiens

<400> SEQUENCE: 22
cucuagaggg aagcgcuuuc ug                                                  22

<210> SEQ ID NO 23
<211> LENGTH: 23
<212> TYPE: RNA
<213> ORGANISM: Homo sapiens

<400> SEQUENCE: 23
gaacgcgcuu cccuauagag ggu                                                 23

<210> SEQ ID NO 24
<211> LENGTH: 22
<212> TYPE: RNA
<213> ORGANISM: Homo sapiens

<400> SEQUENCE: 24
cucuagaggg aagcacuuuc uc                                                  22

<210> SEQ ID NO 25
<211> LENGTH: 21
<212> TYPE: RNA
<213> ORGANISM: Homo sapiens

<400> SEQUENCE: 25
```
gaaagcgcuu cucuuuagag g	21

<210> SEQ ID NO 26
<211> LENGTH: 21
<212> TYPE: RNA
<213> ORGANISM: Homo sapiens

<400> SEQUENCE: 26
aaagugcuuc cuuuuagagg g	21

<210> SEQ ID NO 27
<211> LENGTH: 22
<212> TYPE: RNA
<213> ORGANISM: Homo sapiens

<400> SEQUENCE: 27
caaagcgcuc cccuuuagag gu	22

<210> SEQ ID NO 28
<211> LENGTH: 22
<212> TYPE: RNA
<213> ORGANISM: Homo sapiens

<400> SEQUENCE: 28
cucuagaggg aagcacuuuc ug	22

<210> SEQ ID NO 29
<211> LENGTH: 22
<212> TYPE: RNA
<213> ORGANISM: Homo sapiens

<400> SEQUENCE: 29
cucuagaggg aagcacuuuc ug	22

<210> SEQ ID NO 30
<211> LENGTH: 22
<212> TYPE: RNA
<213> ORGANISM: Homo sapiens

<400> SEQUENCE: 30
aaagugcuuc cuuuuagagg gu	22

<210> SEQ ID NO 31
<211> LENGTH: 23
<212> TYPE: RNA
<213> ORGANISM: Homo sapiens

<400> SEQUENCE: 31
ucucuggagg gaagcacuuu cug	23

<210> SEQ ID NO 32
<211> LENGTH: 23
<212> TYPE: RNA
<213> ORGANISM: Homo sapiens

<400> SEQUENCE: 32
caaagcgcuu cucuuuagag ugu	23

<210> SEQ ID NO 33
<211> LENGTH: 22
<212> TYPE: RNA
<213> ORGANISM: Homo sapiens

<400> SEQUENCE: 33
cuacaaaggg aagcacuuuc uc                          22

<210> SEQ ID NO 34
<211> LENGTH: 21
<212> TYPE: RNA
<213> ORGANISM: Homo sapiens

<400> SEQUENCE: 34
gaaggcgcuu cccuuuggag u                           21

<210> SEQ ID NO 35
<211> LENGTH: 22
<212> TYPE: RNA
<213> ORGANISM: Homo sapiens

<400> SEQUENCE: 35
ccucuagaug gaagcacugu cu                          22

<210> SEQ ID NO 36
<211> LENGTH: 22
<212> TYPE: RNA
<213> ORGANISM: Homo sapiens

<400> SEQUENCE: 36
aucgugcauc ccuuuagagu gu                          22

<210> SEQ ID NO 37
<211> LENGTH: 22
<212> TYPE: RNA
<213> ORGANISM: Homo sapiens

<400> SEQUENCE: 37
caaagugccu cccuuuagag ug                          22

<210> SEQ ID NO 38
<211> LENGTH: 22
<212> TYPE: RNA
<213> ORGANISM: Homo sapiens

<400> SEQUENCE: 38
aacgcacuuc ccuuuagagu gu                          22

<210> SEQ ID NO 39
<211> LENGTH: 20
<212> TYPE: RNA
<213> ORGANISM: Homo sapiens

<400> SEQUENCE: 39
cuacaaaggg aagcccuuuc                             20

<210> SEQ ID NO 40
<211> LENGTH: 22
<212> TYPE: RNA
<213> ORGANISM: Homo sapiens

<400> SEQUENCE: 40
aaagugcuuc ucuuuggugg gu                          22

<210> SEQ ID NO 41
<211> LENGTH: 22
<212> TYPE: RNA
<213> ORGANISM: Homo sapiens

```
<400> SEQUENCE: 41
aucgugcauc ccuuuagagu gu                                              22

<210> SEQ ID NO 42
<211> LENGTH: 24
<212> TYPE: RNA
<213> ORGANISM: Homo sapiens

<400> SEQUENCE: 42
acaaagugcu ucccuuuaga gugu                                            24

<210> SEQ ID NO 43
<211> LENGTH: 22
<212> TYPE: RNA
<213> ORGANISM: Homo sapiens

<400> SEQUENCE: 43
aucuggaggu aagaagcacu uu                                              22

<210> SEQ ID NO 44
<211> LENGTH: 18
<212> TYPE: RNA
<213> ORGANISM: Homo sapiens

<400> SEQUENCE: 44
ugcuuccuuu cagagggu                                                   18

<210> SEQ ID NO 45
<211> LENGTH: 22
<212> TYPE: RNA
<213> ORGANISM: Homo sapiens

<400> SEQUENCE: 45
cucuagaggg aagcgcuuuc ug                                              22

<210> SEQ ID NO 46
<211> LENGTH: 21
<212> TYPE: RNA
<213> ORGANISM: Homo sapiens

<400> SEQUENCE: 46
aaagcgcuuc ccuucagagu g                                               21

<210> SEQ ID NO 47
<211> LENGTH: 20
<212> TYPE: RNA
<213> ORGANISM: Homo sapiens

<400> SEQUENCE: 47
cugcaaaggg aagcccuuuc                                                 20

<210> SEQ ID NO 48
<211> LENGTH: 22
<212> TYPE: RNA
<213> ORGANISM: Homo sapiens

<400> SEQUENCE: 48
gaaagcgcuu cccuuugcug ga                                              22

<210> SEQ ID NO 49
<211> LENGTH: 22
<212> TYPE: RNA
<213> ORGANISM: Homo sapiens
```

```
<400> SEQUENCE: 49
cucuagaggg aagcacuuuc ug                                              22

<210> SEQ ID NO 50
<211> LENGTH: 21
<212> TYPE: RNA
<213> ORGANISM: Homo sapiens

<400> SEQUENCE: 50
caaagcgcuu cccuuuggag c                                               21

<210> SEQ ID NO 51
<211> LENGTH: 22
<212> TYPE: RNA
<213> ORGANISM: Homo sapiens

<400> SEQUENCE: 51
aucgugcauc cuuuuagagu gu                                              22

<210> SEQ ID NO 52
<211> LENGTH: 22
<212> TYPE: RNA
<213> ORGANISM: Homo sapiens

<400> SEQUENCE: 52
acaaagugcu ucccuuuaga gu                                              22

<210> SEQ ID NO 53
<211> LENGTH: 22
<212> TYPE: RNA
<213> ORGANISM: Homo sapiens

<400> SEQUENCE: 53
cucuagaggg aagcgcuuuc ug                                              22

<210> SEQ ID NO 54
<211> LENGTH: 22
<212> TYPE: RNA
<213> ORGANISM: Homo sapiens

<400> SEQUENCE: 54
aaaaugguuc ccuuuagagu gu                                              22

<210> SEQ ID NO 55
<211> LENGTH: 22
<212> TYPE: RNA
<213> ORGANISM: Homo sapiens

<400> SEQUENCE: 55
cucuagaggg aagcgcuuuc ug                                              22

<210> SEQ ID NO 56
<211> LENGTH: 22
<212> TYPE: RNA
<213> ORGANISM: Homo sapiens

<400> SEQUENCE: 56
aaagugcauc cuuuuagagu gu                                              22

<210> SEQ ID NO 57
<211> LENGTH: 20
<212> TYPE: RNA
```

<213> ORGANISM: Homo sapiens

<400> SEQUENCE: 57
cugcaaaggg aagcccuuuc                                                    20

<210> SEQ ID NO 58
<211> LENGTH: 23
<212> TYPE: RNA
<213> ORGANISM: Homo sapiens

<400> SEQUENCE: 58
uucucgagga aagaagcacu uuc                                                23

<210> SEQ ID NO 59
<211> LENGTH: 18
<212> TYPE: RNA
<213> ORGANISM: Homo sapiens

<400> SEQUENCE: 59
ugcuuccuuu cagagggu                                                      18

<210> SEQ ID NO 60
<211> LENGTH: 160970
<212> TYPE: DNA
<213> ORGANISM: Homo sapiens

<400> SEQUENCE: 60

| | | | | | | |
|---|---|---|---|---|---|---|
| cctttatggt | cagtgtttac | agggaagatg | gagggaaaat | tagagtcaga | gattttaggt | 60 |
| tttatggcag | gatttgggga | aagggattc | tggtgtctat | ggctcacttt | gggaaagaca | 120 |
| gtttctagtt | tctatggcta | gccttggggg | agaaggaggg | tcaggaagaa | acttccgctt | 180 |
| ctgaagctgc | ttcggaagcc | tttgttttga | ggttatcggt | ttctgagccc | caatattagc | 240 |
| ctgccacagt | ctaagctttc | aaagcgcctg | tcaaactctt | gtggatctat | gtatttcaaa | 300 |
| gaccaaaatc | aacagctcac | atatgggtc | caagaggagg | gggaggtca | ctgcacgttg | 360 |
| tcacgtgtga | gatctttgtt | gttgttgttg | agatggaatc | tcgctctgtc | acccaggctg | 420 |
| gagtgcagtg | gcaccatctc | agctcgactg | taaccttcac | ctcccaggtt | ctagcaatta | 480 |
| tcctgcctca | gcctcccaag | tatctggaat | tacgggtgcg | tgccatcatg | cccgctaat | 540 |
| tttttttttt | ttttgtatt | tttagtagag | acggggtttt | caccatgttg | gccaggccag | 600 |
| tctcaaactc | ctgaccccaa | gggatctgcc | cacctcggcc | tcccaaagtg | ctgggactac | 660 |
| aggcatgagc | caccgcgcct | ggcctcttgt | gagatctgat | aagaagtcac | gcactagaag | 720 |
| gaagggaaga | gtgtactcca | caaccccaaa | cgatgcgttt | ggaatcattt | caaacccaca | 780 |
| taacaagagt | ttcatacgga | attgggacag | aacatggccc | ctaatgagcc | ccctaaata | 840 |
| attctcaagg | accacttctc | caatgacgaa | ggagattgag | gattttttt | tcctacgttt | 900 |
| attggccgtg | tggatatttt | gccttgtaa | aatatgtgtc | caagccttt | gcccatttct | 960 |
| ccagtgggta | gtatttcctt | tgttttttt | ttttgagaca | aagtctcact | ctgttgccca | 1020 |
| ggctggagtg | cagtggcctg | atctcggctc | actgcaaacc | ctgcctcctg | ggttcatgcc | 1080 |
| agtcttctgc | ctcagcctcc | caagtgctgg | gactacaggt | gcacaccacc | acgccctgct | 1140 |
| aatttttgt | attttagta | gagatggggt | ttcaccatgt | tagctaggat | ggtctcaatt | 1200 |
| tcctgacctc | gtaatctgcc | cgcctcggcc | tcccaaagtg | ctgggattac | aggcgtgagc | 1260 |
| cactgcacct | ggcctaaaag | aatctttaaa | ttgtccatga | gcgatggtgc | gtgcctgtgg | 1320 |
| tcccagctac | ttggaggctg | agaaggaagg | atcccttgag | cctgggagtt | tgaggcagca | 1380 |

```
atgagctatg ctcttaccac tgcactccag cctgggtgaa agaggaagaa gacccttaat   1440
aggcggacca cggtggctca cgcctgtaat ctcaatactt tcagaggcct aggtggaaga   1500
attacttgag accaggagtt caagaccaac ctgggcaaca tagcgagacc ctcatctctc   1560
caaaagtttg aaaagaaaa aaaaaatttt taatgaaaca gaagtcgtta attttatttt   1620
attttctaag acatcttgtt atagcaaaaa gtccttaatt ttaatatagt ctaatttata   1680
tattttcttc attgtaaaaa ttttttgggtc ctatctagca aatgttagct tacctctatg   1740
taataaagac attcttctgt gttgtcttct aaaacaaaac attgttttat tttctgattt   1800
taggtctgca gttcatttgt agattttgt gtctaggatt aggtagggtt aagatcattt   1860
gtggccaggc atggtggctc acaccagtaa tcctaacact tgggaggct aaggcaggag   1920 gatctcttga gcccaggagt ttcagaccag cctggggaac atagaaagac cctgtctctc   1980
tatttttttt ttcagttaaa tatatacttt taaaaagatc atttgtggtg ctatagttgt   2040
gggtgtttaa tttgtaattt actttgttct gttgatctat ctaatttttt ttttagacgg   2100
attcttcctc tgtcacccag gctggagtgc ttcagcctct caatgccatc atgcccagct   2160 aatttttttgg acttgtagta gagacagagt ttcaccatat tgaccaggct ggtctcgaac   2220
tcctggcctt aggtgacccg cccacctcag cctcccaaaa tgctgggatt ataggcatga   2280
gctactgtgt ccagccagat ctgtctaatt tttttttttc tttgagacgc agtctcactc   2340
tgtcactcag gctggagtgc agtggcgtga tcttggctca atgtaacctc cacctcctgg   2400
gttcaagtga ttttcctacc tcagcctcct gagtagctgg gattacaggt gcgtgccacc   2460
acgcctggct aatttttgta tttttagcag agacggggtt ttgccatgtt ggccaggctg   2520
gtctcaaact cctgacttcc agtgatccgc ccaccttggc ctcccaaaat gctaggatta   2580
caggtgcgag ccactgtgcc tgcccagag ctgtctaatt ttaaagaatg tatgaagatt   2640
cagatttagg ttcctgctat tatgttatgg gaaatcttt cctagtttct tctgattaat   2700
ataaatcctt aattttattt ttatttattt ttttactaca gtcctctttt attacttttt   2760 attttctta atttaatat aatgaaaagt tcgatttttc ctgttatggt tagcattttt   2820
ttcttctgtt taagaggtgt ttcctggctg ggtgtggtgg ctcacacctg caatcctagc   2880
actttgggag gccaaggtgg gaggatcact tgaacccagg agttcaagac cagcttgggc   2940
aacatagtga aacccttgtc tccaattttt ttaaattaaa aattaaaaaa ggcggggctg   3000
ggtgtggtgg ctcaccctg taatcccagc actttggac gccgaggcgg gtggatcacc   3060
taaggtcagc agttcgagac cagcctgacc aacatggaga aaccctgtct ctactaaaag   3120
tacaaaatta gctgggcgtg gtggtgcatg tctgtaatcc cagctattcg ggaggctgag   3180
gcaggagaat cgcttgaatc caggaggcgg aggttgcagt gacccgagat tgcgccattg   3240
cactccagcc tgggcaacaa gagtgaaact ctgtctcaaa aaaataaat aaataaaaa   3300 taaaataaaa aagaagtgtt tccctagcgt gaagacatga agctcttctg taaacttcat   3360
tgttctgcct ttacaattca atctacaacc cactagaatt aatcttccgt atatatagca   3420
tggggtggag gtcaaacacc ttttttccat atggatgttc agctgtccca gtgtcattta   3480
tttaaaagac tgtactggac ctggcatggt ggctcacgcc tgtaatccca gcactttggg   3540
aggctgaggc gggtggatca cttgaggtca ggagttcgag accagcctaa ccaacatggc   3600
aaaaccccat ctctgctaaa aatacaaaat tagccaggtt ggtggtgca tgcctgtaat   3660 tccggctact tgggaaactg aggcgggaga atcccttgaa cctcataggc agaggttgca   3720
```

```
atgagccaag atcgcaccat tgcattccag cctgggcaac aagagcgaaa ctctgtctca    3780
aaaaataaga aaaaatagag gccgagaatg gcccttgctg ccaccaacat ggagactttg    3840
taccgtgtcc cgttcttagc gcttgaatgt cccaacctga agctgaagaa gccgccctgg    3900
ctgcacatgc cgttggccat gactatgtat gctctggtgg tggtgtctta cttcctcatc    3960
accagaggaa tcgtttatga tgttacggtt gaaccgccag gtgttggctc tatgactgat    4020
gaacaagggc atcagaggcc agtagctttc ttggcctaca gagtaagtgg acaatattat    4080
tatggaagga cttggatcca gcttcctgtt tacaatggga ggtttaggtt tcataatcct    4140
ggaccgatcg aatgcaccaa atatcccaaa actcaataga tttcttcttc tattcgttgg    4200
attcgtctgt gtcctattga gttttttttca cggctagagt attcgtgaga atgaaactac    4260
cgggctctct gatgggttag agtgccttta agaagaaatc aggctgggtg cagtggctca    4320
cgcctgtaat cccagcactt tgggaggccg aggcgagcgg attatctgag gtcaggagtt    4380
cgagatcagc ctgggcaaca tggtaaaacc ccatccctac tacaaataca aaattagcca    4440
ggcgtggtga cacatgtctg taatcccagc tactcgggag gctgaggcag gagaattgct    4500
tgaacccggg aggcagagga tgcggtgagc cgagatcgca ccattgcact ccagcctgga    4560
caacaagagt aaatctccgt ctcaccaaaa aaaaaaaaa gaaaaaaaaa aagaaatcag    4620
tgcatactgg atttgctcct gtcaatgaag ttttaaaggc tgtccaatcc tctaatatga    4680
gatgtagaaa agaaggaaga gcagcagtaa aagaaatatc tagtgaaaaa ccaggaagtg    4740
tattgaagct tggactagaa tttcttcttt attaaagaga caaatttatc acagtatttt    4800
cttttcctgc tgaccacatt gctataccaa tgatgatgag tggcatttttc ttcttagttt    4860 tttatttctt taagaaaata caagccaggc gcggtggctc acttctgtag tcccagcact    4920 tgggaggcc aaggtgggca gatcacgagg tcaggagttc cagaccagcc tggccaccat    4980
gttgaaaccc catctctact aaaaatacaa aaattagccg ggcgtggtgg tggcggggca    5040
cctgtaatcc cagctacttg gaaggctgag gcaggagaat cacgtgaacc tgggaggcgg    5100
aggctgcagt gagcctagat cgctgccact gcactccagc ctgggcgaca gagcgagact    5160
ctgtttcaaa aaaaaaaaa gaaagaaaga agaaaagaa aatatactgc atacctacaa    5220
ctataatagc aaatatagtg attattttttt acaaccccct taacacttttt tggagatgac    5280 atttctgact ttcagaaatt aacataaaat caagaagcaa gattccatga gctgagaact    5340
ctggacagct ggtcagcttt acctacggag ctttggcttt aactagagtg tgtgatggta    5400
gattatttca gataggtatg taagactgct gcctgaacaa taacatgtat gaaaggaaca    5460
gaaataaata ctaattaaaa aacaaaataa gaaaaaataa aaaataaaca ctactatgga    5520
catggtagct catgcctgta atcctagcac tttgggatgc caaggtgggt ggatcgcttg    5580
aaccaaggag ttcaaggagt tgggagacca gtctgggcaa catagcaaga ccccatctct    5640
aaaaaaaaaa aaaaaaaaag agtactaaag actcagagat agaaaaatgg aaattattca    5700
tattgtctcc agatttttttt tttttttggac ggagacttgc tctgtcaccc aggctggagt    5760
gcagtggcac tatcttggct cactgcaacc tccacctccc aggttcaagc aattctcctg    5820
cctcagcctc ccaagtagct gggattacag gcatacgcca ccaaacccgg ctaatttttgt    5880 actttttagca gagacagggt tttgccatgt tgtcaggct ggtcttgaac ccctgaccctc    5940 aggtgatcca cccgcctcgg cctcccaaag tgctgggatt acaggtgtga gccaccgcgc    6000
ccagccagta gtcttttatc cttgtaacag attaatcttt tctagggaaa tggagacctt    6060
tcattttcat gtcctttttta catccctgtt gattgtatct ctgcctccat tctgttgatc    6120
```

```
ggaatgacac taacttaatt tgggttctct aaagcagaca ctgatacaaa ggcttcagtt   6180
ccagaggttt atttagaatg tgatcctaaa ccaagaggga ggtagcaggg agagtaagac   6240
aggaaaggat ggggagccaa caccttatct aaggacatgt tgaggccagg cgtggtggct   6300
catgcctgta atcccagcac tttgggaatc cgaggcgagc agatcacaag gtcgggagtt   6360
tgagaccagc ctggccaaca tagtgaaact ctgtctctac taaaaatgca gaaaacaggc   6420
cgggtgcggt ggctcacgcc tgtaatccta gcactttgtg aggccgagac gggcggatca   6480
cctgaggttg ggagttagag accagcctga gcaacatgga gaaaccctgt ctctactaaa   6540
aatacaaaaa ttagccttgc gtggtggtgc atgcttgtaa tcccagctac ttgggaggct   6600
gaggcaggag aatcacttga acctgggagg cggaggttgc gatgagccga gatcgtgcca   6660
ttgcactcca gcctgggcga caagagtgaa acttcatctc aaaaaaaaaa aaaacaaaaa   6720
acagaaaaaa ttagctgggc ctggtggcag acgcctgtgg tcctagctac tcaggaggca   6780
aaggcaggag aattgcttga acctgggagg tggagattgc agtgagccga gatcatgcca   6840
ctgcactcca gcctgggtga cagagtgaga ctctatctca aaaaaaaaaa aaaaaaagga   6900
taagttgctg aagtctgtga agtggacaat gagggcttga ttcctttgaa gcctgttgaa   6960
gactgtttac gcttcctctt atcatcccct gcctcatccc ctgtcacaga gatgaaagac   7020
tgggacattt ctgtgccaaa tttcatccca cattgggtga ggcttccct gagacatgtt    7080 gacttcctgc agttcaaagc tactttcttc tttagacagg gtctcgctct gtccccagg    7140 ctagagtgct atagcgtgat ctcgcctcac tgcaagctcc gcctcccggg ttcaagccat    7200
tctcctgcct cagcctcccc agtagctggg actacaggca cctgccacct tgcccggctg    7260
tttttttgta tttttagtag agacagggtt tcaccatgtt agccaggatg gtctcgatct    7320
cctgacctca tgatccgccc accttggcct cccaaagtgc tgacattaca ggtgtgagcc    7380
accgtacccg gcctattttc ttctttagac agggtcttcc tctgtcccct aggctggagt    7440
gcagtggtgt gatcttggct cactgcaacc tctgcccct gggttcaaga gattctcctg    7500
cctcagcctc ctgagcagct gggattacag acatgcgtca ctatgcccgg ctaatttttt    7560
gcattttttg gtagagatgg ggtttcacca tgttggtcag gctggtctcg aactcctggc    7620
ctcaagtgat ctgtctgcct tggcctccca aagtgctggg attacaggtg tgagccaccc    7680
cgcccggggc aaagctattt tccatttta attttttgtt attgttgttt tgagaccaag    7740
tctcactctg ttgcccaggc tggagtgcag tggcatgatc tctaaatttt gtattttag    7800 tagagacggg ttttcacctt gttgcccagg ctggtctcga attcctgacc tcaggtgatc    7860
cacttgcctc agccgcccaa agtgctggga ttacaggcgt gggccaccat gcccagcctg    7920
ccaaagctat tttctatggg ataaatgaca gcagaaagga ccccagagca aaatactaca    7980
aagatgtatg gcacgtgcat gaggtgagag tatggtagaa tcaagtgagt ctctgctttc    8040
atgagactga acagtgaggc tcaggttaaa attagaggtg tacaagagag tatgatatgg    8100
acatctgcta ctgaacaatc cttgtgcttc ttgaaaatgc tcatttccat attttttatt    8160 ttttatttt tttcagatac aaggtctcac tgtgtcaccc aggctagatt gcaggggcac    8220
aattaaggtt cactaaagtc ccaaccccc gggttcaagc aatcctcctg cctcagcctc    8280
tggagtagct gggactgcag ttgcatgcca cagtgcccgg ctaattttt tattttttgt    8340 agaggcaagg gcttgctctg ttgcccagat tggtcttgaa ctcctggcct caaatgatcc    8400
tcccacccgt gcctcccaaa gtgctgggat tacaggcata agccactgca cccagcctca    8460
```

```
tttctatatg taagttcatt tagtcattaa gtcttgaagc aaagatccag ccacgatcta    8520
tataaaattt tcaatacagg ccaggcatgg tggctcacgt ctataatccc ggcactttgg    8580
gaggctgagg cagactgatc actttaggtc aggagttcca gaccagcctg ccaacatgg     8640
tgaaacgcta atacaaaaaa ttagctgggc atggtggtca gcacctgtaa tcccagctgc    8700
tagggaggtt gaggcaggag aatcggttga acctggaggt agaggttgca gtaagtcaag    8760
atcacgccac tgcactccac cctgggaaac agagcaagac tctgttccaa aaaaaaacaa    8820
aaggcaatct ttcctagaaa aaaatagttt ctgcacattc ttaggcacgc atttgtaggc    8880
tgctatagct atttaaaatt ttcaatacaa tatgtttacc agagcaaact acaatcctca    8940
ttgttatgtg ggccccaaac cattactgat actcatctgt ttcccccacg tcgtctacat    9000
ttcctcatgg tgggccagta cttcattttt tgtaactcat ttgcctgcta gggtgactca    9060
ggcctttgtt tctgagagat ctgagtctgg tgttgctagg aaggaaaagg ttaactagtc    9120
tataatccat tctttctccc aacctggtga tgtctgagga ggcatccctt ggtcaaactt    9180
ctttgtaaac atgctaatca gatctcatgg tatttattag aggaaaacaa ccagagattc    9240
ttatctgtga gatgctttca gcaggacata cttgttcttt cttgatgtct tgcagtaaac    9300
aaggaattta ggggttatg ggcatgagcc actggaaaat gtcagcgtca catatttagt     9360
taagagagag agagagaggg gctgggcgtg gtggttcatg cctacaatcc cagcattttg    9420
ggagactgag gcaggaagat cacttgagcc cagaagcgta agatcagcct aggtaacata    9480
atgagacctc gtcttattaa gagtctgatt ctaccctccc ttggtgttat ctcagttact    9540
gtactttac agggctgtgg ttgtgcaact tcctgctggg catggggaat tctctgagtt     9600
ccagacaaga accttcctgc ccaatatgca gcagcaaccc agtctcttca taatgctcgt    9660
ggttgattat ccatgcccgc caactacctc atttctctgc ccagtgcttt atcagcctga    9720
agagcccaca gtcaccaggc agaaaacctt actgtgcttc ttggtgaaag tgttccctct    9780
tcaaaaatga agacatcacg ccagataagg tttggggact agaagcacaa tttcttcaag    9840
tgggtcccta gacaggatat tgataaatgc caattctgtt tcactccctg gtagctacac    9900
ctgtatattc taactactag ggtcacagcc ccttatattg actgttggtt atatgcagat    9960
attgcatctt agaggacagc accccaaacc catgggatgt tatacctggg ctgacacttt   10020
agttgagccc tttaaaaagc cattcctggg ccaagcccgg tggctcacac ctgtaatccc   10080
agcactttgg gaggctgagg cgggcggatc acgaggtcag gagatcgaga ccatcctggc   10140
taacatggtg gaaccctgta tctaccaaaa atacaaaaaa attagctggg cctggtggc    10200
aggcgcctgt agtcccagct attcagaagg ctgaggcagg agaatggcgt gaacccagga   10260
ggtggaggtt gcagtgagct gagactgtgc cactgcactc cagcctgggc gacagagtga   10320
gactctgtct caaaaaaata aataaataaa taaataaata aataaataaa aggccattcc   10380
tggctgggca tggtggctca cgcctgtaat cccagcactt tgggaggccg aggagggcgg   10440
atcacctgag gttgggagtt tgagaccagc ctgaccaaca tggagaaacc ctatttctac   10500
taaaaataca aaattagcct ggcatggtgg cacatgccta atcccagc tacttgggag     10560
gctgaggaag gagaatcgct tgaatccggg aggcagaggt tgcagtgagc agagattgca   10620
ccattgcact ccaacctggg caacgagagt gaaactccat ctcaaaaaaa acaaaaagcc   10680
attcctggcc tggcgcaatg gctcacgcct gtaatcccaa cactttggga ttacgcttgc   10740
caaagtaagt gaattacctg aggtcaggag tttgacacca gcctggccaa catggtgaaa   10800
ccccgtctct actaaaaata cacaattagc tggacatgat ggcaggcgcc tgtaatccca   10860
```

```
gttactcagg aggctgaggg aggagaacct cttgaaccca ggaggcaggg gttgcagtga   10920
gccaagattg cgccattgca ctccagccag ggcaacaaga gtgaaactcc gtctcaaaaa   10980
ataaataaat aaataaataa ataataacca ttatgttatc ccatgatggc agctctttct   11040
gtataaggta ataaatatgc gatgtaaaga gtgtatttca tattaatgca ctgattgttg   11100
tacctttttt tttttttttt tttttttttt gagacagggt cttgctctgt cacccaggct   11160
ggagtgcagt ggcgcaatct cgactcactt caacctctgc ctcccaggtt caagcaatcc   11220
ttctgcctca gcctcctgag tagctgggat cacaggtgcc cgccaccacg cccagctaat   11280
ttttgtactt ttttagtaga cgggggttt tgcctgttgc ccaggctggt ctcaaactcc   11340
tgacctcagg tgatctgccc tccctggcct cccaagggc tgggattaca ggcacaggga   11400
gccaccatgc ccagctgttt ttttgttttg ttttttgttt tttttgagac agagtctcac   11460
tctgtcgccc aggctagagt gcagtggctt gatcttggct cactgcaacc tcggttcact   11520
gaagcctccc agtttcaagc cgtactctta cctcagcctt ctgagtagtt gggattacag   11580
gcgtgagcca ctgtgcccag cctttgttt tgtattttta gtagagatgg gtttcacca   11640 tgttggccag gctggtcttg aactcctggc cacaagtgat ccacctgcct tggcctccca   11700
aagtgctggg attacaagga tgttagaaaa tggctgggcc tggtggctta cacctactcg   11760
ggaaactgag gcacgagaat cgcttgaacc cgggagacgg gcattgcagt gagctgagat   11820
caggccattg cactccagcc tgggcgacag tcacaaaaaa aaaaaaaaag aaagaaagaa   11880
agaaagaaaa cacatcaatt ccaggaaata caaatcagat gagatcgggc gtgttcccgg   11940
tggtatggtc acagaaacag gaagcacaaa tcaatcacct ccaccactgc cctctccggg   12000
ggaaaggatg aaatgtaatc aacttaccac taactagtca gtcattcccc ttaaaggaca   12060
atagcagatc aaggtgtcat catgggcttt ttttttttt ttttgagac agggtctcgc   12120 tctgtcgccc agcctagagt gcagtggcac caccatagct caaccttctg ggctcaagcg   12180
atcctcctgc cttagcctct ggagtactag gactataggt gcatgcctcc atgcctggct   12240
aattgaaaaa ttttttttgt agagacagga tttggctttt ttacccagac tcatctcaaa   12300
ctcctggcct caagcgatcc tcccgcctcg gcctctcact ggtactctta tcacaggcat   12360
gagccagcgt gtctggccct gatcacagcc agaaactccc aggctgtgat aatgagctca   12420
gctttcatga gagacagctc atgctattag gcacatcctt cgtctcttct cctgctaccc   12480
tgctaccgcg tctctgttca tgggtgcatt atacaagcag tggtctgagg atagagcctc   12540
agtgatgccc actgcacaag gcaccctctc ttcctggttg ctcaggatct tctctgtggt   12600
gagcactccc tggagaacat taacatgaga cacagagatc tcatgcctct gcctcttctc   12660
ataattcctt tttttttttt gagagggagt ctcaccgtgt tgcccaggct ggagggcaat   12720
ggtgtgatct cagctcactg caaccttcac cttccaggtt caagtgattc tcctgcctca   12780
gcctcccagg tagctgggc tacaagtgtg tgtcaccgca cccggctaat ttttgtgtct   12840
ttagtagaga cggggtttca ccatgttggc caggctggtc tggaactcct gacctcaggt   12900
gatctgcctg cctcagcctc ccatagtgct gggattacag gtgtgagcca ctgtgcccag   12960
tgccccccct ttttgtgtg tgtcagggtc tcactctgtc acccaggcta gagtgcaggg   13020
gcataatctc ggctcactgc aacatctgcc tccaaggctc aagtggtcct cccacctcag   13080
cctcctgagt aacagggact acaggcacgt gccaccaaac ccagctaatt ttttgtattt   13140
ttggtacaga cgagacttca ccatgttgcc caggctggtc acaaactcct gacctcaagc   13200
```

```
gatccaccag ccttggcttc ccaaaatgct gggaatacag acgtgagcca ccgtgactgg      13260
ccccagctaa ttttttgtatt tttagtagag atgggttttc accatgttgg ctaggctggt      13320
ctcacactcc tcacctcagg tgatccacct gcctctgcct cccacagtgc tgggattaca      13380
ggcataagcc accacgcccc accgtgagac ccccatctct acaaaaaaag ttttaattag      13440
ctgtgcatgg tggcaggcac cctagtccca gctacctact gaggaggctg atcgcttgag      13500
cccaggaggt caaggctgca gtgagctggg atcacagcac tgcactccag cctgggagac      13560
agagggagac tctatctcca aaagaaaaa aagactagag attgtgcccc aggcacagat      13620
catattaatc ccagtgatat ctgggagtg gtggccagac tccttcccag gactggtctt      13680
ccggtttggc aatgagtgtt agtcaaggcg tgaggttctc atgggccgtc tcaagcactc      13740
tgttcgacat ctttttactc tctcccaggc tggggtgcag tggcgtcatc ttggcttact      13800
gtagcctccg cctccagggt tcaagcaatt ctggtgcctc agcctcccga gtagctggga      13860
ttataggcgc ctgccatcac gcctggctaa tttttttttgt atttctagta gagtcagggt      13920
ttcactatgt tgcccaggct ggtcttgaac tcctgacctc aggtgatctg cctgcctcga      13980
cctcccaaag tgctggggtt gactgctcgt ggcccctctg ttgcacatct tgacttctca      14040
gcctccaagg tgattcttta ggacaccaat ttaatccctc taaacatggc aacagagcca      14100
gcggtttcca gccctatttg cgcagtagaa ggattattta caaatcctcg tacttagact      14160
ccacccgcag agattcaagt ggactgagcc tggagtgaag ccgaaggcat tttcttataa      14220
tcctgagaat gataatatac agctgtcttt gaaaccacc actaagactt gtaaactttg      14280
ttcattcaag tcttctttc tcccttaaa agcaggctta tccttgaggt gtgcttttc       14340 agactccagt aagcatcact gagaacactt aattaatata ctgaggcctc tcacaagagg      14400
gaaggagtgg aagaactcct ggagaaggac ttggaaggga gatgttttt tctttctttc      14460 tttcttttt ttttttttgg agacagagtt cactcttatt gcccaggctg gagtgcaatg      14520
gcgtgatctt ggctcactgc aacctctgcc tcccaggttc aagcaattct cctgcctcag      14580
cctccccagt agctgggatc acaggcgcct accaccatgc ccagctaatt tttgtacttt      14640
tttagcagag acgggctgtc gccacgttgg cctggctggt ctcgaactcc tgacctcagg      14700
tgatccgccc acctcggcct cccaaagtgc tgggagtaca gacatgagcc accgtgccca      14760
gccaagatgt ttttcttaac acaaaaagtt tttgtctggg tgtggtggct cacgcctgta      14820
ctcccagcac tttgggaggc cgaggcgggg agatcacttg caatcaggag ttcgagacca      14880
gcctggccaa cgtggcaaat acaaaaatta cctgggcatg gtggcgcttg cctgtaatcc      14940
cagttattta ggaggctgag gcaggagaat tgcttgaatc cgggaggcgg aggttgcagt      15000
gagctgagat caagccactg aactccagcc tgggcgacag agtaagactc catctcaaaa      15060
ataaaaaaaa atttctaaag caagcgcttg ggctgttctg atgtcaacat acagtagctg      15120
gccctacctt taacccagga taaggggcaa aagtatacc aaagatacat gtaatcaaag      15180
ttgctgggtg cagtggccca cgcctataat cccagtgatt gggaggctg aggtgggagg      15240 attacttgat cctggaggtt gagaccagcc tgggtaacac agtgagacct tgtctctgaa      15300
acctaaaata aaataaaata aaataccact gtgctctatc ctgagcaaca gagcaagacc      15360
ctgtctcaaa tataataaaa ataaaaataa tcagtccttg ggtttagcat ctttggacta      15420
atggtaccag catgagggaa agcaggtctt tgtagctctg ataagtgaac tttgacactt      15480
cttagtgttt ttctctaact gtggtgacat acgaataaca tataattaac catttaaaaa      15540
taagcggttc ggtggcattt agtacatcac agtgttgtgc aaccaccacc tctaggtagt      15600
```

```
tccaaaactt tttctttctg tttttttttt tgagacagag tttcgctctt cttgcccggg   15660
caggagggca atgacacgat ctccactcac cgccacctct gcctcccagg ttcaaatgat   15720
tgtcctgcct cagcttcccg agtagctggg attacaggca tgtgccaccg cacccggcta   15780
attttgtatt tttagtagag atgaggtttc tccatgttgg ccaggctggt ctcaaattcc   15840
tgacctcagg tgatccaccc gcctcggcct ctcaagtgct gggattacag atgtgagcca   15900
ccatgcctgg ccccaaaaca ctttcctaac tctaaaataa agtcccataa gcaggtattc   15960
cccactccct cctcctcccg gcctgtccat ccacaaatga atggattaaa caatatggtt   16020
tatccataca atggagtata attcagctgt aaaaggggct tggcgcagtg gctcacacca   16080
gtaatctcag cactttggga ggccgaggcg ggcagatcac ttgaggccag agtttgaga   16140 ccagcctggc caacatggtg aaaccaggtc tctactaaaa atacgaaaat tagccaggcg   16200
tgttagtgca cacctgtaat cccacctact caggagactg aggcatgaga atcacttgaa   16260
tttaggaggc agagaagttg cagtgagctg agatcctgcc actgcactcc agcctgggca   16320
acagagcaag actctgtctc aaaaaaaaaa aaaaaaaga ggaatgagat accgacacat   16380
tataccatga ggataaacct tgaaaacaac atgctcagta aaagaagcca gcacacaaaa   16440
ggttacatat tatataatgt aattttattt tagtttttga aaagctggtc tcctgggctc   16500
aagcgatcct cccttcttgg cctcccaaac tgctgggatt acaggtgtga gccactgtgt   16560
ccggcctatg attttttttt tttaatgaaa tacctggaaa agataaatcc agagaaacag   16620
acggcagatt acaggctctt tttaaattgg tttctgacac tatcacaaga taaaaatgtg   16680
gtttaaaatt gttgcttggt atgtcttatt cacctctaaa gatatactgt tcatcaggcc   16740
gggtgcagtg gctcacacct gtaatcccag cactttggga ggctgaggcg ggaggatggc   16800
ttgaacccag gagttctagg ctgtaatgtg ctctgccaat tgggcatcca cactaagttc   16860
ggcatcaata tggtgacctc ccaccaggtt gcctaagaag tggggaaatg gtctaggttg   16920
aaaatggagc aggtcaaaat tttcatgctg gctgggcaca gtggctcaca catgtaatcc   16980
cagcactttg ggaggccaag gcagatggat cacctgaggt caggagtttg agaccagtct   17040
ggccaacatg gtgaaaccct gtctctacta aaaatacaaa aaaaaaatt agctgggcat   17100 ggtggcatgt gcctataatc ccagctattt gggaggctga gcaggagag ttgcttgaac   17160 ccaggaggca gaggttgcag tgagccggga tcacgccact gcactctaac ctgggcgaca   17220
gagtgagact ccatctcaaa aaaaaaaaa aaaactttca tgctgatcag tagtggaatc   17280
agcttgtgaa ttgccctcca gcctgagcaa cacagactgc ctcttactaa tcccagcact   17340
ttgggaggct gaggtgggag gatggcttgt gcctaagact ttgagactag cctagccaaa   17400
atcccttctc tacaaaaaat gcaaaaatta gctgggtatg gtagtgtgca cctgtagtcc   17460
cagttactca ggaggcttag gtgagaggct cacctaggcc caggaggtta aggctgcatt   17520
gagctatgat tttgccactg cactccaggc tgggcctagg cctttgtagt cacagctact   17580
tgggggcaaa tgtaggagga tcacttgagc ccagtaggtc gaggctgcag tcagctgtgt   17640
tttttgagac atagcaagac cctgtctcaa aagaaaaaa aaagtagct acaagctcat   17700 ttatgcaaag gctaaccact gtcacaagta gagatgtgca gaactgagat tcaaatggat   17760
ggaatggcaa gaaaactgc cacttctgtg aacctgaagt caaactgccc ttgtcgtcaa   17820
gataaaaggt atacatggtg tgagcctggg catctgaaag gtgttgcagc ttttctttt   17880 attttttga gatggagtct cactcctgtc acccaggctg gagtgcagtg gtgcgatctc   17940
```

```
agctcactgc aacctctgcc tcctgggttc aagcaattct cctgcctcag cctcctgagt   18000
agctgggatt acaggtgccc accaccacac ccagctaatt ttcgtatttt tagtagagat   18060
ggggtttcgc catgttggcc aggctggtct cgaactcctg acctcaggtg atccgcctgc   18120
ctcagcctcc caaagtgctg ggattacagg tgtgagccac tgtaattagc caggcttgg    18180 tggtgggtgc ctgtaatccc agctactggg aaggctgagg caggagaatt gcttgaacct   18240
gagaggcgga ggttgctgtg agccgagatc gtgccactgc actccagcct gggtgacaga   18300
gtgagactcc atctctaaat aaataaataa ataaataaaa tgagatgatt tctgagtgag   18360
ttaactaaat caggatatgc agaacaatgc caagcatata ttagccacta aagaatatat   18420
aagttgcctg aaagccccct tagggtttaa acctggactt cattattcac aatcacattc   18480
ccggtcccca ttacggagcc tggtcacctg ggtgcttgtt agatatgaa atcatcagat    18540 cccacccag accgagtcag aaacgttgag ggcaggagtt caagaccagc ctggccaaca   18600
tggcggaaac tccgtctcta ctaaaaatac aaaaattagt caggagtggt ggcacaggcc   18660
tgtgatctca gctactcggg aggctgagac atgagaatcc cttgaacctg ggaggcagag   18720
gctgcagtga gccaagatgg tgtcattgcg ctccagcctg ggtgacagag tgggactctg   18780
tctcaaagaa aaagaaaaaa agaaaagaaa ttgcagcttc tgctcaggaa gtctggagtg   18840
ggccaggatt ctgcatttta caactcccca ggagtgttag tggggctggt ttgtggactc   18900
gcctttgagt cgttggtctc cgctcaatca atattagata aaatgacagt attgggagaa   18960
atccaggggg ctctggagga ccgagggatc atattggagg cagatagggc agagaaaggt   19020
ggaggaggtg ggagtcgggt gtggctgtgg aggaagctac ttaaatccgg atttgatctt   19080
tgctagttct tatccctgga cctgaaccca ggcgcacatc tggattagaa gatgccaggc   19140
tcagaggatc ttcgtaaagg taagccagaa aaaatgagaa ccgaagcaaa gacacgtgaa   19200
gaagtggaaa gcagctggcg gcgggaaaag gcagagggac caggcggccg aagctggtgc   19260
ttcgtccacg tgggtggcag ggacttccca cagaggctgt catcgttttt gttgttgttg   19320
ttttgttttg ttttgtttgt cttttgagac agtctcactc tgtcgctcag gctggagtgc   19380
agtggcacga tttcggctca ctgcaacctc cacctcccag gttcaagcaa ttctcctgcc   19440
tcagcctccc gagtagctgg gatgacaggc acgccacc acacctggct aattttttttt   19500 ttttttgtat tttagtagag ccgggggtt tcaccatatt gaccaggctg gtctcgaact    19560
cctgaccttg tgatccgtct ggctcagcct cccaaagtgc tggggtgaca ggcgtgagcc   19620
actgcacccg gcccaagttt tgtatcttta tagagatggg gtttcaccat gttagctagg   19680
ttggtctcaa gcccctgacc tcatgtgatt ggctggcctc ggcctcccaa agtgctggga   19740
ttacaggcat gagcctcggt gcccggccgc ggctgtcatc tgacagcaca ggcaaatgca   19800
gggaagcctg tttctgcctt caaatccgaa atcttctccc tcgtagttgt gtcctaattc   19860
ttcccacccc gatgcttgtt cttgagcaca ggggaatctg attcctatga ggatgattag   19920
gtcctagata gaatataggc ttagccaagc tggaaatctc atgttcatga gcacttacta   19980
gactctggag ctgctgccaa accatttttca ggcatgatgc gattcagatc ttttagagcg   20040
aggcatgcgg tggctcatgc ctgtaatccc agcactttgg gaggccgagg tgggcagatc   20100
gcttcagccc aggagttcaa gaccagcctg gcaacaaaa caagacgttg tctctacaaa   20160
aaatacaaaa attagccggg catgtcagtg ttgtgtagtt ccagctactc gggaggctga   20220
ggtgagagga tcgcttgagc ctggggaggt tgaggctgaa gtgagctgtg atcatgccac   20280
tgggcaacac agcagtacac tgtctcaaga aaagaaagt aaaggtgac atccgtgaca    20340
```

```
gcagtgatgt tattttttctg cttatttcct tgctatattc ctaaaagaat atacttaatg   20400
aacattgaat aaatgataag aataaaacca tgtccatcca tttcaccttg gattgagttg   20460
cctatttcta cacaaagaaa atagaaccca agaggtaagg cacaagcgat cccttattta   20520
cgtatttatt tatttatta tttattattt tcttgagaca gggtctccct ctgtctcagg   20580
ctggagtgca gtggcataat ctcggctcac cacagcctct gcctctgagg ttcaagcgat   20640
tctcctgcct cagcctcccg agtagctggg actacaggcg tgcaccatca cgcccagcta   20700
atttttgtac ttttagtaga cagggtttt caccatgtta gccagaatgg tcttgatctc   20760
ttgacctcat gatccgcccg ccttggcctc ccaaagtgct gggattacag gcatgagcca   20820
ctgtgcccgg ccaaattttt gtgttttaa tagagatggg gtttcaccat gctggccagg   20880
ctggtctcaa actcatgacc tgatatgatc tgcccgccct ggcctcccaa agtgctggga   20940
ttacaggcgt gagcaaggga tcccatattt aaatgataac agaaaaaag gatggaggaa   21000 ccaaggggga aaggaacaac cttttcctat gaaaatgaca aatgaggctt ggaaaaacaa   21060
ggacaaaagg cagatcaagt tgtcctcccg cttcagcctc ccacagtact gggactgcag   21120
cctgaggcac gaccccggcc agcagtgtct ccatatctaa gaacctcagt cacggccggg   21180
cacagtggct cacgcatgta atcccaacac tttgggaggc cgaggcgggt ggatcacctg   21240
aggtcaggag ttcgagacca gcctagccaa catggtgaaa ccctgtctct gctagaaata   21300
caaaaattat ccgggcatgg tggcgtgcgc ctgtaatccc agctactcgg gaggctgagg   21360
caggagaatc gcttgaactc aggaggtgga ggttgcagtg agctgagatt gtgccactgc   21420
actccagcct cggtgacaga acctcagtca cttgatcatc acgttgtacc tcagtggaaa   21480
ggaaaggaaa gctcaggctt tgagaatgg agttgttagc atttcccatt tgtgtctttt   21540
tcctcctctt tcaaggcaag gaccagatgc attcacacag gaaacgaacc atgttcacta   21600
agaagcaact ggaagatctg aacatcttgt tcaatgagaa cccatacccca aaccccagcc   21660 ttcagaaaga aatggcctcg aaaatagaca tacacccaac agtactgcag gttggaaaat   21720
gatccctctt ctcactaaac tgccttcctg atctaatcta aattcagagt ccctctagga   21780
taattcctga ggtctcattc caatcgccaa tattccccaa acccacactc tcctactcac   21840
gtccccgtaa acctttcttc aaccccctag agcaagaatg ggaaattttt tccagtaaag   21900
gaccaggtag taaataattg aagctttgtg ggccataccg tctctctagc aactatttta   21960
actatgccac cacagtgcga aggcagccac agacaacgta aacaagaggc ccatctgtgt   22020
tcccagaaac tcttttactc aggttggagc acggtggtgc aatcacagct cactgcagcc   22080
tcgacctccc gggctcaagc aatcctacca cctcagcacc ccaagtagct gggactacag   22140
gtctacaggt gcacactacg cctcccaaag tgttgggatt acaagcatga gcccggctgt   22200
attttatttt ttgtagagat ggggtttcgc tatattgccc aggaggctga tcttgaactc   22260
ctggtctcaa gtgattcacc tgccttggcc tcccaaagtg tcaggattat aggcataagc   22320
cactgcgcct ggcctgaagt ttatacaatt ttcacattac aaaatagtgt tgttttgttt   22380
tgttttaaga cagggtgttg ctcttgccca cattggagtg cagtggcacg atcatagctc   22440
actgcagctt tgaattcctg ggctgaagcc atcctcccac tcagattccc aagtaggtgg   22500
gactacaggt gtgtggtact acagcctccc gagcagctga tactactggt gtgtaccacc   22560
aggcccagcc aatttgtgtg ttttttgtag agatggggtt tcgtcatgtt gcccaggctg   22620
gactcaaact cctgaaatca agtgatccac ccacctcagc ctcccagagt cctgggatta   22680
```

```
taggcatgag ccactgtgcc tggccagtag tattctttta ttttctctct tttttctttc   22740
agtcccaaca cacatacaac acaaaatagt actcttattg tgtttgtttt ttctcaacca   22800
ttttaaaacg taaagcctat tcttagtgca tgggtgatac aaagacaggg ggtggtcaga   22860
tttggccacc agccttagct ggctggcctg agcccagag cagcccctgc gactgatccc    22920
cttgctctcc tatcccctgc tctgggtttt ctgacccctg tctcaatttc tgtccccaaa   22980
atctctcatt tctgctcctt cctgggagta gattgagtag ggttccacaa agaggatgta   23040
agtggccaag ctgtggcact agctgttctc acctagaagt actcatatta tcaactaaaa   23100
ggaaaacttg ggttgggtat ggtggctcat gcctgtaatc ccagcagttt gggaggccga   23160
ggtgggcgga tcatgaggtc aggagttcga gaccagcctg gccaatatgg tgaaaccctg   23220
tctgtactaa aaatacaaaa attagccagg catagtggtg tgagcctgta gtccccgcta   23280
ctcaggaggc tgaggcagaa gcatcgcttg aacctgggag gcggaggttg cagtgagccg   23340
agatggtgcc actgaactcc agcctgggcg acaaggtgag actccatctc aaaaataaaa   23400
taaaataaaa taaaaataaa taaataaata aatattagga gagtttaagg gccaaaaaaa   23460
ggaaaaaaaa agaaaagtta aaaacttaaa ggttaaaaaa aagaatataa ataaataaaa   23520
tacgtttaac aaaataaaaa ttaaaaagta aaaatttttt aaaaatagaa tgacaagtca   23580
tctgaattcc accccattct cttctctctc ttcccttcag gtctggttca agaatcacag   23640
agcaaaactc aagaaagcga aatgcaagca tattcatcaa aaacaagaaa ctccacaacc   23700
gccaatacca gagggtgggg tctccaccag tgtcggcctg agaaatgcag acacactacc   23760
cagattgccc aacgctgctc acccgatcgg cctggtgtac acgggtcatc gagtcccctc   23820
attccagctc atcctgtacc ccaacctcaa ggtccctgca aatgacttca ttggccacag   23880
aatagtccat tttggctgct gccgagatcc taatatatac tgcctctacc ccattttgga   23940
atcccaagtt tgcgctccaa gcttccattc tggctctcct gcctgttcat ctaaccaaag   24000
tcgagagaga tgataaaatac aaaaagtcac atgttgtaat gatgtgtgtg tggtactgtg   24060
acatttgcgt ttggtcttcg tgcctgtttc ctggaaagca gctccagagt tccatggagt   24120
ctccaaagtg ccatcttttt gtattttgtg tgctaatgtt gaccgatagc ttcaggatgg   24180
ggactggtct ctggaaagac cccagtagga ttagagggca aacttctggg aggggaagga   24240
agctgagggt gaggctgatc accattggcc agtggtttca tcagtcatgt ctgggtaagg   24300
aagcatccat caaacccag gaggacaggg tttgaagaga tccctgacag ctaagcatgc    24360
ggacgtacct ggagggtggc atatccgggg agggcatgga agctccgggc ccctcgtcat   24420
acgcctcatc ctagcagggt gcggtggctc atgcctctaa tcccagcacg ttgggaggcc   24480
aaggcaggcg gatcacctga ggtcaggagt ttgggaccag cctggccagc atggcgaagc   24540
ccatctctac taaaagtaca aaaattagcc gggcgtggtg gcttgtgcct gtaatcccag   24600
ctactcggga ggctgaggca ggaggatggc gtgaacccgg gaggcagagg ttgcagtgag   24660
ctgaggggat tgtgccactg cattccagcc tgggtgacag agcaagaatc tgtctcaaaa   24720
aaaagaaaca agaaagcaca gaggaccagc tggaatattt ggaagaccag aaaatgtcct   24780
taaaactcaa aatgcctggg catataggtc aggtccacct agccttttga atcaatgcga   24840
acccttcctc aaggcctgga ggttggcaac acaaaatcac cctgtggaga acctaaagca   24900
ttccctctct gagagttgag tcaattggga ttccaccccc aaaattccta aaaatctcaa   24960
gttcctagaa aattctcaga aaaagcaagc tctcctatac ctcccggct gtactctgat    25020
gcaacttggc aaccatcaga gaatctccat cccccttgaac cttggtcctc tgccaatgtt  25080
```

```
cctcacgcct gtaatcccag cactttggga ggctgaggcg ggcggatggc ttgagcccag   25140
gagttcgaga ccagcctggc cagcatggta aacctcatc tctaccaaaa acatcaaaat    25200
tagccagtct catatactgg tctcaaaata aataaataga ttaaaattta aacataaaat   25260
aaacatgagt gtgttagaaa gaacctactg gcccggcgtg gtggctcaca cctgtaatcc   25320
cagcactttg ggaggcagag gcaggcggat catctgaggt tgggagttcg agaccagccc   25380
gaccaacatg gagaaacccc gtctttacta aaaatacaaa attagccagg catggtggcg   25440
catgcctgta atcccagcta ctggggaggc tgaggcagga gaattgcttg aacccgggaa   25500
ggggaggttg ccatgagccg agattgcgcc attgcactcc aagcctcctg ggcaagaaga   25560
gcaaaactcc atctcaaaaa aaaaaaaaa aaaaggaac ctactgtagg atttggagtt      25620
gagtaatttc agatagaatc aaaggaagag aaaggtctgg attgggtggt gccagcggca   25680
gcttctatga ctgagtatct caatacatct tatctatagg acggctgact agaaagagga   25740
caaacctata atagataaat gggcggcagc cattgcttag ccataggcga atatttgatg   25800
ggttggggct caggacaaat gttaaaaaca atcttaataa cagcatgccg gcccggcggc   25860
ccacacctgt aatcccaggg gatttcagag gtggaggggg aggcggaagg attgcttgag   25920
cccaggaggt tgaggctgca gtgagctgtg attgcaccgc tgcactccag cctgggtggc   25980
agagcgagcc cctatatcaa aacaaacatt atcaagaaaa attattaaat gaataacaaa   26040
aacaggctgg gcacggtggc tcacgcctgt aatccaagta ctttgggagg ctgaggcagg   26100
tggattgctt caactcagga gtttgagacc agcctaggca acacggtgaa accctgtccc   26160
tacaaaaaca caagaagga gtctcgcttt gtcgcccagg ctggagtaca gtggtgtgat    26220
ctcggctcac tgcaacctcc tccatctcct gggttcaagt gattctcctg cctcagcctc   26280
ccaagtagct gggactacag gcatgcacca gcacacctgg ctaattttg tattttagt     26340 agagatgggg tttcatcatg ttggccaggc tggtctcaaa ctcctgacct caggtgatcc   26400
acctgcttca gcctcccaaa gtgctggaat acaggcttg agccaccatg cccagcctct    26460
acaattaatt aaaaaagaac cataacccca aaacttgtac aaccaccagt ccaagaaacc   26520
aagtcacaat ttctgcagca atcagcccca aatgcccagg gcttgatcca tcactcgtag   26580
cttccctagt ttttgtgccc atcccccaac cttgatttca atttaggacc aaccagagaa   26640
acccaatgtt tggctaaaca atcccacagg atcctacttc tggttagctc cctggcggcc   26700
tcccaacgtc agcagccttt ggtcaggaca tatctgaaga cttcgttttt tttctgctat   26760
aaagctttct ttccttttt tttttctcc tgaggtgaag tctaactctg tctcccaggc     26820
tggaatgtag tggcatgatc tcggctcact gcaacctccg cctccctggt tcaagcgagt   26880
ctcacacctc agcctcctga gtagctgaga ttacaggcat gcaccaccac acctggctaa   26940
tttttatggt gtttttttt gtttgttttt ttgtttcttt ttgtagagac ggggtttcac   27000
catgttgccc aggctggtct cgaactccta acctcaaatg ttctgcccaa ctcggcctcc   27060
caaagtgctg ggataacagg cgtgagccac tgcgcctggc catggaacct cactctttaa   27120
agtgtgcagg gaccccagtc attccccact gtgtcgcggt tcccataaca gtgcctgtca   27180
ccaagtatgt tttcaaaata catttttgga agagagagag aaacagaagg ggaggggta    27240 ggaagagaaa gtagggaag aggaaagtga gagagggaga caggaaggga gagggaaggg   27300
agacacagag atgaagacaa agggaaagag acagaggccg ggtacagtgg ctcatgcctg   27360
taatcccagc actttgggag gccgaggtgg cggatcacct gaggtcagca gttccagacc   27420
```

```
agcctggcca acatggtgaa accccgtct ctaccaaaaa tacaaaaatt atctgggagt    27480
gatggtgtgt gcctgtaatc ccagctactc gggaggctga ggcaagagaa tcacttgaac    27540
ctgggaggtg gaggttgtgg tgagccgaga tcgcacccct gaactccatc ctgggcaaca    27600
gaacgaggct ctatctcaaa aaaaaaaaa aaaacagaaa gaaagaaaa gaaaggaac    27660 agcttccaag catctttgga gagggcttc actaacatca aatcctgtct tcctctcatc    27720
accttctagc ccagtatttc cccaacgtga gaataataag aatcatctgg ggagctgtta    27780
aaacccagac tctgagacca gacaggggca tgcttcccag gtgtgggcat gattttttcc    27840
tggggttgta tttaacaaag ttcaaaaccc aggaggtaca atcaaaacct gagccgtctg    27900
gagactcaag acttcttagg gaagacgaaa aagagaaatt ccggccaggt gcagtggctc    27960
tcgcccgtaa tcccagcact ttgggagtcc aaggcaggag gatcgcgtga tcccaggagt    28020
tggagaccag cctggccaac atggtgagac cctcatctct acaaaaaaaa aaaaaaaaa    28080 agagagagag agagaaagaa gttcccagag aaagttccca gaggaaacag gagggaaaag    28140
ggcgaggact gcacccagcc agctagggta tgagtgtgaa ccatagtcta ggggctggg    28200 tgtgaattcc cagtccaggg gctgtgaata cgtggagaca ccgatgctgg ccctgcaccc    28260
agcctcctcc ctgggcgaac tattgactga agccaccct cgtgtcccca ctgttcctgg    28320
tctcaacttc ctcacctgat gaatgggcgg ggagggtaat tccctacgg tggggctttt    28380 ctcactctgt tatgtgttct tacaaaatgt gctctctgat atcatctata tctccctaga    28440
aggaatcatt agtttatctt tttttttttt tgtgggacag ggtttcactc tggtcgccca    28500
ggccggagtg cagtggtgcg atctcggctc actgtaacct ccacctcctg ggttcaagcg    28560
attctcccac ctcagtctcc caaggcctgg tgcggtggct tacgcctgta atcccagcac    28620
tttgggaggc caaggtgggc ggatcacttg gggtcaggag tttgagacca gcctggccaa    28680
tatggtgaaa ctccctcttt actaataata caaaaattgg ccaggcgtgg tggcgggcag    28740
gtgtaatccc agctactcgg aaggctgagg caggagaatt gcttgaaccc agaaggcgga    28800
ggttgcagtg agccgagatc gtgccactgc actccagcct ggggacagag tgaaactgtg    28860
tctcaaataa taataataat aataataata ataatttagg ccaggtgcag tggctcacgc    28920
ctgtaaaccc agcactttgg gaggccgagg cgggtggatc acgaggtcag gagttcaaga    28980
ccagcctggc taacatggtg aaaccccatc tcaactaaat atacaaaaaa attagccggg    29040
cgtggtggca catgcctgta atcccagcta cttgggaggc tgaagcagga gaatcgcttg    29100
aacccaggag gggagggttg cagtgagcca agaccgtgct actgcactcc agcctggcaa    29160
cagagcaaga ctccgtctca aataataata ataataataa tttaaaaaaa aaataaaaaa    29220
taagaaataa aagaatgaac cacaatgtcc ctttgttcta caggccactc ttgtgctatc    29280
cacagttgcc aaaaaccccc acctgccttg tctatggacg cccatcgggt gataccacaa    29340
acacctttga tcctacagat accagggtaa attcagcatc caagtccttg aattcttccc    29400
gtgagtataa gctgccctgg ctcagccctc ttctttgcca ggaacccaat ccttcaaact    29460
tccctcaaag actgggtact tttagcatga ctgctctaga gattctgggt ggggctcaaa    29520
gtttaacctt cagggtcagc aacatttat ggaaagagcc acagagtaaa tatttgaaac    29580
attctcgtac actgacactc agctggactg gcaaagcaga atatctgtgt gtcagtgtgc    29640
gttttattca gccgttgttt gggtcagggt ctgtgggcgg ccctggcag ctaatgccct    29700 cctgtgagga acaatacctc accatcaagc acagtccgtc acatattctt gccctggtcg    29760
ctcgctcttt ctttctttc tttctcttct ttctttcctt tctttctcat tttcgtttct    29820
```

```
ttctttctttt ccttcttttc tttttctttc tgtctctctt tatctatttc tgtttctttc   29880
tctctctctc acctttcttt ctttccttcc ttccttcttt ctcttcctttt ctttctctat   29940 ctctctttct ttctttcctt ccttcttccc ttgtttcctt ctttctttc ttttctttct    30000 ttttcttcct ttcttttctt tcttttctct tctctcttc cttttctttc tctctctctc    30060
tctctctttc tctctttctt tcttttctgac agggtcttgc tgtgtcaccc aggctggaat   30120
gccaagatgc actcataggt cactgcagcc caaataaatt tccccaggct caggtgatcc   30180
tcccacctca cccttccaag tagctaggac aacaggtac atgccaccat gcacgtctaa    30240
tttttatttt tattttttga gactggtctt gctctgtcac ccaggctgga atgcagtggc   30300
acgatcacag ctcactgcag cctcgacaac ccggcccctc caagcaatct ccccctcac    30360 cctcccaagt agctgggacc tcaggcatgt accaccatgc cctgctaatt ttttattgtt   30420
tgtagaggcg gggtctccct atgttgcgca gggtggtctt gaacacctgg cctcaagcaa   30480
tcctcctgcc ttggccaccc aaaatgctgg gatcatgggc gtgagccact gtgcctggtc   30540
tggtcttcct cctttcatcc tcttagtcct tgacctgtcc ctcttctaga gtcctccctc   30600
ttcatgaccc tctcccccttt gttggggctc agaaactgat acctctaaat acagcatgtt   30660
aaaggtgcct caagggccgg gtgcagtggc tcatgcctgt aatcccagca ctttgggagg   30720
ccgaggcagg cagatcactt gaggtcagga gttcaaggcc agaccgacca acatgcaaaa   30780
ccctgtctct actaaaaata tggaaaaaga aaattagttg ggtgctgtga cacacgcctg   30840
taatcccagc tacttgggag gctgaggcag gagaatctgg gaggcggagg ttgcagtgag   30900
ccgaggtcac accactgcac tccagcctgg gcaacagagc gagactctgt ctcaaaaaat   30960
aataagaaat aaataaatga gcctcaaggt ctctgacctc ccccgatcat ctcttccaaa   31020
gcacaggcct ttatctgtgt aagatccaga cctgccaaga ggaataattg tttttcttc    31080 tcctccctgt gagacaaaga atgtaaccac acctgaacag atcccatcac tgtcaatagg   31140
aatgatttcc aggacccatt catgctctct agtaatcctt tattgccctc aatggaattc   31200
ctctagcccc ctcccataat cagtttgcca ggagaacata taagcttctg aaccccttg    31260 ggggatgggc gatcactggc tctccccatg ctcaggttaa agacatttgt aagccttttc   31320
tcctgctaat ctgcttccta tcagttcttt tcagccaacc ttcagagagc caaaggcagc   31380
cttcaccttg gcctcaacac cttccatgcc ttttgcttct cctcctcccc tgcaaagcat   31440
tccccactcc ttgggttccc cactttcaag catcccaccc tccctgttat atgtcatcct   31500
cctcattctc tgctttata accctttaa aattatgggc ccagccaggt gcagtgatgc    31560
atgcctgtaa tcccagctct ttgggaggct gaggcaggca gttcacttga gctcaggagt   31620
cctacacagc tggggcaaca tggtgagacc cccatctcta ccaaattgca atattagcc    31680 gggtgtggtg gtgtgagcct gtattcccag ctactcagga ggctgaggta ggagaatggt   31740
ttgaccccag gagatggaag atgtagtgag ccaagatcac gacactgcac tccagcctgg   31800
gcaacagagc aagatcgagc ctaaaaaaaa aaaaattagg tggggtgcgg tggctcacac   31860
ctgtaatccc agcactttgg gaggtcgagg caggtggaac acctgaggtc aggagtttga   31920
gaccagcctg gccaacatgg caaaacccca tctctactaa aaatacaaaa aaattagctg   31980
agtgtggtgg cgggtgcctg taatcctggc tacttgggag gctgaggcag gagaatcact   32040
tcaacctggg agccagaagt tgcagtgatc tgagataatg ccattgcact ccagcctggg   32100
tgatagagtg agactctatg tcaaaaaaaa aatacataaa aaaattaaaa attaaaaatc   32160
```

| | |
|---|---|
| aatttaaaaa atgccagcta gtatacttttt cctctctccc ttccttttc tatctctctc | 32220 |
| tcttttttt tttttttt tttttttttt ttttttgag acagtttcac tcttgtcgcc | 32280 |
| caggctggag tgcaatggcg tggggatctt ggctcactgc aacctccacc tcctacactc | 32340 |
| aaatgatcct tctgccttag cctcctaagt agctgggatt acagatacaa gcaacaaatc | 32400 |
| ctaattcttg tatttttcgt agaggcaggg ttttgccatg ttctccaggc tggtctcaaa | 32460 |
| gcgaatgctg gccaggctca ttttttaat ttgaattgtg ggaaaactga ggctggatcg | 32520 |
| aatggtcctg gacatgccct ggaacaaaca acatttagct gtgcaaggca cagtgtcagt | 32580 |
| gtctggtatt ggggtgcccc agtctcaagt cccaagaaaa agacaaggca gaccatgaat | 32640 |
| tttgtgtggc tccaactcag ttttcttcat ctgttgcttc acttgcagtg ccagaccaga | 32700 |
| atcactttga cctaaaacta gctacgataa ttaacattca gtatgactca ttacctaaca | 32760 |
| aattcaaaat gtaaggaact gtctttagaa cttgttctat ataaacatgt tattaaggtc | 32820 |
| tgctgcggct gttctatgca gctcttttt ttttttttct ggcgatagga tctcactcta | 32880 |
| tcgcccaagc tggagagcag tggcatgatc acagctcact gcagcctcaa cctcctgggc | 32940 |
| tcaagcaatc ctcccacctc agcctcccaa agtgctggga ctacaggcgt gcacccctgc | 33000 |
| acccaactag ttttgtattt tttgtagaga tggagtgtca ctatgttgcc caggctggtc | 33060 |
| tccaactcct ggcctcaagc aatccaccaa ctcggcctcc caagtgctgg gattacaggc | 33120 |
| ggacgccact gctcccagcc ccagattttt ttctcattta tatttccgca aacctcaaaa | 33180 |
| aaaccccca aggtccctag gtcagtcact tcccactagt aaataagtca gcatctttgc | 33240 |
| aaagatcaaa ggaaaagcaa ttttccttac cacagagcct cttacaggaa agagagctct | 33300 |
| gattttccat atgttcccca accatgctag gatgttcctg tgccctgatg gcattcttac | 33360 |
| taacccattg ttccattcct ttccagcccT ccttcctgta acgtaagtgc aggtgggagt | 33420 |
| tggggattgg tccgctaact gggtatagag aaaacagatg ggtatgctat tctcagtaag | 33480 |
| ggagcttctg tcctgggaaa aatgtggcct ctcctaagga accctatccc attgaatcac | 33540 |
| cctgattcac ttttttttt ttttttttt tttttttg agatggagtc ttgctctgtt | 33600 |
| gcctaggctg gagtgcaatg gtgtgatctc ggctcactgc aacctctgtc tcccggttct | 33660 |
| agtgattctc ctgcctcagc ctcccaagta gctgggacta taggcataca ccaccaagcc | 33720 |
| tggctaattt tttttttt ttttttttt tttgagacgg agtcttactc tgtgccaggc | 33780 |
| tggagtatag tggcgtgatc ccggcccgct ggctcactgt aacctccgcc tcctggattc | 33840 |
| aagtgatttt cttgcctcag cctcttgaat agctgggact ataggcgccc accaccacac | 33900 |
| ccagctaatt tttgtatttt tagtagaaac aggttttcac catgttggcc aggatggtct | 33960 |
| cgatctcttg acctcgtgat ccacacgcct tggcctccca agttctgggg attacaggcg | 34020 |
| tgagccactg cgcccggccc taattttgt gttttagta gagatggggt tttgccatgt | 34080 |
| tggccaggct ggtctggaac tcctggcctt aggtgatctg cccacattgg tcttccaaag | 34140 |
| tggcgagatt acaggcaaga gccactgtgc cctgcctctc acattttctc tcttcccaga | 34200 |
| tttggttcaa gaacttaaga gctaggccat gtgcggtggc tcacgcctgt aatcctagca | 34260 |
| ctttgagagg ccaaggcagg cagatcgctt gaactcaaga gttccagacc acctgggca | 34320 |
| acatggtgag atccctgact acaaaaattc gccaggtgtg gtggcatgtg tctgtagtcc | 34380 |
| ctgctattca ggaagctgag gcaggcggat cgcttcagcc tgggaggtca agactgcagt | 34440 |
| gagctgagat ggagacacag cactccagcc tgagcgacag agccagaccc tgcctcaaga | 34500 |
| aaacaaaaca aaacgataac actggagagc cagagcagga accagtctcc tctccaatct | 34560 |

```
ccaaacctga gagagacatg agtcacactg acggctttgc ctgcctgcga tctctctatg    34620
tgtgttgatt cttgcggaac aaggcgcttc gagcatctcc tctgcccta cgcccgtgac     34680
cctgtccctc ttcttgtctc cattgccccc caagcgggta catttgccca ccttctcacc    34740
tgggacaccc tgggcgtgga tctcctcacc tgcagcgcta ggtgtgctcc cagggtctcc    34800
acatccctaa cccccgcaag gctggcctct ttacctgcaa agcccccgc cgcggcctcc     34860
tccctctacc ataccccaat gccaggctca cttcctgccg cctgcctgga acggggctgc    34920
tcatgcatcc cccacgccct ctgaagcccc cccggcgcac tccacgccct ctcgcctgac    34980
ccctgtttcc gctgccggcg tctccacacc ccctgacgcc gccacgccct ggaccgaggt    35040
ctctagagct gcgcgccggc tgcacgtccc ttaggagttt ccgtgcgcca cgaggcgctg    35100
gcgcgcgtct cccggcccat ccaccccggg cccggcgaca cctttctttg ccacctggaa    35160
ccaacatctt ggttcccttt tgagggatca gaacttgttt aattggaata cggcaaaatt    35220
ctgaattttt ctgccgtctc tattccaact tcagagttct gccgtccagc cctgcgacaa    35280
tcttccggtg ccaacgcggc aggtcagtat gtatccccca cgatgccccc cgggccacgg    35340
gccccctagtt aacaggtttc cctttcgccc gctgcctgga agtatcgcca cctcgccccg    35400
cccaaccccc caccagacag ctctgcagcc acagcccctc atccaaccag gaagtccagg    35460
gcccatctgg cccgctagac ctcgggaaac cacggcgtca gagcacccat taagaggggt    35520
ccaggccggg cgcggtggtt cgcatcaggg cgcccattaa gagggtcca ggctgggcac     35580
ggtggttccc atcagggcgc ccattaagag gggtccaggc cgggcgcggt ggttcgcatc    35640
agggcgccca ttaagagggg tccaggctgg gcacggtggt tcccatcagg gcgcccatta    35700
gaggggtcc aggctgggca cggtggttcc catcagggca cccattaaga ggggtccagg     35760
ccgggcgcgg tcgttcgcat tagagcaccc attaagaggg gtccaggctg gcacggtgg     35820
ttcccatcag ggcgcccatt aagagggtc caggccgggc gcgtggttc gcatcagggc      35880
gcccattaag aggggtccag gctgggcacg gtggttccca tcagggcgcc cattaagagg    35940
ggtccaggct gggcacggtg gttcccatca gggcacccat taagaggggt ccaggccggg    36000
cgcggtcgtt cgcattagag cacccattaa gaggggtcca ggctgggcac ggtggttccc    36060
atcagggcgc ccattaagag gggtccaggc tgggcacggt ggttcgcatc agagcacccg    36120
ttaagagggg tccaggctgg gcacggtagt tcgcatcgga gcaccagtta agaggatgc     36180
aggccgggca cggtggctct aatcccgagca ctttgggagg atcacccgag gtgaggagtt    36240
cgagaacagc ctgccaacg tggtgaaacc ccgtctttac ggaaaaatac aaaattttc     36300
agggcgtggt ggcgggcgcc tgtaatccca gctattcggg aggctgaggt gggagaatcg    36360
gttgaacgcg ggaggcggag gttgcagtga gccagtgagc cgagattgtg ccgctgcact    36420
tccagcctgg gcggcagagt gggactccgt cttgggaaaa aaagggtag tccaggccgg     36480
gcgtggtggc tcaggcctgc aattccagca ctggaggagg ccgcggcagg aggatcgctt    36540
gagaccagga gttaagagac ctgcctgggc aatatagtga gaccctgtg tttgtttgtt     36600
tgttgagacc cttgtgttaa agcaaactaa atatggcctg agaaggactc cgtaattcta    36660
tatttgagtc cttgtggatg aactgcaacc taacttaata ggtacaaaag attgaaaacc    36720
taagttaggc cctgcgtggt ggctcacgcc tgtaatccca gcactttggg aggccgaggc    36780
gcgcgaatca cctgaggtcg ggactttgag actagcctga ccaacatgga gaaacccgt     36840
ctcttctaaa aatacgaaat tagccagacg tggtgactca tgcctgtaat cccagctact    36900
```

```
cgggaggccg aggcgggagg atagcttgaa cccggaaggc ggaggttgca atgagccgag    36960
attgcgccat tgcacactct agcctggtca acaagagcgg gaaactccat atcaaaaaaa    37020 aaaaaagga agcctaactt acgttttatg cgcctgtaac cgccactgag tgttggccaa     37080
tcccagcagc ccagcagctg tacttcatcc actcacaggc tgctgagcat caaactgtg     37140 ttcaaataag gcaaacgctg agcggtaacc aatccagctc tttctgtacc tcacttccga    37200
tttctgtatg tcactttcct tttcttgtcc ataaatttgt tctgaccacg aggcacccct    37260
ggagtccgtc tgaatctgcc gtgactttcg gagctgcccg atttgcaaga ggttcattgt    37320
tcagttgaac tcctttacat ttatttattt tatgtattt attttattta ttttatgtat     37380 tttatttat tttatgtatt ttgttatttt attttatttt attatttta tttttatttt      37440 gtttcatttt tatttttatt ttatttatt tttattttca ttttttttgag acggagtctc    37500 gctctgtggc ccaggcggga gtgcaatggc accatctctg cgcactgcaa cctccgcctc    37560
ctaattcaag tgattctccc gcctcagcct tacgagtagc tggtattaca ggtgcccacc    37620
accacacctg gttaattttt tctgtttta gtagagatgg ggattcacca cgttggcccg     37680
gctggtcttg aactcctgac ctcaagtgat ctgcccacct cagcctccca aagtgctggg    37740
attacaggtg tgagccactg tacctggccc cctttaaatt taattcggct gaagttttc     37800 ttttaacaga tggtgtcaga agcggagtcc agagtagagc ttctaggaac cttcgggagt    37860
gctgagtgaa cacgcaaggt gcctgcggaa cccacttgtg tccattgacc ctccgagtg     37920 gccggggatc gtgggtaagt tccctctcgg atttcagagc tccacagatt tgtgttttga    37980
gctctccgag tttcattgag caaatatctg atccaaactg ggtttggaag ctgtgacaga    38040
aactggactg gttctgggaa tggatctgat gtggtaatta gctggcttgg acccagttag    38100
aggcctctta catgtgactg ggtcagaaag aaactggtag caaatggtaa tattgcagga    38160
ggtgtaaaat ttggctttta aaattaaca gggatgtttg tgttctaccc ctttgtttca    38220
tttttcttgt gcacttaggt attaaaaaaa aaattactgg gtaagttaat caagggaacc    38280
tgagagtaat gaatgccaat attttaggta aaaatgggat ctttttttt tttttttga     38340 gatgaagtct cgtttggtcg cccaggctag agtgcagtgg cgcgatctcg gctcactgca    38400
agctccacct cccaggttca cgccattcta ctgcctcagc ctccccagta gctgggacta    38460
caggcgcccg ccaccacgcc cggctaattt ttttttttg tattttcagt agagacgggg    38520
tttcactgtg atggccagga tggtcttgat ctcctgacct cgtgatctgc ccgcctcggc    38580
ctcccaaagt gctgggatta caggcatgag ccaccacgcc ctgccaaaaa tgggatcctt    38640
aaattctgaa aaactgagtt ccttctggct tatacattag gcacgggaag gagcaaagac    38700
ttacagaaat ggcaaaatct gcctgagcgt ggtggctcac gcctgtaatc ccagcacttt    38760
gggaggctaa ggtgggtgga tcacctgagc tcaggagttc gaaaccagcc tggccaacat    38820
ggtgaaaccc atctctacta aaagacaaa aattagtggg gcgtggtagc ttgtgcctgt    38880
agtcccagct acttatgagg ctgaggcacg agaattgctt gaacccagga gcggagttt    38940 gcagtgagtg gagattgcac cactgtactc caacctgggt gacagagcga gactctgtct    39000
caaaaaataa aaatgctgg gcgcagtggc tcacgcctat aatcccagca ctttagaagg    39060
ccaaggcagg tggatcacct gaggtcggga gtttgagacc agcctggcca acatggtgaa    39120
actctgtctc tactaaaaat acaaaaaatt agccaggtgt ggtggcatgc acctgtaatc    39180
ccagctactt gggaggctga ggcgggagaa tcttgaaccc aggaggctga ggttgcagtg    39240
agccaaggtt gctccattgc actccagcct gggcaacagg agcgaaacac tgtctcgaaa    39300
```

```
ataaataaat aaataaataa aaattaaaaa attaaaatga gggctcccga aagttaaatc    39360
tgctaatctt tcagcttcgt tactatcctg atccaaagga agcagactgc agcaccagtt    39420
ggctgacttt ggataagtaa tggggtccat tttacctgag taaagtatgg gatggggtca    39480
gaggccctcc cctcagtaaa gtcccccttg gttaaaaatg ggttaaagat gacagggccc    39540
agctggggtc aagtttgagc cttgcgagtt cagtattggg tgctaagcac agtggccagt    39600
gtctgtgttt tgtcacgtat tttgcttggg cgccatgatg aaaaaatgtt aattggctta    39660
ccccacgcaa cccccttcggc cacacttgca aaactaagag cttttgctt aaggttccat     39720
aaaacagaaa aagaatttcc tttgtgatgc cgcaggcttg gccctcagga ctatagtgtg    39780
gcaagcagag tcactaggac cacctgggca aagggaacct agaagcctgg catgctggca    39840
aaaggtaaag tatttcttac caattagact gtggcccctc tgtgcaaact ggttagatga    39900
acggtaaaaa tcactgttta tctcctctgt aatgctttga ttaatacaaa aaagaattct    39960
gaggttggtc ttaggaagct gtaataaatc tggtatgctt tgtgtctttc tgtattctgt    40020
cacgaagagg ggtaccttcg gatgaaatgc gtgcccaggg ccgcataagc ccgctgttca    40080
agacggccca gcaaactggt caatcatgtc cttggaagct taacctccta ataccatgtg    40140
gccctgcttt ctcttttcac aacggcaggc caggttcagg gttccattcc cggcttactc    40200
agcgagtact ttctggtgtc accttttacca tgtgttgatt ctcttccctc tgtttcttat    40260
agaacacaga aatattagct gtttggccta gccaaggttg ggtaataaaa gatttaaaag    40320
gacttttttaa aacaagcgct atagttaaaa ctcaggtaca ttaaaagtgg atatttggcc    40380
aggcatcgtg gctcatgctt gtaatcccag tacttgggga ggctgaggca ggtggatcac    40440
ttgaggtcag gaattcaaga caagcctggg caacatggca taactctatc tctactaaaa    40500
aaaaaaaatt agctgggcat gttggtgcac gcctgtaatc ccagctattc aggaaggcgg    40560
gaaaattgct tgaacccggc aggcggagct tgcagtgagc caagatttca ccactgcgct    40620
ccggcctggg tgacagagcg agactccgtc tcaaaaaata aaataaaat aaaaataaaa     40680
taaaataaaa taaataaaat aaaagtgtag tgctcgcttc agcagcacat atactaaaat    40740
tggaatgcta cagagaagat tagcatggcc cctgcacaag gatgacatgc aaattcatga    40800
agcgttccat attttgtgca tcctggcaag atcatttctg tatctgctaa ctagcactaa    40860
agaaatagtg tgaatctaag caaaaatgag tggcacccaa aaacaaaatt gtggttttca    40920
ttaaaaaata taaatattta tataataaaa tatatatgat atataaaaaa taaaatatgt    40980
ataataaaat atacataata tatataaaat aaaaagtat ataaaaaata tatatgtgtg     41040
tgtatattca aattcttttt ttttttttg agacggagtt tcactcttgt cacccaggct     41100
ggagtccaat ggcacgatct cggcttaccg caacctccac ctcctgggtt caagtgactc    41160
tcctgcctca gcctcccgag tagttgggat tacaggcacc tgccaccacg cccagctaat    41220
ttttgtatcc ttagtagaga cagggtctcg ccatgtaggc caggctggtc tgaactcctg    41280
accttgggtg atccacccgc ctcggcctcc caaagtgctg ggattacagg tatgagccac    41340
cgtgcccggc aatgtatata ttcaaattct aacagcctgg gactccttgg gaaaaacagg    41400
aggcaccaga gacgccattt tggaaaaaaa cctgttttcc tcatgaaacc acaggaattg    41460
gaaatggata gattcccctt cagaaatcta aggctctgtt cttttgggga ttcaggatct    41520
ggtataaaaa tgggaccctt aattttggga gacctgtgtt gctttctgct gtgcccactt    41580
attatattgg gccctagaaa ctgcatgctt tcctggtcct ttttgtccaa ggactccacc    41640
```

```
ctaaagccag taatctcaaa taaataaata aacacctaaa tcaaatattt tgaaagaaca    41700
ataaaaacta atgccttta gttcacataa ctttagtaat cttgggaaaa taaaaagttt    41760
taaagattat tgggaaaaat gaagacattt agtctaaatt aggcaggtca gatattaggt    41820
ttgttcgatg ctttaaggtc atcaactgct tcttaggctt ttgaaaattg ttcagtttac    41880
ctacttggga gcattagatt ctagataagg cctgggaaca tgtggaatta gccatgcact    41940
ctatctatgc aaaggttata aagaaaagag attttttttt taattaacaa aaaccacagg    42000
tggttgtgct ccgcctaccc agcacagcag gtgagatggt gcaccctcag tggactgaag    42060
aggccatggg atcccacctc agccggatag cacgctggcc ttcaccttca ttgtgccatg    42120
gcagctttcg tgtgagccac tgactcgtgt acatgttaga ctccttggtc tataagaaag    42180
catcttgtat ggtaaattgt tgttctaaag taaataact ggtttgttca aaaggggat    42240 gctaaggaga agtcagaaag tcaaagcatg ttgtagatgg tctgggaaag tcgtgaaagg    42300
gttcgtgaaa ggaaatttaa gccaccaaaa gtaaagttg ctagttacca ttataacata    42360
tgattgaaac tactgaaaaa atagttttac atggaaagtg tgtgagaaga gtgaaacatg    42420
tttttggtaa aatattttta aaaggcagga gaatgtcaaa tttcacctag ttgagagggt    42480
tatgtgattt ttaaattaga taagaataag ctcacggttt gaacaagttg tggaaggttt    42540
gtaaaaacta atcttgcaaa aaaaattctg tgtgcaaaca cgttgactaa atttaaaggg    42600
gtatttccca gttttccata aattaaacat tgaaatgaaa ggacaaacag ggttctttt    42660 tttgttttt tgttgcccag gctatgggca actatgtagc taggcatgtt ggtgcatgcc    42720
tgtaatccca gctactcagg aagctgaggc aggaaaattg cttgaaccca agaggcagag    42780
gttgcagtga gccaagatcg caccactgca ttccagcctg ggtgacagag caagaccta    42840 tctcgaaaaa aagaaaaaa gaaaagcaat agctccctgg gtgtcaggta tcagtgagaa    42900
tgggaagtca ggtcttctct gactcctagg acattcctct ctctgtcttt gggggttgaa    42960
ttccttgtta gaactccatc ttgttaaagg ggcctcgcac ctgcccttgc cttctgcagc    43020
agccctcctt aatcctctcc aaacttccat ctccagacca ccggattctc ctcatgagtg    43080
ccctgggtgg acattggtga aggtcactg ccttcaggac acaccatagg tacagtcacc    43140
gaggtaaccc agttcaaaga agagcaggat gttcagtatt tacaaaggga tctagcaatt    43200
ggtccaaacc agtcagtgct ggcatgcacc gttcatcgtg ccatcagtgg caagatggag    43260
atctggcaat gcatggctca cagtaagata cacgccctgt gccattccac cctatcatta    43320
gaaaaggagt cttctttttc tttctttctt tcttttttttt tttttttggg agacagggtc    43380
tcactctgtt gcccaggttg tagtgtaatg gtgcaatctt ggctcactgc agcctctgcc    43440
tcctggggtc aagtgatcct ctcacctcag cctcctgagt ggctgagatc acagatgcca    43500
gccaccacgc ctggctaata ttttttgtttg tttgtgttat gtttttgag actgagtctt    43560 gctctgttgc acaggctgga gtgcaatggc gcaatctcgg ctcactgcaa cctccacctc    43620
cctggtacaa gcaattctcc tgtctcagcc tctcaagtag ctgggattac aggcgcctgc    43680
cactacgccc gcctaatttt tgtattttta gtagagacga ggttttgcca tgttggccag    43740
gaatggccag acctcaaatg atctgcccgc ctaggcttcc caaagcgctg ggattacagg    43800
tgtgagccac tgcacccagc caattttgt atttttttt ttttttttt ttgtagagac    43860 agggttttgc cgtgttgccc aggctgatct cgaactcctg acctcaggtg atcaccttcc    43920
ttggcctccc aaagtgttgg gattacaggt gggagccacc atgtccagcc gcttttcctt    43980
tttaaaaaaa atttttttg acataacaga caacaccact ctctttattt tttttataga    44040
```

```
gacggggtct cattatgttg accagtctgg tcttttttaaa ttttattttt ttgagatgga   44100
gtctcactct gttgcccagg ctggagtgta gtggcgggat cttggctcac tgcaacgtct   44160 gtacccccaga ttcaagtgag tctcctgcct caggcttcca agtagctggg attacaggct   44220
catgccacat cgctggctaa tttttttttt ttgtatgttt ttaaatttta tcttttaagt   44280
agagacaggg tttccccatg ttggccaggc tggtcctgaa ctcctgactt caggtgatcc   44340
accctcctca acctcccaaa gtgctgggat tacaggcatg agccaccata cccagccttc   44400
ctgctatttt tgaactacct gtaccaggct ggtttctctg ggtgagggga gtggtcaggc   44460
agaggcaggc cccgtcatgg taagcagcta ggagactgct agagattgac agggcactca   44520
tgagtgccct gggtggacac tggtgaaagg tcactgcctt caggacacac cataggtaca   44580
gtcaccaagg taacccagtt caaagtagag caggatgttg ggtatttaca aaggagatct   44640
agcaattggt ccaaaccagt cagtgctggc atgtaccgtt catcgtgcca tcagtggcaa   44700
gatggagatc tggcaatgca tgggctcaca gtaagataca cgccctgtgc cattccgtag   44760
acgtagatca agcgattatt actgcagaaa tctccgtgga cgtagagcaa gcaattatta   44820
ctgcagaaat tgcaggagca ggttctgcag catgtcacat ccaaagaagc ttcccttgca   44880
agttggtaac cttgagggct tcaataccac acagagttgg tctaggtgat ggctgaccat   44940
ccaggcataa taatttgggg aacaattcca ggatggaggt tatgttgcta gacttgtttg   45000
tccgggaaag tggtagacag gaagttcctg tctgcacacg tctcctggct ccagcccttt   45060
cccctgtcca tctgtcctac agactccgcc tcaggcatgt tgtcttggag gacgtgcaga   45120
aaggcagcca tgcactttct aggtttcgat gccgtcttag agtcactggt caccaggtct   45180
gggtcaaacg ggagtctctg gctgtcaaga ctggactggg aggaatcaca tcgcttcttc   45240
accatcagct ttatctgctt tgccttttcc gacttcagct ttctctgcag ggggtatcag   45300
tggggttgac aaagattgac atcttttgt tatcctcatc cctaatcttg ccactgacat   45360
tcttcagtgc ctaggcgatg ctggcattct ccacaaagat gtgggcctgc attttctcat   45420
agcgaaactg aatcaggagg aagggggcatt gcattgactc tgaatcaaat tcagcagcca   45480
cttctcattt tatgcagatc ttgaactagc agctccctaa ggtccgatct ggcctgtttc   45540
cctctgttct tttctctgga ggttttttggc gctttctctg tgttaacatg ggtttggtct   45600
tgtttatggc aagtgcctct ccatggctgg gtgcggtggc tcacgcctgt aatcgcagca   45660
ctttgggagg ccaaggctgg cgaatcacca gaggtcagtt cgagaccagc ctagccaaca   45720
tggcgaaacc ccgtctctac taaaaatata aaaaaattag ccaggtatgg tggcgggcgc   45780
ctgtggtccc agctactcag gaggctgagg caggagaatc gcttgaaccc gggaggcgga   45840
ggttgcagtg agctgaaatt gtgccattgc actccagctt gggtgacaga gtgagactct   45900
gtttaaaaaa aaaaaaagta agtaaataaa taaatgttga tattatgtag ccatgttatg   45960
tagttttgca tagcctttct ctgtcttata gctatgaaag acaatttcca aaacatagcc   46020
tagaatggag aattgaagat aaagtgagaa ctgttgggca tagtaaccta aaaagggatc   46080
ccctctggtg tggaaagatt gttccaacgc aaaagggact gagatccaga gatggcagtt   46140
gtttgagatc tggaatcttc agaagaggta gatcagactt gctcaggaaa taatgggtcc   46200
taccatcaca gcgggtacgg atggggctac aagatgagag aggctggata ggagagtatt   46260
taaggaaaaa aaaagacag aaaaggacca aaggacagtc tgtgagaccc cagagaatgc   46320
attaaacctg aagaatttct gaacaatgac gtctgatatt caggcttccg ttgtttcttt   46380
```

```
ttgtgctgta atcttccgtg ttttctctgc acatagctca gtaaagctct attcaccagt    46440
taacctagag tctgtcttga gataagcagg gagggctgtg acggctgcac aagggcggag    46500
tggtttgtag acctgaaaag gaacttgtaa gagctggcag atcttaacca ggagagggag    46560
cccctttcca cagcctagaa gcttctgaag tcatttaaat ggaactgaat tatatgaagt    46620
caaatgtcag ttggggaaaa agtcaaactt tattatttat ttatttattt gtaattgtgc    46680
gtatacatat atatatatat atatatatat atatatatat atatatatat aattttttt     46740 aaattatgat ctccgtgata gtaccaaatc aaacttttt tggagacaga gtcttgctct     46800
gtcacccagg ctggagtgca gtggcgtgat ctcggctcac tgcaacctcc gcctcccagg    46860
ttcaagcaat tctcctgcct cagcctcctg aagagctggg attacaggcg cgtgccacca    46920
tgcccggcta attttgtat ttttagtaga gatagggttt caccatgttg gccaggctgg     46980
tcttgaactc ctgacctcag gtgatccacc cgccttggcc tcctaaagtg ttggaattac    47040
tggcatgagc gaccacgctg gcccaaaccc tgcttttac tggagagacg aggtagccct     47100
aagttaaaaa aaaaaaaaa aagaccctgt ttcacttctt ttggatatac ccggggtgac     47160
attgctagat cattctgcaa ttcctccttt tttttttttt ttttttttgct gggggtggga   47220 tagagtctca ctcccaggct ggagtgcaat ggtgtgatct tggctcactg caacctccgc    47280
ctcctgggct caaacgactc tcctgcagtg aggagctggg attacaggtg cctgccacca    47340
caacctgcta atttttttt tatttttgt attttagta cagacggggt ttcactatgt       47400
tggccaggct ggtcttgaac tcctgacccc gtgatccgcc cgccacagcc tctcaaagtg    47460
ctgggatgac aggcatgagc ctccgcgccc agtagatcat tctgtaattc tgtgtttaac    47520
ttttttcccc ctaaacttaa ctgaagtgat atttaacttt ctgaggaatc accaaatcaa    47580
aggtgacttt tgagacaaat acaggaagtg gaggtggttt tcctcatgta gatgaagaca    47640
ttctaaaccc agaactgaaa acacacatgg aatcctttta agtatcagga tgccttggtg    47700
gacaaaatgg atacatccaa cttctcaagg agcttaatat tcagtattaa agctgaggtg    47760
agctcaggtg attcacgcct gtaatcccaa cattttggga ggccaaggca ggcggatcac    47820
ttgagcccag gagtttaaga ccagcctggg caacatagtg agaccctcc ccctgcccc      47880 cgtctctaca aaaataaaa aaattacaga cgcatggtgt agtcccagct acttggcagt     47940
caaaggtaga aggactgttt gaacccagga gtgggttgaa gctgcagtga gccttgattg    48000
taccagtaaa ctttagcttg ggaggcagtt gagaccctgt ctcaaaaaaa aaaagaaagg    48060
aagaatttct ctctcccaac ttcccttggt ttctcctcgc ccccggcta aaagtgatt      48120 ggggacctt taaaaaactt cctgctctcc acagaatggg attacagccc cgagatgatc     48180
cataaaagat tttcaggaag aatgaagagt ttagggagtg aaggttctaa aacagtaaat    48240
agagtgtcac aaagaaatcc attcatctct ttgaaggctg ggtatttgga aaaagagaga    48300
aagaaagctt cattcagaga gcgctcgcct gtatttaggg gtgtttggag ggggcggggt    48360
gactatagaa ttagggtaaa gttcagtgtc ttgcaaatca gccctgaaat agccctgatc    48420
cctgcaggcc tgtctggttt cccaaaccct ccactagctt tcaaatttgc attaaaaagc    48480
ttttggcttg ttcattctgt tctttctttc ttttctttct tttatttatt tattttttt    48540 gagacggagt ctggcactgt cacccagact ggagtgcaat ggcgcgatct ccgctcactg    48600
cagcctctac ctcccgggtt caagcaattc tcctgcctca gcctcccgag tagctgggat    48660
tacaggcgcc caccgccaca cctggcttat ttttaatt tttaatagag atggggtttc      48720
tccatgttgg ccaagctgtt ctcaaacttc tgacctggtg atccacctgc ctcagcctcc    48780
```

```
caaagtgctg ggattacagg cgtgagccac tgcgccaggc cctcattctg ttacttcttt    48840 cttcttttt tcattaattt aagttctggg atacacatgc gggatgtgca ggtttgctac    48900
ataggtaaat gcgtgccgtg gtggtttgct gaacctattg acctaggtat aagcctcac    48960 agccattagc tatttgtcct gatgcccttc tgcctcctgc ccattctttg ttatttcttc    49020
atattccaat taatgttcat tttgaggacc tggctctggc caggcaaggt tccagtctgg    49080
agtcaaactg aggaaagtat tacctttcac aaacacttag accacgttgg gaggggagaa    49140
tgattgtcct ccacatgcgt atgggtgtgt tataaacccc aggaaggtaa atactaagca    49200
aaggcgtgca cagataatta ttgcaactga tgattccacg tcaattgtac tgtactgtga    49260
gtaggtttat aggctgccgt gacaggggcc atcacctggg tacgagggtg ctggcttcct    49320
cttgaagacg tgactttaaa attgtgagtt gaatagatgc aaggatattg cccagtgga    49380 ggaactttga ggggagggg cagggtatcc tggttgggag gaaattacat acagaaattg    49440
gggagtggtg acaacattga ctcttccagt aattgtctgg gtgtggtaac tcaggactgt    49500
aatcccagca ctttgggagg ctgagatggg aggattgctt gagcttggga gttccagatc    49560
agcctaggta acacgaggag atctaaaatt gaaaaaaaac gtagctgggt gtggtggctc    49620
attcctataa tcccaacaac tttgactcag gaggctgaag tgggaggatc ccttaaggtc    49680
aggaggttga ggctgaagtg agctagcact ttgggaggcc gaggtatgtg gattacttga    49740
ggccaggagt tcgagaccag gctggctaac atggtgaaac cccatctcta ctaaaaataa    49800
aaaaattagc caggcatggt ggtgcgcgcc tgtaatccca gtgactcggg aggctgaggc    49860
aggtgaatca cttgaccccct ggaggcagag gctgcagtga gccaagatca taccactgca    49920
ctctagcctg gacaaccaga gtgaaactct gtctcaaaaa aacaataata attttaaaaa    49980 aatttttaa ataaaaaaat taacaaatga cccgcacatc tggggtgaag taagacgagg    50040
ctggcagcat agctctgtca cctgtggtta ggattaatta agctcagctt taaaggctgg    50100
atcttggcct cctgggtttt aattttgact tctccacttc tcagccatgt tttgttttgt    50160
tttgtttgct tgaggaggga caaatcaggc cagcattgag cctctttccc ccgtgtgtca    50220
actgagattg ataattacaa gattaaatga tgcttgtctg tgattttagc atctgttcag    50280
cccatcattc atttcaagag tattgactgg gcttcagggt aggttccatg ttagtactgg    50340
ggacgccgtg ggtgggaggg agactgggtc tccaccctcc tagagttata gtctaggcct    50400
gcggttaagc agatttttgt gcaggaatca aacccactac actacctgtc agaaatcaag    50460
ccctgttcca ggcactggga aactcagaat ttaaaggga tgtaccaggt ctctgtcctt    50520
gcggagcatt atcgatcagt agaagagaga aaataaacaa gcaaacacct gagacaattg    50580
taatagcaat aatgtgatat caataaaatg aaacagagca acagaaatag ggtagatggg    50640
ccgggcgcgg tggctcaccc ctgtaatccc agcactttgg gaggccgagg tgggcggatc    50700
acgaggtcag gagatcgaga ccatcctggc taacacggtg aaaccccgtc tctactaaaa    50760
atacaaaaca ttagccgggc gtggtggcgg gcgcccgtag tcccagctac tcgggaggct    50820
gaggcaggag aatggcgtga agccgggagg cggagcttgc agtgagccga gatgcgcca    50880 ctgcactcaa gcctgggcaa cagagtgaga ctgtctcaac aaaaaagaa agaaaagaa    50940 acagagtaga tggtcttaga aatgacaagg aatcccaatg agaggttcta cctgggacaa    51000
aatagaaaaa tggaaatca taataagctc tggaattggg gcagtggtat tgtttatttc    51060
ctagttgtgg caaatctaat gtaaaatatg gacattaaag aaaactgggt ggagaacata    51120
```

```
gagaactttc tgtactttt  gcaacttttc tgtaagtcta aatttattcg aaggccgggc   51180
gcagaggctc ctgcctgtaa tcccaaaacg ttaggaggct gaagcaggta gatcacttga   51240
gcttggtagt ttgagaccag cctgggcaaa aaagtgagac ttcatctcca ttaaaaattt   51300
aaaaaattag ctggctttgc tggtgagcac ctgcaccaga ctggttagcc tgggcagcat   51360
agtgagaccc cgtttctata aataagataa aaatcagctg ggtgccaggc gtgatggctc   51420
atgcctgtaa tcccagtgct cgggaggcc  gaggggggcg gatcacctga ggtcgagagt   51480
ttgagaccag cctgaccaac atggagaaac cccgtctcta ctaaaagtac aaaaattagc   51540
tgggcgtggt ggcacgcgcc tgtaattcca ggtactaggg aggctgaggc aggagaatca   51600
cttgaacctg ggaggcggag gttgcagtga gctgagatca ctccactgcc ccccagcatg   51660
gctacagagc aagactccgt agcgggatat tgcatgcatg taatcccagc tactctggag   51720
actgaggcag gagaatcatt tgaacctggg ggcggaggt  cacagtgagc caagatcatg   51780
ctattccagc ctgggtgaca gagtgagact acctctcaaa aaaaaaaaa  agaaaaagaa   51840
aaagaaaaag aaatgcattt acagaagcta ggaaaatcaa attcagggag gaggctggag   51900
ggcaaagagt gggtgtggcc agactttaat ccattctcca tctgtggggt ggtccctagg   51960
gtataaaaga gctccagggc ccctgccctg cctttcatcc tcaggatggg aagtcctcac   52020
agagttcagt aagtattggc ttcccatggt gtttctgcac ttcccccggg gtcatatgag   52080
cctcacattt aggttgtaag actcccccta aaatctccaa cactgagtcc tctctatttg   52140
tagtcatgac tccgacacct tgattctctg cccctaatac tctttttttt tttttgagac   52200
ggagtttcac tcttgttgcc caggctgcag tgcagtggtg tgatcttggc tcactgcaac   52260
ctctgcctcc cggattcaag caattctcct gcctcagcct cccgagtagc tgggattaca   52320
ggcatgcacc accatgccca gttgattgtt tttgtatttt tagtagaggt ggggtttcac   52380
catgttggcc aggtctcaga ctccaagcct cgagtcatcc gccctcttca gcctcccaaa   52440
gtgctgggtt tacaggtgtg agccaccatt cctggaccgc attattgatt ttttaaaatt   52500
tttggatttt gttcaattag tgattgagtc tcactgtgtt gcccagatgg gcttgtctcc   52560
caggctggag tgcagtggtg agatcgtgac tcacagtagc ctcaacctcc ctcaccccag   52620
cgtcccgtgt agttgggatg gcaggcatac aggaccatgc ttagctaatt tttttttttt   52680
tttgtagggt tggggtctcc caccattgtc taggctggtc atcaacacct gggcacaaac   52740
atcctctcac cccggcctct gagccactgc acccagtagg ttttaggttc attttatttt   52800
ttatttaggt gtccacaaag gcagcttttt cctttcttt  attttttaaa gacacagggt   52860
ctcactctgt tgcccagggt ggagtgcagt ggccagatct tggctctctg caacctctgc   52920
cttccagact caagtgatcc accttcgtct ccagagtagc tgggactata ggtgtgcaca   52980
aacacaccca gctgagtttt aaatcttttg tagagaaggg ggcctcagta tgtttcccag   53040
gctggttttg aagtcctgtg ctcaagcaat ccttctgcct tggcttccca aactgctagg   53100
attacaggta agccaccaca ccgggcctgt ccacgtaatt taaaaggtgc tggacgtgtg   53160
cggtggctca cgtctgtaat cccagcactt tgggaggctg aggtgggcgg atcacgaggt   53220
caggagttcg agaccagcct ggccaatatg gtgaaaccct gtctctacta aaaatacaaa   53280
aattagccag gtgtggtggc aggcgcctgt aatcccagct tctcaggagg ctgaggcagg   53340
agaattgctt gaacccagga ggcggaggct gcagtgagct gatgatcgct ccatggcact   53400
ccagcctggg caacagagca agactaagaa aaaaaagaa  agaaaagaa  aagaaaaca   53460
aagtaatgta aaggtgtta  ttcaggctgg ggacccccaa agtgctggga ttacaggcat   53520
```

```
gagccccagg gcaggcctag gatttgcatt acaaggctct gcattgttcc tgagaactgg    53580
agagagtgct caatctacct ttcgctattg agcaacattc agaagtcagt tttaaatctc    53640
ttatcttctg catagaggat gtgcctgcag tttccaggta ctggacaata cagggagggt    53700
acttctcagt ctgtggcact cagccttgag ggcactttct ggtgccagaa tgaaagtgct    53760
gtcatagctg aggtccaatg actgaggcga gcaccgaaga aacaccatgg gggggagggg    53820 gggcggggg ctccaggagc cactgcaggt aaaagctaaa ccgtggtgct tgttctgcgc    53880
cataaactgg acttcagccc agctttaagg aaatgaccac ggtctctggg ttgtgaggct    53940
gggttccgta gcagctataa tgcttggatt cagggatagc ctgggtcaca ccattgccag    54000
agaagaggca accaatccag accccaaaag cgggttcttg gatctcttgc tggaaagaat    54060
ttcgaggcaa gtcacaacac agcgaaagaa gcaagctgag gcctgggctc aatcctcctg    54120
cttcgtcctc ccaaagtgct gggattacac gcatgatccc ctgtgccctg ccaatatttg    54180
gtaattataa ctggtggtca gcttacaatg tggctatttc cagaccataa gtaccaactc    54240
tataggtgcc ttgtgagtga gtgccttgct acttcaagca gttactttcg tgtgttatta    54300
aaccagaggc ctgctaagcc tctgtgccta gtaaagatta caatttggaa tgtcagcccc    54360
cagctgtcct gtgtgattgg caggttaggt ccttgttgaa ccagaagcaa ctggccagtc    54420
gtacagatgc aactttcgga ccagtagaaa atttctatgt caacctggag acatagggat    54480
tgtacctttc tgataccta ttagtaaata aatagtattt atttataaat tatgtataat    54540
agtatttatc tgaatatatc ccaagcagcc caagtgtgtt ccagacataa cattttatt     54600 tacatttaaa tatcactaag attagagata cacatctaac tcaggttttc aactagtctt    54660
accattgaaa gaactattgt ggcaggacgc agtggcgcac gcctattatc ctagcacttt    54720
gggaggccga ggagggcgga tcacaaggcc aggagttcga gaccagcctg gccagcatgg    54780
tgaaacccca tctctactaa aaatacaaaa aaattagctg ggcatgatgg cacaggcttg    54840
cagtcccagc tactcggtag gctgaggcag gagaactgct tgaacccggc agacggaggt    54900
tgcagtgagc cgagatcgcg ccaccgaact ccagtctggg caacagagca agacgcttgt    54960
cttaaaaaag agagagaaag aactacttgt tctctgtaag ccatgctggt ttagccaaaa    55020
tgctgcagtt gtgtatggcc agggacgttg aggctgcagt gagccgacgg ctgtgttgcc    55080
gctctgcagt ctgggggaca gagcaagaac ctgtctcaaa aaaacaagaa gttagtgaga    55140
cagacatgcc gttctgttac ttttcccctt gctggttcaa agctaggtag ttgccaatta    55200
aatgtaatct tgtagagcaa aaatgttttt catttttga acaggatct cactctattg       55260 cccagcctgg agtgcagttg tgggaactca cagcaacctc cacctcctgg gtttaggcag    55320
ttcttctgca tcagtctccc gagtagctga gactacaccg tgcccagag gcagtggcc       55380 agatcttggc tctctgcaac ctctgccttc cagattcaag tgagccacct ccgcctcctg    55440
agtagctggg actataagta cgtaccacca tacccagtta attttgcat tttttgtaga     55500 taaggggct aagtatgttt cccaggctgg tttcgaagtc ctgtgctcaa gcaatccttc     55560
tgccttggct tcccaaactg ctaggattac aggtgagcca ccacaccggg cctgtccacg    55620
taatttaaaa ggtgctggac gtgtgcggtg gctcacgtct gtaatcccag cactttggga    55680
ggctgaggtg ggcggatcat gaggtcggga gttcgagacc agcctggcca atatggtgaa    55740
accctgtctc tactaaaaat acaaaaatta gccaggtgtg gtggcaggcg cctgtaatcc    55800
cagtttctca ggaggctgag gcaggagaat tgcttgaacc caggaggcgg aggctgcagt    55860
```

```
gagctgatga tcgcgccatg gcactccagc ctgggcaaca gagcaagact aagaaaaaaa   55920
aaagagaaaa agaaaaagaa aacaaagtaa tttaaaaggt gttattcagg ctggggatcc   55980
ccaaagtgct gggattacag gcatgagccc cagggcaggc ctaggatttg cattacaagg   56040
ctctgcattt ttcctgagaa ctggagagaa tgctcaatct acctttcact attgagcaac   56100
attcagaagt cagttttaaa tctcttatct tctgcataga ggatgtgcct gcagtttcca   56160
ggtactggac aatacaggga gggtacttct cagtctgtgg cactcagcct tgagggcact   56220
ttctggtgcc agaatgaaag tgctgtcata gctgaggtcc aatgactgag gcgagcaccg   56280
aaaaaacacc atgggggggga ggggggggcgg ggggctccag gagccactgc aggtaaaagc   56340
taaaccgtgg tgcttgttct gcgccataaa ctggacttca gcccagcttt aaggaaatga   56400
ccagggtctc tgggttgtga ggctgggttc cgtagcagct ataatgcttg gattcaggga   56460
tagcctgggt cacaccattg ccagagaaga ggcaaccaat ccagacccca aaagcgggtt   56520
cttggatctc ttgctggaaa gaatttcgag gcaagtcaca acacaatgaa agaagcaagc   56580
tgaggccggg cgcggtggct cacgcctgta atcccagcac tttgggaggc tgaggtggat   56640
ggatcacctg agatcactat ttttcttttt attttctgag atggagtttc actcttgttg   56700
cccaggctag agtgcaatgg cacgatctcg gctcacagca acctctgcct cccgggttca   56760
agccattctc ctgcctcagc ctccggagta gctgggatta ctggcatgcg ccaccacgcc   56820
cagctaattt tgtattttta gtagagacgg ggtttctcca tgttggtcag actggtctcc   56880
aactcccaac ctcaggtgat ccgcccgtct cggcctcaca aagtgctagg attacaggcg   56940
tgagccaccg cacccagcct gttttctgca tttttagtag agacagagtt tcactatgtt   57000
ggccaggctg gtctcaaact cccgaccttg tgatctgccc gcctcggatt cccaaagtgc   57060
tgggattaca ggcgtgagcc accgcgcccg gccttatttt tctttttttt ttttttgagac   57120 aggatcccac tctattgccc agcctggagt gcagtgcagt gatctcagct cactgcaacc   57180
tctgcctccc gggttcaagc aattctcctg catcagccgc ccaagtagct gagattacag   57240
ccgtgcctgg cttatgtttt gtgtttttag tggagatggg gtgccaccat gctggccagg   57300
ctggtcttaa actcctgacc tcagttgatc ctcccacctc agtctcccaa agtgctggga   57360
ttacaggtgt gagccaccgc gcccagcaag cataagattt tttgacacat ggaggatcac   57420
ttgctggatg tgcactgaga agtaatgtgc ccatttccca gccacactct cccaaaggct   57480
tttacaggcg ctgtccccgt gaggtggtag aacagaatgt cagaattcaa cacattccaa   57540
cactgtcttc tgttgagctg taggaggact gcctgtggag ggacatgggt tctatgctac   57600
cttgcaggtt ttccctgggg cttgtgatca ctgtctcctt ggtgacatgc aatctgggag   57660
tgctttctgg agtctgataa gaacatactg gcacattgcc tgtgacgtgt gggacccagg   57720
cattttcagt gctgaggtga gtccttgatt gtaactgatg gggactggta tcttaactcc   57780
aggttactga agactaggaa tttcttgcct tacagtaaaa ttgcaaagaa gagtagcata   57840
agaggtagat cagaagactg cagaatagat taacaaatga atgcccaaat gaggatgcta   57900
aacttggatt tgcatcaaga agacagatat tggtcgggcg tggtggctca cgcctgtaat   57960
cccagcactt tgggaggctg aggcgggtgg atcatcctgg ctaacacggt gaaacccgt   58020 ctctactaaa aaatacaaa aaattagcc gggcgtggtg gcaggcgcct gtagtcccag   58080
ctgctgggga ggctgaggca ggagaatggc atgaacccag gaggcggagc ttgtagtgag   58140
ccgagatcgt gccactgcac ttcacctggg gcgacagagc gagactctgt ctcaaaaaaa   58200
aaaaggacag gtattaggat agttttgaag cccacttgct cctatcatgg cattgaagca   58260
```

```
tcagtttgct gccaatcact ccttcttctg tgttcataga caggactgtg gaaatgtaca    58320
cttggattct ttcacaggta atgctgagaa atttaaaacc aaaaacggcc gggtgccgtg    58380
gctcctgcct gtaattctag cactttggga ggctgaggcg ggcggatcac aaggtcagga    58440
gttcgagagc agcctggcca atatggtgaa accccatctc cactaaaaat acaaaaatta    58500
gcctggcata gtggcgggcc cctgaagtcc cagctactca ggagactgag tagacgagga    58560
gaatggcttg aacatggggt gcagaggttg cagtgagctg agatcgcacc gctgcactcc    58620
agcctgggca acaagagtga aactctgtct caaaaaaaaa aaaaaatttg aaattaaagt    58680
gtatgattag agtgcatgat tggttctgac tggatgtgta acatgtgcat agccttctca    58740
taaatcaaag gttttatgt gaaacctacc actagtgatg taactgaatt tgtgtaaatg    58800
ctggtgtgtc tgccttttcc tagcaactcc ctgggcagcc tgaggattct ttgaggttat    58860 ttttttcaa gatctggctg ggagcttctg catgagtgct gtgtgaacgt cctccatctg    58920
cagtgtgagg acagcgaacc ctagtgtgag ttaaccacgt aggaagagtt tgaagtcaga    58980
catgacattc agactgaggt cctcaaaact gaggggcatt ttctgtggtt tgaaaggaaa    59040
gtgcacccag ttttggggat gtcaattgtg aatcctcatc ataacccatc ccagtccccc    59100
catcgcattg caccacatgg atgcacccag tggactggcc tttgcttttc tattgtttct    59160
ttttctctcc actgcaatca gctttctcac gttgaatgca ttccatttc taagcgctct    59220 cctaggcaaa aatccctcta atgcaaagca aaatgtctg ttatgcaaca ttgttctgag    59280
accccaggaa ttgcagttaa cttggctcct tagtatgtgc ttcctaaggc gggtggggtg    59340
gctcgcgcct gtagtcccag cactttggga ggcaggcgag gcacttgaaa ccctgtctct    59400
actaaaaata caaaaattag ctggacatgg tggcatgtgc ctgtaatccc agctacttgg    59460
gaggtgcaga caggagcatc gcttgaaccc aggaggcaga ggttgcagtg agccaagata    59520
atggcactgt actgcaacct gggtgacaga gcgagactca aaaaaaaaa aaagtgcttc    59580 ctgtgaaggt ttccttccc ttctgccccc cataccagtc catctattta gtagatgtcc    59640
tggtttctac ccaggatatc atggaccagg ggttctgtct tccagccttg agtacaatgg    59700
tgcgactata gctcactgca gtctcaacct cctgggctca agtgatcatc ctgcctcagc    59760
ctccaagtag ctggtattac agatgcacgt gccccattc ccagagggttc ttaaatttat    59820 gacaaaaacc cagaagcttg gctgaagcag cttgttgggg cccacccaca gattttgttt    59880
ggtgccatag acctggggttg ggatctgggg agccatttt cttagtctca atgtaaatgt    59940
ctaagcattt tcttttttc tttctttttt tttttttgag acagggtttc gctcttgttg    60000
cctaaactgg agtgcagtgg cacaatctcg gctcactgca acctctgcct cctgggttca    60060
agtgattctc ctgcctcagc ctcccaagta gctgggatta caggtgtgca ccaccatgcc    60120
cggctaattt ttttttattt ttttattttt ttattttt gagatggagt cttgctctgt    60180
tgcccaggct ggagtgcagt ggtgtgatct cggatcactg caagctccgc tccttgatt    60240 catgccattc tcctgcctca gcctcccgac tagctgggac tacaggtgcc cgccaccacg    60300
cccagctaat ttttttgtat tttttagtaga cacggggttt cactgtgtta gccagggtgg    60360
tctcggtctc ctgatctcgt gatctgcctg cctcggcctc ccaaagtgct gggattacag    60420
gcttgagtca ctgcccctgg ccaattttt gtattttag tagaaatgga gtttcaccat    60480
gtttcctgcc tatctctcta tgtatttaga cagggtctca ctatgttgcc caggttggtc    60540
tcaaactcct ggactcaagc aatcctcctg cctccaccctt ccaaagtgct gggactacag    60600
```

```
gcttgagcca tcctgcctga ccatttgaga gtttttttttt tttgagatgg agtctctctc   60660
tgtcacccat gctgtagtgc agtagtgtga tcttgcctca ctgcgacctc tgcctcccgg   60720
gttcaagcaa ttctcctgcc tcagcatccc cagtagctgg gattacaggc gcccgccact   60780
acacccagct aattttttgta ttttttagtag agacagggtt tcaccatgtt ggccaggctg   60840
gtctcgaact cctgacctca ggtggtctgc ccacctccgc ctcgcaaagt gctgggataa   60900
gaggcgtgag ccaccgtgcc tgtcttcaac aatgatttct aattgcattt tatggtggtg   60960
attgaacata atgtactttg gtccttctcc attgtatgcc tcgtgtatta tgtgtctcat   61020
aacgtctgtc ccgtcctatg ctatgtgtgc atttgaatgt tggggagggt tcagtagatg   61080
tccattgagt tggtttgcaa acttatttga aacttctact tacttctgcc taattctgct   61140
tattattgag agtggactgc tctgggatgc cttttgtttg cactctgatt tcagatggac   61200
cctgagaatg ctcaagcccc aaaccctcct tgggaagtga agctcaggct gtgatttcaa   61260 gccaggggc gttttctat aactggatga aaagcacctc cagagcttga agctcacagt   61320
ttgagagcaa tcgtctaagg aagttgatgg caatgttaat agttttttaa acaagcatga   61380
aatcagattc ctgtgtttac ttctggatgc tgttgatcca ggaaatgtac ttagaaaatt   61440
cattttaacg gaaatagtca taagcgtctt ggtaattttca tgaagctaca gtgagtaaat   61500
tgcctgagaa tttccctgcc tgaaaggtct tcaggagtgt aattttttttt taatatagct   61560 tatttaatac aaatagagat gcggtctcac tcttgcctag actggtgtgc agtgtcatgt   61620
tcacagctca ctgcagcctc tcaacctccg gggctcaagc atcctcctgc ctcagcctcc   61680
caaagtgctg gaattacagg tgtcagccac cactccctac tcatacttgt atatttctct   61740
ttaaattctg ttgaggtttt atggcctagc ctgtggtcta tcctggagaa tatttgtgtg   61800
catgacaatg tgtatatata tatatatata tatattttttt tttttttttc tttttttga   61860 gatggagttt cactcttgtt gcccagctg gagtacagtg catgaatct cagctcactg   61920 caacctccgc ctcccgggtt caagcgattt tcctgcctca gcctcccgag tagccgggat   61980
taccctccac cacacccggc taattttttgt attttttagta gaggtggggt ttcgccatat   62040
tgaccaaggt ggtcttgaac tcctgacctc aggagtcccg cctcggcctc tcaaagtgct   62100
gagattacag gcgtgagcta ccctgcccag gctgaccatg tatattccta attttttgtac   62160 ttttttttttt ttgagacgga gattcactct tgtggcccaa gctggagtgc aatggcatga   62220
tctcggctca ctgcaacctc tgcctcctgg gttcaagcaa ttctcctgcc tcggcctccc   62280
gagtagctgg gattacaggt gtgcaccacc acgcctgact gacaatatat attcttaaac   62340
agctcagatt ccatttgga tcctcccatc aggactggaa cttaggtgta ctggaactta   62400
ggtgaacact tggctcaaaa ttcattgctg ttctctataa atctagccag ttctcttggt   62460
taaatttaag gtatgtatag tagtcgctgc ttttttctttc ggggacaaa actcaggagg   62520 attgcttctt gattcataag ggcaacctgt tgagattttc acgcaaggaa cccgagatgt   62580
tcatttaatg ggcttataat ttgggattcc agaacacatg caaacagggc aaatgaatgt   62640
ttggctgtat cttttatttttt gtgttcattt cagcctggtc aaggttttag aatccaagga   62700
aaccaataaa cacccagagt gctggagcaa gactgtctcc tgctgtgacc tcaagatgg   62760 aagcagtttc tgttgtctga aaggaaagaa agtgcttcct ttttgagggt tactgtttga   62820
gaaaagcaac cttgaggttg atgctgatgt ttgtaacaca cctgcagagt atacttataa   62880
tcagacttgg gtgatgtgag gttttgtttt tactccaaga tgagggtctc cacccaggct   62940
ggaatgcagt tgcccttcca acctagaact cctgggatga actggtcctc tatgcctcag   63000
```

```
cctgccgagt agctgggact ataatatagg ggtgtgccgc catatttggt agattttca    63060 atttttgta gagatggggc ctcaccctg ccaggatggt ctcaactcct gagctcaagc    63120
aatcctacag gtgtgagcca ccgtgcccat tttaaagata gttgacatga tcaagcatag    63180
tgggacacac agccccagct actgcagagg ctggggtggg agagtctctt gatttcaatg    63240
ctataccgtg cactaatgac acctttgaat agccactgca ctccagcctg gccaacata    63300 gcaagatccc atctcttaaa aaaaaataca ttacatggca cctggttcca gagacaccat    63360
ttgtgttggt caaacaatgg cctcctataa atttagttta atgaatccaa accatgtttc    63420
cttcattaag agagtaaata agcctccaag tctatccagt cttttttgaga cagagcttgg   63480 ctcttgtcac tcaggctaga gtgcaatggt gcaatctcag ctcactgcaa cctctgcctc    63540
ctgagttcaa ggagttctct cacctcagcc tcccaagtag ctagaatgac aggcgcctgc    63600
caccatgacc agctaatttt tgtgttttta ctagagatgg ggtttcacca tgtcggtcag    63660
gctggtctcg aactcctgac ctccgtgatc cacccacctc agcctcccaa agtgccggga    63720
ttacagacga gagccaccac gcccggcctg tccagtcttg ttctgcagtc cccaatgggg    63780 atttttttt tcctgttcat ttgtcttttt attttaatct acttgtccct gacactgaaa    63840
attttccctt cctaacagct taccatcatt tctcagaata gacctgcttc ctctgtgaga    63900
agcttatagt tgattcaacc ctcaaccact aatgccaaca ccctagtga gttcttttga    63960 ctacagctgg accatttatc ctgtttcctg tgggtagcgg ttccaatgta ccattccaac    64020
aggcaaaacc tcgcctctga atacaggttg cttggcaaga tctaaaatgt ttgctgtgcc    64080
taatataaac tattgtaaag aaaatccatc tcaatcacag tgacaaatgt cacatgagac    64140
aaaaccacag atattttcgc aaaaatagg tcctttagaa ccctagaagg gtctctctag    64200
taacaggtgg gatgttcagc agctcttgtt gttgccacag tgagcgatgc ctgttcgtcc    64260
agcccttaac acctcttact ccatggaagt tctgcctgca ctgctttata gaacacctct    64320
tgggttgagg tagagttgga ggggacctca gtgtcccttg ctgatgggat gtgcactgct    64380
tagcaagcgc acggaggtgg agtgcatggg ctctgagttt ttattgggta aatgcagccg    64440
aaatgtagtg tgcatgaaca ggtcaaaaaa ttgcacattt gatttaattt ttaaatttta    64500
gagatggggg tctcactgtg tcacccagac taaactgggc tgtgctccta tgcgtaccct    64560
agtagctggg acttcaggtg aatattaacc catgcatagg caaggagaga ggaaggctct    64620
gacagtctgt gatctcccct cactgcaacc tccaccctct ggactgggaa cgtcagggca    64680
ctgcaccgat gcaggcagga tgagccgagg ggaaaggaga gccaggcatc actggctggg    64740
gacattttgg gtttgatctg gatggagcag gtgtctcctg gagagagagc ccctgggatt    64800
ttcactctgc tccctggctg tcttagtcat ggaatctgac aacagagact cctgcccagg    64860
gccacttcat ttggtttctg gaccccagtg gtccttcctg cctggactta ggatcttttg    64920
gggaagtttg ggatctggca gggcatctgc ataatccata gaaatccctg agagtcactt    64980
cccttggctg acatctccat gttcctaccc attaccttcc aaaggagacc cttaactgaa    65040
ttaccaaagg gggcttccca gagcagggaa acccggttaa ctttctattt caggtcaaca    65100
gtatacttga gatgtacttg aactagaaat gattggttgt ttaggtgtgg gcatttgttt    65160
ttcctaactt agtctccaag aaaaaaaatt attgaggttt tacagcctag cctgtggtct    65220
atcctgaaga atgttcgtgt gtgtgacaat gtacattctt tttttccccc cagctctgtc    65280
aaatcttact gaggagcttt tacggcctag cctgtggtct gtcctggagg gtatttgtgt    65340
```

```
gtacaacaat gtatattctt aaacattatc ttagattcca ttttggatgt tcccatcagg    65400
actgtgtgtt tctgtgctgg aactcaagtg aacactggct caacatcctt agaaatccag    65460
cccaattctc ttggttaaag ataaggtatg tgtggtaggc attgcttttt ctctttgggg    65520
acaaaactca ggaggattgc cccttgatga acaaggctaa cctgctaagc ctttgaagca    65580
aggaactgga gatggtcctt tcaggggttt atgttctgga ttccataaaa catgcaaaca    65640
ggggcaatga atgcaccttt tttatttttta ttttattttt tttttgagat ggagtcttac    65700
tcttgccagt ctggagtgca gtggcacgat ctcggctcac tgcaacttct gcctcctggt    65760
tcaagtaatt cccctgcctc agcctcccga gtagctggga ctacaggtac atgccaccac    65820
aggcggcaaa tggttgtatt tttagtagag acggagtttc accatgttgg ccaggatggt    65880
cgtggtctct tgaccagcct cccaaagtgt gggattcca ggcgtgagcc accgcgcctg     65940
gccaatgaat gcatctttat ttttgtgttc attttaatct ggtaaggtaa attccaacaa    66000 aaacccaga gttttggagt gagaagatct catgcagtca ttctccaaaa gaaagcactt     66060
tctgttgtct gaaagcagag tgccttcttt tggagcgtta ctgtttgaga aaaaccacgt    66120
tgaagttgat gctgatcttg gtaacacatt tgcagagcgt gcttatcatc agacttgcat    66180
gatgttgggg ttctgttttt gtttagtttt tttgcaacac agggtctctt gcccaggctg    66240
gagtgcggtg acacttccaa cctagacctc ttgggctcag ttggtccctg cccccacccc    66300 ctccccttt ttttctctt gagacagtct ctctctgtgg cccaggctgg agtgcagtgg     66360
tatgttctct gctcactgca acctctgcct cccgagtagc tggtattaca ggcacatgcc    66420
accacgcctg gctaattttt gtattttag cagagacgga gtttcatcat gatggccaga    66480
ttagtcttga actcctgacc ttaggtgatc cacctgcctc ggcctcgcaa agtgctggga    66540
ttacaggcat gagccactgt gcctggccca caacgtatat tcttaaatat catcttagat    66600
tccattttgg ttgctcccat cgggactgtg tgtccctgtg ctggaactca agtgaacaca    66660
tggctcaaaa tccattgctg ttctctagaa atccagccca attctcttgg ttaaatataa    66720
ggtatgtgtg gtaggctttg cttttttctct ttggagacaa tactcaggag ggttgcccct    66780
tcgtgaacaa ggctaacctg ctgagccttt gaagcaagga actggagatg gtccttttag    66840
gggtttatgt tctggattcc agaaaacatg caaacaggga caatgaatgc atcttttattt    66900 ttgtgtccat tttaacctgg taaggaaaat tccaacaaaa acccagagtt ttggagcgag    66960
aagatctcat gcagtcattc tccaaagggg agcactttct gtttgaaaga aaacaaagtg    67020 cctccttta gagtgttact gtttgagaaa aaccacgttg aagttgatgc tgatcttggt     67080
aacgcatttg cagagcgtgc ttatcatcag acttgcatga tgttggggtt ctgttttgt     67140 ttagtttttt tgcaacacag ggtttctgtt gcccgggcag gagtgcggtg gcgcttccaa    67200
cctagacctc ttaggctagt tggtccccc tacttttttt gttgttttg ttcttgagac      67260 agagtctcac tatgtgggcc aggcgggcag gcagtgacac attctctgct cactgcaacc    67320
tcggcctccc aagtagctgg tattataggc acgtgccacc acgcctggct aattttttgta   67380 tttttagcag agatggagtt tcaccacatt ggccaggtta gtcttgaact cctgacctca    67440
ggtgatctgc ccgcctctgc tttccaaagt ggtgggatta caggcatgag ccaccctgct    67500
cggactgcag ggtgtttttt tttttttttt taattattat ttgtattttt ttgtgctgcc    67560
aaagcaagca cttgtgtgta ggaatttgt tgtttgttt gtttgtttgt ttgagatgga      67620
gtctcattct tgtcgcccag gctggagtgc agtggcatga tctcggctca ctgcaaccta    67680
cgccttccgg gttcaagcga ttctcctgcc tcagcctcct gagtagctgg gatttcaggt    67740
```

```
gcatgccgcc accccggcta attttttgtcc ttttggtaga atcggggttt tgccatgttg    67800
gtccggctgg tctcaaactc ctgacctcaa ctaatccacc tgcctcggcc tcccaaactg    67860
ctgggattac aggcatgagc caccgcaccc ggtgaggagt tatttttaat gtgagcaaac    67920
agtatattct tttttttttt tttcatagac agggtctcaa caatatatga tgtatattta    67980
atcatatagt cttatcatgt atataatgta gtcatatgta caccaaaccc tgttctacac    68040
acggagaata ctcttgtatc actttgggta tttatttact tgtttctttc tgtgtttttc    68100
ttgtttgttt gtttgttttg ttttgagaca aggtctagct ttatcaccca ggctggagtg    68160
cagtggtgcc atgtcgactt actgcaacct ccacctgcca cctcagcctc ctgagtactt    68220
gtctacaggt gcgcaccacc acccagct aacttttcta ttttttgtgc ataaggtttc    68280
accatattac ccatgctggt tgagctcgaa ctcctgagct caagtgatcc tcctgccttg    68340
ccctctttaa gtgctgggtt tattggtgtg agccaccacg ccccacccat acttgtgtat    68400
ttctgtattt attgaggagc ttatacagca taccctgtgg tctatcctgc aggatgtttg    68460
tgtgtgagac agtgtatatt cttgaacata gtagattcca ttttggatgc tcccatcggg    68520
actgtgtgtc cctgtgctgg aactcgagtg aacacttggc tcaaaatcca ttgctgttct    68580
ctagaaatcc agctcaattc tcatggttaa atataaggta tatgtggtag gcattgctttt  68640
ttctctttgg ggacagaact caggaggatt gccccttgat gaacaaggct aacctgctga    68700
ttctttgaag caaaggactg gagatggtcc ttttaggggt ttatgttctg gattccagaa    68760
aacatgcaaa cagggccaat aaatgcatct ttttgttttg ttttgttttg ttttttgagat   68820
ggagtctcgt tctgtcaccc aggctggagt gcagtggcac aatcttggct cactgcaagc    68880
tcagcctcct gggttcacgc cattctcctg cctcagcttt ccaagtagct ggggctacag    68940
gtgcccacca ccacgctagg ctaattttt gtatttttag tagaggcggg gtttcaccct     69000
gttagccagg atggtcttga tctcctgacc tcgtgatctg cccgcctcgg cctcccaaag    69060
tgctgggatt acaggcatga gccactgcgc ccggccccaa taaatgcatc tttattttg    69120
tgtccattta aacctggtca aggaagattc ccacaaaaaa tccacggtgc tggagcaaga    69180
ggatctcagg ctgtgaccct ctaaagggaa gcgctttctg tggtcagaaa gaaaagcaag    69240
tgcttccttt tagagggtta ccgtttggga aaagcaatgt tgaagttgat gctgatcttg    69300
gtaaaatatt tgcagagcgt gcttatcatc agacttggat gatggtgggg ttttgctttt    69360
gttttgttgt attccaagac aaggtccctg ttgcccaggc tggagtgcgg tgacacttca    69420
acctacattt cttgggctcc ggtcgttttt gtttgtttgt ttgtttgttt gacagggagt    69480
ctcactgtgt gtctcagcaa tgcagtggca ctatcttggc tcactgaaac ctcagcctcc    69540
tgagtagctg ggatcacagg tgcgtgcaac cacgcccatc taattttgt attttttgca    69600
ttttcagtag agacggggtt tcaccgtgtt agccaggatg gtctcgatct tctaacctcg    69660
tgatccgccc gcctcggcct cccaaagtgc tgggattata ggcgtgagcc accgcgcccg    69720
gccgagaaac taatctttg agatgaactc tgagatgtgg attttagctt gtttgcagcc    69780
accaccactc tagttttgga agattttcat caccccgaag aggcttatac tcatttgcag    69840
tcagtaccca cccacctctt ccaccagac cgtggcaacg actccccatc tctctagctc    69900
tggatctgcc tcttgtaggc cggtcacgta gaccaatctt gtatgggtgt ccagttgagg    69960
ataatggggtt ggtcctggtt gtctgcaatg tgaatcttac cactgaaggg tggtccctgg    70020
agggaagcag gaggctggga gaactgggcg gaacatcctg tgggaatgga gtggggcggg    70080
```

```
cagaccctga tgtctgggaa gctcacaagg gtggaagacc ccatcttcct ccctgagaac   70140
tgcaaggtga ccctcctggg gcactggaag gagtgaaggc ctctgggctg ggaacgtcag   70200
ggcactgcac cgatgcaggc aggatgagcc gaggggaaag gagaagcagg catcattctc   70260
tggggacatt ttgggtttga tctggatgga gcaggtgtct tctgggagag agagcccctg   70320
ggattttcac tctgctccct ggctgtctta gtcatggaat ctgacaacag agactcctgc   70380
ccagggccac ttcatttggt ttctggagcc cagtggtcct tcctgcctgg acttgggatc   70440
ttttggggaa gtttgggatc tggctgggcg tctgcataat ccatagaaat ccctgagagt   70500
cacttccctt ggctgacatc tccatgttcc ttacccatta ccttccaaag gagacccctta  70560 tctgaattac caaaggggggc ttcccagagc agggaaacct ggttaaattt gtatttcaga  70620
ttaacagtat acttgagatg tacttgaagt agaaatgatt ggctgtgggt gtcggcattt   70680
gttttttcta attttaaata tgggaccatc atgaatttgg gtgtcacttt gtgcagggga   70740
cgtgggaatc gctgtcattt tttttttttt taacatatg ctgccagaga aggcacttag   70800
gtggagaaat tactcttcgt gtgagcattc agtatataga acttccttt ctgggggcag    70860 tgtcttatat atgatacaca ttttatcata tcatcttcta tagataatat aatgattaac   70920
acaaaacact cttctacaca cacagaatac tcttgtatca ctttgggttt ttttttccttc  70980 gtgtgtgtgt gtgtgtgtgt gtgtgtgtgt gtgtgtgtgt gttatgagac aaggtctggc   71040
tctgtcaccc aggctgcagt gcagtgttgc agtcttggcc catgccccac cgcagcctct   71100
ggaatagctg tctgcaggcc aggcacggta gctcaggcat gtcgtctcag cactcttgga   71160
gaccaaagca ggctaatcac ctggagtcag gagtttgaga ccagcctggc caagatggtg   71220
aaacctcatt tctactaaaa gtacaaaaat tagccgggcg cggtggctca cgcctgtaat   71280
cccagctctt agggaggcag aggcaggagg atagcttgag cccaggagtt tgagacctgc   71340 ctggcaata cagtgagacc ctgttctcca caaaagaaa agaaaaaaa gaaaaaaaa      71400 ttttaaaaat gcaaaattag gtgggcatcg tggcacgtgc ctgtaatccc aggtacccca   71460
gaggctgaga caggagaatt gctggaaacc tggaggcaga gcttgcagtg agctgagatc   71520
acggccctgc actacagcct gggcaacaaa gtgagacttg tttcaaaaaa aaaaaaaaaa  71580
tttattgagg agcttttatg gcctagcctg tgttctatcc tggagaatgt gtgtacaaca   71640
gtgtatattc ttaaacatca tcttagattc catttggat gcttgcatgg ggactgtgtg    71700
tccctgtact gggacttatg tgaacacttg gcttcaaatc cattgctgtt ctctagaaat   71760
ccagcccaat tctcatggtt aaatataagg tatgtgtggt aggcattgct ttttctcttt   71820
ggggacagaa ctcaggagga ttgtctcttg atgaacaagg ctaacctgct gagcctttga   71880
agcaaggaac tggagatggt ccttttaggg gtttatattc tggattccag aaaacatgca   71940
gagagagtca ataaatgtat ctttatttt gtgtccattt taaccaggtg aggaaaattc    72000
cgtcaaaaaa cccagacttt tggagcgaga agatctcatg cagtcattct ccaaaagaaa  72060
gcactttctg ttgtctgaaa gcagagtgcc ttcttttgga gcgttactgt ttgagaaaaa   72120
ccacgttgaa gttgatgctg atcttggtaa cacatttgca gagcgtgctt atcatcagac   72180
ttgcatgatg ttggggttct gtttttgttt agttgttttg catcatgggg tctctgttgc    72240
ccaggctgga gtgcggtggc gcttccaacc tagatctctt gggctcaagt ggtcccgtgc   72300
ttgctttttt ttttttttctt gaaacagagt ctctgtctct ggcccaggct tgagcgcagt  72360
ggcatgttat ctgctcactg caacctctcc tcccaagtag atgggattac aggtgcacgt   72420
gccacgacgc ctggctaata tttgcatttt tagcagagat gcagtttcat catgatggcc   72480
```

```
aggttagtct ccaactcctg acctcaggtg atccgcctgc ctcagcctcc caaaatgctg    72540
agattatagg tgtaagccac ccagcctagc ctccaatttt ttttaatgtg tgctgccaat    72600
gcaagcacat atgtgtagga attattttc atgtgagcac atagtatatg gaacttaatt    72660
tttattgatg tacggtctca aaatatata ttttatcata ttcttattat acatgtaaca    72720
tagtcatata cacacaaaac actcttctat acacagagaa tactctcgta tcactttggg    72780
taattttttg tttgtgtgtg tatgttttg tttttttttt agataaggtc tgggtctgtc    72840
acccaggcta gagtgcagtg gtgccatctc agcttattgc aacctccacc tgccacttca    72900
gcctcttgag tagctgtcta caggcgcaca ccaccacgcc cggctaactt ttctgttttc    72960
tctacacatg aggtatcacc atgttgccca ggctggtctc aaactcttga actcaagtga    73020
tactcctgcc tcagcctcct aaagggctgg gtttagaggt gtgagccacc acacctcacc    73080
tgtacctgtg tgtttctgct catttattg aggagctttt acagcctggc ctgtggtctc    73140
tcctggaggg tgtttgtgtg tgtgacaatg catattcttc aacatcgtag attccatttt    73200
ggatgccccc gtcgggactg tgtgtcactg tactggaact cgagtgaaca cttagctcaa    73260
aatctattgc tgttctctag aatccagccc aattctcatg gttaaatata aggtatgtat    73320
agtcggcatt gcttttgaa acaaggaact ggagatggcc ctgataggg tttatgttct    73380 ggattccaga aatcatgcaa acagggccaa taaatgcatc tttattttg tgtccatttt    73440 aacctggtca aggaaaattc caacaaaaaa tcaatggtgc tggagcaaga agatctcagc    73500
ctgtgaccct ctagagggaa gcgctttctg ttgtctgaaa gaaaagaaag tgcatctttt    73560
tagaggatta cagtttgaga aaagcaacgt taacgttcat gctgatctcg gcaatacatt    73620
tgcagagcgt gcttatcatc agacttggat gagggtgggc ttttgttcct ggtttgtttg    73680
ttttctaaga cggggtctct tttgcccagg ctggagagca gtggcacttc caacctagct    73740
ctcttgggct caggtggtcc tctttgcagg gtcacgatct ctgctcacta caatctcccc    73800
ttcccgggtt gaagtggttc tcccatctca gtctcctgtg ttgctgggag tacaggccca    73860
tgccaccacg cccggctaat ttttgtattt ttagcagaga tggggtttca ccgtgttgac    73920
caggatggtc tccatctcct gacctcgtaa tccacctgcc tcggcctccc aaagtgctgg    73980
gtttacagtc atgaaccact gcacccggcc tttgatctta attttcaata tgagacccat    74040
catgaatttg gcatcacct ctgcacaggg gccatggtga tctctgtcac tccattcatt    74100
tcttatgtgt ggagcaaaca tttatgtgta ggagtaattc tttatgtgag catacagtat    74160
atggaacttt ctttttttt gagatagggt ctggaaaata aatgatgtac agccaggcgc    74220
atgagtatat gagcagtttt tgtgtgtata cgacatgagc ggtggctcat gcctgcaata    74280
tcaacacttt ggcaggttga ggcgagtgga tcacttgagg tcaggagttt gagaccagcc    74340
tgaccaacat ggtgaaaccc tgtctctact aaaaatacaa aaaattagcc agctatggtg    74400
gcgcacgcct gtattcccat ctgctgggga agttgaggga ggagaatcac ttgaacggac    74460
agatggaggt tgcagtgagc caagatcacg ccaccacact ccagcctggg cgagagaata    74520
agactgtctc aaaaaaaaaa tatatatata catatatatt tatatagaga gagagactct    74580
gtctcaaaaa aaaaaatata tatatgggtg tgtttgtgtg tatatatata ttatatatga    74640
tgtatatttc atcatatagc catatatata attatataca caaaaaatac tcttctacac    74700
acagagatga ctgatatcac tttggggtgg ttttgcttg tgtgttcttt taaatttttt    74760
tttgcaacaa gatctggctc agtcgcccag gttggagtgc agtgtttcag tcttggctca    74820
```

```
ctgcaacctt cgcctcccac cccagcctcc tgaattagtg tctacaggca tgtaccacca   74880
cacctggcct acatttgtat ttttttacag acagggtttc accgtgttgt acacgctggt   74940
cttgagctcc tgagctcaag tgaatctcct gccttggcct cctgatgtgc tgggattaga   75000
ggtatgagcc accacaccca actggtactt gtgtattcct gttcaaattt tattgaggag   75060
cttttaccac ctagcctgtg gtctatcctg gaggatgttt gtgtgtgcga caatgtatat   75120
agttcaacat cttagatcac attttggatg tttccaatgg gactgtgtgt ctccgcactg   75180
gaactcaaat gaacacttgg ctcagaatcc atttgctgtt ctctggaaat ccagtccaat   75240
tctcttggtt aagtataagg tatgtctagt aggcattgct ttttctgttt gagaacaaaa   75300
ctcgggagga ttgtcccttg atgaacaagg ctaacctgct gagcctttga agcaaggaac   75360
tggagatggt ccttttcagg cgttttattc tggattccag aaaacatgca aacagggcca   75420
ctaaatgcat ctttattttt ctgtccattt aaacctggtc aaagaaaatt ccaacacgaa   75480
acccagagtg ctggagcaag aagatctcaa gctatgagtc tacaaaggaa agcgctttct   75540
gttgtcagaa agaagagaaa gcgcttccct tttgagggtt acggtttgag aaaagcagtg   75600
ttgaagttga tgctgatctt ggtaatacat ttgcagagca tgcttatcat cagacttgga   75660
tgatagcggg gttatgtttt ggttttgtgt ttttctaaga cagggtctcc gttgcccagg   75720
ctggagtgcg gtggcacttc caacctagct ctcttgggct caagtgatcc tcttttatt   75780 tatttatgta ttcattttg agatggagcc tggctctgtc acccaggctg gagtagagtg   75840
ggatgatctc cactcattgc atcctctgcc tcccaggttc agaaattct cccacctccg   75900 tgtcactagt agctgggatt acaaatgctc accactatga cctgccagtt tttgtacttt   75960
tggcacagac ggggtttcac catgtttgcg gggctggtct caactcctga cctcaagtga   76020
tctgcctcct tggcctccca cagtgctggg gattatagat ataagccacc gtgcccggcc   76080
cattcctgtc tttttaattt aatctgctcg tccctgacat cgaaaatttt tcttgcttaa   76140
cagcttccac ttatttctcg gaatagacct ttttctgcag gaagggtgta gttgattcaa   76200
ccctcaccca ctcatgccaa ccgtagtgag tgctgtgact gcagctgcac tgtttatcct   76260
gttttctgca ggtaattttt ccagtgtacc attccaacct gcaaaacctc acatttaaat   76320
gcaaatttct tggtaagctg tgaaatgttg gctgtggcta atatgagaaa caagctatta   76380
tagacaagat gaatctcagt tgcagtgata aatgtcacat gggacaaaac cacagatact   76440
ttcacaaaaa ccttgaggac cctagaaggg cctccctagt aacaggtggg atgcgcatcc   76500
gctcttgttg ccatagtgag tgatgcctgt tcgtccagcc ctcaacacct ttcactccgt   76560
ggaagttatg cctgcactgg tttacagaac ctcccttgac ttgacttgag gtagagttga   76620
agggaacctc agtgtccctt gcagatggga tgtgcattgc ttcgcaagag cacagaggtg   76680
gagtgcatgg gctttgagtt tttattgggt aaatgaagct gaaatacagg gtgtatgacc   76740
acgttatcaa cgcacacttg atttaggttt tgtattttag acacggggt gtgagctgcc   76800 aaagcaagga cttatgtgta ggaattattc ttttctgtgag catacagtat atggaacttt   76860
cttttctttg agacagggtc tcaaaaatat atgatgtatg ccaggtgcg gtggatcacg   76920 cctgtaatcc cagcagtttg ggaggccgag gcggtggat aacctgagat caggaggcg   76980 agaccagact ggccaacatg gtgaaaccat gtctctgcta aaaatacaaa aaattagcca   77040
gggctggtgg cgcacgcctg tagtctcagc tactccggag ggtgaggcag gagactatca   77100
ctttgagtgt gtgtctttgt gtgtgtgtgt gtgtgtgtgt gtgtgtgtgt atgtgtttct   77160 agttttttaca agacacagcc tgactatatc accgaggctg gagtgcagtg gtgcaatgtt   77220
```

```
ggctcactgc aacctccacc tgccaccgca gcctcctgaa ttagtgtcta caggtatgca   77280
ccaccacacc tggctcactt ttgtattttt tgtacagatg aagcttcacc atgttgccca   77340
ggcttgtctg gaactcttga gctcaagtga tcctctcact tcggcgtcct gaagtgctgg   77400
ggttagagat gtgagccacc gcacccaaca ggtacttgtg tatttttta ttgaggagct    77460 tttacagcgt agcctgtggt ctctcctgga ggatgtttgt gtgtgcgaca atgtacattc   77520
ttcaacatct tagattccat tttggatgcc cccatgggta ctacatgtgc ctatactgga   77580
actcaagtga acacttggct caaaatccat tgctgttctc tagaaattca gttcgattct   77640
cttggttaaa gataaggtat gagtgtagg cattgctttt tctctttggg ggcaaaactc    77700
aggaggattg ccccttgatg aacaaggcta acctgctgag cctttgaaag aaggaactgg   77760
agatggtcct tttaggggt ttatattctg gattccagaa aacatgcaaa cagggccagg    77820
aaaaatgcat ctttattttt gtgtccattt aaacctggtc aaggaaaatt ccaacaataa   77880
acccagagtg ctggagcaag aagatctcag gctgtgaccc tccagaggga agtactttct   77940
gttgtctgag agaaaagaaa gtgcttccct ttggactgtt tcggtttgag taaagcagcg   78000
ttgaagttga tgctgatctt ggtaatacat ttgcagagca cgctcatcat cagactcgga   78060
tgatgttggg gttctgattt tgttttctc caagacaggg tctctgttgc ccaggctgga    78120
gtgcagtggc agttccaacc tagctctcct gggcccaaga gaccctctat ttatttattt   78180
atttatttat ttatttattt atttatttat tcattcattc atttagagat ggaatctggc   78240
tctgtgaccc aggctggagt gcagtaggac aatctccact cactgcaacc tccatctccc   78300
aggttccagc agttctgcca cctcagcctc ccatgtagct gggattacag gcgcccacca   78360
ccatgtcatg ctaatttttg tattttagc agagatgggg ttacaccatg tttgctgggc    78420
tgttctcaac tcctgacttc aagtgatttg cctccctggc ttcccaaagt gctggtatta   78480
caggcgtgag ccactgtgtc cggcctcaag tggtcttcct gagtcagcct cccaagtagt   78540
tgggattaca tggggcgtga cacaacactt ggttcagctt ttaattttg gtagagatgg     78600 ggtctctgtt gctcaggacg gtctcaactc ctgagctcaa gcgatcctac aggtgtgagc   78660
caccttgtcc tgatgaccca tttcaaagat agttgacttg gccaggcatc atggggcaca   78720
cagtcccagt tactgcaggg gccggggcgg gagggtgctt tgattttaag gctataccgt   78780
gcacagatcc cacctttgaa tagccactgc actccagcct gggccaacat agcaagatcc   78840
catttcttta aaaacagatt acatagcacc tggtcccaca gatttcattt gggttggtca   78900
tgtcatacaa tggcctccca tcaatttagt ataatcaatc caaaccatgg ttccttcatt   78960
aagagagtgg gtaatcctcc aagtccatcc agtctattct gtaatcccca gtgggtgtcc   79020
gtattgatac aatttctttt tgttcctgtt cactcgtgtc tttttagtgt aatctgcttg   79080
tccgtaacac tgaaatttgt ttttccccaa catcttgcca tcatttctcg gaatagacct   79140
gctttctctg caggaagggt gtagttgatt caaccctcac ccactaatgc aaccccagt    79200 gagttctttg actgtagctg ccatgtttat cctattttct ttgggtaacg attccaaggt   79260
accattccaa tgggcttaaa ccttgcatct aaatgccagt tacttgctaa gatgtcaaat   79320
gtgtcttata ttagctgtgg ctaatataag aaactgttgt agacaagatg aatctcagtc   79380
acagtgataa atgtagcatg caacaaaacc agttgttttc acaaaaatct tgaggaccct   79440
agaaggggct ccctcgtaac aggtggaatg cacagcagct cttcttgttg ccatagtgag   79500
cgatgcatgt tcttccagtc ctcaacacct tttatttatt tatttattta tttatttatt   79560
```

```
ttattattat tattttttt tgagacagag tctcgctctg tcacccaggc tggagtgcaa      79620
tggtgtgatc tcagctcact gcaaccactg cctcccgggt tcaagcgatt ctcttgcctc      79680
agcctcacgt gtcgctagga ctacaaccgt gcaccaccac gcccggctaa tttttgtatt      79740
tttaatagag acagggtttt gccatgttgg ccaggttggt ctggaactcc tgacctcagt      79800
tggtccacct gcctcagcct cacaaagtgc tgtaataca ggtgtgagcc aacacgcccg       79860
gctatcaaca acttttccta cgtagaaatt attcgggcac tggtttatag aacctcacgt      79920
gggttcacgt agaattgaag gggacctcag cgtcccttgc agatgggatg tgcaatgtat      79980
ttgagatgta ctcgaacatt gctgttgagg tgtgggcatc ttttgctttt tcctaatttt      80040
aaatatggga ctagtctggg tatggtgact tccaccagta attctagcac tttgggaggc      80100
tgagacagga ggatcacctg aggtcagttg ttcgagacca gtctggccag catggtgaaa      80160
ccccgtctct actaaaaata caaaaattag ccgggtgtgg tggcactcac ctgtaatccc      80220
agctactcgg gaggctgagg caggagaatc acatgaatct gggaggcgga ggttacagcg      80280
agcagagatc acaccgttac actcctgcct gggcaacagt gtgagactct gtctctaaat      80340
aaataaataa ataaaaataa aaataattag gtgaatatgg gaccagcatg gacttgggtg      80400
tcgcctttgt gcagtggcca ggatattcta tgtcatttaa attttttat gtgtacttcc       80460 aaagcaagca gttatgtata ggaattattc ttcctataag catgcaatat ttggaacttt      80520
ctttgagaca gggtctcaaa aatacatgat gtatatttca ttttatattc ttatatatta      80580
tgtacacaca aaatactctt ctaaacacag agaatactcc gatatcacct agggtgtgtg      80640
tgcgtgtgcg tgtgtgtgcg tgtgtgtgtg gttcttttct gagacaatat ctgcctctgt      80700
cacccaagat ggagtgtggt ggtgcaatct cggcttactg caacctccac ctcccaccta      80760
agcctgctga attagtctct acaggcatgc accaccacac ctggctaact tctgtaattt      80820
ttgtacacat ggggtctcgc catgttgccg gggctggtct cgagctcctg aggcaggtga      80880
tcctcctgcc tgggcctcct aaagttcgag gagttagagg tctgagccac tgggccccac      80940
ttgtacttgt gtatttctgc tcaaattta ttgagtagtt tttacatcct agcctgtgat       81000
ctactctgga gagtgtttgt gcatatgaca gtgtatattc ttcaacatcg tagactccat      81060
tttggatgct cccttcgtga ctgtgggtcc tgtactggaa ctcgagtgaa cacttggctt      81120
aaaatccatt gctgttctcc agaaatcctg cccaattttc tcggttaaag gtacgtgtag      81180
taggcattgc tttttctctt tggggacaaa actcaggagg attgcccctt gatgaacaag      81240
gctaacctgc tgattctttg aagcaaggaa ctggagatgg tccttataga gttttatatt      81300
ctggattcca taaaacatgc atacagggtc aataaatgca tctttatttt tgtgtctatt      81360
ttaacttggt caaagaaaat tccaggaaaa aatccacggc atcagagcaa gaagatgtca      81420
ggctgtgacc ctcttgaggg aagcactttc tgttgtctga agaagagaa agtgcttcct       81480 tttagaggct tactgtctga gaaaagcaac gttgtagttg atgctgatct ttgtaatatc      81540
tttgcagagc acgcttataa tcagacttgg atgatgttgg ggttttgttt ttcttttgtt      81600
tttttatcta agactgggtc tctgttgccc aggctgaagt gcagtggcac aatcttggct      81660
caccacaacc tccgcctccc gggttcaagt gattcttctg cctcagcctc caagtagct       81720 gggattatag gactgcgcca ccatgcctgg ctaattttgt attttagta gagacagggt       81780 ttctttagga gcttttaagg cctcccttgt agtctatcct ggaggatgtt tgtgtgtgca      81840
acaatgtata ttcttcaaca tggtagattc cattttgact gctctaatca ggactgtgtg      81900
tccctgtgct ggaaatcaag tgaacacttg gctgaaaatc cactgctgtt ctctagaaat      81960
```

```
ccagcccaat tctcttggtt aaatataagg tatgcatagt aggcattgct ttttctttct    82020
ggacacaaaa ctcaggagga tttcccctttg atgaacaagg ctaacctgct gagcctttgt    82080
aggaaggaac gggagatggg cttttttaggg gtctatgttc tggattccag aaaacatgca    82140
aacagagcca ataaataggt ctttattttt gtctctattt taacctggtc aaggaaaatt    82200
tctacaaaaa acccagggtg ctggagcaag aagatcccat gctgtgaccc tctagaggga    82260
agcgctttct gttgtctgaa agaaaagaaa gtgcatcctt ttagaggttt actgtttgag    82320
gaaagcaaca gtgaagttga tgctgatctt ggtaatacat ttgcagagca tgcttatcat    82380
cagacttgga tgatggtggg attctgtttt tattttgttt tttttctaa acagagtct      82440 ctcttgccca ggctggagta gggtagcact ccaacgtag atcttttagg ctcaaacggt      82500
cctctttttt tttttttttt ttttgaggcg gagtcttgct ctgtaccca gacgagagtg     82560 caatggcgcg atcttgtgtg caagctcacc tcctgagttc aagcaattct tctgccccag    82620
cctcccaagt agctgggact acaggtgcct gccaccactt ccagctaatt tttgtatttt    82680
tagtagagac agggtttcac cacgttggcc aggctggtct caaactactg acctcaagat    82740
ccacccacct cagcctccca aagtgctggg attacaggcg tgggccattg tgcccagcgg    82800
tcctcttttt tgagatggag tcttgctctg tgacccaggc tggagtgcag tggcaggaac    82860
ttcgctccct gtaccctcca cctcccagat tcaagccatt ctctcctgag tcagcctccc    82920
tagtagctga gatcgcagac atgagccacc atacccagct aattttttgta ttttttatta   82980 ttatttattt actcatcgat ttttgaaaca gagtcttact ccgtccatca ggctggaggt    83040
cagtggcaca atcccacgtt caagcaattc tcctgcctca tcctcccgag tagctgggat    83100
cacaggcgca caccaccacg cccggctaat ttttgtgttt ttttgttttg ttgtttttt     83160 ttttttttgt agagacaggg tttcaacatg ttggccagcc cagtctccaa ctcctgacct    83220
taagtgagcc catacacaat caagaagaga gcgagacctg ttcttttttt ctgtctttga    83280
ctatttgaga cagtcttgct ctgtcacccg agatggagta cattagtgtg atcttggctc    83340
actgcaacct ctgcctcctg gactcaagca attctctttt tttttttttt ggagaaagag    83400
cctctctgtg tctcccaggc tggactgcag tggtgtgatc tcagctcact gcaacctcag    83460
ccttccaagt agctgggatt gcagacatgt acccccatac cagctatata tatatatgta    83520
ttttagacac agtttcacca tgttagccag gccattcttg aatcctgacc tcaggtgatt    83580
tgccgacgta ggcctcccga agtgctggga ttacaggtat gagccactgc actcagcctt    83640
ttttcctaat tttgaatatg ggacccatta tgaatttggg tgtcacctat gtgcggggc     83700 tatggaaatc tctgtcaccc cattcatttg tgtgtgctgt caaagcacca atatgtggga    83760
attatgcttt atgtgagcat atagtatatg gaacttggt ttttttttat acagggtctc     83820
aaaaaaaaat gagtatattt catcacaatg ttctgtgtat aattccatac acacaaaata    83880
gtcttctata cacagagaac actcttatat cactttggag ttgttttttgt ttgtgtattt   83940 tgttttaatt tttatgagac agggcctggc tatgtcgctg aggctggagg gcagtggtga    84000
gatcttggct cactgcaacc tccacctgcc acctcagcct cctggattag tgtctacagg    84060
caggcaccac caccccctggg taagttctgt atttttggta ctgatgaggt tcagcacgt    84120 tccacaggct ggactcttaa ctcctgcgat caagtgatcc tcccgctgtt caaattttac    84180
tgaggagctt ttaaggcctc gcctgtggtc tgtcctgtag tgtccctgtc ctggaactca    84240
agtgaatact tggtttaaaa ttgattgctg ttctctagaa atccagccca attctcttgg    84300
```

```
ttaaatataa ggtatgtgta gtaggcactg ctttttcttt ctggaggcga aactcaggag   84360
gattgcccct tgatgaacaa ggctaacctg ctgagccttt gaagcaagga actggagatg   84420
gtcgttttag gggtttatgt tctggattcc agaaaacatg gaaacagggc caataaatgc   84480
atctttattt ttgtgtccat tttaacccag tgaaggaaga tttcaaccaa aaacccacgg   84540
tgctggagca agaagatctc aagctgtgac tctccagagg gatgcacttt ctcttatgtg   84600
aaaaaaaaga aggcgcttcc ctttagagcg ttacggtttg ggtaaagcaa cgttgaagtt   84660
gatgctgatc ttggtaatat atttgcagag catgcttata attaagactt ggatgatggt   84720
gggtttctgt tttgtttttt gttttaaatc agagtctcac tctgtcaccc aggctggagt   84780
gcaatggcgc aatctcggct cactgcaact tccccctcct gggttcaagt gattctcctg   84840
cctcagcctc ctgagtagtt aggattacag acatgcgcca cctcacccgg ctcagttttt   84900
gtatttggtg gagatggggt ttcaccatgt tagtcaggct ggtcttgaac tcctgatctc   84960
aggtgatcca cctgcctcag cctcccaaag cattgggatt acaggcgtga gccaccacgc   85020
caggcctgtt caacatctta gatttcattt tggatgttcc tgtgaggact gcgtgtccct   85080
gtgctggaac tcaagtgaac gcttggctca aaatccattg ctgttctcta gaaatccagc   85140
caaattctat tggtgaaata taaggtatgt ctagtagtca ttgcttttc ctttggaga    85200 caaaactcag gaggattgcc ccttgatgaa caaggctaac ctgctgagcc tttgaaacaa   85260
ggaactggag atggtccttt caggggttta tattctggat tccagaaaac atgcaaacag   85320
ggccagtaaa tgcatcttta tttttgtgtt cattttaacc tggtcaagga aaattgctac   85380
aaaaaaccca gggtgctgga gcaagaagat ctcatgctgt gaccctctag agggaagcgc   85440
tttctgttgt ctgaaagaaa agaacgcgct tccctataga gggttaccct ttgagaaaag   85500
cagcattgaa gttgatgctg atcttgctaa tacatttgca gagcatgctt atcatcgac    85560 ttggatgaag gtggggttct gtttttttt ttttctaag acaggatctc tgttgcccag    85620 gctgaatgt ggtggcactt ccaacctagc tctcttgggc tcaaatggtc ctctcttttg     85680
ggatagagtc ttactctgtg acccaggctg gagtgcagtg gcgtgatctc agcttactgc   85740
cacctccacc tcccagtttc aagccgttct cctgcctcag attcctgagt atctgggatt   85800
ataggtacct gacaccacgc ctggctaata cttgcatttt tctttcttttt ttcttttcttt   85860 ttttttttt tttttttga gatggagtct tactctgtca ccaggctgga gtgcagtggt   85920
gcgatcttcg cttatttcaa cctccgcctc ccagtttcaa gtgattctcc tgcctcagcc   85980
acccgactaa ctaggatttc aggcatgcac cacacgcctg gctaattttt tgtatttta    86040 gtagagacag ggtttcacca tgttggtcag gctggtctcg aactcccgac ctctggtgat   86100
cttcccgcct tggcctccga aagtgctggg attgcaggca ttagccaccc cgcccggcca   86160
ttatatattc ttatatatat aataccatat acgtgcaaaa tactcttcta catgaagaga   86220
atactcttat atcactttgg ggttttttt gtttgtttgt gtgtgtgtga gtgtatgttt   86280
tatttgtttt tggataaggt ctggctctgt cacccagtct agagtgcagt tgtgccatct   86340
ctctcagctc actgcgactt ctacctccca cctaagcctg ctgaattagt gtctacaggc   86400
atgcaccacc acacctggct ccgttttgta ttttttatac acatgggctt acaccatgtt   86460
gccgagactg gtctcgaaca cctgagctca ggtgatactt cagtttcagc ctcctaatgt   86520
gctgggatta gaggtgtgag ccaccgtgcc ccactgtag ttgtgtgttt ctgttcaaat    86580
tttattgagg agttttagg gcctagcctg tgatctaccc tggaggatgt ttgtgtgtac   86640
aacaatgtat attctttaac atcgtagatt ccattttgga tgctcccatc gggactgtgt   86700
```

```
gtccctgtgc tggaactctg gtgaacacct ggctcaatat ccatttctct tctctagaaa   86760
tccagcccag ttctcttggt taaatataag gtacatatgt ctatgaggca ttgcttttgc   86820
tctttgagaa caaaactcag gaggattgct ctttgatgaa caaagctaac ctgctgatcc   86880
tttgaagcaa ggaactggag atggtccttt tagggggttta tattctggat tccagaaaac   86940
atgcaaacag ggccaataaa tgcatctttg tttttgtgtc cattttaacc gggtgaagga   87000
aaattccaac aaaaaaccca gagtgttgga gcaagaagat ctcatgctgt gaccctctag   87060
agggaagcac tttctcttgt ctaaaagaaa agaaagcgct tctctttaga ggattactct   87120
ttgagaaaag caacgttgaa gttgatgctt atcttggtaa taaatttgca gagaatgctt   87180
ataatcagac gtggatgatg ttggtgtttc atgtttgttt tgttttgttt ttaatacagg   87240
gtgtctgttg cccaggctgg agtgtggtgg tccctctcca acctagatct cttgggttca   87300
agtggccctc ttttttgggt cagagtcttg ctctgtggcc ctggctggag tgcagtgtca   87360
ggatctctgc tcactacaac ctctgcctcc tgggtaaaag cgattctcct gcctcagcct   87420
cccaagcaac tgggattaca ggcatgtgct accatgcccg gctaattttt gtaatttcct   87480
ttatttattt ttgagacaga gtcttactct ttcgcccagg ctggagtgca gtggtgcaat   87540
ctcggctcac tgcaacctcc aactcccacc tcagcctcct gaatagctgt ctacaggcat   87600
gcaccaccac acctggctaa cttttgtatt ttttgtacag acatggtttc tccatgttgc   87660
ctgggctggt cttgaactcc tgaactcaag tgatcctccc acctcggcct cctaaagtgc   87720
tgtgattaga ggtatgagcc accgtgcccc acctgtactt gtgtgtttct gctcaaattt   87780
tattggggag ctttatggt atagcctgtg gtctctctgg agaatgtttg tgtctatgac   87840
aatgtatatt cttcagtatg ttatgttcca ttttggatgc ttgcatgggg actgtgtgtc   87900
cctgtactga aactcaggtg aacacttggc tctccgtcca ttgctgttct ctagaaatcc   87960
agcccagttc ccttggttaa agataaggta tgtctagcag gtattgctct ttctcttgca   88020
gacaaaactc aggaggattg ccccttgata aacaaggcta acctgctgat tctttgaagg   88080
aaggaactgg agattgtcct tttaggggtt tatattctgg attccagaaa acacacaaat   88140
agaaaacagg gcaaataaat gcatctttct tttcgagtcc attttaacct ggttaaggaa   88200
gattccaaca aaaaatccac ggtgccacag caagaagatg tcaggctgtg tccctctaca   88260
gggaagcgct ttctgttgtc tgaaagaaaa gaaagtgctt cctttagag ggttaccgtt   88320 taagaaaagc aacgtttagg tggatgctga tcttggcaat aatacatttg cagagcatgc   88380
ttatcatcag agttggatga tggtgggggtt ctgtttttttt gtttttttttt ttctgagaca   88440 gagtgtctat tgcccaggct ggagtgcagt ggcacttta acctagatct cttgggctca   88500
agtggtcctc ttttttggga taatctcaca ctgtgaccca gtccggagta cagtggcatg   88560
aacaccactc attgcatgct ttgcctccca ggttcaagtc attcttatga cccagcttcc   88620
agagcagctg ggattacagg catgagccac cacactggct aatttttgta tttttaatag   88680
agatggggtt caccatgttg gccaggctgg tctccaacta ctgacctcat gatccaccca   88740
cgtcggcctt ccaaagtgct gggattacag acgtgagcca ctgtgcccgg ccaacacaga   88800
gaatactctt atatcacttt ggggttgttt ctgtttgtgt attttttaaa tatttttga   88860 gacacagtct ggcgctatta cctaggttgg agtgcagtgt tgtgacctcg gctcacagca   88920
acctctacct cccagctgag cctcctgagt tagcatctgc aggcatgaac cacaacacct   88980 ggtaacctttt gtattttttgg acacatgagg tttcaccatg ttgcccaggc tagtcttgaa   89040
```

```
ctcctgagct caagtaatcc tcctgcctcc gactcctaaa gtgctgggat tacaggtgtg    89100
agccactgca ccccacctgt acttgtgtat ttctgttcaa attttattga ggagctttta    89160
cggcctagac agtagtctat cctggagaat gtttgtgtgt atgacaatgt atattctttt    89220
tttttatttt tattttttgg agacggagtc tcactctgtc acccaggctg gagtgcaatg    89280
gcatgatctc ggttcactga aacctccgcc tcctgggttc agcgatcct cctgtctcag     89340 cctgctgagt agctaggatt acaggtgggc gcctggctaa tttagattcc attttggatg    89400
ctcccatcgg gactgtgtgt ccctatgttg gaactcaggt gaacgcttgg ctcaaaaatc    89460
cattgctgtt ctctagaaat cctgcctaat tctcttggtt aaagataagg tatatgtagc    89520
aggcattgct ttttctcttt ggggacaaaa ctcaggagga ttgcgccttg atgaacaagg    89580
ctaacctgct gagcctttga agcaaggaac tggagatggt cctttaggg gtttatgttc     89640 tggattccag aaaacatgca aacagggcaa ataaatgcat ctttattttg tgtccatttt    89700
aacctggtca aggaaaattc caacagcaac atcaaaaaac cagtgttgga gcaagaatat    89760
gtcatgctgt ggccctccag agggaagcgc tttctgttgt ctgaaagaaa acaaagcgct    89820
cccctttaga ggtttacggt ttgagtaaag cagcgttgaa gttgatgctg atcttggtaa    89880
tacatttgca gagcgtgctt atcatcagac gtggacgatg gtggggttct gttttggttt    89940 tgttttttc taagacaggg tctccgttgc ccagactgga gtgcggtggc acttctacct     90000
agatctcttg ggctcagatg gtcttctttt tatttcattt ttttaattgt ttgagatgga    90060
gtctcactct gtcacccagg ctggagtaca gtggcaggat ctccacaact acagcctccc    90120
aggttccaga cattctccca cctcagcctc cgagtagct ggaattataa gcacccaccg     90180
ccatgccctg cttttgtat tttagacaa gaaagggttt caccatattg gccaggctca      90240
tctcaactct tgcccttaag taatcctcct ccctggcctc ccaaagtgct gagattacag    90300
gcgtgagcca ccgcgcccag cctcaagtgg tcctcttgag tcagcctctc aagtagttgg    90360
gactacgtgg ggcgtgccac catacttggc taagttttta attttttggta caattggggt   90420 ctcttttttcc caggatagtc tcatctccac agcttatgtg gtcctacacg tgtgagccac   90480
ctcgtcttga tgacccattt caaagagagt tgacatggcc aggcattgtg gggcacacag    90540
tcccagccac tgcagaggcc agggtcggag ggacctttga tttccagact gtaccatgca    90600
ctgatcacac cttcgaatag ccactgcgct ccagcctggg ccaacatagc aagatcccat    90660
ctctttaaaa acagattaca tggcacctgg ttacagaggc tccatttggg ttggttatt     90720 gaaatgggtc tcccatcaat ttagtgtaat caatcgaaat catttccttc attaagagag    90780
taagtagccg gggcatggtg cctcatgcct gtaatcccag cactgtggga ggcaaaggca    90840
ggcggatcgc ctgaggtcag gagttcaaga ccagcctggc caatatgtg aaaccctatc     90900 actactaaaa atacaaaaat tagccgggtg tggtggcgtg aacctaggag ctgaggttg     90960 cagtgagctg agattgcacc attgcactcc aacctgggcg actgagctgg acttaaaaaa    91020
aaggtaagta agccttcaag tctatccaat cttaatttgt aatctcaaat ggatgtccat    91080
attaacaaaa ttttcttgtt tttcctgttt gtgtctttt agtttaatct tcttgtcctt     91140
gacactgaaa ttttttctc tccaacaact tgccgtcgtt tctcggaata gagctgcttt     91200
ctctgcagga agggtgtagt tgattcaacc gccacccact cacgccagcc ccggtgagtt    91260
ctttgactgc agcttccctg attatgctat ttcttcgggg taatgaaccc aaggtacctc    91320
gcatttaaag gctagttgct tggtaagctg tgaaatgttg gctgtggcta atatgagaaa    91380
caaactatgg tagacaagat gagtctcagt ggcagtgata attgtcacat gggacaaaac    91440
```

```
cacagatact tttcacaaaa accttgagga ccctagaagg gcctctctag taacaggtgg   91500
gatgcgccgc agctctcgtt gttgccgtag tgagcgatgc ctgttcgtcc agccctcaac   91560 acctttact  ccgtggaagt tatgcctgca ctggtttaca gaacctccct tgacttgggt   91620
tgaggtagag ctgaagggaa cctcagtgtc ccttgcaggt gggatgttca ctacgtagca   91680
agagcacaaa ggtggagtgc gtgggctttg agtttctatt gggtaaatga agctgaaatg   91740
tagggcacat gagcacgtca tcaatgtaca attgatttaa tttttgtatt ttagaaacgg   91800
aggtctcgct atgccgccca gggtagaatg tgctctctcc ctctcctctt cctagtatct   91860
gggactacag gtgaatattt taatctatgc acaggcaaga agagggcaag gagggttctt   91920
ttgttctgtc tttgactttg tgaggcagtg tcactctgtc actcaagctg gagtgcaata   91980
atgtgatctc ggctcactgc aacctctgcc tcctgggttc aagcaatttt tttttttttt   92040
tttttttgag tcagtatctc actctgtccc tcagggtgga gtgcagcggc ccagtctctg   92100
ctcctgcaac ttctgactcc caagtaggta caattgcaga cacgtgtcac cacgcttggc   92160
aaaatttttt ttgtattttt agagctggga ttttaccttg ttggcgaggc tggtctggaa   92220
ctcctgacct caggtgactc gcccaccttg gcctcccaac aagttatgct gatcttggta   92280
ataacttcgc agagcgtgct tccatcagac atggaggatg gtggggtcct gttttgttgt   92340
tgttgttttt ctaagatagg gtctcttgcc caggctggag tgtgttggca cttccaacct   92400
aggtgtcttg ggctcaaatg gtcctctttt ttcggacagt cttgctctgt gacccatgct   92460
ggagtgtagt gacgtgatct cagctcactg caacctccac ctcccagttt taggcagttc   92520
tcctgcctca cattcctgag tagctgggat tataggtgcc tgacaccatg cctggctaat   92580
atttgcatgt tatttattca tgtatttatt tgttttgaga tggagtctca ctgtcactca   92640
ggccagaggg cagtggcagg acctcggctc actcaaacct tgcctctca  ggttcaagca   92700 agtcttctgc ctcaacctcc tgagtagctg gaatcacagg cacccgtcac cacgcccggt   92760 tactttgta  tttttttttt caccatgttg gccaggctgg tctgaaaccc ctgacttcat   92820
gtgagccgcc cgcctcagcc acccaaagtg gtgggattac aggcataagc cactgcgccc   92880
ggccaacaat gtatattttt caacatggga gattcagttt tgaatgctcc catcgggact   92940
gtgtgtccct gtgctggaac tcaagtgaac gcttggctca aaatccattg ctgttctcta   93000
gaaatccagc ccaattctct tggttaaatg taaggtatgt gtagtaggca atgcttttc    93060 tggagacaga actcaggagg attgtccctc gatgatctag gctaacctgc tgagactttg   93120
aagcaaggaa ctggagatgg tccttttagg gttttatgtt ctggattcca gaaaacatgc   93180
aaacagggcc aataaatgca tcctcatttt tgtgtccatt ttaacctggt gaaggaaaat   93240
tccaacaaaa aacccacagt gctggagcaa gaagagctca ggctgtgacc ctctagaggg   93300
aagcactttc tgttgcttga aagaagagaa agcgcttcct tttagaggat tactctttga   93360 gaaaacaac  attgaagtta atgctgatct tggagatcat gcttataatc agacttggat   93420
gatgttgggg ttttgtgggg ttttttggt  tttttttcct aagacagggt gtctgttgcc   93480
caggctggag tatggtggcc cctccaacct agatctcttg ggttcaagtg gccctctttt   93540
ttgggacaga gtcttgctct gtgacccgg  ctggagctca gtatcaggaa ctttgctcac   93600
tgcaacctct gcctcccagg ttcaaatgat tctcctgcct cagcctcccg agcagctggg   93660
attacaggca tatgccacca cgcccagcta ttttttgtat tattgttatg tatttatttt   93720
ttaacttatt cattttagag acagagtctc actctgtcgc ccaggctgga gtgcagtggt   93780
```

```
gcgatctcgg ctcactgcaa cctccaactc ccagctcagc ctcctgaata gctgtctgca    93840
ggcatacacc accacacctg gctaactttt ggttttttg tacagatgtg gtttccccat    93900
gttgcccagg ttggtctcga actccttagc tcaggtgatc ttccaccttg gcctcctaaa    93960
gtgctaggat tagtggtgtg agctgttgtg ccccacctat actcgtctgt ttctgctcag    94020
attttattga ggagcgttta cagggtagcc tgttgtctac cctgcaggat gtttgtgcct    94080
acaacagtgt atattcttca acatcttaga ttccatttcg gatgccccca tgaggactgt    94140
gcgctcctgt actggaactc aagcgaccac ttggctcaaa atccattgct attctctaga    94200
aatccagccc aattctcttg gttaaagata aggtatgtgt agtaggcatt gccttttctc    94260
tttgggaaca aaactcagga ggattgcccg ttgatgaaca aggctaacct gctgattctt    94320
tgaagcaaag aactgcagat ggtcctttta gggattatg ctctggattc cagaaaacat    94380
gcaaacaggg caaataaatg catctttatt tttgcgtcca ttttaacctg gtcaaggaag    94440
attcccacaa aaaatccaca gtgccagagc aagaagatct caggctgtcg tcctctagag    94500
ggaagcactt tctgttgtct gaaagaaaag aaagtgcttc cttttagagg gttaccgttt    94560
gagaaaagca acattgaagt tgatgctgat cttggtaata cattttcaga gcatgcttat    94620
catcagagat ggatgatggt gggcttctgt ttttgttttg attttttctt ttttttttt    94680 ttgagatgga gtttcgttct tgctgcccaa gcactagtat gtaggaatta ttctttatgt    94740
gagcatatag tacatggaac tttgttttt tgagacaggg tctccaaaat atatacatgt    94800
tatcatataa tcttctatgt ataattatat tcacacaaaa tagtcttctg cacacagaga    94860
atactcttat atcactttgg ggttgttttt gtttgtgtat tttttttttt tttaatttt    94920 tttgagacac catctggctc tattgcccag gctggagtgc agtgttgtga cctcaactca    94980
ctgcagcctc tacctcccac ctcagcctcc tgaattagtg tctacaggca tgaaccacta    95040
cacctggcta tcttttgtat tttacagat gaggttttac tatgttgggc aggctagttt    95100
tgaactcgag ctcatgtaat tttcccgcct tcgactccta aagtgctggg attagaggtg    95160
taagccactg cactccaccc gtacttctgt acaaatgtta ttgaggagct tttacggcct    95220
aggcagtgct ctatcctgga gaatgtttgt gtgtaagaca atgcatattc tttttttctt    95280
tcctgtcacc caggctggag tgcattggca cgatctcgtc tcactgcaac ctccgcctcc    95340
cgggttcaag caattctcct gcctcagcct cctgagtagc tgggattaca ggtgggcacc    95400
accacgcctg gcaaatttag attccatttt ggatgctccc atcatgactg tgtgtccctg    95460
tgctggaact caagtgacca tgtgactcaa tccattgctg ttctctagaa atccacctca    95520
attctcttgg ttaaaggtaa ggtatgtgta gtgggcattg ctttttctcc ttggagacaa    95580
aacttaggag gattcccctt gatgaacaag gctaatctgc tgagcctgga gattgtcctt    95640
ttagaggttt atgttctgga ttccagaaaa cggtcaaaca gcgaataaat gcatctttat    95700
atttgtgtcc atcttaacct ggtcaaggaa aatttcaaca aaaatcccag atggctggag    95760
cgagaagatc tcatgctgtg actctctgga gggaagcact ttctgttgtc tgaaagaaaa    95820
caaagcgctt ctctttagag tgttacggtt tgagaaaagc aacgttgaag ttgatgctga    95880
tcttggtaat acattcgcag agcatgctta tcaggcttgg atgacggcag ggttctgttt    95940
tggttttatt tttttccaag accagtctct gttgcccagg ctggagaggg aggggttgca    96000
ctccaaacta gatctcttgg ggtcatgtct tgctctatta ttattattaa ttcttatttt    96060
tgtgtgtgtg tgagacggag tctcgctctg tcaccaggtt ggagtccagt ggcggaatct    96120
cagctcactg caacctccga ctccgtggtt caagcgattc tcctgcctca gcctcctgag    96180
```

```
tagctgggat tacaggcacg caccgccatg ccgagctaat ttttgtattt ttagtagaga    96240
ccgggtttca ccacgttggc caggatggtc tcaaactcct gacctcatga tccacccgcc    96300
tcggcctccc aaagtgctgg gattacaggt gtgagcctcc gtgcccagcc tgttatttta    96360
ttttgtttta ttttattat tttatttat tttgagatgg agactggctc tgtcgcccag    96420
gctggaatgc agtggcagga tctccactca ctgtaactcc cacctctgtc gcccaggctg    96480
gagtgcagtg gcaggatctc cactcaccgt ggagttccag tgattctttc accttagcct    96540
cgcaaatagc tggtattaca agcacccacc aacacaccct gccaattttt gtattttag     96600 acaagaaagg gtttcgccat gttggccagg ctggtctcga ctcctgacct taagtgatcc    96660
acctccctgg cctcccaaag tgctgggatt acaggcgtga ccaccacgt ccagcctcaa     96720 gtggtcttct tgtcagcctc gcaagtagtt gggctcaggt tttaatttt ggtagagatg     96780 gggtctcttt tgcctgggat ggtctcagct gagcttaagt gatcctaaat gtgtgagcca    96840
ccttgtccca tttcaaagat aggtgacacg gccaggcatc ctgggacaca cagggtccca    96900
gttactgcaa aggctagggt gggagggtcc tttgatttta aggctatacc atgcactgat    96960
cacacctttg aatagccact gcactccggc ctgggccaca tagcaagatc ccatctcttt    97020
aaaaacgcag attacatgcc atctggttcc tgaggctcca tttgggttgg tcacttcaaa    97080
tacaggcctt tcatcagttt agtttaatca atccaaacca tgtttccttc attaggagag    97140
taagggccag gtgtgtaatc caagcacttt gggagactga agcaggcgga tcaggaggtc    97200
aggagttcga gaccagcctg accaatatgg tgaaaccccg tctctactaa aaatacaaag    97260
attaagtggg cgtggtggtg cgtgcttgta atcccagcta ctcaggaggc tgaggcagca    97320
gaatctcttc aacccaggag gcggaggttg cagtgagcca agatcgcgca ggtgcactcc    97380
agcctgggcg acagagcgag gctccatctc aaaacaaaac aaaacaaaaa atataggcct    97440
ccacatctat ccagtctatt ctgtaatccc aatggatgtc aatattaata caatgttctt    97500
attttttcta tttatttgta tcttttagt tgaatctcct tgtccctgac actaaattt     97560 ttttatttt atttatttat tttttttgaa acagtcttgc tctgtcgccc aggctgcagt    97620
acagtggcgc aatctcggct tactgtagcc tctgtctccc gggttccagt gattctcctt    97680
ccccaactcc cgggtaactg ggattttcag gcacacacca ccaccccagc taattttttt    97740
gtacgtttag tagagacagg gtttcaccat attgggcagg ctggccttga actcctgaac    97800
taaggtgatc cgcccacctc ggcctcccaa agtgctggga ttagggataa ggctaacctg    97860
cttattcttt gtagcaagga actggagatg gtcattttag gggtttatgt tctggattcc    97920
agaaaacatg caaacagggc caataaatgc atcctcattt ttgtgtccat tttaacctgg    97980
gcaaggaaaa ttccaacaaa aaacccgag ttctggagca agaagatctc atgctgtgac     98040
cctacaaagg gaagcacttt ctcttgtcca aggaaaaga aggcgcttcc ctttggagtg     98100
ttacggtttg agaaaagcag cgttgaagtt gatgcttatc tcgtaatac atttgtagag     98160 catgcttatc atgaggcttg gacgatggcg gggttctgtt ttggttttgc ttttttattc    98220
taagacagga tctctgttgc ccaggctgga gtgcggtggc acatccaacc taggtctttt    98280
ggattcaaat ggttttttta gcggacagag tctctctatc acccaggctg aagtgcagtg    98340
gtgtgatctc ggctcactgc aacctccacc tcccaggttc aagcgagtct cctgcctcag    98400
cttcccaagt aggtgagatt acaggtgccc atcaccacac ctggataata ttttcatttt    98460
ttaaaattca tttatttatg tttttgagat ggagtctcac tgttacccag gctggagggc    98520
```

```
cgaggcgtga tctctgctca gtgcaacctc tgcctcccgg attcaagcaa ttcttctacc   98580
tcagcctcct gagtagctag aattacggga gcccaccacc acacctggct acttttttgtt  98640 ttttgttttt tgttttttt ttagtagaga tgggatttca ccatgtttgc caggctggtc   98700
tcaaacccct gacctcaagt tagccaccgg cctctgcctc ccaaagtgct gggattacag   98760
gcatgagcca ccacgcctgg cctaatttt atatttcag cagaggcggg gtttcaccat    98820
gttggccagg ctggttgcga actcctgacc tcaggtgatc tgcccacctc agcctcccaa   98880
agtgctaaga ttacaggcgt gagccaccac acatggccat taacacctt tagtccatgg    98940 aaattattct ggcactgatt tataaagcct catgtggggt caggtagagt caaaggggga   99000
cctcagtgtc ccttgcagat gggatgtgct cagcaagagc acggaggtgg agtgcatggg   99060
gtttgagttt tcactgggga aatgaaacca acatcttggg tgcatgacca ggtcatatat   99120
gcagtcatat atgcaatatg catggtggtg ggtgcctcta atcccagcta ctcaggaggc   99180
tgacgcagaa gaatcgcttg aacccaggag gcagaagttg ccatgagccg agatcccacc   99240
accgcatcca gcctgggcgg cagagtgaga ctccgtgtca aaaaaagaa gatctcaggc    99300 agtgaccctc tagatggaag cactgtctgt tgtataaaag aaaagatcgt gcatcccttt   99360
agagtgttac tgtttgagac aagcaacgtt gaagatgctg ctgatcttgg taatacattt   99420
gcagagcgtg cttatcatca gacttgcatg atgtcggggt tctgtttgtg atttgaaatt   99480
tttccaagac aggctttcta ttgcccaggc gtgggtggat agcaccttcc accaagattt   99540
cttgggctta agtggtcctc ttttttattt ttgatttttt gagacacact cttgtttcgt   99600
tgggagtgca gtagcaggat ctctgctcac cggaaactcc acctctcggg ttccagtgat   99660
tctcccacct cagcctgccg aattgttggg aattcaggca tcaggcaccc accatcgtgt   99720
cctgcactct tgctgcccat cctggagagc actggcatga tctaggctca ctgcaacctc   99780
cgcctcctgg gttcgagtga tgcttctgcc tcagcctccc aggtagttgg gattacaggc   99840
acctactgcc ccacccagct aattttatg tttttagtag agacgggttt caccatgttg   99900
gccaggctag tcttgaactc ccgctttcag gtgatccact agcctgtggt ctatcctgga   99960
ggatgtttgt gtgtgtgaca atgtatattc ttcaacatct tagactccat tttggatgct  100020
cccatcggaa ctatgtatcc ctgtgctgga actcaagtga acactcagct caaagtccat  100080
tgctgttctc tagaaatcca gcccagttct cttggttaaa tataaggtat gtgtagtagg  100140
cattgctttt tctctttaga ggcaaaactc aggagggttg ccccttgatg aacaaggcta  100200
acctgcagag cctttgaaga aaggaactgg agatggtcct tttaggggtt tatgttctgg  100260
attctagaaa acaggcaaac agggccaata aatgcatctt tattgttgtg gccatttaa   100320 cctggtcaag gaagatttca acaaaaaacc cagagtgctg gagcaagaag atcccatgct  100380
gtgaccctcc aaagggaagc gctttctgtt tgttttctct taaacaaagt gcctcccttt  100440
agagtgttac cgtttgggaa aagccacgtt gaagatgatg ctgatcttgg taatacattt  100500
gcagaccatg cttgtaatca gacttggatg atgttgggag tctgttttt tgtttgtttg  100560 tttggttggt ttttttgttt gttaggtttt tgttttttgt tttggtgtgt gtgttttgtt  100620
ttgtgttttt tttttttct aagacaaggt ctctgttgcc caggagagac tagagaagca  100680 cttttttaaga taggcctgtt gggctcagat ggtcctttta tgggatacag tcttgctctg  100740
tgacccagac tggagtgcag tggcgcgatc ttggctcaat gcaacctcca cctcccgggt  100800
tcgagtgatt ctcctgcctc agcttcctgg gtagctggga ttacagatgc ctgacatcac  100860
actcggctaa tatttgtatt tttcttttt attcattcat tcattttga gatggagtgt   100920
```

```
tgctgtcacc cagcctggag ggcagtggca tgatcccggc tgactccaac ctctgcctct   100980
caggttcaag ccattctcct gcctcagtct cctgagtagg tggaattaca ggcacccacc   101040
actacaacca gctactttt gattttgatt ttttttttt tttttttttt ttagtaaagg   101100
tggggtttca ccatgttggc caggctagtc tcaaaccct gacctcaagt gagccgctgg    101160
cctcggcctc ccaaagtgct gagaatacag gcgtgagcca ccgggcacag ccatcagcac   101220
cttttacttt atgaaatttt ttctggcact ggtatagaac ctcacgtggg gtcaggtgga   101280
gttgagggga cctcagtgtc cctgcagatg ggatgagcaa gagcacggag gtggagtgca   101340
tggggcttca gtgtttattg gggaaatgaa gctgaaatct gggtgcatga ccaggagata   101400
aatgcatgag acggcggtct cactatgctg ccctggctga agtgggctta gatcctcctg   101460
cctctgcccc tccccagtcc ttggtagatg ggaccacatg tgaatattaa ccccccatgc   101520
acagacaaga agaaagtaag gactgttctt tggttcatac ctgaccccag ttaaacttgt   101580
attttagata aacaatgtat ttgagatgta cttgaacaac aaacgatttg ctgttcaggt   101640
gtgggcatct ttgttttgtt ttttttttc ctaattttaa atatgggact agtgtgcata   101700
tggtggctct tgtctgtaat tcctgcactt tgtgaggctg agacaggagg atcacctgag   101760
atcagttgtt cgagaccagc ctggccaaca tgaagccagg aggctgagct ttcagtgagc   101820
tgaaatcttc tgctgcactc caccctgggc aacagagtga gactcagtct caagaaagta   101880 aaaaatagc cgggcgcggt ggcgcatgcc tgtaatccca gcactttggg aggccgagac   101940
gggaggatca cctgaggtca ggagttcaag accaacaggg ccaacatggc aaagcctcgt   102000
ctctactaaa aatacaaaaa ttagctgggt gcaatggtgc acatctgtaa ttccagctac   102060
tccggaggct gaggcaggag aatcccttga acccaggagg aggagatttc agtgagctga   102120
aatcaagcca tggcattcca gcctgggcca gagagcaaca ttccgtctca aaaataaatg   102180
aataaataaa ataaataaaa ataaatagat aaatatggga catcataaat ttgggtgtca   102240
cctttgtgta gcagccagcg taatctctgt cattccaatt ttttttatg tgaactgcca   102300 aagcaagcac ttgtgtagga attttttcttc ctgtgagcat acaatatatg gaactttctt   102360
tgacacaggg tctcagaaat atatggtata tatttcgtta tatatatact tatatataat   102420
ataatcatat acacacaaaa tactgttcta aatacagaga atactctgat ataaccttgg   102480
gtattttttt ctttctttgt gtgtgtatgt ttttatttg tttggctggt tttttttgt    102540 ttttgttttt tgtttttgt tttttgtttt tgtttttgtt ttgagacaga gtctcactct   102600
gtcgccgagg ctggagtgca gtgacaggat ctcgggtcac tgcaagctcc gcctaccggg   102660
ttcacgccat tctcctgcct cagcctcctg agtagctggg accacaggca cccaccacca   102720
cacctggcta atttttttt gtatttttag tagagacagg gtttcgccat gttagccagg   102780
atgatctcga tctcctgacc tcgtgatcca cccgcctcgg cctcccaaag tgctgggatt   102840
acaggcgtca gccaccgcgc ccggccagtt ggttattttt gagacaaggt ctggctctat   102900
cacccaggct ggagtgtagt ggtgcgatct tggctcactg caacctccac ctcccaccta   102960
aacctgctga attagtgtct acaggcatgc accaccacac ctggctcact tttgtgtttt   103020
tcatacacat gggtttacac catgttgctg gggctggtct caggaactcc tgagctcagg   103080
tgatcctccc gtcttggccc cctaatgtgc taggattaga ggtgtgagcc aacccacccc   103140
acccatactt acgtatttct gttcagattt tattgagttt ttatgaccaa gcctatggtc   103200
tatcctggag aatatttgtg tatgtgacaa tgtatattct tcaacatcgt agactcgatt   103260
```

```
ttgggtgctc ccatcgggac tgtgtgtacc tgtcctggaa ctcaagtgca cccttggctc    103320
ataatccatt gctcttctcc agaaatctta ccaattctcc tgcttaaata taagctacgt    103380
gtagtaggca ttgttttttc ttagcagata cgaaactcag gaagattgtc ctatgataaa    103440
caaggctaac ctgctgattg tttgaagcaa ggaactggag atggtccttt tagggtta     103500 tgttttggat tccagaaaac gtgtaaacag gccaatacg  tgcatcttta ttttgtgtcc    103560
agtttagcct ggtcaacaaa aatgtcaaca aaaacccag  agtgctggag taagaaggtc    103620
tcgggctgtg actctccaaa gggaagaatt ttctcttgtc taaagaaaa  gaacgcactt    103680 cccttagag  tgttaccgtg tgagaaaagc aatgctgaag ttgatgctga tcttgcaaat    103740
aactttgcag agcctgctta taatcagact ttgacaatgg tgggcgtctg tttttttttt    103800
tctaagacag gatctctgtt gcccaggctg gagtatggtg gcacttccaa cctaggtctc    103860
ttgggctcaa atggtcctct ttttggac   agagtcttgc tctgtgaccc aagctagacc    103920
acagtggcac gatcttggct cacggcaatc tctgcctccc agtttcaagt gattcccctg    103980
cctcaacttc ctgagtagct gggattatag gtgtctgaca ccatgactgg ctataatttt    104040
catttttctt atttatttat ttttgagtct cgctgtctct caggctggag tgcagtggca    104100
gcctttgcct cttgggttca agcaattttc ctgcctcagc ctcccaagta gttggaatta    104160
tatgtgtcac catcatgccc tttttgtttt ttttagtag  aaaatgggtt tcaccacgtt    104220
ggccaggcta gtctcaagcc cctgacctca agtgatcctc cgcctcaga  ctcccaaagt    104280 gctgaaaatg caggcgtgag ccactgcacc gagccatcaa caccttctac tccatggaaa    104340
tgatactggc gctggtttat agaacctcac ttggggtcgg gcagatttaa aagggacctc    104400
aggctgggtg tggtggctga cgcctgtaat cccagcactt tgggaggccg aggcgggtgg    104460
atcacgaggt caggagatcg agaccatcct ggctaacatg gtgaaaccct gtctctacta    104520
aaaatacaaa aaattagcca ggcgtggtgg cgggtgcctg tagtcccagc tactcgggag    104580
gctgaggcag gagaatggtg tgaacccggg aggcggagct tgcagtgagc cgagatggca    104640
ccactgcact ccagcctggg cgacagagca agactctgtc tcaaaaaaat aaataaataa    104700
ataagggggt gggggacctc attgtcccctt gcagatggga tgtgccctgc ttagcaagag    104760
cacggaggtg gagtgcatgg cttttgagttt tcactggggc acggaggtgg agtgcatggc    104820
tttgagtttt cactgggtaa atgcagctga actcttggct gcacgaccag gtcatatgtg    104880
caacgagaca ggggtctcac tatgctgccc aggctaaaat gggcttaggt cctttgcct   104940 ccacctctcc ccagtcctta gtagctggga ctacatgtga atattaacca tgcacaggca    105000
agaggaaaga aaggaccgtt ctttggttca cacctagccg ccagtcaaat tagtatttta    105060
gatgaagact gcatttgaga catacttgaa caacaaatga tttgctgttt aggtgtgggc    105120
atctttcttt tttcctagtt ttaataatgg caccaggcag agtacagtgg cccacgcctg    105180
taattccagc actttgggag gctgagacag gaggatcacc tgaggtcggg aatttgattc    105240
cagcctggcc aacatggtgc agccccatct ctactaaaaa tacaaaatta gcccagcatg    105300
gtggtggtat atgcttgtaa tcccagctac tctggaggct gaggcaggag agtcgcttga    105360
agctggaagg ctgatctttc aatgagctga gatcacgcca ctgcactcaa gcctcggcaa    105420
aaagagtgag actccatctc aaaaacataa aaaataggcc agacacggtg gtccactcct    105480
gtaatcccag cactttgaga ggccaggaca ggcggatctc ctcaggtcag gagtccaaga    105540
ctagctgggc aaacaaggca aaacctcgtc tatactaaaa ttaggaaaaa tggctgggaa    105600
cagtggtgga cacctgtaat ctcagctact tgggaggcca cggcaagaga atctcttgaa    105660
```

```
cctgggaaaa ggagattgca gtgagacgaa atcacaccat tgtactccat cctgggtgac 105720
agagtgagat tctgtttcaa aaattaaata aataggccga gcacagtgac tcatgcctgt 105780
aatcccagaa ctttgggagg ccgaggtggc ggatcacctg aggtcgggag ttcaagacca 105840
gcctaaccaa cacgtagaaa ccccatctct actaaaaata caaaattagc cgggcatggt 105900
ggcgcatgcc tgtaatccca gctgctcggg aggttgaggc aagagaatca cttgaaccccc 105960
aggggggcgga ggttgtggtg agccgagatt gtgccattgt attccagcct gggcaacgag 106020
tgaaactctg tctctaaata aataaataaa actattaaat aaacattaaa cgttaaaaaa 106080
taaaaataga taaatatgag atcatcatga atttgagtgt cacctttgcg cagggcccat 106140
ggtaatcttt gtcattccaa ttttttcatg cgtgctgcca aagctagcac ttgtgtgtag 106200
gaagtattct tcctgtgagc atacaatata tggaagtttc ttttattatt attatttttt 106260
atgttttttgc gactgagttt tgctcttgtc gcataggctg aagtgcaatg gtgtgatctg 106320
ggctccctgc gatgtccacc tcttgggtta aagcgactct cctacctcag cctcctgagt 106380
agctgggatt acaggcatac acttccaggg ctagctaatt tgttgtattt tagtagacgg 106440
gatttctcca tgttggtcag gctggtctca aactcccgac ttcaggtgat ctgcccacct 106500
tggctttcca aagtactggg attgcagaca gccaccgcgg ctggccttca tatattctta 106560
tatatataat atcatgtaca cacaaaagac tcttttacac cctgagaata ctcttatatc 106620
actttgggca ttttttttgtt ggtgtgtgca ttttttgttt gttcgttcgt ttgttttttga 106680
gacaagatct ggccctgtca cctatgctgg agtgcagtgg tgtgatctcg gctcccggca 106740
acctcaacct cccacctcag cctcctgaat tagtgtctac aggcatgcac ctctatacct 106800
ggctaacttt tgtattttta cagatgaggt tttaccatgt ttcccaggct ggtgtctaac 106860
tcctgagaat ataaggtata tgtagtaggc gttgcttttt ctctttgaag acaaacccca 106920
ggacagttgt ccctcgatga acaaggctaa cctgctgaac gtttgaagca aggaactgga 106980
gatggtcttt gtatcggttt atgttctaga ttccagaaaa tatgcaaaca ggaccaataa 107040
atgcatcttt attttgtgt ccattttgac caggtcaagg aaaatttcaa caagaaaccc 107100
agagtgccgg agcaagaaga tctcaagctg tgagtctaca aagggaagcc cttctgttg 107160
tctaaaagaa aagaaagtgc ttctctttgg tgggttacgg tttgagaaaa gcaacgttga 107220
agttgatgct gatttcggta atacatttgc agagcatgct tatcacactt ggacgatggt 107280
ggggttctgt tttggttttg ctttttttatt ctaaggctct gtgttgctca tgctggagtg 107340
cagtgacatg tccaatatat ctcttggctt caaatggtca gcctgggcaa cacagggaaa 107400
ttctgtctca aaaataaac aaatgaataa aatacaaaaa taaagccggg catggtggct 107460
catgcctgta atcccagcac tttgggaggc cgatgcaggt agatcatctc aggtcaggag 107520
tttgagacca gtctgaccaa cgtggtgaaa atccgtctct actaaaaata caataacaac 107580
aaaaattagc ccagtgtggt ggtgggcacc tgtaatccca gctacttagg aggctgaggc 107640
aggagaattg cttgaacccg ggaggcagag gctgcagtga ccgagattg tgccacagca 107700
tccagccagg atgacagagt gagattccgt ctgaaaaaaa aaaaaaaaa aaaagctgg 107760
gcgctgtggc tcacgcctgt aatcccacca ctttgaaagg ccgaggcggg tggatcacga 107820
ggtcaggaga tcgagaccat cctggctaac acggtgaaac cccatctcta tttaaaaata 107880
caaaaaatta gccgaggcgtg gtggtgggtg cctgtagtcc cagctacccg ggaggctaag 107940
gcttgagaat ggcttgaacc caggaggcgg agcttgcagt gagccgagat cgtgccattg 108000
```

```
cactctagcc tcggcaacag agcaagactc cgtcaaaaag aaacaaaaac aaaaacaaaa   108060
aaaagaaccc tacagtactg gagcaagaag acctcatgct gtgaccctct agatggaagc   108120
actgtctgtt gtctaagaaa agatcgtgca tccctttaga gtgttactgt ttgagaaaag   108180
caacgttgaa gatgctgctg atcttggtaa tacatttgca gagcgtgctt atcatcagac   108240
ttgcatgatg ttggggttct ctttggtttg ttttttttcca agacaggttc cctgttgccc   108300
aggcgggagt gggtggcacc tccaaccgag atctcttggg ctcaagtggt gatcttttta   108360
tttttgattt tttgagatgc gctctcattc cgtttcccag gctggagtgc agcggcagga   108420
tccctgttga ccgaaaactc cgcctcccag cttccggcga ttctcccacc tcagcctgcc   108480
gaatagttgg gaatagagat gcccgccatc gtgtcctgct agttattatt tttattgttg   108540
ttgttgttgt tgagatggag tttcactctt gatgtccagg ctggagtgca gtgttgcaat   108600
ttaggctcac tgcaacctcc acctcctggg ttcaagcgat tctcctgccg cagcctcctg   108660
ggtagctggg attacaggtg cctactgccc cacccagcta attttttgtgt tttgaataga   108720 gactgggttt caccatgttg gcaggctgg tctcaaactc ccgacctcag gtgatccacc   108780
agccttggcc tcctaaagtg ctgggattac aggcgtgagc caccgcccct aatctcacgt   108840
ggtcctctag agtcagccta gactctggtc tatcctggag gatgtttgtg tgtgagacaa   108900
tgtatattct tcaacatcag cccaattctc ttagctaaat gtaaggtatg agtagtaggt   108960
attccttttt ctctttgggg acaaaactca ggacgatcgc cccttgatga acaaggctaa   109020
cctgctgagc ctttgaagca aggaattgga gatggtcctt tcaggggttt atgttctgga   109080
ttccataaaa catgtaaaca gggccaataa atgcatttt atttttgtat ccgttttaac   109140
ctggtcaagg aaaattccaa caagaaaccc agagtgctgg agcaagaaga tcccatgctg   109200
tgaccctcta gaggaagcac tttctgtttg ttgtctgaga aaaacaaag tgcttccctt   109260 tagagtgtta ccgtttggga aaagcagtgt tgaagttgat gctgatgttg gtaatatatt   109320
tgcatgctta ttatcagact tggatgatgt tggggttctg ttttgttttt gttttctaag   109380
acagggtctc tgtggcccag gctggagtac agaggcactt ccaacctagg tctcttgggc   109440
tcatatggtc cttttgggga cagtcttcct ctgtgaccca ggctggagtg cagtggcacg   109500
atcttggctc actgcaatct ccacctcgcg ggttcaagct attctcctgc ctcagcttcc   109560
tgaatagctg ggattgcagg ggcccgacat cacacttggc taatatttgt attttttcttt   109620 tttattcatt tatttatttt tgagatggag tctcgtttcc ccagctggag agcggtggca   109680
tgatcccgac tgactccaac ctctgcctct caggttcaag caattctcct gcctcagcct   109740
ctgaagtagc tgaaactaca ggtggccgcc accacgcctg gctacgtttt gaattttttt   109800 ttttttttttt ttcagtagag atggggctta ccatgttggc caggctggtc tcaaacccct   109860
gacctcaagt gagccactca ccttggcctc cgaaaatgct gagaatacag gcatgagcca   109920
ccaccgcgcg cctcccaaag gcgtgagcca tggtgcgtgg ccatcaacac ctcttacttt   109980
atggaaattt ttctggcact ggtatagaac ctcacatggg gtcaggtgga gttgagggga   110040
cctcagtgtc cctgcagatg ggatgagcaa gagcacggag gtggagtgca tggggcttca   110100
gtgtgtattg gggaaatgaa gctgaaatct tgggtgcatg accaggagat aaatgcatga   110160
gacgggggtc tcactatgct gccctggcta aagtggtctt agatcctcct gcctctgccc   110220
ctcccaggcc ttgttagatg ggactacatg taaatattaa cccatgcaca ggcaggaaga   110280
aagtaaggac cattttttgg ttcgtcccgg ccctcagtta aacttgtgtt ttagataaac   110340
aatgtatttg agatgtgctt aaacaataaa tgatacgcta tttaggtgtg ggcatctttg   110400
```

```
tttcccccta attttaatga tgggactagt ccaggtatgg tggctcctgc ctataattcc   110460
agcactttgg gaggccgaga caggaggatc acctgaggtc agttgttcga gaccggcctg   110520
gccaacatgg tgaaaccccg tccatactaa aaatacaaaa atcagccagg cctggttgca   110580
cacacctgta atcccagcta ctcgggaggc tgaggcagga gactcgcttg aagccaggag   110640
gctgagcttt cagtgagctg agattgcgcc actgcattcc agcctgggca actgagtgag   110700
tctcagtgtc aacaaagtaa ataatagtct aggcacagcg gcacacgcct gtaatcccag   110760
cactttagga ggctaagacg ggaggatcac ctgaggtcag gagttcaaga ccaacggggc   110820
caacgtggca aagccttgtc tctactaaaa ctacaaaaat tagctgggtg cggtggtgca   110880
catctgtgat tccagctact cgggaggcca agacaggaga accacttgaa cccaggagga   110940
ggcgatttca gtgagctgta atgaagccat ggcattccag cctgggccac agagcaagat   111000
tccgtctcaa aaataaataa aacaaataaa aatacgtaga taaatacggg accgtcgtga   111060
atttgagtgt caccttt gtg gagcagccac ggtaatctct gtcattccaa ttttttttat   111120
gtgcactacc aaagcaagaa cttgtgtagg aattattctt cctgtgagta tgcgatgtat   111180
ggaactttcc ttgagacagg gtctcaaaaa tatatcatgt atattttata tattcttatc   111240
atatataata taatcatgta cacacaaaat actcttctaa atacagagaa tactctgata   111300
tcaccttgcg tatttttgt ttgcatgtgt ctgtgtttgg ttgttttttt tttgtcatat   111360
ttttgtatcc ctacttatat atttatttt aattttatta ttatacttta agttctaggg   111420
tacatgtgca caacgtgcag gttagttaca tatgtataca tgtgccatgc tggtgtgctg   111480
cacccattaa ctcatcattt agcattaggt atatctccta atgctatccc tcccgctac   111540
ccccacccaa caacagtccc cggtgtgtga tgttcccctt cctgtgtcca tgtgttctca   111600
ttgttcagtt cccacctatg agtgagaaca tgcggtgttt ggttttttgt ccttgcgata   111660
gtttgctgag aatgatggtt tccagtttca tccatgtccc tacaaagggg ttggttattt   111720
ttgagacaag gtctgactct atcgcccagg ctggagtgta gtggtgccat ctcggctcac   111780
tgcaacctcc acctcccacc taatcctgct gaattagtgt ctgcaggcat gcacaaccac   111840
atctggctca cttttgtatt ttttatacac atgggtttac accatgttgc aggcgctggt   111900
ctcaaactcc ctcccaagct caggtgatcc tctgtctcag cctcctaaag tgctgggatt   111960
agaggtgtga gccaccacac cccactggta tttgtgtgtt cctgttcaaa ttttattgag   112020
gagttttttat aaccaagcct gtggtccatc ctggaggatg tttgtgtgca tgacaatgta   112080
tattcttcaa catcgtagac tcgatgttgg atgctcccat cgggactgtg tgtccctgta   112140
ctggaactcg agtgaacact tggctctaag ttcattgctg ttttctagaa atccagccca   112200
attctcttgt ttaaatataa ggtgcacgta gtaggcattg ctttttcttt ctggagacaa   112260
aactcaggag gattgcccct tgatgaacaa agctaacctg ctgagacttt gaagcaagga   112320
actggagatg gtccttttaa gggtttatat tctggattcc agaaaatgtg caaacagggc   112380
caataaatgc atctttattt ttgtgtccat tttaacctag tcaaagaaaa ttacaacaaa   112440
aaatccacag tgctggagca agaagatctc atgatgtgac catctggagg taagaagcac   112500
tttgtgtttt gtgaaagaaa gtgcttcctt tcagagggtt actctttgag aaaagcagca   112560
ttgaagttga tgctgatctt ggtaatacat ttgaagagca tgcttatcat cagacttgga   112620
tgatcttggg gttttgtttt tttctaagac agggtgtctg tagcccaggc tcgagtgcgg   112680
tggcacttcc aacctagatc tcttgggctc aacaagtagc cctcttttc ggacagagtc   112740
```

```
tcgcgctgtg accctagctg gagtgcagtg gcaggaactt ggctcactgc cacctctgcc    112800
tcctgggttc aagcaattct cctgcctcag cctcccgagc agggttatag gcatgtgcca    112860
ccacacctgg ctaattttg catttttatta tcgattgatt gattgattgt tgagacagag    112920
tctcactctt ttgcccaggc tgtagtgcag tggtgtgatc tcggctcact gcaacctcca    112980
cctcccacct cagccttctg aatacctgtc tacaggcatg caccaccaca cctgccaac    113040
ttttgtgttt tttgtacaga tgaggtttca ccatgttgcc caggctggtc ttgaacccct    113100
gagctcaagt gatcctccca cctcggcctc ctaaagtgtg agtcactatg tcccgcccta    113160
cttgtgtgtt tctgcttaca ttttattgag gcgatttttt ttttttttt gagacggagt    113220
cttggtctgt tacctaggct ggagcgcagt ggcgcgatct tggctcactg caagctccgc    113280
ctcccaggtt catgccattc tcctgcctca gcctcctgag tagctgggac tacaggcgcc    113340
caccaccacg cccggctaat tttttgtat tttagtaga gatggagttt caccttgtta    113400
gccaggatgg tctagatctc ctgaccttgt gatcctcccg cctcggcctc ccaaagtgct    113460
gggattacag gcatgagcga ccgtattgag gcgcttttac aacatagcct gtggtctatc    113520
ctggggaatg tttgtgtgtg tgacaatgta tattcttaga catcttagat tccattttgg    113580
atgctcccat cggtactatg tgttcctata taggaactca agtgaacact tggcttaaaa    113640
tccattgctc ttgtctagaa atttagccca gttatcttgg ttaaagataa ggtgtgtctg    113700
gtaggcattg attttctttt ccggagaaaa aacttaggag gatttcctct tgatgaacaa    113760
ggctagcctg ctgagccttt gaggcatggg acctggagat gatcctgtga ggggtttatg    113820
tttttggatt caggaaacac accagcagga caaataattg catctttatt tttgtgtcta    113880
ttttcaccag gctaaggaag attccaacaa catatccatg gtgctgaagt aagaagatct    113940
cgtgctgtga ccctctagag ggaagcactt tctgttgaaa gaaagaaca tgcatccttt    114000
cagagggtta ctctttgaga agagcaacgt ttagtttgat gttgatcttg gtagtacatt    114060
tgcagagcat gcttttatca tcagacttgg ctgatggtgg tgttctgttt tttgttgttg    114120
ttttctacaa caggatgtct gttgcccagg ctagggtgtg gtggcactta caacctagat    114180
ctctagggct caaatggtcc tcttatttgg ggcagagtct tgctctgtga tccaggctgg    114240
agtgcagtgg caggaactct gctcactgca acctccgcct cccgggttca agtgattttc    114300
ctgccttggt tttctgagta ggtgggatta caggcgcaca ccaccacacc cagctagtat    114360
ttgtagtttt ctttattatt cttttttta ttttaatttt tgagacgaag tctcgctgtt    114420
gcctacggtg gagtgcagtg gcgtgatctc ggctctctac aacgtctgcc tcccaggttc    114480
aagcaattct gctgcctcag cctcccgagt agctggaatc aacaggaaca caccaccatg    114540
cctggctact ttttgattt ttttttagta gagacggagt ttcaccatgt tggccaggct    114600
ggtctcaaac tcctgacctc atgtgagcca cccacctcgg ccttccaaag tgctggaatt    114660
acaggcatga accacgacgt ctggcctaat ttttgtattt ttagaagaga cagggtttca    114720
ccatgttggc caggctggtc tcagctcctg acctcaagtg atcctccccc tcggcctccc    114780
aaagtgctgg gattacaggc gtgagccacc tcgcccagcc tcaagtggtc ctcttgactc    114840
agcctcccat gtagttggga ctacatgggg cgtgccacca cacttggcta agtttttaat    114900
ttttcataca gatatgatct ctgttgctca ggaaggtctc aacacctgag ctcaaggatt    114960
ccacaggcgt gagccacatt ctcctgctga cccttttcaa agatagttga catggccagg    115020
catcatgggg cacacagtcc cagccaccgc agatcccggg gtgggagggt cctttgattt    115080
ccagactatt ccatgcactg atcacacctt gttttttttgt ttgtttgttt gtttgttgt    115140
```

```
ttgtttgaca gagtctcagt ttgttgcctg gcgggagtgc aatgatgtga tctcgggtga    115200
ctgcaacctc tgcctccaag gttcaagtga ttctcctgcc tcaccctcca aagtagctgc    115260
ggttacaggc atgcaccacc acacccagct cagtttttgc atttggtaga gacaggtttt    115320
caccatgttg gtcaggctgg tctcgaactc ctgatttcag gtgatccacc tgcctcagcc    115380
tcccaaagag ctgggattat aggcgttagc ctatgcgccc ggtctgtatt tcctaatttt    115440
aaatatggga cccatggtga atttgggtgt cactgtgtac aggggacatg ggaatctctg    115500
tcattccaat ttttttaatg catgctgttc tgtgtaggaa ttattcttcc tgtgagcaaa    115560
caacatagag agctttcttt ttttgacacc gggtctcaaa aatatatcat atacatttta    115620
ttataatgtc tgatattgat aatataatca tacacacaca aaatactctt ctgtacacag    115680
agaatactga tatcactttg gggttttttt gtttgcgtgc gttttttggg attttgggt    115740 gttttttttt tttttttga gacaacatct ggctctgttg cccatgctgg agtgcagtgg    115800
tgcaattggc tccctgcaac ctccacctcc cacctcccac ttcagcctcc taaagagctg    115860
aatacaggca tgcaccacca cacctgacta acttttgtat tttttgtaca cacagggttt    115920
accatgtttc ccaggctgga ctggaactcc agagctcaag tgatcctccc gacttggcct    115980
ccttaagtac tgcagttaga ggtatgagcc gccgagaccc accgtacttg tgttttccta    116040
ttcaaatatt attgaggagc ttttatggcc taacctgtgg tctatcctgg aggttgtttg    116100
tgcgtacaat acatagtctt caatatcttt tttttttttt tcatttttg agagggagtt    116160 tcgctcctgt cacctaggct ggagtgcaat gacatgatct cagttcactg caacctccgc    116220
ctcctgggtt caagtgattc tcctgcctca gcctcctgag tagctgggat tacaggcacc    116280
cgccaccatg cctagctaag tttgtatttt cagtagagac gggcttctcc atgttggtca    116340
ggctgggctc agactcctga cctcaggtga tccgcccgcc tcggcctccc aaagtgccgg    116400
gattacaggc gtgagccacc gcgcccagtc atcatatatt cttatcatat atatagtagg    116460
atgtttgtgt atataacaat gtacattttc aacattgtag attccatttt ggatgctccc    116520
attgggactg tgtgtccctg tgctggaact caagtgaaca cttggctcaa aatccattgc    116580
tgttctctag aaatccagcc caattctctt ggttaaatat aaggtatgtg tagtaggcat    116640
tgctctttct ctttagagac aaagctcagg attgccccctt gatgaacaag gctaacctgc    116700
tgattctttg aagcaaggaa ctggagatgg tccttttagt ggtttatgtt ctggattcca    116760
gaaaacatgc aaacagggcc aatacatgca tctttacttt tgtgtccatt ttaacccggt    116820
gaaggaaaat tccaacaaaa aacccacaat gctggagcaa gatctcaggc tgtgaccctc    116880
tagagggaag cgctttctgt tggctaaaag aaaagaaagc gcttcccttc agagtgttaa    116940
cgctttgaga aaagcaacgt tgatcttggt aatacacttg cagagaatgc ttataatcaa    117000
ccatggaagg tggtgggggtt ttgtgtttgt ttgttttgtt ttgttttcta agacagggtg    117060
tctgttgccc aggctggagt gtggcggccc ctccaaccta gatctcttgg gttcaagtgg    117120
ccctcttttt tgggacagag tcttgctctg tgaccctgcc ctggctggag tgtcctgtca    117180
ggatctccac tcactgcaac ctctgcctcc tggggtcaag ggattctcct gcctcagcct    117240
cccgagcagc tgggattaca ggtatgtgcc accacctg gcttatttat ttatttattt    117300
atgagacaga gtcttgctgt gtcatccatg ctggagagca gtggtgcaat ctcggctctc    117360
tgcaacctcc acctcccacc tcagtctcct gaattagtat ctacaggcat gtaccaccat    117420
acctggctaa cttttgtatt tttacagatg aggttttacc atgtttcccg ggctggtgtc    117480
```

```
taactcctga gctcaagtga tcctcctgcc ttggcctacg taagtgctgc ggttagaggt 117540
gtgagccacc gcgccccacc tgcccttgtg tatctctgtt caaatgttac tgagaagcat 117600
ttacgggata atgcccggag gatgtttgtg tgtgtgacag tgtacattct tcaacatctt 117660
agattccatt ttggatgctc ccctcgggac tgtgtgtctc tgtcctggaa ttcaagtgaa 117720
cacctggctc tccatccatt gctgttctct agaaatccag cccaattctc ttggttaaat 117780
ataaggtagg tgtagtaggc attgcttttt ctctttgggg acaaaactca ggaggattgc 117840
cccttgatga acaaggctaa cctgctgatt ctttgaagca aagaactgga gatggtcctt 117900
ttaggggttt ttattcagga ttccagaaaa catgcaaaca gggccaaaaa ttgcatcttt 117960
atttttgtgt ccattttgac ctggtcaagg aaaatttcaa caagaaaccc agagtgccgg 118020
agcaagaaga tctcaagctg tgactgcaaa gggaagccct ttctgttgtc tgaaagaaga 118080
gaaagcgctt ccctttgctg gattacggtt tgagaaaaac aacactgaag ctgatgccga 118140
tcgtggtaat acatttgcag agcatgctta tcatcaggct tggacaatgc cggggttctg 118200
ttttcggttt tgcttttttta ttctaagaca ggatctctgt tgcccaggct ggagtgcagt 118260
gacatgtcca acccaggtct cttgaattca aatggtcctt tttaggggggc agagtctttc 118320
tctgtcaccc aggctgatat gcagtgaggc gatctcggct cactgcaacc tctgcctccc 118380
aggttcaagc aattctcctg cctcggcttc ccaagcagct gagattacag gcgttcatca 118440
ccatacctgg atgatatttg tatttttttaa aatttattta tttatttatt tttgagacgg 118500
agtctcgctg tcacccagtc tggagggcag tggcacaatc tcggctcact gcaacctctg 118560
cctcccggt tcaagcaatt cttctgcctc agcctcctga gtagctggaa ttacagaagc 118620
acaccaccgc acctagttac ttttgtata tttttttaa gtagagactg gatttcaccg 118680
tgttggctag gctggtctca aattcctgac ctcaagtgat ccacccacct ctgactccca 118740
aatttctggg atcacaggta tgcgccccca tgcctggcct aatttttgta ttttagcag 118800
agacgtggtt tcaccatgtt ggccaggctg aactcagctc ctgaccttag gtgatctgcc 118860
cgcctgggcc tcccaaagtg ctgagaatac aggcgtgagc caccgtgcct ggccattaac 118920
acctttggt ccacggaaat tattctggca ctggtttata gaacctcgct tggggtcagg 118980
tagagttgaa ggggacccca atgtccttgc aggtgggatg tgcactgctt agcaagaaca 119040
cggaggtgga atgcatgggg tttgagtttt tattggagaa ataaagccaa atcttgggt 119100
gcatgaccag gtcgtatatg caacaatacg ggcgtctcac tatgccgccc aggctaatgt 119160
gggcttagat cctcctgcct ctgcccctcc ccagtcctta gtagctggga ctacatgtga 119220
atattaactc acgtacagga agaggaaagt aaggactgtt ctttgattca cgtcccaccc 119280
ccagttaaat ttgtatttta gataaacaat gtatttgaga tgtacttgaa caacaaatga 119340
tttgctgttt agatgtgagc atctttttt gctcctgatt ttaaacatag acaaggtca 119400
ggtatggtgg ctcacgcctg taattccatc attttggtag gcagagacag gaggatcacc 119460
tgaggtcagc tgcttgagac cagcctggcc aacatggtga aaccccatct gtactaaaaa 119520
tacaaaaatt agccatgcgt ggttgtgctg cacgcctgta atcccagcta ctcaggagga 119580
tgaggcagga gaatcgcttg aagccgggag gcagaggttg cagtgagctg agatcgcgcc 119640
agtgaactac agcctgggca aaagaataag attcaatctc aaaaaaataa aaataggcc 119700
aggcacggtg gcacacacct gtaatgctag cacttttgga ggtcgagacg ggggcatcac 119760
ctcaggtcag gagttgaaga ccagctgcgg catcacggca aagcctcatc tctacgaaaa 119820
atacaaaaat tagccaggtg cagtggcagg tgcctgtaat accagctact cgggagacca 119880
```

```
aggcaggaga atcgttccaa ctgggcggca gaggttgcag tgagccaaga tcgtgccact 119940
gcactgcagc ctgtcgacag agtaagactt ggtctaaaaa aaaaaaataa ataaataaat 120000
aaaagataaa tatggaacca tcatgaattt gggtgtcacc tctgtgtggg ggccagggta 120060
atctctgtca atccaatttt tttttatgtg caccagcaaa gcaagcactt atgtttaggt 120120
attattcttc ctgtgagcat acaatatgta gatctttatt ttctttgaga catggtctca 120180
aaaatgtatg atgtggctgg gcacagtggc tcaagcctgt aatcccagca ctttgggagg 120240
ctgaggcgtg tggatcaccc gaggtcagga gttcaagacc agcctggcca acatggtgaa 120300
aatccgtctc tacgataaat acatatatat atatatgtat atatgccggg catggtggca 120360
ggtacgggta atcccagcta cttgggagcc tgaggcagga gaatcgcttg aacctgggag 120420
gtagaggtta ctcatatcac tatgagattg ttttttgttc ttgtgtgtgt ggttttttgtt 120480 tgttttttgag acaaggtctg gctctgtcac ccaggcaaaa gtgtagtagt gcgatctcgg 120540
cttactgtaa cctccatctc ccacctatgc gtcctgaatt agtgtgtcta caggcatgca 120600
ccaccacagt gggctacctt ttttttttga gagggaattt tgctcttgtt gcacaggctg 120660
gagtacaatg gcaagatttc agatcactgc aacctccgcc ttccgggttc atgtgattct 120720
cctgcctcag cctcccaagt agctgcgatt acaggcatgc accatcacac ttggctaatt 120780
ttgtattttg agtagataca ggtttcccca tgcttgtcag gctggtctcc aactcctgac 120840
ctctagtgat ccacctgcct cggactccca aattgctggg attacaggca tgagctacca 120900
cacccagcca cctggctaac ttttgtagtt tttctacaga ctacaaaatg gtttcaccat 120960
tttacctgag actacaaaat ggtttcacca ttttacctga gactacaaaa tggtttcacc 121020
attttacctg agctggtctc caacacctga gctaaagtga tcctcctgcc tcggcctcat 121080
aaaatgttgg gattagaggt gtgagccacc gtgcctcacc cgtacttgtg tatttcttta 121140
tttttattga tttatttatt ttgagacaga gtttcactct tgttgcccaa gctggagtgc 121200
aatggcacaa tctcggctca atgcaacctc cttctcttag gttcaagcga ttctcctgcc 121260
tcagcttccc gggtagctgg gattaaaggc gtccaccacc acacccagct aattttttgtg 121320 tttttagtag agacagggtt tcagcatgtt ggccagactg gtctcaaact cctaacctca 121380
ggtaatccac ctgcctcagc cttccaaact gctgggatta caggcatgag ccactgcgcc 121440
tagcctcaag tggtcctctt aagtcagcct aaactgtggt ctatcctgga ggatgcttgt 121500
gtgtgtgaca atttatattc ttcaacgtct tagattctat tttggaggct cccaagggga 121560
ttgtgtgtcc ctgtgctgga actcaagtga acacttggct gtacatccat tgctgttctc 121620
tagaaattca gcccaattct cttggttaaa gataaggtat gtgtagtagg cattgctttt 121680
tctttccaga gacaaaactc aggaggattg ccccttgatg agcaaggcta acctgctgat 121740
tctttgaagc aaagaaccag agatggtcct tttaggggtt tatgttctgg attccagaaa 121800
acaggcaaac aggaccaata aatatatttt tattttttcta tccactttaa cctggtcaag 121860
gaaaattcca acaagaaacc cagagtgctg gagtgagaag atcccatgct gtgaccctct 121920
agagggaagc actttctgtt gtctgaaaga aaccaaagcg cttcccttg gagcgttacg 121980 gtttgagaaa ctcaatgttg aagttgatgc tgacttcagt aatacatttg tagaggatgc 122040
ttatcatcag acttggatga tatcggggtt ctgtgctttt ttttttttt ttctcctaag 122100 acaaaatctg tattttccag gctggagtcc ataagcactt ccaacctagg tctcttgcgc 122160
tcagatagtc ctcttttttg ggacagagtc ttgctctgtg acccaggctg gagtgcagtg 122220
```

```
gcgtgatctc ggctcactgc aacctctgtc tcctgggctc aagcaattct ccttcctgag   122280
cttcctgagg agctgggatt acaggcgcct gacatcatcc ttggctaaca tttgtatttt   122340 tctttttat  tcatgtattt atttactttt cagatggagt ctcgctgtcg accaggctag   122400
agggcagtgg cacgatcccg gctgactaca acctgtacct ctcaggttca agcaattctc   122460
ctgcctcagc ctctggagta gctggaatta caggaacaca ccaccaggcc cggctacttt   122520
ttgtattatt attattatta ttatttttt  tttttttcac taaagagggg gtttcaccat   122580
gttgtccaga gaatacaagc atgagccact gcgcagccat caacaccttt tactgcatgg   122640
aaattattct ggcactggta tagaacctca catggggtca ggtggagttg aggggacctc   122700
agtgtccctg cagatgggat gagcaagagc acggaggtgg agtgcatggg gcttcagtgt   122760
ttattgggga aatgaagctg aaatcttggg tgcatgacca ggaaataaat gcatgagaca   122820
ggggtctcac tgtgccgccc tggctaaagt ggtcttagat cctcctgcct ctgcccctcc   122880
ccagtcctag gtagatggga ctacatgtga atattaaccc atgcacagac aagaagaaag   122940
taaggactgt tattttgttc gtacccagcc cccagttaaa tttatcatat atataatata   123000
tcatatatat aacataatca tatacacaca aatgctgat  ttgaatacag agaatactct   123060
gatatcactt tgggtatttt ttggtttgtt tctgtgtgtg tgtgttttat ttgtttggtt   123120 ggttatttt  gagacaaggt ctggctctat cacccaggct ggagtgtagt ggtgcgttct   123180
cagctcactg caacctccgc cttccaccta agctgctgc  attagtgtct acaggcatgc   123240
accaccacac ccggctcact tttgtatttt ttgtacacat ggggttacac catgttgccg   123300
gggctggtct cgaactcctg acctcaggtg attctcccgt cttggcctcc taaagtgcta   123360
gaattagagg tgtgagccac cgtgccccac ctgtacttgt gtatttatgt taaaattgtg   123420
ttaaggagtt tttatgacca agcctgtgat ctattctgga gaatatttgt gcgtatgaca   123480
atgtatattc ttcaacatcg tagattccat tttggatgct cccactggga ctgtgtgcct   123540
atactggaac tcaagtgaac acttggctca aaatccattg ctgttctcta gaaatccagc   123600
ccaattctct tggttaaata taaggtatgt gtagtaggca ttgcttttc  tttctagaga   123660 caaaactcag gaggattgcc ccttgatgaa caaggtaacc tgctgattct ttgaaacaag   123720
aaactggaga tggttccttt aggggtttat gttctggatt ccaggaaaca tgcaaacagg   123780
gcccacaaat gcatctttat gtttgtgtcc attttaacct ggtcgaagaa cattccaaca   123840
aaaaatccac catgcaccga gcaagaatat ctcaggctgt gaccatctgg aggtaagaag   123900
cactttctgt tttgtgaaag aaaagaaagt gcttcctttc agagggttac tctttgaaaa   123960
aagcaacgtt gaagttgatg ctgatcttgg taatacattt ggagagcatg cttatcatca   124020
gacgtggatg acggttgggt tttgtttttg ttttattttt tatcttaggc agggtctctg   124080
ttgcccaggc tggagtgtgt tggcacttcc aacctagatc tcttggtctt aaatggtcct   124140 cttttttgggg ggcggagtct cactctgacc caggctggag tgcaatggca ggaactcccc   124200
tcactgcaac ctccacctcc cgggttcaag cgattctcct gcctcagttt ccgagtcgc   124260 taggattaca ggctcactcc tccacacctg gctaatattt gtagttttct ttattattca   124320
tttatttatg tgttttttgag aaggagtctc gctgtcgccc aggctggagt gcagctgcac   124380
aatctcagct cactgcaact tctgccactg gagtaactgg gatttcaggt gcgtgccacc   124440
acacttggcc aatttttttat gtgtgtattt ttagacccgg gttttcccca tgttggccag   124500
gctggtctgg aactcctgac ctcaggtgac ccatgcacct cggcctccca gagtgctggg   124560
attacaggca tcagccaccg cacccggccc tgtctctgac ttttgcgaac tgaggaagta   124620
```

```
accttttgaa atttactctg aagtgtgaat gattttagca tattttcaac caccaacatt   124680
ctagttcagg agattttcat caccccaaag aggcttattc ccatttgcag tcagttccca   124740
ccccactctt ccacccagac cgtgacaaac actttgcatc tctctagctc tggatctgcc   124800
tcttgtgggc atgtcacata gatcagtttt gaataggtgg cctgttgtga ccactgtaat   124860
tgaggataat gggttggtcc tggttgtctg cagtgtgaat cttaccactg aagggtggtc   124920
cctgatgga agcaggaggc tgggagaact gggcggaaca ccctttggga atggagtcgg    124980
gcgggcagac cctgatgcct gggaagctca caagggtgga agaccacatc ttcctccctg   125040
agaactgcaa ggtgaccctc ctggggtact ggaaggagtg aaggcctctg gactgggaac   125100
accagggcat tgcaccggtg caggcaggat gagccaaggg gaacggagag ccaggcatcg   125160
ctaactggcg acaatttggg tttgatctgg acggagtctg tgtcttctgg tagagagaac   125220
ccctgggatt ttcgctctgc tcctggctgt ctttcagtca tggaatctga tgacaaagac   125280
tcccgcccag agccaagaca tttggtttct ggacccagt ggtcctttct gcctggactt    125340
gggatctttt ggggaagttt gggatctggc agggcatctg cataatccat agaaatccct   125400
gagagtccct tcccttttgct gacatctcca tgttcctacc tattagcttc caaaggagac  125460
tcctatctga attgccgaag gcagcttccc aggccaggga tacccagtta aatttgtatt   125520
tcagatcaat agtatatttc agatgtactt gaacaagaaa tgatttgctg tttaggtgtg   125580
ggcatttgta tttccccctt ttttttttt tttttttttt tttgacagag ttttgctctt    125640
cttacccagg ctggaatgca atggcacaat cttgactcac tgcaacctcc acctcccagg   125700
ttcaagcgat tctcctgcct cagcagcccg agtagctggg attacaggca tgcgccacca   125760
cacccggctc agttttttgca tttagtggag atggggttc accatgttag ccaggctggt    125820
ctcaaactcc tgacctcaag tgatttccct gcatcggcct cccaaagtgc tgggattata   125880
ggcatgagcc tccacgccta gcctcaagtg gtcctcttga gtcaacctag actacagtct   125940
atgctagaga atgtttgtgt gtgtgacaat gtatgttctt gaacatcata gattccactt   126000
tggatgctcc tgtcgggact gtgtgtccct gtgctggaac tcaagtgaga gttggctgaa   126060
aatccattgc tgttctctag aaatccagcc caagtctctt ggttagagat aaggtatgtc   126120
tagtgggcat tgcttttct ttttggggac aaaactcaga aggattgccc cttgatgaac    126180
aaggctaacc tgctgattct ttgaaggaag gaactggaga tggtcttta gggggtttata   126240
ttctggattc cagaaaactt gcaaacaggg ccaatacatg catctttata tttgtgtccg   126300
ttttgaactg gttaaggaaa atttcaacaa gaaacccaga gtgccggagc aagaagatct   126360
caagctgtgg gtctgcaaag ggaagcccTT tctgttgtct aaaagaagag aaagcgcttc   126420
cctttgctgg attacggttt gagaaagcga cgttgaagtt gatgcatttg cagagcatgc   126480
ttatcatcag gcttggacaa tggcggggtt ctgttttggt tttgcttttt cattctaaga   126540
caggatctct gttgcccagg ctggagtgcg gtggcagtgg catgtccaac ctagccctct   126600
tggattcaaa tggtcctttt ttgcaagcaa agtctctctc tctcacccag gctggagtgc   126660
agtgatgtga tctcggctcg ccgcaacccc cgcctcctgg gttcaagcga ttctcctgct   126720
tcagcttccc aagtagctga gattacaggc acccatcacc acacctggat aatatttgta   126780
tttttaaaaa ttcatttatt tatttatgag acggagtctc gctgtcaccc atgctggagg   126840
gcagtgacac gatctcggct cactgcaatc tctgcctcct gggttcaagc aattcttcct   126900
cagcctcctg actagctgga attacaggag cacaccaccg cacctggcta cttttttgtat  126960
```

```
tttttttttta gtagaaatgg gatttcacca tgttggttag actggtctca aactcctgac  127020
ctcaagtcat ccgcccacct ctgactcttt ctgggattgc aggtatgcgc ccccacgcct  127080
ggcctaattt ttgaatgttt agcagagatg gggtttcacc atgttggcca ggctgaactc  127140
agctcctgac cttaggtgat ctgcctgcct cggcctccca aagtgctgag aatacaggcg  127200
tgagccaccg cgcctggcca tcaacacctt ttaccccaca gaaattattc tggcactggt  127260
ttatggaact tcacttgggg tcaggtagag gtgaagggga ccccaatgtc ccttgcagat  127320
gggatgtgta ctgctcagca agagcatgga ggtggagtgc atggggtttg agttttcatt  127380
ggggaaatga agctgaaatc ttgggtgcat gaccaggtcg tatatgcaac gagacgggcg  127440
tctcactatg ccgcccaagc taaagtgggc ttagatcctc ctgcctctgg ccctcccag   127500 tccttagtag ctgggactac atgtgaatat taactcatgt acaggaagag gaaagtaagg  127560
actgttcttt gattcatgcc ccacccccac ttaaatttct atttcagata aacaatgtat  127620
ttgagatgta cttgaacaac aaatgatttg ctgtttaggt gtgggcatct ttttttgttc  127680
ctaattttaa gtataggaca aggctgggta ccacggctca cacctgtgat tccatcattt  127740
tgggaggcca agacaggagg atcacctgag gtcagttgtt tgagaccagc ctggccaaca  127800
tggtgaatcc ccatctctac taaaaataca aaacttagcc cagtgtggtg gtggtacacg  127860
cctgtaatcc cagctactca ggaggctgag gcaggagaat cacaggaagc cgggaagctg  127920
agctctcagt gagctgagat cgcaccactg aactccagcc taggcaacag tgagactcaa  127980
tctcaaaaaa ataaaaaata ggccgggtgc ggtggcacac gcttgtaatc ccagcacttt  128040
gggaggtcga cgggtggga tcacctcagg tcagagttca agagcagccc cgccatcaag  128100
acaaaacctc ctctctacta aaaatgcaaa atatagctag gcgtggtggt acacacctgt  128160
agtctcagct acgtgggagg cggcagcagg agaatctctt gaacccgtga aaggagatt   128220 gcagtgagct aaaatcacac cattgcactg cagcctgggc gactccatct caaaaaataa  128280
atacataaat aaataaatac ataaatacat aaaaaataac ccagagtact ggagcaagaa  128340
gatctcaggc agtgaccctc tagatggaag cactgtctgt tgtctaagaa aagatcgtgc  128400 atcctttag agtgttactg tttgagaaaa tcaacgttga agatgctgct gatcttggta   128460
acacatttgc agagcgtgct tatcatcaga cgtgcatgat gttggggttc tgttgttttt  128520
gttttttttt tccaagacag tgtctctgtt gcccagacta gagtgggtgg cacctccaac  128580
cgagatctct gggctcaag tggtcctctt tttattttt gatttttga acccactct     128640 ggtttcactg ggagtgcagt agcagaatct ctgttgaccg gaaactccac ctctcaggtt  128700
ccagtgtttc taccacctca gcctgccgaa tcattgggaa ttcagttgcc tgccatcagg  128760
tcttgctaat tattattgtt tttttgtttt tttttttga ggcggagttt cgctcttgtt   128820
gcccaggctg gagggcaata gcgcgatctc ggctcaccgc aacctcggcc tcccgggttc  128880
aagtgattct cctgcctcag cctcccagat agctggaatt acaggtgcct accaccccac  128940
ccagctaatt tttgtgtttt cagtagagat ggggtttcac catgttgggc aggctggtct  129000
caaactcctg acctcaggtg atccaccagc cttggcctcc caaagtactg ggattacagc  129060
tgtgagccat caccctaat ctcaaatggt cctgtagagt cagcctagac tgtggtctat   129120
cttggaggat gtttgtgtgt gagacaatgt atattcttca acattgtaga ttccattttg   129180
gatgcttcca tcgggactgt gtgcccctgt cctggaactc agctgaacac ttggctcaaa  129240
atccattgct gttctctgga aattctgccc taatctcttg gttaaatata aggtatgtgt  129300
agtaggcttt gcttttctc tttggggaca aaactcagga gggttgcccc ttggtgaaca   129360
```

```
aggctaacct gctgagcctt tgaagcaagg aactggagat ggtccttttta ggggtttatg   129420 ttctggattc cagaaaatat gcaaacaggg ccaataaatg catctttatt ttgtgtgtat   129480
tttaacctgg tcaaggaaaa ttccaacaag aaacccagag tgctggagca agaagatccc   129540
atgctgtgac cctctagagg aagcactttc tgtttgttgt ctgagaaaaa acaaagtgct   129600 tcccttttaga gttactgttt gggaaaagca gtgttgaagt tgatgctgat gttggtaata   129660
tatttgcatg cttatcatca gacttggatg atgttgggggt tctgggtttt ttttgttttc   129720
taagacaggg tctctgtggc ccaggctgga gtacagaggc acttccaacc taggtctctt   129780
gggctcaaat ggtccttttt gggacagagt cttgctctgt gactcaggct ggagtgcagt   129840
ggtgcaatct cagctcactg caccctccac ctcctgggtt caagtgattc tcctgcctca   129900
gcttcctggg attacaggca cctgacatca tgcccagcta atatttgtat ttttctttt    129960 tattcattca tttatttatt ttttaggtgg agtcttgctg ttgccaagtc tggagggcca   130020
tggcacgatc ccggctgact ccaacctctg tctctcaggt tcaagcaatt ctcctgcctc   130080
agcctcctga gtagctggaa ttacaggcgc ttaccaccac gcctgactgc ttttcgaatg   130140
tgtgcgtatg tgtgtgtatg tgtgttagag agaaagagag agagagagat ggagtttcac   130200
tcttgttgcc caggctggag ggcaatgaca tgatctcggc ccatacaacc tcagcctcct   130260
gggttcaagt gattctcctg cctcagcctc ctgagtagct aggattacag gcatgtgcca   130320
ccacacctgg ctaattttgt attttttagta gatatgggggc ttccccatgt tggtcaggct   130380
ggtctcgaac tcctgacctc aaatgattca cctgcctcag tctcccaaag tgctgggatt   130440
acaggtgtga gccaacatgc ccggcctgaa tttttttttt tttttttttt ttttcaagta   130500
aagacggggt ttcaccatgt tgaccaggct ggtctcaaac ctctgaactc acgtgagctg   130560
ctcgcctcgg cctcccaaag gcatgagcca tggtgcgtgg ccatcaacac ctcttacttt   130620
atcgaaattt ttctggcact ggtatagaac ctcacgtggg gtcaggtgga gttgaaggga   130680
cctcagtgtc cctgcagatg ggatgagcaa gagcacggag gtggagtgca tgggggcttca   130740 gtgtttattg gggaaatgaa gctgaaatct tgggtgcgtg accaggaaat aaatgcatga   130800
gacgggggtc tcactatgcc accctggcta aagtgggctt agatcctcct gcctctgccc   130860
cccgcagtcc ttgctagatg ggactacatg tgaatattaa cccatgcaca gacaagaaga   130920
atgtaagaac cattatttgg ttcacaccgg gccctcagtt aaacttgtat tttagacaaa   130980
caatgtatct gagatgtcct tgaacaacaa atgatttgct gttcaggtgt gggcatcttt   131040
gttttttccc taattttaat gatgggacta gtctgggtac ggtggctccc gcctgtaatt   131100
ccagcacttt gggaggctga ataggagga tcacctgagg tcagttgttt gagaccagcc   131160
tcgccaacat gatgaaacct cgtctgaact aaaaatatag atattagcca gacgggggtgg   131220 tggtgcaccc ctgcaatccc agctactcag gaggctgagg caggagaatc acttgaagcc   131280
aggaggctga gctttcagtg agctgagatt gagccactgc actccagcct gggcaacaga   131340
gtgagactca gtctcaaaaa agtaaaaaat aggctgggtg tgggccgggc gcggtggctc   131400
acgcctgtaa tcccagcact ttgggaggcc gaggtgggtg gatcacaagg tcaggagact   131460
gagaccatcc tggctaacac ggtgaaaccc tgtctctagt aaaaatacaa aaaaaaaaa    131520 aaaattagcc agacgtgatg gtgtgcgcct gtactcctag ctactcagaa ggctgaggca   131580
ggagaatggc ctgagcccgg gaggcggagc ttgcagttag ctgagatcgc accactgcac   131640
tccagcctgg gtgacagagc aagactccgt ctcaaaaaaa aaaaaaaaa aaaaaaggcg   131700
```

```
gggtgtggta gtgcacatct gtaatcccag catttcggga ggccaagaca ggaattacct 131760
gaggtcagga gttcaagacc aacagggcca acatggcaaa acctcgtctc tactaaaaat 131820
acaaaaatta tctgggtgca gtggtacaca tctgtaattc cggctaccca gaggctgagg 131880
caggagaata gcttgaaccc aggaggagga gatttcagtg agctgaaatc acaccattgc 131940
acttcagcct gggccacaga gcaagattgt gtctcaaaaa taaataaata ataaaatga 132000
cataaaatca ataaataaaa ataaatacat aaatacagga acatcattaa tttggatgtc 132060
accttttgtgc aggggccagg gtaatctctg tcattccaat ttttttatg tgcactgcca 132120
aagcaagcac tcatgtagga attatccttc ctgtgagcat ataatatatg gaacattctt 132180
tgagacaggg tctcaaaaat atgatgtgta tttcatcata tatataatat aatcgtatac 132240
acacaaaata ctgtttaaat acagagaata ccctgatatc accttgggta tttttctttg 132300
tttctgtgtg tgtgtgtgtg tgtgtgtgtg tgtgtgtgtg tgtgtttgtt tggttatttc 132360
tgagacaagg tctggctcta tcgcccaggc tggagtgtag tggtgtgatc tcaactcact 132420
gcaacctccg ccccccacct aaacctgctg aattagtgtc tacaggcatg caccagcaca 132480
cctggctaac ttttgtattt tttgtacata tggggttaca ccatgttgcc ggggctggcc 132540
tctaactcct gagctcaggt gatcctcccg cctcagcccc taaagtgctg ggattagagg 132600
tgtgagccac cgcaccccag ccatacttgt gtatttctat tcaaatttta ttgaggagtt 132660
tttaccgccc agcctgtggt ctatcctgga gaatgtttgt gtgtgcgaca atgtatattc 132720
ttcaccatcg tagattccgt tttggatgct cccatcggga ctgtgtgtcc ctgtgctgga 132780
actcgagtga acacttggct caaaatccac tgctgttctc tagagatctg tagggtccag 132840
ccctactggg cctgtgggtt tttctcttcg tgagcagata ggagagattg tagaaataaa 132900
gacacaagac aaagagagag aagaaaaggc agctgggcct gggggaccac taccaccaag 132960
acgtggagac cggtagtggc cccgaatgcg tggccgcgcc gttatttatt gtatacgagg 133020
caaaagggca gggtaagaag tgtgagtctt ctctaatgat aggtaagatg acgcgagtca 133080
cgtgtccacc ggacaggggg ccccttccct atttggtagc ttaggcggag agagattggg 133140
gacagcttac gtcattattt cttctatgta tttctcggag agatcaaaga ctttaatact 133200
ttcacttatt ctgctaccgt tatctagaag gcggagccag gtgtgcagag cggaacgtga 133260
aagtggacca ggagcgtgac cgctgaagca cagcatcaca gggagacgtt taggccacca 133320
gacggctgcg ggcgggcttg actgatgtca ggctttccac aagaggtggt ggagcagagt 133380
cttctctaac tcccctggag aaagggagac tccctctccg ggtttgggaa ggtaaggggg 133440
tccttcccag gcactggcgc taccgctgtg ctaagtgacg ggtgccttcc ccctggtgtt 133500
accgctggac cagggagccc tctagtggcc gtgtccgggc atgacagagg gctcacgctc 133560
ttgtcttctg gtcgcttctc accgtgtccc ttcagctcct atctctgtat ggcctggttt 133620
tccctaggtt atgattgtag aacaaagatt attataatat tggaataaag agtaatgcta 133680
caaactaatg attaataata ttcatatata atcatatcta taatctattt ctagtataac 133740
tagtcttatt ctatatattt tctttgttat actggaacgg cttgtggtga gtttctttat 133800
tataccggaa cagcttgtgc cttcggtctc ttgcctcggc acctgggtgg cttgccaccc 133860
acagaaatcc tgcccgtttc tcttggttaa atataatgta tttctagtag gcattgcttc 133920
ttctttccag agacaaaact caggaggatt gtgctatgat aaacaaggct aacctgctga 133980
ttctctgaag caaggaactg gagatggtcc ttctaagggt ttatattctg gattccagga 134040
aacatgcaaa caggacccat aaatgcatct ttattttggt gcccatttttg acctggtcag 134100
```

```
gagaattcca acaaaaaatc cacggtgttg gagcaagatc tcaggctctc aggctgtggc   134160
catctagagg taagaagcac tttctgttgt cttaaagaaa agaaagtcct tttttttttt   134220
tttttttttt tttgagacaa tgtctcgctc tgtcgcccag gctggaatgc agtggcgtga   134280
tcttggctca ctgcaagctc cgcctcccgg gttcatgcca ttctcctgcc tcagcctcct   134340
gtgtagctgg gactacaggc gcccgccacc aagcccggct aattttttgt attttagta    134400 gagacggggt ttcatcttgt taggcaggat ggtctcgatc tcctgacctc atgatccacc   134460
cgcctcggcc tcccaaagtg ctgggattac aggcgtgagc caccacgccc gcccagaaag   134520
tgctttcttt cagagggtta cggtttgaga aaagcagcat tgaagttgac gctgatcttg   134580
gtaatacatt tgcagagcat gcttatggtc agacgtggat gatggtgggg ttttgttttt   134640
gttttgtttt ttatctgaga cagggtgtct ctgttgccca ggctggagtg cagtggcaca   134700
tccaacctag atctcttggg ctcaagtggt cctctttttg aaacagagtc tcactctgtt   134760
accctggctg gagttcagtg gcaggaactt ggctcactgc aatctctgtc tcctgggttc   134820
aagcaattct ctggcctcag cctcccgagc agggttacag gcatgtgcca ccacgcccgg   134880
ctaatttttg cattttttta attgatttat ttgtttgttg ttgagacagt ctcactctgt   134940
tgcccaggct gtagtgcagt ggtgtgatct cagctcaccg caacctccac ctcccatgtc   135000
agcctcctga atacctgtct ccaggcatgc acccccacac ctggctaact tttgcatttt   135060
ttgtacagat gaggtttcac catgttgccc aggctggtct tgaaccoctg agctcaagtg   135120 gtcctcccac ctcggcctcc taaactgctg tgattaatgg tgtgagccac cgtgccacac   135180
ccgtacttgt ttgtttctgc tcaaattgta ttgaggagct tttacatcct agtctgtggt   135240
ctatcctgga ggatgtttgt gtatataaca atgtacattt tcaacatttt agattccatt   135300
ttggatgctc ccatcgggac tgtgtgtccc tgtgctggaa ctcgagtgaa cacttggctc   135360
aaaatccatt gctgttctct agaaatcctg ccctattctc ttggtgaaat ataaggtatg   135420
tctagtcggc attgattttt ctttctggag acaaaactca ggagggttgc ccctgcatga   135480
acaaggctaa cctgctgagc ctttgaagca aggaactgga gatggttttt ttaggggttt   135540
atattctgga ttcagaaaaa catgcaaaca gggacaatga atgcatcttt attttctgt    135600 ccatttaac ctggtaaacg aaaatttcac caaaaaccc agagtcctgg agcaagaaga     135660
tctcaggctg tgaccctcca aagggaagaa ctttctgttg tctaaaagaa agaacgcac    135720 ttccctttag agtgttaccg tgtgagaaaa gcaacgttga agctgatgct gatcttggta   135780
ataagtttgc agagcctgct tatcatcaga cttggacgac ggtgtagttc tgttttggtt   135840
ttgagttttt tgtttgtttg ttttgttttg cttttgagat ggaggcttgc tctgtcgccc   135900
aggctggagt gcagtggcgt gttctcagct cactgcaacc tccgcctccc aggttcacgc   135960
cattcttctg cctcttgagt agctgggact acaggcgccc gccaccacgc ctggctaatt   136020
tttgtatttt ttagtagaca cagagtttca ctgtgttagc caggatggtc ttgatctcct   136080
gaccttgtga tccacccgcc ttggcctcca aaagtgctgg gattacaggc gtgaaccact   136140
gcgcccggcc ttaattttg tatttttagt agagacagga ggctgagctt tcagtgagct    136200
gagttcgttc cactgcactc cagcctgggc aacagagtga gactccatct caaaaaaata   136260
aaaaataggc cgagcgtggt ggcacatgcc tgtaatccca gccctttggg aggccgagac   136320
aggtggatca cctgaggtca ggagttaaag gctggctggg ccaacaaggc aaaacctcga   136380
ctctactaaa aatacaaaat tacacctgta atcttagctg cttgggggc tgtggcagaa     136440
```

```
gaacctcttg aacccaggaa gaggagattg cagtgagacg aaatcatacc attgcactct   136500
agcctgggcg acagagcgag attctgtctc aaaaaataaa taagtagggc agacagggtg   136560
gctcacgtct gtaatcccag cactttggga ggcaaggcgg gtaaatcaca aggtcaggag   136620
ttcgagacca gcctggccaa catggcgaaa ccccatctct actaaaaata caaaaaagta   136680
gctgggcatg gtggctggca cctgtagtcc cagctacttg ggaggctgag gcaggagaat   136740
cgtgtgaacc caggaagcgg aggttgcagt gagccgagat cgggccattg cactccagcc   136800
tgggcgacag tgcgagactc tgtatcaaaa ataagtaaat aaataaacaa aataaaagta   136860
aaaagaatta aatagataaa tatggtacca ttatgaattt gagtgtcacc tttgtgcagg   136920
ggtcatggta atctttgtta tttcaatttt tttatgcgta ttgccaaagc aagcacatat   136980
gcgtaggaat tatacttcct gtgagaatac aatatatgga gctttctttt ttgttttttc   137040
tgtttgtttg ttttttgaga cacagtttca ctcttgttgc ccaggctgga gtgcaatgtc   137100
acgatctcag ctcacggcaa cctctgcctc ctgggttcaa gcgattctcc tgcctcagcc   137160
tcccaagtag ctgggattgc ttgcatgtgc caccaagcct agctaatttt ttgtatttag   137220
agtagagatg gggtttctcc atgttggtca ggctggtctc gaactcctga cctcagatga   137280
tccatccacc tcagcctccc aaagtgctgg gattacagat gtgagccacc atgcccggcc   137340
atgatatatt tttatatatg taatatcaca tacacacaaa atactcttct atgcacagag   137400
aatagtctta tatcactttg ggtatttgtg tgtgtgtgtg tgtgtgtgtg tgtgtgtgtg   137460
tgtgtgtgtg tgttttgttt ggttggttat ttttgagaca aggtctggct ctgtcatcca   137520
ggctggagtg tagtggtgtg atctcagctc actgcaacct ccaccccgga cctaagccta   137580
ctgaattagt gtctacaggc acgcactacc acacctggct cacttttgta ttttttgtac   137640 acatgggggtt tcacaatgtt gccggggctg gtctcaaact cctgtgctca ggtgatcctc   137700
ccatcacggc ctcctaaagt gctggaatta gaggtgtgag ccgccacgcc ccacctgtac   137760
ttgtgtatct ctgttcaaat gttactgagg agcttttaca gcgtaacctg tggtctatcc   137820
tggaaaatgt ttgtgtgtga gacaatgtac attcttcaac atcttagatt gcagtttgga   137880
tgctcccgtc aggactgtgt gtccctgtgc tgggactcaa gtgaacactg gctctccat    137940 ccattgctgt tgtctagaaa tccagcccaa ttctcttggg taaatatgag gtatgtgtag   138000
taggcattgc tttttctttc tggagacaaa gctcaggagg attgcccctt gataaacaaa   138060
gctaacctgc tgattctttg aagcaaggaa ctggagatgg tccttttagg ggtttatatt   138120
ctggattcca gaaacatgc aaacaggacc aataaatgcg tgcttatttt tgtgtctgtt    138180
ttaacctggt caaggaaaat tccaacaaaa aatccacgat gctggagcaa aagatctca    138240 ggctgtgtcc ctctagaggg aagcgctttc tgttgtctga agaaaagaa atggttccc     138300 tttagagtgt tacgctttga gaaaagcatc gctgatcttg gtaacacatt tgcagagaat   138360
gcttataatc agacgtggat gatgttgaag ttttgcgttt gttttgtttt gttttttttc   138420
ctagacaggg tgtctgctgc ccaaactgga gtgcggtggc acttccaacc tagacctctt   138480
gggtttaagt ggccctctat tttgggatag agtcttgctc tgtggccctg gctggagtgc   138540
agtgtcagga actctgctca ctgcgacctc tgcctcctag gttcaagcga ttctcttgcc   138600
tcagcctcct gagcagctgg gattacgggc atgtgccacc atgcctggct aattttttgta  138660 ttttttatta tttatttatt tatttatttt tgagacagag tctcgctctg tcacccaggc   138720
tgaagtgcag tggtgcgatc ttggctcacc gcaacctcta cctcccacct cagcctcctg   138780
aacagctgtc tccaggcgtg caccaccaca cctggctaac ttctgtattt gttttacagt   138840
```

```
catggtttca ccatgttgcc cgggctcatc ttgaactcct gagctcaagt gatcctcccg 138900
cctcagcctc ctaaagtgct gtgagccacc gtgtcccaac agtacttgtg tgtttccgtt 138960
caaattgtat tgaggagctt ttacagcata gcctgtggtc tctccgggag aatgttttttg 139020
tttacgacaa tgtatattct tcaacatcgt agattccatt ttggatgccc tcattgggac 139080
tgtgtgtccc tgtactggaa ctcaagtgaa cacttggctc aaaatccatt gctgttctct 139140
agaaatccag cctaattctc ttggttaaag gtaaggtatg agtagtaagc attgcttttt 139200
ctctttggga acaaaactca ggaggattgc cccttgatga acaaagctaa cctgttgatt 139260
ctttgaggga aggaactgga gatggtcctt ttaggggttt atgttctgga ttctagaaaa 139320
cacacaaacc ggacaaataa atgcatcttt attttttgtgt ctattttaac ctcgtcaagg 139380
aagattccaa caaaaaatcc acagtgccgg agcaagaaga cctcaggctg tgacactcta 139440
gagggaagcg ctttctgttg tctgaaagaa aggaaagtgc atccttttag agtgttactg 139500
tttgagaaaa gcaacattga agctgatgct gatcttggta ataaatttgc agcgaatgct 139560
tataatcaga cttggatgat gttgggcttc tgagttttttt tttgtttttgt tttgtttagt 139620
tttgggggttt ttctgttttt tgttttttgt ttttttttttt tttgaggccg agtcttgctc 139680
tttcgcccag gctggagtgc agtggcgcta tctcggctca ctgcaagttc tgcctcccgg 139740
gttcacgcca ttctcctgcc tcagcctcct gtgtagctgg gactacaggt gcccgccagc 139800
acacccggct aattctttgt attttagta gagacggggt ttcaccgtgt tagccaggat 139860
ggtctcgatc tcctgacctc gtgatccacc cgcctcagcc tcccaaagtg ctgggattac 139920
aggcgtgagc caccgcgtcc agccttgtta ttgttttttga gactgagtct tgctctgtgg 139980
cccaggctgg agcgcagtgg cgtgatctcg gctcactgca acctccatct cccaggctca 140040
agcaattctc ctgcctcagc ctcctgagta gctgggatta caggcctgtg ccaccatgcc 140100
cggctaatta tttgtatttt tagtagagac agggtttgca ccatgttggc caggctggtc 140160
tcgaactcct gacctcaggt aatccaccca cgtcgatctc ccaaagtgct gggattacaa 140220
ctgtgagcca ctgcgcccgg cctgttttttc tctaccacag ggtgtctgtt gcccaggctg 140280
gagtgcggtg gcatttttaa catagatctc ttgggctcga gtggtccttt ttttttggttc 140340
agtcttgctt tgtgacccag gctggagggc agtggcagaa actctcctca ctgcaacctc 140400
cgcctcctag gttcaagcca ttctcctgac tcagcctcct gagcagctgg gattaccggt 140460
gtgagccacc acacccagct aatttttgta tttttattta tttgtttatt tatttattta 140520
ttgttgagac ggagtcttgc tgtgtctccc aggctggagt gcagtggcgc gatcgtggct 140580
tactgcaacc tcctcctcct tggttcaacc aattctcctg cctcagcctc ctgagaagct 140640
aggattacag gcatgcacca ccatgcctgg ctaatttaga ttccattttg gatgctccca 140700
tcaggactgt gtccctgtac tggaactcag gtgaacactt ggttcaaaat ccgtcgcttt 140760
tctctagaca tccagctcag ttctcggtaa agataaggta tgtgtagtag gcattgcttt 140820
ttcccttttag agacaaaact caggaggatt gccccttggt gaacaaggct aacttgcaga 140880
ttctttgaag caaggaactg gagatggtcc tttagggggt ttatgttctg gattccagaa 140940
aacatgcaaa cagggccaat acatgcatct ttattttttgt gtccgttttg acctggtcaa 141000
ggaaaatttc aacaagaaac ccagagtgcc ggagcaagaa gatctcaagc tgtgactgca 141060
aagggaagcc ctttctgttg tctaaaagaa aagaaagtgc ttcccttttgg tgaattacgg 141120
tttgagaaaa gcaacgttga agttgatgct gatctcggta atacatttgc agagcatgct 141180
```

```
tatcacactt ggacggtggt ggggttctgt tttggttttg ctttttattt ctaagacagg   141240
gtctgtgttg cccatgctgg agtgcggtgg cacatcccac ctaggtctct tggattcaaa   141300 tggtccttt tgggggcaga gtctctctat caccgaggct ggagtgcagt gatcccatct    141360
tggctcacta caacctccgc ctcccaggtt caagcaattc tcctgcttcg gcctcccaag   141420
tagctgagat ttacaggtgc ccatccccac acctggataa tatttggttt tattcatgta   141480
tttatttatt tttaagatgg agtctcactg tcacccagac tggagggcag tggcacgatc   141540
tcggctcgct gccacctgcg cttccctggt tcaagtaatg cttctgcctt agcctcctga   141600
gtagctggaa ttacagaagt acaccaccac acctggctac tttttatatt tcatttttaa   141660
tacagactgg atttcaccat gttggctagt atgatatata ttttgtcata tattcttata   141720
tatataatca tatacacaca aaatactctt ctgcacacga agagtattct tatatcgctt   141780 tgggttttt tgtttgtgtg tttgttttgt gtttgtttct ttgttttga dacaacgtct     141840 ggctctgttg ctcaggctaa agtgtagtat tgcaagctca gctcactgca acctccacct   141900
cccacctaaa gtcccctgaa ttagtgtcta caggcatgca ccaccacacc tggctcactt   141960 tttttctga gaaggaattt tgcttttgtc gctcaggctg gagtgcaatg gggtgatttc    142020
agctcactgc aacctctgac tcccggcttc aagcaattct cctgcctcag cctcccaagt   142080
agctgggatt acaggcatgc accaccacac ctggctaatt ttgtattttt agtagagatg   142140
ggtttcacct tctttctcag gctggtcttg aactcctgac ctcaagtgat ccacctgcct   142200
cgacctccca agtgctagg attacaggtg agagacattg cacctggcca cctaactttt    142260 gtagttttt tacagacagg gcttcaccat attgcccaag ctggtctcca gctactgagc    142320
tcaagtgatg ctcctgtctc ggccactgtc cctcacccaa acttgtgtat tcttttctt    142380 ttctttttt tttttttt ttgagatgga gtctggctct gtcacccagg ctggagtgca     142440
gtggcacgat cttggctcac tgcaagctcc gcctcccag ttcatgatat ttttctgcct    142500
cagcctccca agtagctggc actacaggca cccgccacca cgcctggcta atttttttgta  142560 tttttagtga agacggggtt tcactggatt agccaggatg gtcttgatct cctgagctcg   142620
tgatctgcct gccttggcct cccaaagtgc tgggattaca ggcttgagcc accgcaccca   142680
gcttttttgt tttttgttt tgtttttttg agatggggtc tcgctctgtc acccagcctg    142740
gagtgcaatg gcacgatctc ggttcactgc atcctacccc tcccgggttc aagcgattct   142800
cctgcctcat cctcccaagt aactgggatt acaggtgccc accaccgcgc ctggctaatt   142860
ttttgtattt ttagtagaga cggggtttca ccgtattagc caggatggtc ttgatctcct   142920
gacctcgtga tctccctgcc tcagcctccc aaagtgctgg gattacaggt gtgagccact   142980
gcacccggcc ttttttttt tttttttt tttgagatgg gatctcgctc tgtcacccag     143040
gctggagtgc aacggcatga tctcagctca cggcaacctc ccctccgg gttcaggtga     143100 ttctactgcc tcagcctccc aagtagctgg gattacaggt gcccacgacc acgcctggct   143160 aatttttgt attttagta gagatggggt ttcatcaagg tggccaggct ggtctcaaac     143220
tcctgacctc atgatctact ggcctcggcc taccgaagtg ctgggattac aggcatgagc   143280
caccgcgccc agcttctgta tttcttttca aattttattg aggattttt atgtcctagc    143340 ctgtggtcta tcctggagga tgtttgtgtg tgagacaatg tatattcatc aacatcttag   143400
attccatttt gattgcttcc gtagaaactg tgtgtccttg tgctggaact ccggtgaaca   143460
cctggctcaa tatccattgc tcttctctag aaatccagcc cagttctctt ggttaaatat   143520
aagatatgtg tagcaggcat tgctttttct ttccagagac aaaactcagg aggattgccc   143580
```

```
cttgatgaac aaagctaacc tgctgattct ttgaagcaag taactggaga tcctccttt   143640 aggggtttat attctggatt ccagaaaaca tgcaaacagg gccaataaat gcatctttat 143700
gtttctgtcc attttaactt gatctaggaa aattccaaca aaaaacccac ggtgctggag 143760
caagatctca ggctgtgacc ttctcgagga agaagcact ttctgttgtc tgaaagaaaa 143820
gaaagtgctt cctttcagag ggttacggtt tgagaaaagc aacgttgaag ttgacgctga 143880
tcttggtaat acatttgcag agcgtgctga tcatcagacg tggataatgg tggggtttg  143940 ttttttatct aagacagggt gtctgttccc caggctggag tgcggtggca cttccaactt 144000
agatctcttg ggttcaagtg gccctctttt tgggacagag tctcactctg tggccctggc 144060
tggagtgcag tggcaggaac ttggctcact gcaatctctg cctcctgggt tcaagcaatt 144120
ctcctgcctc agcctccgga gcagctgggg ttacaggctg tgccaccatg cccagctaac 144180
ttttgcattt ttattattga tttattgatt tatttttgag acagggtctg gctctgtcac 144240
ccaggctata gggcagtggt gcgatctcgg ctcactgcaa cctccacctc ccacctcagc 144300
ctcctgaata cctgtctcca ggcatgcact accacacctg cctaactttt gtatttttg  144360 tatagatgag gtttcaccat gttgcccagg ctggtctcgg accttgagc tcaattgctc 144420 ctcccgcctg ggcctccaaa actgctgtga ttaatggtgt gagcaagcgt gccctactct 144480
tgtgtgtttc tgctcaaatt ttatggagga gcttttacat cccagcctgt ggtctatcct 144540
ggagaatgtt tgtgtgtgtg acaatgtata ttcttcaaca ttttagattc catttggatg 144600
ctcccatccg gactgtgtgc ccctgtactg gaactcaagt gaacacttgg ctcaacatcc 144660
attgctgttc tcatgaattc caggccaatt gtcttggtta aagacaaggt atgtgggctg 144720
ggcgtggtgg ctcatgcctg taatcccagc actttgggag accgaggtgg gaggatcacg 144780
aggtcaggag ttcgagacaa gcctgaccaa cacggtgaaa cccatctcta ctaaaaatac 144840
aaaaattagc tgggcgtggt ggctccacca gtaatctcag ctacttggga ggctgaggca 144900
ggagaattgc ttgaacccag gaagcggagg ttgcagtgag ctgagatcgc gccactgcac 144960
tccagcctgg gtgacagagc gagacttcat ctcaaaaaat aaaaaataaa aaggtatgtg 145020
tagtaggcat tgcttttct ctttgtagat aatactcagg aggactgcct cttgaacaag 145080
gctaacctgc tgagcctttg aagcaaggaa ctggagatgg tccttttagg gggttatgtt 145140
ctggattcca gaaaacatgc aaataggggac aatgaatgca tctttatttt tctgtccatt 145200
ttaacctggt caaggaaaat ttcaacaaga aacccagagt gctggagcaa gaagatctca 145260
agctgtgagt ctacaaagga aagcgctttc tgttgtctga aagaaaagaa atcgcttccc 145320
tttggagtgt tacggtttga gaaaagcagc gttgaagttg atgctgatct cggtaataca 145380
tttgcagagc atgcttatca cacttggacg gtggcgggt tctgttttgg ttttgctttg 145440
ttattctaaa acagggtctg tgttgcccat gctggagtgc ggtggcacat cccacctagg 145500
tctcttggat ttaaatggtc cttttttggg gccagagtct ctctctgtca ccgaggctga 145560
agtgcagtca tcccatcttg gctcactaca acctccgcct cccaggttca agcaattctc 145620
ctgcttcagc ttcccaagta gctgagattt acaggcgccc atcccacac  ctggataata 145680 tttgggtttt tttttatt  atttttaaga tggggtctca ccgtcaccca ggctgtagtt 145740
cagtggcttg atctcggctt actgcaatgt atgccaccca ggatcaagtg attctcctgc 145800
cccagactcc tgagtagctg gaattacacg cacctgccac tacacccggc tacttttga  145860 atttttttt ttttttttaa agtaaagatg ggctttcacc atgttggcca ggctggtctc 145920
```

```
aaaccccctga cctcaagtca gctgcttgcc tcagcctccc aaagtgctga aatacaaac    145980
atgagccact gcgtggccat caacacctct tactttatgg aaattttttct ggcactggta   146040
tagaacctca cgtggggtca ggtggagttg aggggaccte agtttcccttt gcagatggga   146100
tgtgcactgc tcagcaagag cacagaggtg gagtgcatgg ggcttcagtg tttattgggg   146160
aaatgaagct aaaatcttcg gtgtgtgacc aggagataaa tgcatgagat ggggatctca    146220
ctatgctgcc caggctgaag tgggcttaga tcctcctgcc tctgcccctc ccagtccctt    146280
ggtacatggg actacatgtg aatattaacc ccccatgcac agacaagaag aaagtaagga    146340
ctgttctttg gttcatacct gaccccagtt aaacatgtat tttagataaa caatgtattt    146400
gaaatgtact tgaacaacaa atgatttgct gtttaggtgt gggcatcttt ttttttcttc    146460
ctaactttaa atatgggact agtccaggta cggtggctca tgcctgtaat tccagcactt    146520
tgggaggcgg agacaggagg atcacctgag gtcagttgtt cgagaccaga ctggccaaca    146580
tggtgaaacc tcgtctgtac taaaaataaa aaaattagtg agacgtggtc ttggtgcatg    146640
cctgtaatcc cagctactcg ggtggatgag gcaggagaat tgcttgaggc tgggaggctg    146700
agctttcagt gagctgagat caagcctctg cactccagcc tgggcaacag agtgagactg    146760
agtctcaaaa aagtaaaaaa tcagctgggt gcgctggcaa acacttgtaa tcccagcact    146820
ttgggaggcc gagacgggag gatcacctga ggtcatgttc aagactaaca gggctgaaat    146880
agcaaaacct catctctatt aaaaatacaa aaattagctg ggtgcagtgg tgtatatctg    146940
tatttccagc tacttggagg ctaaggcagg agaatcgctt gaacccagga ggaagagatt    147000
tcagtgagct gaagccatgc cattgcactc cagcctgggc acagagcaa gattccatct     147060
caaaaataaa ataaataata aaatgaaat taaatagata aaataaata gataaatatg     147120
agaccatcat gaatttggat gtcacttttg tgcaggggcc agggtaatct ctgtcattcc    147180
aatttttttt atgtgcactg ccaaagcaag cactcatgtg taggaattat tcttcctgtg    147240
agcatataat atatggaact ttgagacaga gtctcaaaca tatataatgt atattttatc    147300
atatattctt tatatataaa atatcatata gacacaaaat actgttctaa atacagagaa    147360
tactctgata tcaacttggg tattttttgt ttctgtgtgt gtgtattttg tttggttggt    147420
tattttttgag acaaggtcta gctctatcac acaggctgga gtgtagtggt gcgttctcgg   147480
ctcactgcaa cctccgcctc ccacctaagc ctgctgcatt agtgtctaca ggcatgcacc    147540
accacacccg gctcactttt gtattttttg tacacatggg gttacaccat gttgccgggg    147600
ctggtctcga actcctgagc tcaggtgatt ctcctgtctt ggcctcctaa agtgctggga    147660
ttagaggtgt gagccaccat gccccatcgg tacttgtgat ttaggttcaa attttgatga    147720
gtttttatga ccaagcctgt ggtctatcct agagaatgtt tgtgtgtttg acaattcaac    147780
atcgtagagt tgatttttggg tgctcccatt gggactgtgt gtccctgtac tggaacttga   147840
gtgaacactt ggctcataat ccattgctct tctctagaaa tccagcccaa ttctcttggt    147900
taaatataag gtatgtgtag caggcattgc ttttttccttc cagagacaaa actcaggagg   147960
attgcccctt gatgaacaag gctaacctgc tgattctttg aagcaaagaa ctggagatgg    148020
tcctttaga ggtttatatt ctggattcca gaaaacatgc aaacagggcc aataaatgca    148080
tctttatgtt ttcgtccatt ttaacttgat ctaggaaaat tccaaaaaaa aaacccacg    148140
gtgctggagc aagaagatct caggttgtga ccttctcgag gaagaagca ctttctgttg     148200
tctgaaagaa aagaaagtgc ttcctttcag agggttacgg tttgagaaaa gcaacgtcga    148260
agttgacgct gatcttggta atacatttgc agagcgtgct gatcatcaga catggataat    148320
```

```
ggtggggttt tgttttttgtt ttattttttt atctaagaca aggtatctgt tgcccaggct  148380
ggagtgcggt ggcacttcta acctagatct cttgggttca agtggccctc ttttcgggat  148440
agagtcttct ttgctctgtg gccctggctg gagtgcagtg gcaggaactc ggctcaccgc  148500
aacctctgcc tcctgggttc aagcaattct cctgcctcag cctgtcgagc agctgggtt   148560 acagacatgt gccaccacgc ctggctaatt tttgcatttt tattgtcgat cgattgattg  148620 attttttgaga cagagtctgg ctctgtcacc caggctgtcg ggcagtggtg cgatcttggc 148680
tcactgcaac ctccacctcc cacctcagcc tctgaatac ctgtctacag gcatgcacaa   148740
ccacaccttg ctaactttg tattttttgt acagatgagg tttcaccatg ttgcccaggc    148800
tggtctcgga ccctgagct caagtactcc tcaaacctgg gcctcctaaa ctgctgtgat   148860
taatggtgtg agccaccgtg ccctactctt acttgtgtgt ttctgctcaa attttattaa  148920 ggagcttta tggcctcgcc tgtggtctgt cctggaggat gttttgtgtgt gtgacaatgt   148980 atattcttca acatcttcga ttccatttg ggtgcctcca tggggactgt gtgtccctgt    149040
actggaacgc aagtgaagac ttggctcaga gtccatttgc tgttctctag aaatccagcc 149100
taatcctctt gtgcaaatat aatatatatc tagtaggcat tgcttttct ttctggagac    149160 aaaacacagg aggattgccc cttgatgaac aggactaacc tgctgattct ttgaagcaag  149220
gaactggaaa tggtcctttt agggatttat gctctggatt ccagaaaaca cgcaaacagg  149280
gccaataaat gcatctttat ttttgtgtcc attttgacct ggtcaaggaa gattccaaca  149340
aaaaatccac agtgccggag caagaagatc tcaggctgtg tccctctaca gggaagcgct  149400
ttctgttgtc tgaaagaaag gaaagtgcat cctttagag tgttactgtt tgagaaaagc    149460
aacgttgaag ttgatgctga ttttggtaat acatttgcag agcatgctta tcatcagact  149520
tggatgatgt tgggttctgt ttttgctttg tttttttttc caagacagtg tgtttgttgc   149580
ccaggctgga gtgcggtggt acttcccacc tagatctctt gggctcaaga ggtctttttt  149640 tattttttctt tctcaagaga gagtctggtg gtgacaccca ggctggagtg cagtggtgca 149700
ttatcagctc actgcagcct tcccctcccc ggttcaagtg attctttcac ctcagcctcc   149760
cgagtagctg ggattacagg tgtgggctac cacacccggc taatttttgt attttttagca 149820 gagacagggt tttaccatgt tggggaggct ggtctcaact cctgtcctca agcgatccac   149880
ctcccttgcc tcccaagtac tgagattaca ggcgtgagca actgcgcccg gcctcaagtg   149940
gtcctcttaa gtcagcctac caagttttgg gactacatgg ggcatgccac cacacttggc  150000
taagttttta atttttttt tttttttttt tttttttttt gagacggagt ctcactctgt     150060
cgcccaggct ggagtgcagt ggcaagatct cggctcactg caagctcggc ctccggggtt  150120
cacgccattc tcctgcctca gcctcccgag tagctgggac tacaggtgcc cgccaccacg  150180
cctggctagt tttttgtatt tttagtagag acggggtttc accctgttag ctaggatggt   150240
ctcaatctcc tgacctcgtg atccacccgc ctcggcctcc caaagtgctg ggattacagg   150300
cgtgagccac cgcgcccggc cgatagtttt taatttttga tagaaaggga atctctcttg    150360
cctaagatgg tctcaactcc tgagctcaag ggatcctaaa ggtgtgagcc gccttgtcct   150420
gatgacccat ttcaaacgta gctgacatgg ccaggcatca tggggcacac agtcccagct   150480
actgcagaag ccggggtggg agggtccttt gatttccagg ctataccatg tgctgatcac   150540
acttttgatc ccgagtagct gggattacag gcagccaccg ccaggccggc taattttat    150600 ttatttactt atttttttcag acggtgtttc cctcttgttg cccaggctgg agtgcaatgg 150660
```

```
catgatctcg gatcactgca acctccacct ccctggttca agcgattctc ctgcctcagc 150720
ctcccgagca gctgggatta caggcatgca tcaccacgcc cggctaattc tttgtatttt 150780
tagtagagat gggatttctc catgttggtc aggctgatct tgaactccca accttaggtg 150840
atccacccac ctcggcctcc caaagtgctg ggattacagg catgagccat tgtgcccggc 150900
ccatttcatt tattttatg tgtgctgctg aagcaagcac ttatgtgtag gaattgttct 150960
tcctgtgagc atatgttggc cagcctggac cacataccaa gatcccatct ctttaaaaac 151020
acagattacg tggcacctgg cacctggtcc cagagacttc atttgggttg gtcatttgaa 151080
acactagcct cccatcaatt tagtgtaatc aatccaaatc atgtgtcctt cattaagaga 151140
ctaagaacgc ctccacgtct atccagtcta ttttgtaatc cccaacggtt gtcaatatta 151200
ataaaatttc ttttctttt cctattcatt tgtgtcttta gttttcttc cccaaaaact 151260
tgccatcatt tctcggaata gacctgcttt ctctgcagga agggtgtggt tgattcaacc 151320
cttacccact aatgccaacc ccagtgagtt cttttatcct attttctatg ggtaacgatt 151380
ccaaggtacc attccaccgg gcaaaagctc acatctaagt gtcagttgct cggtaagatg 151440
tgaaatgttt gctgtggcta atataagaaa caaactattg tagacaagat gaatctcagt 151500
ggcagtgata aatgtcgcac aagacaaaac cacagatcct tttttttttt tttttttttt 151560
ttagacaaag tttcactctt gttgcccagg ctggagtgca atggtgcgat ctcggctcac 151620
tgcaacctcc gcctcctgga ggcgattcaa gcgattctcc tgcctcagcc tcccaagtag 151680
ctgggattac aggcatgcac caccacgccc aggtaatttt gtattttag tagagacggg 151740
gtttcgccat gctggtcagg ctggaactcc tgacctcaga tgatcctccc acctcagcct 151800
cccaaagtgc tgggattaca ggcgtgagcc actgtgcccg gccaaccaca gatactttca 151860
cgaaagcctt tagggcccta gaggggctc cctagtaaca ggtgggatgc gaggcagctc 151920
tcgttgttgc cgtagtgagc gatgcctgtt cgtccagccc tcaacacctt ttactccgtg 151980
gaagttatgc ctgcactggt ttacagaacc tcccttgact tgggttgagg tagagctgaa 152040
gggaacctca gtgtcccttg caggtgggat gtgcactgct tagcaagagc acggaggtgg 152100
agtgcatggg ctttgagttt ttattgggaa aatgaagctg aaatgtaggg cgcatgacca 152160
catcataaat gcacatttga tttaattttt ctatttatt tttatttatt tattttgaga 152220
tggagcctcg ctctgttgcc caggctggag tgcactggcc tgatctcggc tcactgcaac 152280
ctccacctcc cgggttcaag caattattgt gcctcagcct cccaggtagc tgggattaca 152340
cgcatgcttc cacgcccggc cgattttgt attttagta gagacggggt ttcaccatgt 152400
tggccaggct ggtttcaaaa tcctgacctc aagtgatccg cccgcctcgg cctctcaaag 152460
tcctgagatt acaggcgtga ccaccatga ccagcctaat ttttctattt tagagacagt 152520
ggtctagcta tgccacccgg gctaaactag gctttagaga tcttcctgcc tctgcccctc 152580
cacggtctct ggtagtttgg actacaaatg aacattagca tatttgcaac caccaccact 152640
ctagttttgga agattttat caccccaaag aagcttatac ccatttgcct tcagtaccca 152700
ccccctctt ccactcagac cctggcaact actctacatc tctctagctc tggatttgcc 152760
tcttgtgggc atttcacaaa aaccagtctt gaatgggtgg cctgttgtga ccacttttaa 152820
tataatgggt tggttctggt tgtctgaagt gtgaatcttg ccaatgaagg atggtccctg 152880
gatggaagca ggaggctggg agaactgggc ggaacatcct ttcggaatgg agtggggtgg 152940
gcacaccctg atgtctggga agctcacaag ggtggaagaa cccatcttcc tctctgataa 153000
ctgcaaggtg accctcctgg ggcactggat ggagtgaagg catctggact gggaacacca 153060
```

```
gggcattgca ctggtgcagg caggatgagc cgagggaaa ggagtgccag gcatcattct  153120
ctggtgacag tttgggtttg atctggatgg agcaggtgtc ttctggtaga gagagtccct  153180
gggatttttg ctctgctcct ggctgtcttt cagtcatgga atctgatgac aaaggctccc  153240
actctgggcc acttcatttg gtttctggag cccagtggtc ctttctgccc ggactcagga  153300
tcttttgggg aaatttggga cctcgcagga catctgcaca atccatagaa atccctgaga  153360
gccccttccc tttgctgaca tctccgtatt cctacctatt gccttccaaa aaagaccct   153420
tatctgaatt gccaaagggg gcttcccaga gcagggaaac ccggttaaat ttgtatttca  153480
gattaacagc atatctagaa tctactcgaa caagaagtga tttgttgttt aagtgtgaga  153540
aattttttc ccctaattt aaatacggaa cccatcatga atttggctgt cacctttgcg   153600
cagggccgt gggaacctat catttcattg tttaatgtgt gctgccaaag caagcactta   153660
agtgtgggaa ttattcttca cgtgaggata caatagatgg aacgttatta cttttttctt  153720
tcataattga gattttattg gttgaagatc ggtacagaca tttcaatttg tacacaattc  153780
ttaacatacg taccgaaaat ctaaaaagcc atgtattgta aatcgttttg ttttgttttg  153840
ttttttgag acagagtttc gctcttgtca cccaggctgg agcgcaatga cgcaatctcg   153900
gctcaccgca acctccgcct cccgggttca agcaattctc ctgcctcagc ctcccaagta  153960
gctgggatta caggcaaatg ccaccatgcc cggctaattt ttgtattttt ttttttttaa  154020
gtagagacag gcttctgcc tgtcggtcag gctggtctcg aattcccgac ctcaggtgat   154080
ctgcccgcct cggcctctta aagtgctgag attacaggcg tgagccaccg cacccggcca  154140
tgtattgtaa ttcttctaca aagttattcc ggcgactttc cagcttaaaa tttggaagca  154200
cattttcctt aagaggctat caagtaccag tatcttcaca tgttgatcag ctgttacgga  154260
cgtccctcca attcacaact aaaaatagca tgtaccctac atattcaaat ttttcatctt  154320
tcacaacgca gaaacaaact tattaggaga acagaactac cacaatcaaa gatgttacag  154380
agtccacaca attctaacag ggagagccat ggtcagggag tggttttctt taggaaacaa  154440
ttccaaaata cgacaggaga atagaagtaa tttaaaatgt tcaagacact aaatgcagag  154500
ctgattccat gctgccattt aatatgcttt gtattatagg atataaacac gaaccctggc  154560
cgggtgcagt ggctcacgcc tgtaatccca gcactctggg aggccgaagt gggcagatca  154620
cctgaggtca ggagttcaag accagcctgg cccacatggt gaaacccat ccctactaaa    154680
aatatgaaaa ttagccaggc atggtggtgc gcgcctgtaa tcccagctac tccggatgct  154740
gaggcatgag aatcgcttga acccgggagg tggagattgc agtgaactga aatcacgcca  154800
ctgccctcca gcctgggcga caagaacaag actctgtttc aaaaaaaaaa aaaaaaaaa   154860
agttctgga actactaaaa aacttgcatt tacaaaatag ttgataaaaa gattcctctg   154920
ggttttacaa gaagcgagac agggagcact gatgagacgt ggtatacggt gaatcagact  154980
gggcatcaga ggctgggcct cctcagtttt cctttcccca ttttctgcag ataaatcttt  155040
agtttcttgg ttagccactt ctgcccgttt tcccttttgct cccctttgcc cttctgttca  155100
cactttttg tctgaagatg tatccttcgt tgctgccttt ttcggcttca tttccactgg   155160
ttttttttgtt ttgttttgtt ttgttttgtt tgagacgtag tttcacccctg ttgctcaggc  155220
tggagtgcaa tggcgtgatc tcggctcaca gcaacttctg ccttccggtt caagcgattc  155280
tcttgcctca gcctcccgag tagctgggct tataggcgcg caccgccatg cccggcttat  155340
ttttgtattt ttagtagaga cgggggtttc accatgttgg ccaggctggt ctcgaactcc  155400
```

```
tgacctcagg tgatccgccc gcctcagcct cccaaagtgt tgtgattaca agcgtgagcc   155460
accgcacccg gccttgcttc cacttttgca ggagcaggtt tagctgacaa ccgtgcgatc   155520
tcctcgtggg ctcttccttg gcggcccta tggcggagct aacctgcctc ttgggcatcc    155580
tggtggcgga gagggcgcgt gccggctgtc tgcgggccgc ggctgccgag agccttggcg   155640
aagctgggct gcctggcggc tgcggctcct cccgccgccc gagctgctga gacccacagc   155700
ggggtcggtg ggagaaccga atggaacccg aaactttctt attttgagac aggatctggc   155760
tctgtcaccc aggctggagt gcttggctca ctgcaacgtc tgcctcaagt gatccttcca   155820
cctcaacctc ccaagtagct gagattacag gcgcgcgtgc cactatgcct ggctaatttt   155880
tgtactcttt gtagagatgg gggtctcgct atgttgccca cgctggtctt gaactcctgg   155940
gctcaaatga tcctcctggc ctggcttccc aaagtgctgg ttgtaacgcc agcagtttgg   156000
gaggccacag tcggcgggat ggattagcta gcaacaaaca ttccaggcag agaatggtgc   156060
tctctcaact ctcagtcagc aaggggctag tatatattga aggggctcag ggcatgtcac   156120
cccaaagtca tcgcgtcagc atatggatta tttcgacctg gaagcctgtg ggaaaaagca   156180
gatgcatctg acctccccct tcctacgtaa aagtagattg taaaatttat caagaggaaa   156240
acgcccttcc tgcgccagga agagaagaat gttcctatca gcaggggcca ggagtccata   156300
tgctaaacaa ctcagctact aaccctatc ttccttaagt tcccactgt ttcctggtca     156360 cttcccctag cccaagcctc tttgtcttgt cacatcccca caactatca ttcctttttt    156420 ttttttgagg tggagtttag ctcttgttgc ccaggctaga gtgcgatggc gcaatcttgg   156480
ctcactgcaa cctctgcctc ccgggttcaa gtgattctcc tgcctcagcc tcccaagtag   156540
ctgggattac aggcgcccac caccacgctc ggctgatttt ttgtattttt agtagagatg   156600
gggttttgcc atgctggcca ggctggtctt gaactcctga tctccggtga tccgcccgcc   156660
tcagcctccc aaagtgctgg gattgattac aggcgtgagc caccgcgccc ggccatcatt   156720
ctcttttttg ttttgttgtg gttgttgttg tttgagacag cgtctggctt tgtcacccaa   156780
gctggagtgc agtggcgcca tctcagctca ctgcgacctc tgcctcccgg gttcaagcaa   156840
ttctcatacc tcagcctccc gagtagctgg aaccacaggc atgagccacc atgcccggct   156900
agttacaggg ttttcctatg ctctccaggc tggagtgcag tggcgcaatc atagttcact   156960
gcagtcttca actcctgggc tcaagcaatc ctcccacctc agcctcttaa actgctggga   157020
ttacaggtgg tagccatcat gccctgcccc agagaagtct ttaggcttca gccaggcacg   157080
gtggctcagg ccggtaaacc cagcactttg ggaggctgag gtgggaggat cgcttgtgcc   157140
caggagttga aggctgcaat cagctatgac tgcaccacag cactccagtc tgggcaacaa   157200
agtgagaccc tgtctcaaaa aacaacaccg taggcccagc acggtggctc ctgcctgtaa   157260
tcccagcact ttgggaggcc aaggcaggtg gatcacttga ggtccagagt tcaggaccag   157320
catgaccaac atggtgaaac cccgtctcta ctaaaaatat acaaattagc caggtgtggt   157380
ggcagacacc tgtaatccca gctacttggg agactgaggg aggataattg cttgaacccg   157440
ggaggcggag gttgcggtga gccaagatcg cgccattgca ctccagcctg gttgacagag   157500
caagaccctg tctcaaaaag aaaggaaaag aaaagaata caccagaagg tacccagaga   157560
ggccagtgtg gatgtacagc cagcacataa gatgctggtt agggacaggc gcagtggctc   157620
acgcctgtaa tcccagcact ctgggaggcc caggcagggg gatcacctga ggtcaggagt   157680
tcaagaccag cctggccaac atggcgaaac cccgtctgta ctagcaaata caaaaattac   157740
ttgggcgcgg tggcacgtgc tataatccca gctactccgg aggctgaggg tggaaaattg   157800
```

```
cttgaacccg ggaggctgag gttgcagtga gccgagatcg caccactgta ctccagcctg    157860
ggcaacaaga gcgaaactcc gtctcaaaaa attaaataaa taggccgggc gcggtggctc    157920
acgcctgtaa tcccagcact ctgggaggcc gaggagggcg gatcacgggg tcaggagatc    157980
aagaccatcc tggccaacat ggtgaaaccc cgcctctact aaaaatacaa aaacttcgcc    158040
ctgtatggcg gcacacggct gtattcccag ctactcggga ggctgaggca ggagaacggc    158100
ttgaacccgg gaggcagagg ctacagtgag ccgggatcac accgctgcac tccggcctgg    158160
gcagcaagag caaaactctg tctcaaaaaa caaaaaacag aaaaacaaaa agaatcaagt    158220
aagtcgaagc cacactgata acagccaatt tttgtgaacc aagggagtgt caattcaaga    158280
atttacatag atgtctactt ttgctatctc ctatgtgcca agcaagatac aggctctggg    158340
caatcagaaa caaagagac tcactcgttc ctctcacagt actcagtcct tactgagata    158400
aggacaaaag aaaatgtcct gtctggaatg cagggaaacc agaacttcag gtcagggac    158460 atttccattg aattgtgtgg agttgaagct gaaaatactt ttttttttt tttttttttt    158520 acatcacggc atggtttatt acgtgatttt tttactatac aaacaaaaa tacagaaatg    158580 caatatgtga atacagctaa atgcagaatg gtgacttttt tctcttcaag aggccatgat    158640
tcccatttct agtaaaataa agagaccgca tacaggttgg ttgtgagatt cacaattttg    158700
cctagaaatg atctataaat gcattttttcc cccctgctac ctaccgtaaa tcgtaaaaag    158760
ggagttaaag caaagtttcc ttgttggttc ctaccatatg gaagatgcta tattctattt    158820
tagcagggtc aatatttgga aaatatctaa attaaatatt attacaaaaa tgaagctgta    158880
atgagattct ggctaaagag ggcactaaat gagaataata tatatttaaa gaatccaaaa    158940
caaacaaaca aaaagaggtt attataaaaa gctctaggtg cactgtaagc atataggggtt    159000 ttttttttcat gtgttttttt ttaaacaatg gaagtgtcaa aaatagggtc aactgtgtta    159060
gactaaatta cattattgta tatgctgcat tgaatggaac ctttgtatta taattatcat    159120
agagaagcac agtttgcatc atattatggc aattcatcgt caatgaaaac cttccagagt    159180
ccttttattt tggaatctcc tgtaaactat caaaccacca gaacatgact gtacaacagt    159240
aaaatgttct cttgcattaa actgaagaga cctgtttaat aaaaaaagaa aaagaaaatg    159300
taggaaaggt acttagagct gttacttttct aagtacacaa caccctagac aattcgaggc    159360
atcttaatct ccatcaagaa caacaacaac aaaaataatt tttgtcatgt tgttaaatcc    159420
atcattatgg atcaaactgg tgcaacttgg tcaaatgaat ccaacaaaca ctgatgtcca    159480
agctggcata ttggcaacta atacacaact ggtggtcaat agagagttta aaagatcttc    159540
cctttcttgt tgttcttttc caaggttctc aaagagttct gttgctctaa aatacgttgt    159600
tgagcttccc agtttgcttt ctcatcctca aactgacgac gtttctcctc taattctttg    159660
tgccgtgctc ccaaattctt tttcagttgc acatggcact gctggagcta atcacagca    159720 caatatatac cccaaggata ctgccttcct ctgacccttt ttccattaac ttcagtgata    159780
atatcactac ccaccacagc aagaggtaaa cggtccttta tcttttttaac acgtttcttt    159840 tcttcttcat catctgtttc tggaaattca tatattttaa ttttatgttc ttggatttct    159900
ttcattatct gttttgtaaa ctgttgacat tcctctggtg tgagtgtgtc tgctttggca    159960
gtaagtggga tgatattcac ttttttcatgc aaatgtttca taaactcaac atccagtggt    160020
ttaagtctca acaaaaggca atgtcaagta gttacaaaca tgcactaccc aatcctgcct    160080
gaaggtggga gtcttcagtt atgtaatggt cctgttatca ggcatctgac gtctgctcac    160140
```

```
tcgcgattct gcatttaggt agtcctcaaa tttactatca atgtaatcga taacaggctg    160200
ccagcaatta ctactatcca ctgcatctcc aaatcctgag gtatcaacta tcctgagcag    160260
caactaaaca ccaccttctt tgattaaaac tttggattgt tccatccagg cttctatttt    160320
cccatagagg tccaaaaaac gcccttgttt gttaagttga tatatgtaaa ccttttctcc    160380
aggctgttcc ttgaggttta cataattggg aactccttca agcatctgta aataaacctt    160440
ttcagctgta gatctctcta ttttcagtta atttgcagac caccaactat aggagccaag    160500
ttgaaagaga aaaagtttc tcttcccagc actttcttta ggatgctttt cattgcttcc     160560
caactggagg cctcgcccct cacccacct gccctagtcc tcagctgcct ccagttctgt     160620
ccacttaaat acagactccc ggtagtagag aacttttta aaattttatt attattatta    160680
ttattattat tgacacagtc ttactctgtc gtccaggctg gagagcagtg gcacaatctc    160740
agctcactgc agcctctgcc tcctgggttc cagcgattct cctgcctcag cctcctgagt    160800
agctgggatt acagcaccc gccaccatgc ccggctaatt tttgtatttt tggtagagac     160860
gggggtttca ccatgttggc caggctggtc ttgaactcct aacctcaggt gatcctccta    160920
cctcggcctc ccaaagtgct gggattacag gcgacagcca atgtgtgcac                160970
```

```
<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
actgggacga catggagaaa a                                                21

<210> SEQ ID NO 62
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 62
gccacacgca gctc                                                        14

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 63
tgcaaggaaa gcattgaaca a                                                21

<210> SEQ ID NO 64
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 64
gaggagtcac ctggacaatc act                                              23

<210> SEQ ID NO 65
<211> LENGTH: 22
```

```
<212> TYPE: DNA
<213> ORGANISM: Artificial Sequence
<220> FEATURE:
<223> OTHER INFORMATION: Synthetic oligonucleotide

<400> SEQUENCE: 65
cacatgaagc agcacgactt ct                                              22

<210> SEQ ID NO 66
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 66
aactccagca ggaccatgtg at                                              22

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gcggtggttg cccaacagga                                                 20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
acgacccgtg gtcatcttta                                                 20

<210> SEQ ID NO 69
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 69
tagaggatca cgtaattgca gga                                             23

<210> SEQ ID NO 70
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 70
gttgtcaaag ctgagccttc tat                                             23

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
```
atgccagacc gtcttgatac a                          21

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 72
tgacccaagt atttcagccc a                          21

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 73
gaacaacggt ttcgctcttt g                          21

<210> SEQ ID NO 74
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 74
gcttctacat taggccagac ttt                        23

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 75
acccgcttaa cagcgtcaac a                          21

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
ccaaagaggt gcgggagttt                            20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
gccaatgagg gttcgagttc                            20

<210> SEQ ID NO 78
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 78
aacaacatcc cgtcgttcat c                                              21

<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 79
acgaatccca gtgtgttttg g                                              21

<210> SEQ ID NO 80
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 80
tgctcaaaaa cggtatggac at                                             22

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
caaccaagca aatgtgagga                                                20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
ggagacttgc ctggtgaaaa                                                20
```